United States Patent [19]

Dürckheimer et al.

[11] Patent Number: 5,089,490

[45] Date of Patent: * Feb. 18, 1992

[54] CEPHEM DERIVATIVES

[75] Inventors: Walter Dürckheimer, Hattersheim am Main; Dieter Bormann, Kelkheim; Eberhard Ehlers, Hofheim am Taunus; Elmar Schrinner, Wiesbaden, all of Fed. Rep. of Germany; René Heymes, Romainville, France

[73] Assignee: Hoechst Aktiengesellschaft, Frankfurt am Main, Fed. Rep. of Germany

[*] Notice: The portion of the term of this patent subsequent to Jul. 19, 2005 has been disclaimed.

[21] Appl. No.: 572,150

[22] Filed: Aug. 23, 1990

Related U.S. Application Data

[62] Division of Ser. No. 187,833, Apr. 29, 1988, which is a division of Ser. No. 891,850, Mar. 30, 1978, Pat. No. 4,758,556.

[51] Int. Cl.$^5$ .................. C07D 501/36; A61K 31/545
[52] U.S. Cl. ..................................... 514/206; 540/227; 540/225
[58] Field of Search ................ 514/202, 206; 540/227

[56] References Cited

U.S. PATENT DOCUMENTS

| 4,091,211 | 5/1978 | Montavin et al. | 544/27 |
| 4,264,595 | 4/1981 | Numata et al. | 544/25 |
| 4,355,160 | 10/1982 | Ochiai et al. | 544/27 |
| 4,514,565 | 4/1985 | Ochiai et al. | 540/227 |
| 4,758,556 | 7/1988 | Dürckheimer et al. | 540/227 |

Primary Examiner—Nicholas S. Rizzo
Attorney, Agent, or Firm—Curtis, Morris & Safford

[57] ABSTRACT

Cephem derivatives of the general formula

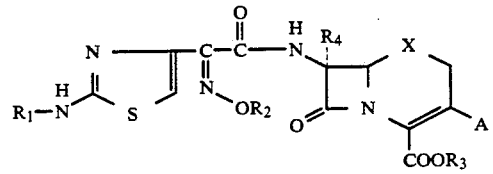

in which the $R_2O$ group is in the syn-position, a process for their manufacture and pharmaceutical formulations which are active against bacterial infections and contain these compounds.

13 Claims, No Drawings

CEPHEM DERIVATIVES

This application is a division of application Ser. No. 187,833, filed Apr. 29, 1988, which in turn is a divisional application of prior application Ser. No. 891,850, filed Mar. 30, 1978, now U.S. Pat. No. 4,758,556 issued July 19, 1988.

The invention relates to cephem derivatives of the general formula I

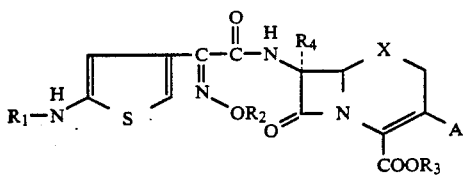

in which $R_1$ denotes hydrogen, an optionally substituted alkyl, acyl, arylsulfonyl or alkylsulfonyl group or an amino-protective group which is known from peptide chemistry, $R_2$ denotes hydrogen or an optionally substituted alkyl, alkenyl, alkinyl, cycloalkyl, aralkyl, acyl, aryl, arylsulfonyl, alkylsulfonyl or heterocyclic group, $R_3$ denotes hydrogen, an ester group or a cation, $R_4$ denotes hydrogen, a lower alkoxy group or a group which can be converted to this, X denotes sulfur, oxygen, $-CH_2-$ or $-NH-$ and A denotes hydrogen, an optionally substituted alkoxy or alkenyloxy group, halogen or a group $-CH_2Y$, in which Y represents hydrogen, halogen or the radical of a nucleophilic compound, and in which the $R_2O$ group is in the syn-position, with the exception of those compounds, in which X denotes sulfur and $R_4$ denotes hydrogen and simultaneously a) $R_1$ denotes hydrogen or a group K, $R_2$ denotes hydrogen, a group K or saturated or unsaturated alkyl with 1 to 4 carbon atoms $R_3$ denotes either hydrogen or an equivalent of an alkali metal, an alkaline earth metal or of a base L, A denotes a group $-CH_2OCOCH_3$, but if $R_2$ denotes a group K, $R_1$ denotes also a group K, and, if $R_2$ denotes hydrogen, $R_1$ also denotes hydrogen, or b) A denotes either a group $-CH_2-S-R'$ (in which R' denotes either an acyl group with 2 to 4 carbon atoms, a 2-methyl-1,3,4-thiadiazolyl group, or a 1-methyl-tetrazolyl group), or A denotes methyl, $R_1$ denotes hydrogen or a group K, $R_2$ denotes saturated or unsaturated alkyl with 1 to 4 carbon atoms, $R_3$ denotes hydrogen, an equivalent of an alkali metal, an alkaline earth metal or of a base L, or $R_3$ denotes a group M, but if $R_1$ denotes hydrogen, $R_3$ cannot denote a group M, or c) $R_1$ denotes hydrogen or a group K, $R_2$ denotes saturated or unsaturated alkyl with 1 to 4 carbon atoms, A denotes a group $-CH_2OCONH_2$, $R_3$ denotes either hydrogen or an equivalent of an alkali metal, an alkaline earth metal or of a base L, or d) $R_1$ denotes hydrogen, a group K or a chloroacetyl group, $R_2$ denotes saturated or unsaturated alkyl with 1 to 4 carbon atoms, A denotes a group of the formula

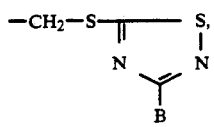

with B standing for alkyl with 1 to 4 carbon atoms or alkoxy with 1 to 4 carbon atoms, $R_3$ denotes hydrogen, an equivalent of an alkali metal, an alkaline earth metal or of a base L, or $R_3$ denotes a group M, but if $R_1$ denotes hydrogen, $R_3$ cannot denote a group M, or e) A denotes a group $-CH_2OCOCH_3$, $R_1$ denotes hydrogen, a group K or a chloroacetyl group, $R_2$ denotes the group

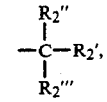

wherein $R_2'$ denotes either a $-CO_2R_1'$ group, in which $R_1'$ denotes alkyl with 1 to 3 carbon atoms or hydrogen, or $R_2'$ denotes a nitrile group or $R_2'$ denotes a carbamoyl group, $R_3$ denotes hydrogen, an equivalent of an alkali metal, alkaline earth metal or of a base L, or $R_3$ denotes a group M, $R_2''$ and $R_2'''$, which may be the same of different, denote hydrogen or alkyl with 1 to 3 carbon atoms, but if $R_1$ denotes hydrogen, $R_3$ cannot denote a group M, and in the case where $R_1$ denotes hydrogen, if $R_2'$ denotes a $-CO_2R_1'$ group, in which $R_1'$ denotes hydrogen, $R_3$ denotes hydrogen, but if $R_1$ denotes a group K, $R_2'$ cannot denote the $-CO_2R_1'$ group, in which $R_1'$ denotes hydrogen, or f) A denotes chlorine or methoxy, $R_2$ denotes hydrogen, saturated or unsaturated alkyl with 1 to 4 carbon atoms, a group K or a chloroacetyl group, $R_1$ denotes hydrogen, a group K or a chloroacetyl group, $R_3$ denotes hydrogen, a group M or an equivalent of an alkali metal, an alkaline earth metal or of a base L, but if $R_2$ denotes a group K, $R_1$ also denotes a group K, and if $R_2$ denotes a chloroacetyl group, $R_1$ also denotes a chloroacetyl group, and, if $R_2$ denotes hydrogen, $R_1$ also denotes hydrogen and, if $R_1$ denotes hydrogen, $R_3$ cannot denote a group M, wherein in the above paragraphs a) to f) K denotes a tert.-butoxycarbonyl, trityl, benzyl, dibenzyl, trichloroethyl, carbobenzyloxy, formyl, trichloroethoxycarbonyl or 2-tetrahydropyranyl group, L denotes trimethylamine, triethylamine, methylamine, propylamine, N,N-dimethylethanolamine, tris-(hydroxymethyl)aminomethane, arginine or lysine and M denotes a benzhydryl, tert.-butyl, benzyl, p-methoxybenzyl or trichloroethyl group.

The invention furthermore relates to a process for the manufacture of cephem derivatives of the general formula I, which comprises a) reacting lactams of the general formula II

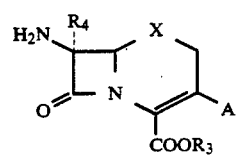

wherein A, X, $R_3$ and $R_4$ have the meanings indicated above, but $R_3$ cannot represent hydrogen, with reactive derivatives of a carboxylic acid of the general formula III

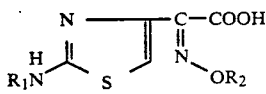

(III)

in which the radicals $R_1$ and $R_2$ have the meanings indicated above, but $R_1$ cannot by hydrogen, or b) reacting cephem compounds of the general formula IV

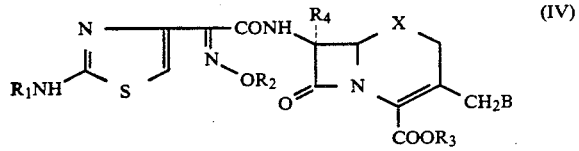

(IV)

in which the radicals $R_1$, $R_2$, $R_3$, $R_4$ and X have the meanings indicated above, but $R_3$ cannot represent an ester group, and B represents a group which can be replaced by a nucleophile, with a compound containing the nucleophilic radical Y in the presence of bases to give compounds of the general formula I in which A represents —$CH_2Y$, and, if desired, in the compounds manufactured according to a) or b)

α) converting a resulting salt into the free carboxylic acid and optionally further esterifying this, or converting a resulting salt directly into an ester, β) saponifying a resulting ester and optionally converting the resulting product into a salt, γ) splitting off a radical $R_1$ and/or $R_2$, if this denotes a protective group, δ) if $R_1$ represents hydrogen, introducing a radical $R_1$, which denotes optionally substituted acyl, alkylsulfonyl or arylsulfonyl, by reaction with the corresponding activated carboxylic and sulfonic acid derivatives, and ε) if $R_4$ represents a group which can be converted into a lower alkoxy group, carrying out this conversion, it being possible for one or more of the reactions given under α) to ε) to be used.

The present invention relates to compounds of the general formula I in which the substituents can have, for example, the following meaning.

$R_1$ can represent hydrogen, optionally substituted alkyl with 1–6 carbon atoms, preferably tert.-butyl, tert.-amyl, benzyl, p-methoxybenzyl, benzhydryl, trityl and phenylethyl, benzyl, benzhydryl and trityl also being amino-protective groups which are known from peptide chemistry, aliphatic acyl with 1–6, preferably 1–4, C atoms, such as, for example, formyl, acetyl or butyryl, it also being possible for such an acyl group to be further monosubstituted or polysubstituted, for example by halogen, such as, for example, fluorine, chlorine or bromine, which can also lead, for example, to the chloroacetyl or trichloroacetyl radicals, which are known from peptide chemistry as amino-protective groups, by aryl, in particular phenyl, which can also carry still further substituents, such as, for example, a heterocyclic radical defined under $R_5$; alkyl with 1–4 C atoms, preferably methyl; alkenyl with 1–4 C atoms, preferably allyl; alkoxy with 1–4 C atoms, preferably methoxy; alkylthio with 1–4 C atoms, preferably methylthio; halogen, preferably chlorine or bromine; sulfamoyl, carbamoyl, carboxyl or trifluoromethyl; alkoxycarbonyl with 1–4 alkyl C atoms, such as, for example, methoxycarbonyl; cyano or nitro; amino; alkylamino with 1–4 C atoms, such as, for example, methylamino or ethylamino; dialkylamino with 1–4 C atoms, such as, for example, dimethyl- or diethyl-amino, or amidino, by a nucleophilic radical, defined under Y, preferably —$SR_5$, by aryloxy, in particular phenoxy, by arylmercapto, in particular phenylmercapto or by arylamino, in particular phenylamino, it also being possible for these aryloxy, arylmercapto and arylamino radicals, for example, to carry the substituents indicated above for aryl (as a substituent of the aliphatic acyl $R_1$), by an optionally substituted hetero-aromatic 5-membered or 6-membered ring with 1 to 4 hetero-atoms, in particular nitrogen, sulfur or oxygen, such as is described in detail under —$SR_5$, by hydroxyl, by alkoxy with 1–4 C atoms, in particular methoxy or ethoxy, by alkylthio with 1–4 C atoms, in particular methylthio or ethylthio, by alkylamino with 1–4 C atoms, in particular methylamino or ethylamino, or by dialkylamino with 1–4 C atoms, in particular dimethyl- or diethyl-amino, which can be closed to form a 5-membered to 7-membered ring which can be optionally interrupted by hetero-atoms, such as, for example, oxygen or nitrogen, such as, for example, morpholine, piperazine or N-alkyl-piperazine in which alkyl has 1–4 C atoms, preferably N-methylpiperazine, aromatic acyl, preferably benzoyl, it also being possible for the aromatic group to be substituted, such as is indicated above for the aryl substituents of the aliphatic acyl radical $R_1$, hetero-aromatic acyl, the hetero-aromatic 5-membered or 6-membered ring with 1 to 4 hetero-atoms, which can also be further substituted, as described above for aryl, being one such as is described in detail under —$SR_5$, optionally substituted alkylsulfonyl with 1–4 C atoms, in particular methylsulfonyl or ethylsulfonyl, arylsulfonyl, preferably phenylsulfonyl, which can be substituted in the manner indicated above for aryl, in particular by nitro, amino or alkyl with 1–4 C atoms, such as, for example, methyl, or an amino-protective group which is known from peptide chemistry (compare, for example, Houben-Weyl, volume XV/1, page 46 (1974)), in particular alkoxycarbonyl with 1–4 alkyl C atoms, which is preferably substituted by halogen or cyano, such as, for example, methoxycarbonyl, tert.-butoxycarbonyl, trichloroethoxycarbonyl or cyano-tert.-butoxycarbonyl, or arylalkoxycarbonyl with 1–4 alkyl C atoms, in particular phenylalkoxycarbonyl, it also being possible for the aryl radical to be further substituted, for example by nitro or lower alkoxy, preferably benzyloxycarbonyl, p-nitro- or p-methoxy-benzyloxycarbonyl, 3,5-dimethoxybenzyloxycarbonyl or 2-biphenylyl-4-isopropoxycarbonyl, or trialkylsilyl, in which alkyl can consist of 1–4 C atoms, such as, for example, trimethylsilyl or tert.-butyldimethylsilyl.

$R_2$ can denote, for example, hydrogen, alkyl with 1–4 C atoms, such as, for example, methyl, ethyl, propyl or butyl, preferably methyl, or cycloalkyl with 3–8, preferably 3–6, C atoms, such as, for example, cyclopropyl, cyclobutyl, cyclopentyl or cyclohexyl, it also being possible for alkyl and cycloalkyl to be further monosubstituted or polysubstituted, for example by alkyl with 1–4 C atoms, preferably methyl, by cycloalkyl with 3–8, in particular 3–6, C atoms, such as, for example, cyclopentyl or cyclohexyl, by alkoxycarbonyl with 1–4 alkyl C atoms, preferably methoxycarbonyl or ethoxycarbonyl, by carboxyl; cyano; carbamoyl, which can be monosubstituted or disubstituted by optionally substituted, for example hydroxyl-substituted, alkyl with 1–4 C atoms, it also being possible for 2 substituents to be closed to form a 5-membered or 6-membered ring which is optionally interrupted by O or N, such as, for example, morpholino, piperazino, N-methylpiperazino or pyrrolidino, by alkylcarbonyl with 1–4 alkyl C atoms, in particular acetyl, by sulfo or sulfamoyl, by alkoxysulfonyl with 1–4 C atoms, in particular methoxy- or ethoxy-sulfonyl, by a phosphono group, by hydroxyl, by halogen, preferably chlorine or bromine, by alkoxy with 1–4 C atoms, in particular methoxy or ethoxy, by alkylthio with 1–4 C atoms, in particular methylthio or ethylthio, by acyloxy, in particular aliphatic acyloxy with 1–4 C atoms, such as, for example, acetoxy or benzoyloxy, by carboxyalkoxy with 1–4 alkyl C atoms, in particular carboxymethoxy, or by aryl, preferably phenyl, which can be substituted, as indicated above for the aryl substituent of the aliphatic acyl radical ($R_1$), alkenyl with 2–6, preferably 3–5, C atoms, such as, for example, allyl or crotonyl, which can also be further substituted, for example by alkyl with 1–4 C atoms, preferably methyl, by halogen, in particular chlorine or bromine, by carboxyl or carbamoyl, which can be substituted, as indicated above under alkyl ($R_2$), or by alkoxycarbonyl with 1–4 alkyl C atoms, in particular methoxycarbonyl or ethoxycarbonyl, alkinyl with 3–5 C atoms, preferably propargyl, which can also be further substituted, for example by aryl, preferably phenyl, aliphatic, saturated or unsaturated acyl with 1–7, preferably 1–4, C atoms, such as, for example, formyl, acetyl, propionyl, butyryl, hexanoyl, acryloyl, crotonoyl or propioloyl, which can also be further substituted, for example by halogen, such as, for example, chlorine, bromine or fluorine, which leads, for example, to a chloroacetyl, dichloroacetyl or bromoacetyl radical, by amino, by alkylamino with 1–4 C atoms, preferably methyl- or ethyl-amino, or by dialkylamino with 1–4 C atoms, in particular dimethyl- or diethyl-amino, which can also be closed to form a ring which is optionally interrupted by hetero-atoms, such as oxygen, nitrogen or sulfur, such as, for example, morpholine, piperazine or perhydrothiazine, aromatic acyl, such as, for example, benzoyl or naphthoyl, which can also be substituted, for example by alkyl with 1–4 C atoms, in particular methyl, by halogen, preferably chlorine or bromine, by alkoxy with 1–4 C atoms, in particular methoxy, by dialkylamino with 1–4 C atoms, in particular dimethyl- or diethyl-amino, which can also be closed to form a ring which is optionally interrupted by hetero-atoms, such as, for example, oxygen or nitrogen and which has already been described above, or by trifluoromethyl, heterocyclic acyl, which is derived from heterocyclic 5-membered or 6-membered rings with 1 to 4 hetero-atoms, such as, for example, sulfur, oxygen and nitrogen, such as, for example, thenoyl, furoyl, nicotinoyl, isonicotinoyl or picolinoyl, and which can also be further substituted, for example by substituents such as are indicated above for aromatic acyl ($R_2$), optionally substituted arylsulfonyl, in particular phenylsulfonyl, p-tolylsulfonyl and p-amino-phenylsulfonyl, optionally substituted alkylsulfonyl with 1–7, preferably 1–4 C atoms, in particular methyl- or ethyl-sulfonyl, aryl, preferably phenyl, or, for example, 1- or 2-naphthyl, which can also be further substituted, for example by substituents such as are indicated above for aromatic acyl ($R_2$), or a heterocyclic group, which is derived from a heterocyclic 5-membered or 6-membered ring with 1–4 hetero-atoms, such as, for example, sulfur, oxygen and nitrogen, such as, for example, thienyl, furyl, pyridyl or picolinyl, and can also be further substituted, for example by substituents such as are indicated above for aromatic acyl ($R_2$).

$R_3$ can represent, for example, hydrogen, an ester group or a cation.

If $R_3$ denotes an ester group, possible examples of this are straight-chain or branched alkyl with 1 to 12, preferably 1 to 6, C atoms, such as, for example, methyl, ethyl, i-propyl, tert.-butyl, hexyl as well as, for example, octyl or dodecyl, straight-chain or branched alkenyl with 2 to 12, preferably 3 to 5, C atoms, such as, for example, allyl, crotyl, pentenyl as well as dodecenyl, or straight-chain or branched alkinyl with 3–12, preferably 3–5, C atoms, such as, for example, propinyl, butinyl, pentinyl as well as dodecinyl, it also being possible for these alkyl, alkenyl or alkinyl groups to be monosubstituted or polysubstituted by identical or different substituents, for example by halogen, in particular chlorine or bromine, whereby, for example, a trichloromethyl radical results, by hydroxyl, by alkoxy with 1 to 4 C atoms, in particular methoxy or ethoxy, once or twice, preferably twice, by carbocyclic or heterocyclic aryl, such as, in particular, phenyl, or radicals which are derived from hetero-aromatic 5-membered or 6-membered rings with 1 to 4 hetero-atoms, such as, for example, sulfur, oxygen and nitrogen, such as, for example, thienyl, furyl or pyridyl, which can also carry still further substituents, for example those which have been given above in detail for the aryl substituent of the aliphatic acyl group ($R_1$), by carbocyclic or heterocyclic aryloxy, such as, in particular, phenoxy, or radicals which are derived from hetero-aromatic 5-membered or 6-membered rings with 1 to 4 hetero-atoms, such as, for example, sulfur, oxygen and nitrogen, such as, for example, pyridinoxy, which can also carry further substituents, such as have been indicated above, for example, for the aryl substituent of the alkyl radical $R_3$, by carboxyl or cyano, by carbamoyl, which can also be substituted, for example by one or two alkyl groups with 1–4 C atoms, preferably methyl; or lower aralkyl, preferably benzyl, by alkoxycarbonyl with 1–4 alkyl C atoms, such as, for example, methoxycarbonyl, by alkylcarbonyloxy with 1–6, preferably 1–4, alkyl C atoms, such as acetoxy, pivaloyloxy or also hexamoyloxy, by cycloalkylcarbonyloxy with 3–7 cycloalkyl C atoms, such as, for example, cyclohexylcarbonyloxy, by aroyloxy, such as, for example, benzoyloxy, by carbocyclic or heterocyclic arylalkylcarbonyl with 1–4 alkyl C atoms, such as, for example, phenylacetyl or thienylacetyl, by carbocyclic or heterocyclic aryloxyalkylcarbonyl with 1–4 alkyl C atoms, such as, for example, phenoxy or thienyloxy, by alkylcarbonyl with 1–6, preferably 1–4, alkyl C atoms, such as, for example, acetyl, propionyl or butyryl, which can also be monosubstituted or polysubstituted, for example by oximino; alkoximino, as defined in more detail under $R_2$, in particular methoximino; or alkoxycarbonyl with 1–4 alkyl C atoms, in particular methoxy- or ethoxycarbonyl; by carbocyclic or heterocyclic arylcarbonyl, such as, for example, benzoyl or thenoyl, which can also carry further substituents, such as, for example, alkyl with 1–4 C atoms, such as, preferably, methyl or ethyl; alkoxy with 1–4 C atoms, preferably methoxy or ethoxy; halogen, preferably chlorine or bromine; sulfamoyl; trifluoromethyl; alkylamino with 1–4 C atoms, such as methyl- or ethyl-amino; or dialkylamino with 1–4 C atoms, such as diemthyl- or diethyl-amino, which can also be closed to form a 5-membered to 7-membered ring which is optionally interrupted by hetero-atoms, such as, for example, oxygen, nitrogen or sulfur, such as, for example, morpholine or piperazine, or by optionally substituted aryl, preferably phenyl, trialkylsilyl with 1-4 C atoms in the alkyl group, such as, for example, trimethylsilyl, or indanyl or phthalidiyl.

If $R_3$ denotes a cation, it represents an inorganic metal ion or an organic ammonium ion. Examples which may be mentioned are, in particular, pharmacologically acceptable alkali metal ions or alkaline earth metal ions, preferably the sodium, potassium, calcium or magnesium ion, the ammonium ion and, from the organic ammonium ions, in particular, an optionally substituted, alkylated ammonium ion, such as, for example, the triethylammonium or diethanolammonium ion, as well as the morpholineammonium, benzylammonium, procaineammonium, L-arginineammonium and L-lysineammonium ion.

$R_4$ can represent, for example, hydrogen, lower alkoxy with 1-4 C atoms, preferably methoxy, or a group which can be converted into such an alkoxy group, such as, for example, halogen, preferably bromine, or saturated or unsaturated alkylthio with 1-4 C atoms, such as, for example, methylthio, ethylthio, i-propylthio or allylthio.

A can denote, for example, hydrogen, alkoxy with 1-4 C atoms, such as methoxy, ethoxy or butoxy, in particular methoxy, it also being possible for the alkyl chain, with the exception of the α-C atoms, to be substituted, for example by hydroxyl or by halogen, preferably chlorine or bromine, alkoxycarbonyl with 1-4 alkyl C atoms, in particular methoxy- or ethoxy-carbonyl, alkenyloxy with 3-6 C atoms, such as, for example, allyloxy, which can be substituted in the same manner as the alkoxy group (A) above, halogen, preferably chlorine or bromine, or —CH$_2$Y, wherein Y, in addition to hydrogen or halogen, such as, for example, fluorine, chlorine or bromine, can also represent the radical of a nucleophilic compound.

Examples which may be mentioned of such radicals of a nucleophilic compound, preferably of a S-, N- or O-nucleophilic compound are: acyloxy, hydroxyl, alkoxy, amino, alkylamino, dialkylamino, mercapto, optionally substituted pyridinium, quinolinium or isoquinolinium, optionally substituted carbamoyloxy or carbamoylthio, azido or a group —SR$_5$, wherein R$_5$ denotes an optionally substituted acyl, alkyl or aryl radical or an optionally substituted 5-membered or 6-membered heterocyclic ring which is optionally fused to an aromatic 5-membered or 6-membered ring, or the radical

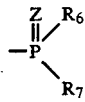

in which Z represents sulfur or oxygen and R$_6$ and R$_7$, which can be identical or different, represent alkyl, alkenyl, alkoxy, alkenyloxy, optionally substituted phenyl or a carbocyclic ring with 3-8 C atoms.

Some of the groups which are possible, according to the invention, as the nucleophilic radical Y are illustrated in more detail in the following text.

If Y represents acyloxy, possible acyl radicals are, for example, aliphatic acyl radicals with 1-4 C atoms, such as, for example, acetoxy or propionyloxy. Acetoxy is particularly preferred.

If Y represents alkoxy, possible radicals here are straight-chain or branched alkoxy radicals with, for example, 1-8 C atoms, preferably with 1-4 C atoms, such as, for example, methyl, ethyl, n-propyl, i-propyl, n-butyl or i-butyl.

If Y represents a pyridine, quinoline or isoquinoline radical, it is bonded via nitrogen and can be substituted, for example by lower alkyl, such as, for example, methyl or ethyl, lower alkoxy, such as, for example, methoxy or ethoxy, or carbamoyl. However, it is preferably unsubstituted.

If Y represents a carbamoyloxy or carbamoylthio group, this group can be monosubstituted or polysubstituted on the nitrogen, for example by lower alkyl with 1-4 C atoms, such as, for example, methyl or ethyl, it also being possible for the two substituents to be linked with one another to form a ring, for example to form a 5-membered or 6-membered ring, which can also be interrupted by a hetero-atom, such as, for example, oxygen, sulfur or nitrogen. The unsubstituted carbamoyl group is preferred.

Y can furthermore represent azido, as well as monosubstituted or disubstituted amino. Possible substituents are, in particular, alkyl with 1-4 C atoms, such as, for example, methyl or ethyl, it also being possible, in the case of a dialkylamino group, for the substituents to be closed to form a 5-membered or 6-membered ring which is optionally interrupted by hetero-atoms, such as, for example, morpholine or piperazine. The amino group can, for example, also be substituted by alkoxy with 1-4 C atoms, such as, for example, methoxy or ethoxy, or by aryl, preferably phenyl, which can also carry further substituents, such as, for example, alkyl with 1-4 C atoms, preferably methyl, sulfamoyl, trifluoromethyl or halogen, such as, for example, chlorine or bromine.

If Y denotes amino, in order to avoid the formation of a ring R$_3$ must represent an ester group. This can also then be appropriate if Y denotes a hydroxyl, mercapto or monosubstituted amino group.

If Y represents a group —SR$_5$ and R$_5$ represents an acyl radical, possible acyl radicals are optionally substituted aliphatic, aromatic or heterocyclic acyl radicals, for example aliphatic acyl with 1-4 C atoms, such as, for example, acetyl or propionyl, aromatic acyl, such as, for example, benzoyl or toluoyl, and heterocyclic acyl which is derived from 5-membered or 6-membered rings with 1-4 hetero-atoms, such as, for example, nitrogen, sulfur or oxygen, such as, for example, nicotinoyl, isonicotinoyl, picolinoyl, furoyl, thenoyl, thiazoloyl, oxazoloyl, triazoloyl or thiadiazoloyl. The acetyl and propionyl radicals are preferred. R$_5$ can also denote optionally substituted aryl, preferably phenyl, the substituents corresponding to those which can be in the aryl substituting the aliphatic acyl radical (R$_1$).

If R$_5$ denotes an alkyl radical, a possible radical here is straight-chain or branched alkyl with, for example, 1-8 C atoms, preferably 1-4 C atoms, such as, for example, methyl, ethyl, n-propyl, i-propyl, n-butyl or i-butyl, in particular methyl and ethyl, which can also be optionally substituted, for example by amino, hydroxyl, carboxyl or carbalkoxy with 1-4 alkyl C atoms, in particular methoxycarbonyl, or by phenyl which is optionally substituted by alkyl or alkoxy with 1-4 C atoms, in particular methyl or methoxy, nitro or halogen, in particular chlorine or bromine.

If R$_5$ represents a heterocyclic radical, possible radicals are optionally substituted five-membered or six-membered rings which have 1 to 4 hetero-atoms, such as, for example, oxygen, sulfur and/or nitrogen, in particular nitrogen, optionally together with sulfur or oxygen as ring atoms.

If the radical $R_5$ denotes a heterocyclic radical, it can also be bonded to a fused aromatic 5-membered or 6-membered ring system, for example a pyridine or triazole ring, preferably to a benzene ring, but the heterocyclic ring which is not fused to a ring system is preferred. The heterocyclic ring system which forms the radical $R_5$ can also be completely or partially hydrogenated, but preferably non-hydrogenated.

The following fundamental ring systems may be mentioned as examples of the radical $R_5$: thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl and purinyl, as well as benzo-fused derivatives, for example benzoxazolyl, benzthiazolyl, benzimidazolyl and indolyl.

5-membered ring systems with a sulfur or oxygen atom and 1 to 3 nitrogen atoms, such as thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, are preferred. Furthermore, 5-membered ring systems with 2 to 4 nitrogen atoms, such as imidazolyl, preferably imidazol-2-yl, triazolyl, preferably 1,3,4-triazol-5-yl and 1,2,3- and 1,2,4-triazol-5-yl, and tetrazolyl, preferably 1H-tetrazol-5-yl and 2H-tetrazolyl, are preferred. Benzofused derivatives, in particular benzoxazol-2-yl, benzthiazol-2-yl and benzimidazol-2-yl, are also preferred.

Furthermore, preferred possible ring systems are 6-membered ring systems with 1 to 3, preferably 1 to 2, nitrogen atoms, such as, for example, pyridyl, such as pyrid-2-yl, pyrid-3-yl and pyrid-4-yl, pyrimidyl, preferably pyrimid-2-yl and pyrimid-4-yl, triazinyl, preferably 1,3,4-triazin-2-yl and 1,3,5-triazin-4-yl, pyridazinyl, in particular pyridazin-3-yl, and pyrazinyl. The pyridyl, pyrimid-2-yl, pyrimid-4-yl and pyridazinyl radicals, in particular the pyridine N-oxides and pyridazine N-oxides, are preferred.

If the radical $R_5$ denotes a heterocyclic radical, it can be monosubstituted or polysubstituted, examples of possible substituents being the following: straight-chain or branched alkyl groups with, for example, 1 to 15 carbon atoms, such as, for example, methyl, ethyl, n-propyl, i-propyl, n-butyl, tert.-butyl, n-hexyl, undecyl and pentadecyl, preferably those with 1-4 carbon atoms, such as, for example, methyl and ethyl, as well as low-molecular alkyl groups with 1 to 4 carbon atoms, such as, for example, methyl, which are substituted, for example by aryl, such as, for example, phenyl or thienyl, by aryloxy, for example phenoxy, by low-molecular alkoxy, such as, for example, methoxy and ethoxy, by low-molecular alkoxycarbonyl, such as, for example, methoxy- or ethoxy-carbonyl, by halogen, such as, for example, chlorine or bromine, by hydroxyl, by aliphatic acylamido, preferably with 1 to 4 C atoms, such as, for example, acetamido, by aromatic acylamido, such as, for example, benzamido, by amino, by alkylamino with 1 to 4 C atoms, such as, for example, methyl- or ethyl-amino, by dialkylamino with 1-4 C atoms, such as, for example, dimethyl- or diethylamino, it also being possible for the alkyl radicals of the dialkylamino group to be closed to form a 5-membered to 7-membered ring which is optionally interrupted by hetero-atoms, such as, for example, oxygen or nitrogen, such as, for example, morpholino or piperazino, by trifluoromethyl, by cyano, by carbamoyl, by carboxyl, by carboxyalkoxy with 1-4 alkyl C atoms, such as, for example, carboxymethoxy, by cyanoalkoxy with 1 to 4 alkyl C atoms, such as, for example, cyanomethoxy, by carbamoylalkoxy with 1-4 alkyl C atoms, such as, for example, carbamoylmethoxy, by alkoxycarbonyloxy with 1-4 alkyl C atoms, such as, for example, methoxycarbonyloxy, by sulfo, by alkylsulfo, preferably with 1-4 C atoms, such as, for example, methylsulfonyl, by sulfamoyl, by phosphonyl, by alkylcarbamoyl with 1-4 alkyl C atoms, such as, for example, methylcarbamoyl, by dialkylcarbamoyl with 1-4 alkyl C atoms, such as, for example, dimethylcarbamoyl, by alkyl- or dialkyl-sulfamoyl with 1-4 C atoms, such as, for example, methyl- or dimethyl-sulfamoyl, by carboxyalkylcarboxamido, preferably with 1-4 alkyl C atoms, such as, for example, succinamic acid, by cyanoalkylcarboxamido, preferably with 1-4 alkyl C atoms, such as, for example, malonic acid mononitrile-amide, or by alkoxycarbonylalkylcarboxamido, preferably with 1-4 C atoms in each alkyl group, it also being possible for the carboxamido nitrogen to be further substituted, such as, for example, methyl-succinamate and methyl N-methyl-succinamate.

If $R_5$ denotes a heterocyclic radical, it can furthermore be substituted by cycloalkyl with 3 to 8 C atoms, such as, for example, cyclopentyl and cyclohexyl, or by alkoxy with 1-4 C atoms, such as, for example, methoxy and ethoxy, alkenyl with 2-4 C atoms, such as, for example, allyl, alkenyloxy with 3-5 C atoms, such as, for example, allyloxy, alkyl- and alkenyl-thio with 1-4 C atoms, such as, for example, methylthio and allylthio, alkoxycarbonyl with 1-4 alkyl C atoms, such as, for example, methoxycarbonyl, alkylcarbonyl with 1-4 alkyl C atoms, such as, for example, acetyl, arylcarbonyl, such as, for example, benzoyl, carboxyalkoxycarbonyl with 1-4 alkyl C atoms, such as, for example, carboxymethoxycarbonyl, cyanoalkoxycarbonyl with 1-4 alkyl C atoms, such as, for example, cyanomethoxycarbonyl, carbamoylalkoxycarbonyl with 1 to 4 alkyl C atoms, such as, for example, carbamoylmethoxycarbonyl, alkoxycarbonylamino with 1-4 alkoxy C atoms, such as, for example, ethoxycarbonylamino, carboxyalkylthio with 1-4 alkyl C atoms, such as, for example, carboxymethylthio, amino, arylamino, such as, for example, phenylamino, heteroarylamino, such as, for example, pyrid-2-yl-amino and pyrid-4-yl-amino, monoalkyl- and dialkyl-amino with 1-4 C atoms, such as, for example, methylamino, dimethylamino, ethylamino and diethylamino, it also being possible for the two alkyl substituents to be closed to form a 5-membered to 7-membered ring which is optionally interrupted by hetero-atoms, such as, for example, oxygen or nitrogen, such as, for example, morpholino, piperidino, pyrrolidino and piperazino, carboxyalkylamino with 1-4 alkyl C atoms, such as, for example, carboxymethylamino, cyanoalkylamino with 1-4 alkyl C atoms, such as, for example, cyanomethylamino, alkoxycarbonylalkylamino with 1-4 alkoxy and alkyl C atoms, such as, for example, methoxycarbonylmethylamino, sulfoalkylamino with 1-4 C atoms, such as, for example, sulfomethylamino, sulfamoylalkylamino with 1 to 4 C atoms, such as, for example, sulfamoylmethylamino, alkylsulfamoylalkylamino with 1-4 alkyl C atoms in each case, such as, for example, methylsulfamoylmethylamino, dialkylsulfamoylalkylamino with 1-4 alkyl C atoms in each case, such as, for example, dimethylsulfamoylmethylamino, alkoxysulfonylalkylamino with 1-4 alkoxy and alkyl C atoms, such as, for example, methoxysulfonylmethylamino, oxido, hydroxyl, hydroxyalkyl with 1-4 alkyl C atoms, such as, for example, hydroxymethyl and hydroxyethyl, carboxyalkylcarbonyloxy with 1-4 alkyl C atoms, such as, for example, carboxymethylcarbonyloxy, cyanoalkylcarbonyloxy with 1 to 4 alkyl C atoms, such as, for example, cyanomethylcarbonyloxy, alkoxycarbonylalkylcarbonyloxy with 1-4 alkyl C atoms in each case, such as, for example, methoxycarbonylmethylcarbonyloxy, carboxyalkoxy with 1-4 alkyl C atoms, such as, for example, carboxymethoxy, cyanoalkoxy with 1-4 alkyl C atoms, such as, for example, cyanomethoxy, alkoxycarbonylalkoxy with 1-4 alkoxy C atoms, such as, for example, methoxycarbonylmethoxy, carbamoylalkoxy with 1-4 alkyl C atoms, such as, for example, carbamoylmethoxy, carbamoylalkylcarbonyloxy with 1-4 alkyl C atoms, such as, for example, carbamoylmethylcarbonyloxy, sulfoalkoxy with 1-4 C atoms, such as, for example, sulfomethoxy, sulfamoylalkoxy with 1-4 C atoms, such as, for example, sulfamoylmethoxy, nitro, cyano, halogen, preferably chlorine, trifluoromethyl, mercapto, carboxyl, carbamoyl, carboxyalkylaminocarbonyl with 1-4 alkyl C atoms, such as, for example, carboxymethylaminocarbonyl, carbamoylalkylaminocarbonyl with 1-4 alkyl C atoms, such as, for example, carbamoylmethylaminocarbonyl, alkoxycarbonylalkylaminocarbonyl with 1-4 alkoxy and alkyl C atoms, such as, for example, methoxycarbonylmethylaminocarbonyl, aryl radicals, such as, for example, phenyl, substituted phenyl, such as, for example, alkoxyphenyl with 1-4 alkoxy C atoms, such as, for example, methoxyphenyl and ethoxyphenyl, alkylthiophenyl with 1-4 alkylthio C atoms, such as, for example, methylthiophenyl, halogenophenyl, such as, for example, chlorophenyl, hydroxyphenyl, aminophenyl, alkylamino- or dialkylamino-phenyl with 1-4 alkyl C atoms, such as, for example, methylamino- or dimethylaminophenyl, alkylphenyl, in particular alkylphenyl with 1-4 alkyl C atoms, such as, for example, tert.-butylphenyl, tolyl or cetylphenyl, hydroxyalkylphenyl with 1-4 alkyl C atoms, such as, for example, hydroxyethylphenyl, halogenoalkylphenyl with 1-4 alkyl C atoms, such as, for example, trifluoromethylphenyl or chloromethylphenyl, alkoxyalkylphenyl with 1-4 alkoxy and alkyl C atoms, such as, for example, methoxymethylphenyl, alkenylphenyl with 2 to 6, preferably 3-5, alkenyl C atoms, such as, for example, allylphenyl, alkenyloxyphenyl with 2-6, preferably 3-5, alkenyloxy C atoms, such as, for example, allyloxyphenyl, cyanophenyl, carbamoylphenyl, carboxyphenyl, alkoxycarbonylphenyl with 1-4 alkyl C atoms, such as, for example, methoxycarbonylphenyl, alkylcarbonyloxyphenyl with 1-4 alkyl C atoms, such as, for example, acetoxyphenyl, sulfophenyl, alkoxysulfophenyl with 1-4 alkoxy C atoms, such as, for example, methoxysulfophenyl, sulfamoylphenyl, nitrophenyl, biphenyl or optionally correspondingly substituted naphthyl radicals or heterocyclic radicals which are derived from heterocyclic 5-membered or 6-membered rings with 1 to 4 hetero-atoms, in particular nitrogen, sulfur or oxygen, such as, for example, pyridyl, furyl, quinolyl, isoquinolyl, thienyl, thiazolyl, N-pyrrolyl, pyrrolyl, imidazolyl, pyrazolyl, isoxazolyl, tetrazolyl and triazolyl.

If $R_5$ denotes a heterocyclic radical, possible substituents are also: cyanoalkylaminocarbonyl with 1-4 C atoms, such as, for example, cyanomethylaminocarbonyl, carboxyalkylcarboxamido with 1-4 C atoms, such as, for example, succinamic acid, alkoxyalkylcarboxamido with 1-4 C atoms, such as, for example, methylsuccinamate, cyanoalkylcarboxamido with 1-4 C atoms, such as, for example, malonic acid nitrile-monoamide, alkylcarbamoyl with 1-4 C atoms, such as, for example, methylaminocarbonyl, dialkylcarbamoyl with 1-4 C atoms, such as, for example, dimethylaminocarbonyl, it also being possible for the two alkyl radicals to be closed to form a carbocyclic ring with 5-7 C atoms, which can be interrupted by nitrogen, sulfur or oxygen, such as, for example, morpholinocarbonyl, alkoxycarbonylalkoxyalkyl with 1-4 C atoms, such as, for example, methoxycarbonylalkoxyalkyl, alkylcarbamoylalkoxyalkyl with 1-4 C atoms, such as, for example, methylcarbamoylmethoxymethyl, alkoxyalkylaminocarbonylalkyl, such as, for example, methoxymethylaminocarbonylmethyl, an amino group or an amino group which is monosubstituted by lower alkyl, it being possible for the amino group to be acylated by lower aliphatic or aromatic carboxylic acids, such as, for example, acetamido or benzamido, as well as an aryl or hetero-aromatic radical which is substituted by trifluoromethyl or alkylcarboxyl with 1-4 C atoms. The number of C atoms, 1-4, indicated in this paragraph in each case relates to an alkyl group contained in the radicals.

Of the 5-membered rings with 2-4 hetero-atoms, such as nitrogen, sulfur and oxygen, preferably at least one hetero-atom being nitrogen, and 6-membered rings with 1-3 hetero-atoms, in particular nitrogen atoms, which are preferred, according to the invention, for $R_5$, the following radicals of the general formulae II-VII may be mentioned as examples of particularly preferred radicals. In the definitions of the substituents, in each case "lower" denotes a carbon atom number of 1-4, or, in the case of an unsaturated radical, a C atom number of 2-4.

a) A thiazolyl radical of the general formula V

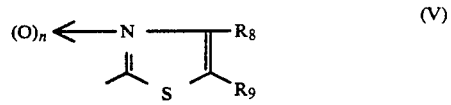

in which $R_8$ and $R_9$ can be identical or different and represent hydrogen, straight-chain or branched lower alkyl, which can be optionally substituted by halogen, lower alkoxy, hydroxyl, amino, lower alkylamino, lower dialkylamino, trifluoromethyl or phenyl, straight-chain or branched lower alkenyl, a carbocyclic ring with 3-8 carbon atoms, amino, lower alkylamino, lower dialkylamino, lower aliphatic acylamido, lower carboxyalkyl, lower alkoxycarbonylalkyl, lower carbamoylalkyl, carboxyl, carbamoyl, cyano, cyanoalkyl, lower alkoxycarbonyl, lower carboxyalkylaminocarbonyl, lower alkoxycarbonylalkylaminocarbonyl, cyanoalkylaminocarbonyl, lower carboxyalkylcarboxamido, lower alkoxycarbonylalkylcarboxamido, lower cyanoalkylcarboxamido, lower carboxyalkylthio, an optionally substituted hetero-aryl radical or a phenyl radical which is optionally substituted by one or two halogen atoms, lower alkyl, lower alkoxy, hydroxyl, lower alkylamino, lower dialkylamino, lower alkylthio, cyano or trifluoromethyl, it being possible for $R_8$ and $R_9$ together to form an optionally substituted carbocyclic ring with 5–7 carbon atoms, and n represents 0 or 1.

Examples which may be mentioned are, in particular: 1,3-thiazol-2-yl, 4-methyl-1,3-thiazol-2-yl, 4-tert.-butyl-1,3-thiazol-2-yl, 4-n-propyl-1,3-thiazol-2-yl, 4-ethyl-1,3-thiazol-2-yl, 5-amino-1,3-thiazol-2-yl, 5-acetamido-1,3-thiazol-2-yl, 5-methylamino-1,3-thiazol-2-yl, benzothiazol-2-yl, 5-chloro-benzothiazol-2-yl, 4-methyl-3-oxy-1,3-thiazol-2-yl, 3-oxy-4-phenyl-1,3-thiazol-2-yl, 4-(4-chlorophenyl)-3-oxy-1,3-thiazol-2-yl, 3-oxy-1,3-thiazol-2-yl, 4-(4-bromophenyl)-3-oxy-1,3-thiazol-2-yl, 3-oxy-4-(p-tolyl)-1,3-thiazol-2-yl, 4-(p-methoxyphenyl)-3-oxy-1,3-thiazol-2-yl, 4-methyl-3-oxy-5-phenyl-1,3-thiazol-2-yl, 5-methyl-3-oxy-4-phenyl-1,3-thiazol-2-yl, 5-methyl-1,3-thiazol-2-yl, 4-trifluoromethyl-1,3-thiazol-2-yl, 4-phenyl-1,3-thiazol-2-yl, 4,5-dimethyl-1,3-thiazol-2-yl, 4-(3-pyridyl)-1,3-thiazol-2-yl, 4-carboxymethyl-1,3-thiazol-2-yl, 3-carboxy-4-methyl-1,3-thiazol-2-yl, 4-carboxy-1,3-thiazol-2-yl, 4-ethoxycarbonyl-5-amino-1,3-thiazol-2-yl, 5-amino-4-carboxy-1,3-thiazol-2-yl, 5-carboxymethylaminocarbonyl-1,3-thiazol-2-yl, 5-carboxymethylcarboxamido-1,3-thiazol-2-yl, 5-carboxymethyl-4-phenyl-1,3-thiazol-2-yl, 4-(5-nitro-thien-2-yl)-1,3-thiazol-2-yl, 4-(4-carboxythien-2-yl)-1,3-thiazol-2-yl, 4-(1-methyl-pyrrol-2-yl)-1,3-thiazol-2-yl, 4-(5-carbamoyl-fur-2-yl)-1,3-thiazol-2-yl and 5-carboxy-4-methyl-1,3-thiazol-2-yl.

b) A pyridyl radical of the general formula VI

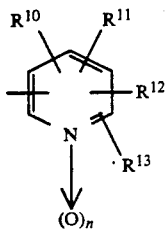

in which $R^{10}$ to $R^{13}$ can be identical or different and denote hydrogen, halogen, lower, straight-chain or branched alkyl or alkenyl, trifluoromethyl, lower alkylcarbonyl, amino, lower alkylamino, lower dialkylamino, carboxyl, carbamoyl, cyano, lower alkylaminocarbonyl, lower dialkylaminocarbonyl, lower alkoxycarbonyl, hydroxyl, lower alkoxy, lower hydroxyalkyl, mercapto, lower alkylthio or nitro and n represents 0 or 1.

Examples which may be mentioned are, in particular: 1-oxy-pyrid-2-yl, 3-methyl-1-oxy-pyrid-2-yl, 4-methyl-1-oxy-pyrid-2-yl, 1-oxy-pyrid-4-yl, 5-methyl-1-oxy-pyrid-2-yl, 6-methyl-1-oxy-pyrid-2-yl, 3-ethoxy-1-oxy-pyrid-2-yl, 5-bromo-1-oxy-pyrid-2-yl, pyrid-2-yl, pyrid-3-yl, pyridin-4-yl, 3-hydroxy-pyrid-2-yl, 3-nitro-pyrid-2-yl, 5-nitro-pyrid-2-yl, 2-amino-6-methyl-pyrid-3-yl, 4-chloro-1-oxy-pyridin-2-yl, 2-carboxy-pyrid-4-yl, 3-carboxy-pyrid-5-yl and 4-carboxy-pyrid-5-yl.

c) Oxadiazolyl, thiadiazolyl and triazolyl radicals of the general formulae VII, VII a and VII b

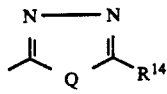 VII

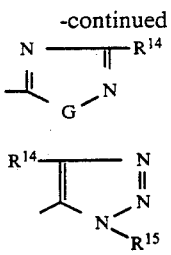

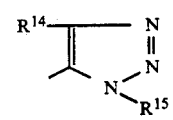

in which Q represents oxygen, sulfur or $>$N—$R^{15}$ and G represents oxygen or sulfur, and wherein $R^{14}$ denotes hydrogen, lower, straight-chain or branched alkyl, lower straight-chain or branched alkenyl, a carbocyclic ring with 5–7 carbon atoms, hydroxyl, lower hydroxyalkyl, lower alkoxy, mercapto, lower alkylthio, lower alkoxyalkyl, an amino group, which can be optionally substituted by one or two lower alkyl radicals which together can also form a carbocyclic ring with 5–7 carbon atoms, lower aliphatic or aromatic acylamido, a lower aminoalkyl group, which can be optionally substituted by one or two lower, branched or straight-chain alkyl radicals, which together can also form a carbocyclic ring with 5–7 carbon atoms, or acylated by a lower aliphatic or aromatic carboxylic acid, trifluoromethyl, lower alkoxycarbonylalkylamido, lower carboxyalkylamido, lower cyanoalkylamido, lower alkoxycarboxyalkoxyalkyl, lower carboxyalkyl, lower alkoxycarbonylalkyl, lower cyanoalkyl, carboxyl, carbamoyl, cyano, lower carbamoylalkyl, lower alkoxycarbonyl, lower alkylcarbamoyl, lower dialkylcarbamoyl, lower sulfoalkyl, lower sulfamoylalkyl, lower alkylsulfamoylalkyl, lower dialkylsulfamoylalkyl, lower alkylcarbamoylalkyl, lower dialkylcarbamoylalkyl, lower alkoxycarbonylalkoxyalkyl, lower carboxyalkoxyalkyl, lower carbamoylalkoxyalkyl, lower alkylcarbamoylalkoxyalkyl, lower alkoxyalkylaminocarbonylalkyl, lower carboxyalkylthio and an aryl or heterocyclic radical, preferably a phenyl, naphthyl, thienyl, furyl, thiazolyl, pyrrolyl, imidazolyl, pyrazolyl, isoxazolyl, quinolyl, isoquinolyl or pyridyl radical, which is optionally substituted by one or two halogen atoms, hydroxyl, lower alkoxy, lower, straight-chain or branched alkyl, lower, straight-chain or branched alkenyl, trifluoromethyl, cyano, amino, carboxyl, lower alkoxycarbonyl, sulfo, carbamoyl, sufamoyl, lower alkylcarboxy, lower alkylcarbonyl, lower alkylamino, nitro or dialkylamino, or an arylamino or heteroarylamino group or lower arylalkyl, and in which $R^{15}$ can be hydrogen, lower, straight-chain or branched alkyl, lower, straight-chain or branched alkenyl, lower carboxyalkyl, lower alkoxycarbonylalkyl, lower cyanoalkyl, lower sulfoalkyl, lower sulfamoylalkyl, lower alkylsulfamoylalkyl, lower dialkylsulfamoylalkyl, lower alkylcarbamoylalkyl, lower dialkylcarbamoylalkyl, lower alkoxycarbonylalkoxyalkyl, lower carboxyalkoxyalkyl, lower carbamoylalkoxyalkyl, lower alkylcarbamoylakoxyalkyl, hydroxyl, lower hydroxyalkyl, an amino group, which can be optionally acylated with a lower aliphatic carboxylic acid or alkylated with one or two lower alkyl radicals, lower arylalkyl, lower alkoxyalkyl, a carbocyclic ring with 5 to 7 carbon atoms, a pyrrolyl radical, which can be optionally substituted by one or two lower alkyl groups, or an aryl or heterocyclic radical, preferably a phenyl or pyridine radical, which can be optionally substituted by carboxyl, cyano, trifluoromethyl, carbamoyl, amino, lower alkylamino, lower dialkylamino, lower alkyl, sulfo, sulfamoyl, lower alkoxycarbonyl, hydroxyl, lower hydroxyalkyl, lower alkylcarbonyl or lower alkoxy.

Examples which may be mentioned are, in particular: for

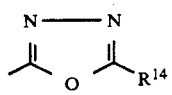

1,3,4-oxadiazol-5-yl, 2-methyl-1,3,4-oxadiazol-5-yl, 2-phenyl-1,3,4-oxadiazol-5-yl, 2-(4-fluorophenyl)-1,3,4-oxadiazol-5-yl, 2-(2-bromophenyl)-1,3,4-oxadiazol-5-yl, 2-(2-methoxyphenyl)-1,3,4-oxadiazol-5-yl, 2-cyclohexyl-1,3,4-oxadiazol-5-yl, 2-(2-pyridyl)-1,3,4-oxadiazol-5-yl, 2-(3-pyridyl)-1,3,4-oxadiazol-5-yl 2-(4-pyridyl)-1,3,4-oxadiazol-5-yl, 2-(2-furyl)-1,3,4-oxadiazol-5-yl, 2-(3-furyl)-1,3,4-oxadiazol-5-yl, 2-(2-thienyl)-1,3,4-oxadiazol-5-yl, 2-propyl-1,3,4-oxadiazol-5-yl, 2-butyl-1,3,4-oxadiazol-5-yl, 2-(2-hydroxyphenyl)-1,3,4-oxadiazol-5-yl, 2-ethyl-1,3,4-oxadiazol-5-yl, 2-(4-nitrophenyl)-1,3,4-oxadiazol-5-yl, 2-(3-thienyl)-1,3,4-oxadiazol-5-yl, 2-(4-chlorophenyl)-thienyl-1,3,4-oxadiazol-5-yl, 2-(2-thiazolyl)-1,3,4-oxadiazol-5-yl, 2-(3-nitrophenyl)-1,3,4-oxadiazol-5-yl, 2-(2-tolyl)-1,3,4-oxadiazol-5-yl, 2-(3-tolyl)-1,3,4-oxadiazol-5-yl, 2-(4-hydroxyphenyl)-1,3,4-oxadiazol-5-yl, 2-benzyl-1,3,4-oxadiazol-5-yl, 2-(1-naphthyl)-1,3,4-oxadiazol-5-yl, 2-(2-pyrrolyl)-1,3,4-oxadiazol-5-yl, 2-(4-imidazolyl)-1,3,4-oxadiazol-5-yl, 2-(5-pyrazolyl)-1,3,4-oxadiazol-5-yl, 2-(3,5-dimethyl-4-isoxazolyl)-1,3,4-oxadiazol-5-yl, 2-(ethoxycarbonylmethoxymethyl)-1,3,4-oxadiazol-5-yl, 2-(carboxymethoxymethyl)-1,3,4-oxadiazol-5-yl, 2-carbamoyl-1,3,4-oxadiazol-5-yl, 2-(N-methylcarbamoyl)-1,3,4-oxadiazol-5-yl, 2-(N-ethylcarbamoyl)-1,3,4-oxadiazol-5-yl, 2-(N,N-dimethylcarbamoyl)-1,3,4-oxadiazol-5-yl and 2-(N,N-dimethylaminomethyl)-1,3,4-oxadiazol-5-yl, for

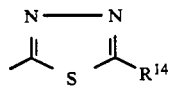

1,3,4-thiadiazol-5-yl, 2-butyl-1,3,4-thiadiazol-5-yl, 2-propyl-1,3,4-thiadiazol-5-yl, 2-phenyl-1,3,4-thiadiazol-5-yl, 2-amino-1,3,4-thiadiazol-5-yl, 2-ethyl-1,3,4-thiadiazol-5-yl, 2-acetamido-1,3,4-thiadiazol-5-yl, 2-methylamino-1,3,4-thiadiazol-5-yl, 2-(N-methylacetamido)-1,3,4-thiadiazol-5-yl, 2-isobutylamino-1,3,4-thiadiazol-5-yl, 2-piperidino-1,3,4-thiadiazol-5-yl, 2-pyrrolidino-1,3,4-thiadiazol-5-yl, 2-aminomethyl-1,3,4-thiadiazol-5-yl, 2-acetamidomethyl-1,3,4-thiadiazol-5-yl, 2-benzamido-1,3,4-thiadiazol-5-yl, 2-(β-piperidinoethyl)-1,3,4-thiadiazol-5-yl, 2-(2-pyridylamino)-1,3,4-thiadiazol-5-yl, 2-(3-pyridylamino)-1,3,4-thiadiazol-5-yl, 2-(1,3-thiazol-2-yl-amino)-1,3,4-thiadiazol-5-yl, 2-(1,3,4-triazolyl-2-amino)-1,3,4-thiadiazol-5-yl, 2-(tetrazolyl-5-amino)-1,3,4-thiadiazol-5-yl, 2-dimethylaminomethyl-1,3,4-thiadiazol-5-yl, 2-methylaminomethyl-1,3,4-thiadiazol-5-yl, 2-ethyl-1,3,4-thiadiazol-5-yl, 2-trifluoromethyl-1,3,4-thiadiazol-5-yl, 2-mercapto-1,3,4-thiadiazol-5-yl, 2-methylthio-1,3,4-thiadiazol-5-yl, 2-(2-pyridyl)-1,3,4-thiadiazol-5-yl, 2-(3-pyridyl)-1,3,4-thiadiazol-5-yl, 2-(4-pyridyl)-1,3,4-thiadiazol-5-yl, 2-(2-thienyl)-1,3,4-thiadiazol-5-yl, 2-(2-furyl)-1,3,4-thiadiazol-5-yl, 2-(3-furyl)-1,3,4-thiadiazol-5-yl, 2-methyl-1,3,4-thiadiazol-5-yl, 2-isopropyl-1,3,4-thiadiazol-5-yl, 2-(4-methoxyphenyl)-1,3,4-thiadiazol-5-yl, 2-(4-chlorophenyl)-1,3,4-thiadiazol-5-yl, 2-(1-naphthyl)-1,3,4-thiadiazol-5-yl, 2-(2-quinolyl)-1,3,4-thiadiazol-5-yl, 2-(1-isoquinolyl)-1,3,4-thiadiazol-5-yl, 2-(β-methoxycarbonylpropionylamido)-1,3,4-thiadiazol-5-yl, 2-(β-carboxypropionylamido)-1,3,4-thiadiazol-5-yl, 2-carboxymethoxymethyl-1,3,4-thiadiazol-5-yl, 2-ethoxycarbonylmethyl-1,3,4-thiadiazol-5-yl, 2-carboxymethyl-1,3,4-thiadiazol-5-yl, 2-(α-carboxyacetamido)-1,3,4-thiadiazol-5-yl, 2-(α-cyanoacetamido)-1,3,4-thiadiazol-5-yl, 2-(methoxycarbamoyl)-acetamido-1H-1,3,4-thiadiazol-5-yl, 2-(N,N-dimethylcarbamoylmethyl)-1H-1,3,4-thiadiazol-5-yl, 2-(N,N-diethylcarbamoylmethyl)-1H-1,3,4-thiadiazol-5-yl, 2-(N,N-dipropylcarbamoylmethyl)-1H-1,3,4-thiadiazol-5-yl, 2-(N,N-dibutylcarbamoylmethyl)-1H-1,3,4-thiadiazol-5-yl, 2-(2-acetamidoethyl)-1,3,4-thiadiazol-5-yl, 2-(2-aminoethyl)-1,3,4-thiadiazol-5-yl, 2-hydroxymethyl-1,3,4-thiadiazol-5-yl, 2-(2-hydroxyethyl)-1,3,4-thiadiazol-5-yl, 2-(isobutyryloxymethyl)-1,3,4-thiadiazol-5-yl, 2-(ethoxycarbonylmethoxymethyl)-1,3,4-thiadiazol-5-yl, 2-(carbamoylmethoxymethyl)-1,3,4-thiadiazol-5-yl, 2-(N-methylcarbamoyl)-1,3,4-thiadiazol-5-yl, 2-isobutyl-1,3,4-thiadiazol-5-yl, 2-methoxypropylaminocarbonylmethyl-1,3,4-thiadiazol-5-yl, 2-carboxyethyl-1,3,4-thiadiazol-5-yl, 2-sulfoethyl-1,3,4-thiadiazol-5-yl, 2-carboxy-1,3,4-thiadiazol-5-yl, 2-phenylamino-1,3,4-thiadiazol-5-yl, 2-o-carboxybenzoyl-amino-1,3,4-thiadiazol-5-yl, 2-(1-carboxyethylthio)-1,3,4-thiadiazol-5-yl and 2-(1-carboxy-1-methylethyl)-1,3,4-thiadiazol-5-yl, for

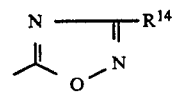

1,2,4-oxadiazol-5-yl, 3-methyl-1,2,4-oxadiazol-5-yl and 3-phenyl-1,2,4-oxadiazol-5-yl, for

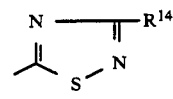

1,2,4-thiadiazol-5-yl, 3-phenyl-1,2,4-thiadiazol-5-yl, 3-methylmercapto-1,2,4-thiadiazol-5-yl, 3-methyl-1,2,4-thiadiazol-5-yl and 3-ethyl-1,2,4-thiadiazol-5-yl, for

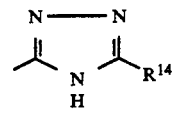

2-methyl-1H-1,3,4-triazol-5-yl, 2-ethyl-1H-1,3,4-triazol-5-yl, 2-amino-1H-1,3,4-triazol-5-yl, 1H-1,3,4-triazol-5-yl, 2-trifluoromethyl-1H-1,3,4-triazol-5-yl, 2-(β-piperidinoethyl)-1H-1,3,4-triazol-5-yl, 2-(β-diethylaminoethyl)-1H-1,3,4-triazol-5-yl, 2-hydroxy-1H-1,3,4-triazol-5-yl, 2-(4-pyridyl)-1H-1,3,4-triazol-5-yl, 2-tert.-butyl-1H-1,3,4-triazol-5-yl, 2-(3-pyridyl)-1H-1,3,4-triazol-5-yl, 2-(2-pyridyl)-1H-1,3,4-triazol-5-yl, 2-acetamido-1H-1,3,4-triazol-5-yl, 2-propionylamido-1H-1,3,4-triazol-5-yl, 2-benzamido-1H-1,3,4-triazol-5-yl, 2-(2-thienyl)-1H-1,3,4-triazol-5-yl, 2-(2-furyl)-1H-1,3,4-triazol-5-yl, 2-(3-furyl)-1H-1,3,4-triazol-5-yl, 2-methoxymethyl-1H-1,3,4-triazol-5-yl, 2-(4-sulfamoylphenyl)-1H-1,3,4-triazol-5-yl, 2-phenyl-1H-1,3,4-triazol-5-yl, 2-(4-methoxyphenyl)-1H-1,3,4-triazol-5-yl, 2-(4-chlorophenyl)-1H-1,3,4-triazol-5-yl, 2-(2-methylpyrid-4-yl)-1H-1,3,4-triazol-5-yl, 2-phenoxymethyl)-1H-1,3,4-triazol-5-yl, 2-ethoxymethyl-1H-1,3,4-triazol-5-yl, 2-(2-ethoxyethyl)-1H-1,3,4-triazol-5-yl, 2-aminoethyl-1H-1,3,4-triazol-5-yl, 2-acetamidomethyl-1H-1,3,4-triazol-5-yl, 2-ethoxycarbonylmethyl-1H-1,3,4-triazol-5-yl, 2-($\beta$-carbomethoxypropionylamido)-1H-1,3,4-triazol-5-yl, 2-carboxymethyl-1H-1,3,4-triazol-5-yl, 2-carboxymethoxymethyl-1H-1,3,4-triazol-5-yl, 2-ethoxycarbonylmethoxymethyl-1H-1,3,4-triazol-5-yl, 2-ethoxycarbonyl-1H-1,3,4-triazol-5-yl, 2-carbamoyl-1H-1,3,4-triazol-5-yl, 2-carbamoylmethoxymethyl-1H-1,3,4-triazol-5-yl and 2-(N-ethylcarbamoylmethoxymethyl)-1H-1,3,4-triazol-5-yl, for

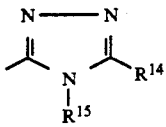

in which $R^{15} \neq$ hydrogen 2-amino-1-methyl-1,3,4-triazol-5-yl, 1-methyl-1,3,4-triazol-5-yl, 1-methyl-2-trifluoromethyl-1,3,4-triazol-5-yl, 1,2-dimethyl-1,3,4-triazol-5-yl, 2-hydroxy-1-methyl-1,3,4-triazol-5-yl, 1-methyl-2-(3-pyridyl)-1,3,4-triazol-5-yl, 1-methyl-2-(4-pyridyl)-1,3,4-triazol-5-yl, 2-(2-furyl)-1-methyl-1,3,4-triazol-5-yl, 1-methyl-2-(2-thienyl)-1,3,4-triazol-5-yl, 1-methyl-2-(2-pyridyl)-1,3,4-triazol-5-yl, 2-(3-furyl)-1-methyl-1,3,4-triazol-5-yl, 1-methyl-2-phenyl-1,3,4-triazol-5-yl, 1-ethyl-1,3,4-triazol-5-yl, 1-ethyl-2-(3-pyridyl)-1,3,4-triazol-5-yl, 1-ethyl-2-(4-pyridyl)-1,3,4-triazol-5-yl, 1-ethyl-2-(2-pyridyl)-1,3,4-triazol-5-yl, 2-(3-furyl)-1-methyl-1,3,4-triazol-5-yl, 1-ethyl-2-trifluoromethyl)-1,3,4-triazol-5-yl, 1-ethyl-2-(2-furyl)-1,3,4-triazol-5-yl, 1-ethyl-2-(2-thienyl)-1,3,4-triazol-5-yl, 1,2-diethyl-1,3,4-triazol-5-yl, 1-propyl-2-(3-pyridyl)-1,3,4-triazol-5-yl, 2-(2-furyl)-1-propyl-1,3,4-triazol-5-yl, 1-propyl-1,3,4-triazol-5-yl, 1-isopropyl-1,3,4-triazol-5-yl, 1-allyl-1,3,4-triazol-5-yl, 1-butyl-1-(2-furyl)-1,3,4-triazol-5-yl, 1-cyclohexyl-1,3,4-triazol-5-yl, 1-benzyl-1,3,4-triazol-5-yl, 1-hydroxy-1,3,4-triazol-5-yl, 1-methoxymethyl-1,3,4-triazol-5-yl, 1-phenyl-1,3,4-triazol-5-yl, 2-methyl-1-phenyl-1,3,4-triazol-5-yl, 1-(4-chlorophenyl)-1,3,4-triazol-5-yl, 2-hydroxy-1-phenyl-1,3,4-triazol-5-yl, 2-amino-1-phenyl-1,3,4-triazol-5-yl, 1-phenyl-2-propyl-1,3,4-triazol-5-yl, 2-(1-piperidinomethyl)-1-phenyl-1,3,4-triazol-5-yl, 2-($\beta$-diethylaminoethyl)-1-phenyl-1,3,4-triazol-5-yl, 1-(4-ethoxyphenyl)-2-($\beta$-piperidinoethyl)-1,3,4-triazol-5-yl, 1-(4-chlorophenyl)-2-dimethylaminomethyl-1,3,4-triazol-5-yl, 1-phenyl-2-(4-pyridyl)-1,3,4-triazol-5-yl, 1-(3-pyridyl)-1,3,4-triazol-5-yl, 2-hydroxy-1-(2-pyridyl)-1,3,4-triazol-5-yl, 1-(4-pyridyl)-1,3,4-triazol-5-yl, 1-(2-pyridyl)-1,3,4-triazol-5-yl, 1-(4-ethoxyphenyl)-2-hydroxy-1,3,4-triazol-5-yl, 1-(4-chlorophenyl)-2-hydroxy-1,3,4-triazol-5-yl, 1-amino-2-trifluoromethyl-1,3,4-triazol-5-yl, 1-amino-2-(2-hydroxyphenyl)-1,3,4-triazol-5-yl, 1-amino-2-phenyl-1,3,4-triazol-5-yl, 1-amino-2-(4-fluorophenyl)-1,3,4-triazol-5-yl, 1-amino-2-(2-bromophenyl)-1,3,4-triazol-5-yl, 1-amino-2-(2-methoxyphenyl)-1,3,4-triazol-5-yl, 1-amino-2-(4-pyridyl)-1,3,4-triazol-5-yl, 1-amino-2-(2-thienyl)-1,3,4-triazol-5-yl, 1-amino-2-cyclohexyl-1,3,4-triazol-5-yl, 1-amino-2-methyl-1,3,4-triazol-5-yl, 2-ethyl-1-amino-1,3,4-triazol-5-yl, 2-phenyl-1-phenylamino-1,3,4-triazol-5-yl, 2-ethyl-1-ethylamino-1,3,4-triazol-5-yl, 1-amino-2-methylthio-1,3,4-triazol-5-yl, 1-amino-2-mercapto-1,3,4-triazol-5-yl, 1-amino-2-benzyl-1,3,4-triazol-5-yl, 1-acetamido-2-ethyl-1,3,4-triazol-5-yl, 2-ethyl-1-(2,5-dimethyl-pyrrol-1-yl)-1,3,4-triazol-5-yl, 2-ethyl-1-(pyrrol-1-yl)-1,3,4-triazol-5-yl, 1-methyl-2-(4-sulfamoylphenyl)-1,3,4-triazol-5-yl, 1-allyl-2-(4-sulfamoylphenyl)-1,3,4-triazol-5-yl, 1-phenyl-2-(4-sulfamoylphenyl)-1,3,4-triazol-5-yl, 1-amino-1,3,4-triazol-5-yl, 1-(4-ethoxy-phenyl)-2-(4-pyridyl)-1,3,4-triazol-5-yl, 1-(4-ethoxyphenyl)-2-(3-pyridyl)-1,3,4-triazol-5-yl, 1-(4-methoxyphenyl)-2-(4-pyridyl)-1,3,4-triazol-5-yl, 1-(4-ethoxyphenyl)-2-phenyl-1,3,4-triazol-5-yl, 1-(4-ethoxyphenyl)-2-(4-aminophenyl)-1,3,4-triazol-5-yl, 1,2-diphenyl-1,3,4-triazol-5-yl, 1,2-di-p-tolyl-1,3,4-triazol-5-yl, 1-allyl-2-phenyl-1,3,4-triazol-5-yl, 1-amino-2-carboxymethyl-1,3,4-triazol-5-yl, 2-carboxymethyl-1-methyl-1,3,4-triazol-5-yl, 2-carboxymethoxymethyl-1-methyl-1,3,4-triazol-5-yl, 1-carboxymethyl-2-trifluoromethyl-1,3,4-triazol-5-yl, 1-carbamoylmethyl-2-trifluoromethyl-1,3,4-triazol-5-yl, 1-sulfoethyl-2-trifluoromethyl-1,3,4-triazol-5-yl, 2-ethoxycarbonylmethoxymethyl-1-methyl-1,3,4-triazol-5-yl, 2-carbamoyl-1-methyl-1,3,4-triazol-5-yl, 2-carbamoylmethoxymethyl-1-methyl-1,3,4-triazol-5-yl, 2-ethoxycarbonyl-1-(4-methoxybenzyl)-1,3,4-triazol-5-yl and 1-amino-2-carboxymethylthio-1,3,4-triazol-5-yl, and for

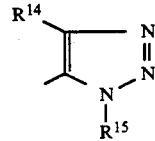

1H-1,2,3-triazol-5-yl, 1-methyl-1,2,3-triazol-5-yl, 1,4-dimethyl-1,2,3-triazol-5-yl, 1H-4-methyl-1,2,3-triazol-5-yl, 1,4-diethyl-1,2,3-triazol-5-yl, 4-carboxy-1H-1,2,3-triazol-5-yl, 4-(2-carboxyethyl)-1H-1,2,3-triazol-5-yl, 4-(3-carboxypropyl)-1H-1,2,3-triazol-5-yl, 4-(1-carboxy-1-methylethyl)-1H-1,2,3-triazol-5-yl, 4-(2-carboxy-2-methylpropyl)-1H-1,2,3-triazol-5-yl, 4-N-methylcarbamoyl-1H-1,2,3-triazol-5-yl, 4-N-ethylcarbamoyl-1H-1,2,3-triazol-5-yl, 4-N-propylcarbamoyl-1H-1,2,3-triazol-5-yl and 4-N-butylcarbamoyl-1H-1,2,3-triazol-5-yl.

d) A triazolyl radical of the general formula VIII

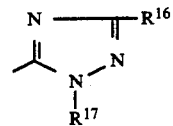 (VIII)

in which $R^{16}$ and $R^{17}$, which can be identical or different, denote lower, straight-chain or branched alkyl, lower, straight-chain or branched alkenyl, lower alkoxyalkyl, hydroxyl, hydroxyalkyl, lower alkoxy, lower alkylcarbonyl or an optionally substituted phenyl radical, and furthermore $R^{16}$ can represent hydrogen.

Examples which may be mentioned are, in particular: 1-methyl-1,2,4-triazol-5-yl, 1-butyl-1,2,4-triazol-5-yl, 1-phenyl-1,2,4-triazol-5-yl, 1-methoxymethyl-1,2,4-triazol-5-yl, 1,3-dimethyl-1,2,4-triazol-5-yl, 1-allyl-1,2,4-triazol-5-yl, 3-hydroxy-1-methyl-1,2,4-triazol-5-yl, 3-hydroxy-1-isopropyl-1,2,4-triazol-5-yl, 3-hydroxy-1- phenyl-1,2,4-triazol-5-yl, 3-ethyl-1-methyl-1,2,4-triazol-5-yl and 3-methyl-1-phenyl-1,2,4-triazol-5-yl.

e) A pyrimidinyl and pyridazinyl radical of the general formulae IX, IX a and IX b

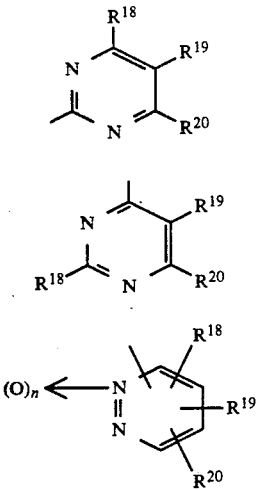

in which $R^{18}$ to $R^{20}$, which can be identical or different, denote hydrogen, halogen, lower, straight-chain or branched alkyl, lower, straight-chain or branched alkenyl, mercapto, lower alkylthio, hydroxyl, lower hydroxyalkyl, lower alkoxy, lower alkylcarbonyl, lower alkoxyalkyl, an amino group which can be optionally substituted by one or two lower alkyl radicals, lower carboxyalkyl, carboxyl, cyano, lower alkoxycarbonyl, a carbamoyl group which can be optionally substituted by one or two lower alkyl groups, which in turn can form a carbocyclic ring with 5-7 C atoms which can be optionally interrupted by nitrogen or sulfur, lower alkoxycarbonylalkylamido, lower carboxyalkylamido, lower cyanoalkyl, an optionally substituted phenyl radical or lower carboxyalkylthio and the heterocyclic rings can also be partially hydrogenated and n represents 0 or 1.

Examples which may be mentioned are, in particular: for

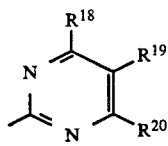

4,6-diamino-pyrimidin-2-yl, 4-amino-6-hydroxy-pyrimidin-2-yl, 5,6-diamino-4-hydroxy-pyrimidin-2-yl, 4,5-diamino-pyrimidin-2-yl, 4-hydroxy-6-methyl-pyrimidin-2-yl, 4,6-dihydroxy-pyrimidin-2-yl, 4-hydroxy-pyrimidin-2-yl, 4-hydroxy-6-propyl-pyrimidin-2-yl, pyrimidin-2-yl, 4-methyl-pyrimidin-2-yl, 4,6-dimethyl-pyrimidin-2-yl, 4-mercapto-pyrimidin-2-yl, 4-methylthio-pyrimidin-2-yl, 1,4,5,6-tetrahydropyrimidin-2-yl, 4-hydroxy-6-methyl-pyrimidin-2-yl-5-acetic acid, 4-hydroxy-pyrimidin-2-yl-5-carboxylic acid, 4-amino-pyrimidin-2-yl-5-carboxylic acid, methyl 4-amino-pyrimidin-2-yl-5-carboxylate, ethyl 4-amino-pyrimidin-2-yl-5-carboxylate, 4-hydroxy-pyrimidin-2-yl-5-acetic acid, 4-hydroxy-5-piperidino-carbonyl-pyrimidin-2-yl, 4-chloro-pyrimidin-2-yl-5-carboxylic acid, 4-(β-carboxypropionylamido)-6-hydroxy-pyrimidin-2-yl and 5-cyanoethyl-4-hydroxy-6-methylpyrimidin-2-yl, for

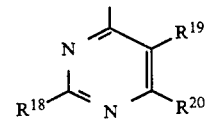

2-hydroxy-pyrimidin-4-yl, pyrimidin-4-yl, 5-ethoxycarbonyl-6-methyl-2-phenyl-pyrimidin-4-yl, 6-ethoxy-5-ethoxycarbonyl-2-phenyl-pyrimidin-4-yl, 5-ethoxycarbonyl-6-amino-2-phenyl-pyrimidin-4-yl, 5-cyano-2-hydroxy-6-methyl-pyrimidin-4-yl, 5-acetyl-2,6-dimethyl-pyrimidin-4-yl, 5-ethoxycarbonyl-2,6-dimethyl-pyrimidin-4-yl, 2-hydroxy-6-methyl-pyrimidin-4-yl, 6-mercapto-2-methyl-pyrimidin-4-yl, 6-mercaptopyrimidin-4-yl, 2-amino-6-mercapto-pyrimidin-4-yl, 6-mercapto-2-methylthio-pyrimidin-4-yl, 6-carboxymethylthio-pyrimidin-4-yl, 6-carboxymethylthio-2-methyl-pyrimidin-4-yl and 2-amino-4-carboxymethylthio-pyrimidin-4-yl, and for

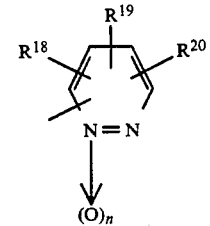

6-methoxy-2-oxy-pyridazin-3-yl, 6-butoxy-2-oxy-pyridazin-3-yl, 6-ethoxy-2-oxy-pyridazin-3-yl, 6-chloro-2-oxy-pyridazin-3-yl, 2-oxy-pyridazin-3-yl, 6-methyl-1-oxy-pyridazin-3-yl, 6-methyl-2-oxy-pyridazin-3-yl, pyridazin-3-yl, 6-hydroxy-pyridazin-3-yl, 6-chloro-1-oxy-pyridazin-3-yl, 5-ethoxycarbonyl-6-hydroxy-pyridazin-3-yl, 5-carboxy-6-hydroxy-pyridazin-3-yl, 4-ethoxycarbonyl-6-hydroxy-pyridazin-3-yl, 4-methyl-6-hydroxy-pyridazin-3-yl, 4-ethyl-6-hydroxy-pyridazin-3-yl, 5-ethoxycarbonyl-6-hydroxy-4-methyl-pyridazin-3-yl, 5-ethoxycarbonyl-4-ethyl-6-hydroxy-pyridazin-3-yl, 4-ethoxycarbonyl-5-ethyl-6-hydroxy-pyridazin-3-yl, 4-ethoxycarbonyl-6-hydroxy-5-methylpyridazin-3-yl and 6-mercaptopyridazin-3-yl.

f) A tetrazolyl radical of the general formula X

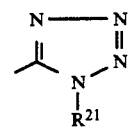

in which $R^{21}$ represents hydrogen, lower, straight-chain or branched alkyl, lower, branched or straight-chain alkenyl, lower alkoxyalkyl, an optionally substituted aryl or heteroaryl radical, a carbocyclic ring with 5-7 C atoms, lower arylalkyl, lower carboxyalkyl, lower cyanoalkyl, lower alkoxycarbonylalkyl, lower sulfoalkyl, lower sulfamoylalkyl, lower alkylsulfoalkyl, lower alkylsulfamoylalkyl, lower dialkylsulfamoylalkyl, lower carbamoylalkyl, lower alkylcarbamoylalkyl, lower dialkylcarbamoylalkyl, lower aminoalkyl, lower hydroxyalkyl or lower alkylamidoalkyl.

Examples which may be mentioned are, in particular: tetrazol-5-yl, 1-ethyl-tetrazol-5-yl, 1-allyl-tetrazol-5-yl, 1-phenyl-tetrazol-5-yl, 1-butyl-tetrazol-5-yl, 1-benzyl-tetrazol-5-yl, 1-(4-fluorophenyl)-tetrazol-5-yl, 1-isopropyl-tetrazol-5-yl, 1-(2-pyridyl)-tetrazol-5-yl, 1-cyclohexyl-tetrazol-5-yl, 1-(2,4-dichlorophenyl)-tetrazol-5-yl, 1-(2-tolyl)-tetrazol-5-yl, 1-(4-nitrophenyl)-tetrazol-5-yl, 1-(4-dimethylaminophenyl)-tetrazol-5-yl, 1-methoxymethyl-tetrazol-5-yl, 1-methyl-tetrazol-5-yl, 1-propyl-tetrazol-5-yl, 1-cyclopentyl-tetrazol-5-yl, 1-(4-chlorophenyl)-tetrazol-5-yl, 1-carboxymethyl-tetrazol-5-yl, 1-carboxyethyl-tetrazol-5-yl, 1-cyanomethyl-tetrazol-5-yl, 1-sulfomethyl-tetrazol-5-yl, 1-sulfoethyl-tetrazol-5-yl, 1-sulfopropyl-tetrazol-5-yl, 1-sulfamoyl-tetrazol-5-yl, 1-sulfamoylethyl-tetrazol-5-yl, 1-(2-N,N-dimethyl-sulfamoylethyl)-tetrazol-5-yl, 1-(3-sulfamoylpropyl)-tetrazol-5-yl, 1-(2-sulfo-1-methylethyl)-tetrazol-5-yl, 1-(4-sulfobutyl)-tetrazol-5-yl, 1-(2-carbamoylethyl)-tetrazol-5-yl, 1-(N-methylcarbamoylmethyl)-tetrazol-5-yl, 1-(N,N-dimethylcarbamoylmethyl)-tetrazol-5-yl, 1-(2-carbamoylpropyl)-tetrazol-5-yl, 1-(3-carboxypropyl)-tetrazol-5-yl, 1-(2-carboxy-1-methylethyl)-tetrazol-5-yl, 1-(4-dimethylaminophenyl)-tetrazol-5-yl, 1-acetamidoethyl-tetrazol-5-yl, 1-(2-hydroxyethyl)-tetrazol-5-yl, 1-ethoxycarbonylmethyltetrazol-5-yl, 1-(2-aminoethyl)-tetrazol-5-yl and 1-(3-methoxypropyl)-tetrazol-5-yl.

If in the definition of the radicals $R^8$ to $R^{21}$ substitutents or references to particular ring systems occur which are not explained in more detail, they correspond to the preceding statements concerning the general substitution possibilities of the radical $R^5$ in the meaning of "heterocyclic radical". At the same time, they are illustrated further by the particular accompanying tabular summary of specific radicals.

Further examples of heterocyclic $R_5$ radicals which may be mentioned are: 1,2,3-thiadiazol-5-yl, 1,2,4-thiadiazol-3-yl, 1,2,5-thiadiazol-3-yl, 1,2,3-oxadiazol-5-yl, 4,5-dimethyloxazol-2-yl, 4-phenyl-oxazol-2-yl, benzoxazol-2-yl, oxazolin-2-yl, imidazol-2-yl, imidazolin-2-yl, benzimidazolin-2-yl, 1-methyl-imidazolin-2-yl, 2-furyl, 2-thiophenyl, 2-pyrrolyl, 2-thiazolinyl, 3-isoxazolyl, 3-pyrazolyl, thiatriazol-5-yl, purinyl, pyrazinyl, 2-methylmercapto-6-phenyl-1,3,5-triazin-4-yl, 5-methyl-6-hydroxy-1,3,4-triazin-2-yl, 5-phenyl-4H-1,3,4-thiadiazin-2-yl, 5-hydroxy-4H-1,3,4-thiadiazin-2-yl, 3-hydroxy-[4,5-b]-pyridazin-6-yl and tetrazol-[4,5-b]-pyridazin-6-yl.

If $R^5$ represents the radical

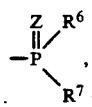

the radicals $R^6$ and $R^7$, which can be identical or different, can have the following meanings: straight-chain or branched alkyl with 1–4 C atoms, such as, for example, methyl, ethyl, propyl, butyl or isobutyl, preferably methyl, straight-chain or branched alkenyl with 2–4 C atoms, such as, for example, allyl, straight-chain or branched alkoxy with 1–4 C atoms, such as, for example, methoxy, ethoxy, propoxy or isobutoxy, straight-chain or branched alkenyloxy with 1–4 C atoms, such as, for example, allyloxy, aryl, in particular phenyl, which can also be substituted, for example by alkyl or alkoxy with 1–4 C atoms, in particular methyl or methoxy, or by halogen, in particular chlorine, or a carbocyclic ring with 3–8 C atoms, such as, for example, cyclohexyl.

Examples which may be mentioned are, in particular:

α) If Y denotes

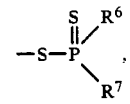

the radical of dimethyl-dithiophosphinic acid, butyl-methyl-dithiophosphinic acid, ethyl-methyl-dithiophosphinic acid, isobutyl-methyl-dithiophosphinic acid, methyl-phenyl-dithiophosphinic acid, diphenyl-dithiophosphinic acid, O-methyl-methyl-dithiophosphonic acid, O-ethyl-methyl-dithiophosphonic acid, O-ethyl-ethyl-dithiophosphonic acid, O-ethyl-propyl-dithiophosphonic acid, O-methyl-(4-methoxyphenyl)-dithiophosphonic acid, O-methyl-isobutyl-dithiophosphonic acid, O-methyl-cyclohexyl-dithiophosphonic acid, O,O-dimethyl-dithiophosphoric acid, O,O-diethyl-dithiophosphoric acid and O,O-di-propyl-dithiophosphoric acid, and β) if Y denotes

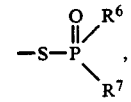

the radical of O-methyl-methyl-thiophosphonic acid, O-ethyl-methyl-thiophosphonic acid, isobutyl-methyl-thiophosphinic acid, O-ethyl-ethyl-thiophosphonic acid and O-ethyl-propyl-thiophosphonic acid.

The cephem compounds of the general formula II which are to be employed according to the invention are known from the literature or can be manufactured according to information in the literature, for example according to the information in E. F. Flynn, Cephalosporins and Penicillins, Chemistry and Biology, Academic Press, New York and London, 1972, or, if X represents oxygen or $CH_2$ in the formula II, according to J. Amer. Chem. Soc. 96, S. 7582 and 7584 (1974). Compounds in which A denotes —$CH_2S$— heterocyclic ring, and $R_3$ denotes ester groups are the subject of German Offenlegungsschrift 2,359,402.

In order to obtain the compounds of the formula I with the $R_2O$ group in the syn-position, which in the present text is represented throughout as

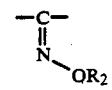

to differentiate from the anti-position

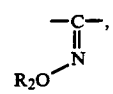

it is appropriate to ensure that the starting material of the general formula III is already present as the syn-compound. If the mild reaction conditions customary for reactions with syn-compounds are then adhered to, synend products are as a rule obtained. Nevertheless it can sometimes happen that small amounts of the corresponding anti-compound are also obtained as an impurity in the end product, and, if desired, this impurity can be separated off by methods which are known in the laboratory, such as, for example, recrystallization.

The carboxylic acids of the general formula III used for the acylation can be manufactured by various processes.

Thus, for example, compounds of the formula III in which $R_1$ denotes hydrogen and $R_2$ denotes alkyl are obtained by reaction of thiourea with

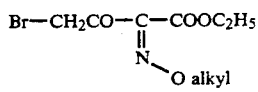

and subsequent saponification of the ester group, whereby the reaction should appropriately be effected with a stoichiometric amount of thiourea at room temperature in a water-containing solvent, such as, for example, acetone, and the reaction should not be carried out for longer than a few hours, for example a maximum of about 2-3 hours.

It is also possible to react the α-carbonyl group of a 2-aminothiazole-4-glyoxylic acid alkyl or aralkyl ester, substituted on the amino group by $R_1$, with a hydroxylamine compound of the general formula $H_2N-OR_2$ and then to saponify the resulting ester in a manner which is in itself known.

The manufacture of the aminothiazole-glyoxylic acid esters used for this reaction is described in German Patent Application P 2,710,902.0. Most of the hydroxylamine derivatives required for the reaction are known, or they can be easily manufactured according to the information in the literature.

The reaction of the two components is carried out under the conditions, described in the literature, for the reaction of glyoxylic acid derivatives with carbonyl reagents.

Compounds of the formula III in which $R_1$ represents an acyl group can be obtained easily and in high yields by acylating the compounds described above of the general formula

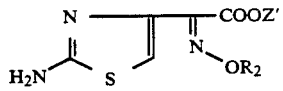

in which Z' represents lower alkyl or aralkyl, with reactive carboxylic acid derivatives.

It has proved favorable to use acid halides, in particular acid chlorides and acid bromides. However, it is particularly advantageous to employ symmetric or unsymmetric anhydrides. The acylation is carried out in the presence of bases, such as, for example, triethylamine, preferably at room temperature or, in particular, at temperatures which are lowered still further, in organic solvents which do not interfere with the reaction, in particular in halogenated hydrocarbons, such as, for example, methylene chloride, chloroform or tetrachloroethylene. The resulting esters are then converted into the free carboxylic acids.

If in the formula III $R_1$ in the meaning of acyl represents an aliphatic acyl radical which is also substituted by a nucleophilic radical defined under Y, such as, for example, a nitrogen- or oxygen-nucleophile, but in particular by the S—nucleophilic group $R_5-S-$, $R_5$ having the meaning indicated above, the acylation described above is appropriately carried out with activated α-halogenoalkyl acid derivatives, such as, for example, chloroacetyl chloride, α-bromopropionyl chloride or bromoacetyl bromide, which can also further carry an aryl, preferably phenyl, in the α-position, and the halogen is then reacted with a mercaptan of the formula $HS-R_5$ and thus replaced by $-SR_5$.

The replacement reaction is carried out in organic or inorganic solvents, preferably in water, in the presence of organic or inorganic bases, such as, for example, triethylamine or sodium bicarbonate, for example at temperatures between about 10° and 80° C., but in particular at room temperature.

If in the formula III the radical $R_1$ represents an arylsulfonyl or alkylsulfonyl group, these compounds of the formula III are obtained by reacting activated alkylsulfonic acid derivatives or arylsulfonic acid derivatives with compounds of the formula

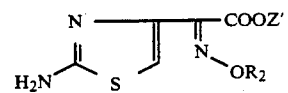

and then saponifying the product.

Possible activated sulfonic acid derivatives are, in particular, the sulfonic acid halides known from the literature, such as, for example, sulfonic acid chlorides, as well as the symmetric anhydrides.

The reaction is carried out in the presence of bases in organic solvents which do not interfere with the reaction. Suitable bases are, above all, organic bases, such as, for example, N,N-dimethylaniline or triethylamine. Examples of possible organic solvents which do not interfere with the reaction are halogenated hydrocarbons, such as, for example, methylene chloride or chloroform, or tertiary amides, such as, for example, dimethylformamide or dimethylacetamide. The reaction is appropriately carried out at room temperature.

If in the general formula III the radical $R_1$ represents a group which can be easily removed again, its introduction into the amino group can be effected in the manner known from peptide chemistry for amino-protective groups (compare the book mentioned below by Schröder and Lübke, The Peptides, volume 1 (1965), page 3). If such a group is, for example, triphenylmethyl, its introduction can be effected with triphenylchloromethane, the reaction appropriately being carried out in an organic solvent, such as, for example, halogenated hydrocarbons, in the presence of bases.

Chloroform and methylene chloride have proved particularly suitable halogenated hydrocarbons here. Bases which can be mentioned are, in particular, tertiary amines, such as, for example, triethylamine or N-methylmorpholine.

The mercaptoheterocyclic compounds $R_5SH$ used as a starting material are known from the literature or can be manufactured according to information in the literature.

It is appropriate, not only in the manufacture of starting material which contains a group

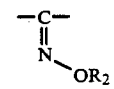

in the syn-position, but also in all further reactions, to use reaction conditions which are as mild and gentle as possible, such as are known to the expert, from the literature, for reactions with syn-compounds, such as, for example, no elevated temperatures, no prolonged reaction times, no substantial excesses of an acid reactant and the like, in order to avoid any possible flipping over of the oxime group into the anti-form.

The reactive derivatives of the carboxylic acids of the general formula III

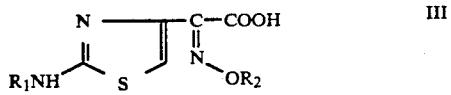

which are employed, according to the invention, for the acylation reaction a) and which are capable of amide formation can be obtained from the carboxylic acids by processes which are known from the literature. Examples of reactive derivatives which may be mentioned are the activated esters, such as, for example, p-nitrophenyl esters or trichlorophenyl esters, azides or anhydrides. A preferred process for activating the carboxyl group consists in converting it into a symmetric anhydride. The processes for the manufacture of symmetric anhydrides are known from the literature and correspond to the methods generally used in peptide chemistry. For example, the inner anhydrides, which are subsequently reacted with the aminocephemcarboxylic acids of the formula II in organic solvents, are obtained from the carboxylic acids of the general formula III using condensing agents, such as, for example, N,N-disubstituted carbodiimides, such as, for example, dicyclohexylcarbodiimide.

The manufacture of the compounds of the general formula I by acylating compounds of the formula II with the carboxylic acids of the formula III can be carried out under variable experimental conditions, for example using various solvents. Examples of suitable solvents are organic solvents, such as, for example, halogenated hydrocarbons, for example methylene chloride or chloroform, but also water or mixtures of water and organic solvents, which are mixed intensively with water. In order to carry out the reaction well, it is appropriate to dissolve the aminolactam derivatives of the formula II.

If aminocephem esters of the general formula II in which $R_3$ thus represents one of the ester groups defined above are used, the reaction is preferably carried out in organic solvents, in which most of the esters are readily soluble. Examples of such solvents which may be mentioned are halogenated hydrocarbons, such as, for example, methylene chloride or chloroform, but also tertiary amides, such as, for example, dimethylformamide or dimethylacetamide.

The ester groups listed above under $R_3$ include on the one hand those such as, for example, are known from peptide chemistry as carboxyl-protective groups which can be easily split off (compare, for example, E. Schröder and K. Lübke, The Peptides, volume 1, Academic Press, New York and London, 1965, page 52). However, they preferably include ester groups, the use of which can be therapeutically advantageous in the administration of the end products. In this case also the restrictions can be somewhat flexible, since, for example, a benzhydryl ester is therapeutically usable and at the same time can also serve as a protective group.

If the aminocephemcarboxylic acids of the general formula II ($R_3$=hydrogen) are used, the compounds must be dissolved, with the addition of bases.

Suitable bases which can be used for dissolving the 7-aminocephemcarboxylic acids, as well as a number of 7-amino-$\Delta^3$-cephem-4-carboxylic acids, are inorganic or organic bases. Thus, tertiary amines, such as triethylamine, N,N-dimethylaniline or N-methylmorpholine, have proved particularly suitable for the preparation of solutions in organic solvents, and alkali metal bicarbonates, such as sodium bicarbonate or potassium bicarbonate, and tertiary amines have proved particularly suitable for the prepartion of aqueous solutions. In general, the bases are added in at least stoichiometric amount, relative to the desired reaction. An excess of base of, for example, about 0.1 to 2, in particular about 0.2 to 0.8, moles can be advantageous.

In the case of compounds of the formula II which are sensitive towards bases, depending on the course of the reaction the pH can be kept constant at about 4 to 8, preferably 6 to 7, by continuously adding the base.

The aminolactam derivatives of the formula II can be dissolved in a wide temperature range. However, appropriately it should not exceed a temperature of about 40° C. In the case of derivatives which are sensitive towards bases, it is advisable, however, to choose a temperature range from about 0° to 15° C.

The activated derivatives of the carboxylic acids of the general formula III are added to the aminocephem derivatives of the formula II, which are present in solution or appropriately in suspension. The reaction is carried out in a manner which is in itself known. If water or mixtures of water and organic solvents are used as the reaction medium, it is advisable to maintain the temperature in a range from about −5° to +10° C. If organic solvents are used, it is also possible to carry out the acylation at temperatures up to about 65° C., preferably at room temperature.

In order to carry out the reaction better, the activated carboxylic acid derivatives of the formula III are taken up in a solvent which does not interfere with the reaction and are introduced in dilute form. If the acylation is carried out in an aqueous medium, it is possible to use, for example, anhydrous ketones, such as acetone or methyl ethyl ketone, or, with intensive stirring, ethers, such as, for example, diethyl ether or diisopropyl ether, as solvents for the activated carboxylic acid derivatives.

If the acylation is carried out in a non-aqueous medium, it is advisable to use the same solvent for diluting the acid derivatives as is used for the acylation.

In order to achieve higher yields, the activated acid derivatives of the formula III are employed in an at least stoichiometric amount. An excess of about 5–25% can prove appropriate.

Compounds of the formula I in which A denotes $CH_2Y$ can also be obtained by reacting compounds of the formula I in which A denotes —$CH_2B$, B having the meaning indicated initially, with a compound which contains the nucleophilic radical Y. B can represent, in particular, acyloxy with 1 to 4 carbon atoms, preferably acetoxy, halogen, preferably chlorine or bromine, an azido group, a carbamoyloxy group or a 2-mercaptopyridine-N-oxide radical. The use of the said pyridine compound as a group which can be exchanged is described in Tetrahedron Letters, Volume 23, (1972), page 2345.

Compounds containing the nuclephilic radical Y which may be mentioned are, in particular, compounds of the formula HS—$R_5$, hydrazoic acid and optionally substituted pyridine, quinoline or isoquinoline compounds.

The reaction proceeds particularly smoothly if $R_3$ in the general formula I represents hydrogen or a cation.

The synthesis is preferably carried out by reacting one mole of a compound of the general formula IV with one mole of a compound containing the nucleophilic radical Y, in particular of the compounds mentioned above as preferred, in a solvent which does not interfere with the reaction.

An excess of the nucleophiles, in particular of the thiol, pyridine, quinoline or isoquinoline component, has an advantageous effect on the yield. Should small amounts of the corresponding anti-compound be obtained here, they can be removed in the customary manner, for example by recrystallization.

Examples of solvents which do not interfere with the reaction are water, acetone, chloroform, nitrobenzene, methylene chloride, ethylene chloride, dimethylformamide, methanol, ethanol, ether, tetrahydrofuran, dimethylsulfoxide or any other solvents which do not have an adverse effect on the reaction. Strongly polar solvents are favorable, preferably water. Of the solvents, the hydrophilic solvents, preferably acetone, methanol, ethanol, dimethylformamide and dimethylsulfoxide, can also be used in mixtures with water.

The reaction is carried out in a pH range from 5 to 8, preferably at the neutral pH value.

If the compound IV ($R_3$=hydrogen) or the nucleophilic compound, in particular HS—$R_5$, is used in the free form, the reaction is preferably carried out in the presence of a base, for example an inorganic base, such as an alkali metal hydroxide, alkali metal carbonate or alkali metal bicarbonate, such as, for example, sodium bicarbonate or potassium bicarbonate, an organic base, such as a trialkylamine, or a tertiary ammonium base. The compounds of the formula IV and the HS—$R_5$ can also be employed directly in the form of their salts, preferably the sodium or potassium salts.

The reaction temperature can be varied within a wide range. As a rule, the reaction is carried out at room temperature or the mixture is warmed up to the reflux temperature of the solvents or solvent mixtures used, but appropriately not above about 80° C.

The isolation of the compounds of the formula I from the reaction medium can be effected by methods which are in themselves known and which depend on the solubility of the resulting compounds.

Thus, for example, the reaction products can be taken up in water, if appropriate after evaporating off the organic solvent, and after appropriate purification operations, such as, for example, filtration or centrifugation, can be precitated in the form of the free carboxylic acids ($R_3$=hydrogen) by adding mineral acids, appropriately in an approximately stoichiometric amount, to the clarified reaction mixture. Suitable mineral acids are, in particular, dilute acids, such as dilute hydrochloric acid or sulfuric acid. It is also possible to use very low-molecular organic acids, such as, for example, formic acid or trifluoroacetic acid, or also arylsulfonic acids, such as, for example, toluenesulfonic acids or naphthalenesulfonic acids. Lyophilization of the solution can occasionally also be appropriate.

The amidocephem acids of the formula I usually precipitate as amorphous solids, or in the crystalline form. They can be separated out, if appropriate, as the free acids by extraction at pH 2 to 1. Various water-immiscible organic solvents can be used as extraction agents, for example halogenated hydrocarbons, such as, for example, methylene chloride, or esters, such as, for example, ethyl acetate or n-butyl acetate, but also ketones, such as methyl isobutyl ketone.

The amidocephem acids of the formula I formed are isolated from the extracts, for example, by evaporation of the solvent and trituration, for example with ether. If symmetric anhydrides of the carboxylic acids of the formula III have been used as the starting component, the carboxylic acid constituent liberated during the acylation must also be separated off by customary experimental methods, which depend, for example, on its solubility, crystallinity or ease of extraction.

If desired, protective groups which have been introduced for intermediate protection of the amino group of the aminothiazole radical can be removed by processes which are known from the literature, such as are described, for example, for peptide chemistry. For example, if $R_1$ represents a triphenylmethyl group, the splitting off is effected in an acid medium. Mixtures of formic acid and water, in particular mixtures of water and formic acid in the ratio 1:1 to 4:1, have proved suitable.

The compounds of the formula I containing a free amino and carboxyl group can be isolated by known experimental methods, for example in the case where a triphenylmethyl group is split off as triphenylcarbinol, by filtering off the triphenylcarbinol and then concentrating the solution.

Esters obtained in the reaction according to the invention, the ester group of which has a protective group for the carboxyl group, such as, for example, p-methoxybenzyl, p-nitrobenzyl or tert.-butyl esters, can, if desired, also be converted into the free carboxylic acids of the formula I in a manner which is known from the literature. However, as already mentioned, it is also possible to retain for therapeutic use ester groups which also serve as carboxyl-protective groups, such as, for example, benzhydryl esters.

Compounds of formula I having a free α-oxime group ($R_2$=hydrogen) can be prepared by the process of the invention, for example by exchange of B in the definition of acetoxy in compounds of formula IV in which $R_2$ denotes hydrogen or by splitting off a group $R_2$ having the character of a protective group from compounds of formula I in known manner by acid hyrolysis or hydrogenolysis, groups of this type being, for example tert.butyloxycarbonyl, dibenzyl, carbobenzyloxy, formyl, trichloroethoxycarbonyl, 2-tetrahydropyranyl, preferably triphenylmethyl.

For acid hydrolysis there may be used, for example, formic acid, trifluoroacetic acid or acetic acid which can be used either in anhydrous form or in aqueous solutions. Zinc/acetic acid may also be used.

Preferred agents for acid hydrolysis are anhydrous trifluoroacetic acid, aqueous formic acid or acetic acid if tert.butoxycarbonyl or triphenyl methyl shall be split off. Dibenzyl or carbonbenzyloxy, for example, are preferably split off by catalytic hydrogenation agents.

If $R_2$ denotes chloroacetyl, this may be split off also with thiourea, preferably in a neutral or acid medium (cf. JACS 90 (1968), page 4508).

Simultaneously with $R_2$, a radical $R_1$ denoting a protective group can be split off by acid hydrolysis, hydrogenolysis or with thiourea. It is the same with the radical $R_3$ provided it can be eliminated by hydrolysis or hydrogenolysis. In the case of compounds containing radicals $R_1$, $R_2$ and $R_3$ having the function of protective groups which can be split off in different manner only, for example by hydrolysis and hydrogenolysis or with different hydrolysis agents, these methods should be applied successively The resulting acids of the formula I can be converted into their physiologically acceptable salts, in particular into alkali metal salts, such as, for example, the sodium salts, or into salts with organic bases, preferably tertiary amines, such as, for example, the procaine salt.

The conversion into salts can be effected in a manner which is in itself known by reacting a carboxylic acid of the general formula I with the desired base, for example with sodium bicarbonate, or the sodium salts of organic carboxylic acids, such as, for example, sodium acetate, sodium propionate, sodium hexanoate or sodium 2-ethyl-hexanoate, or potassium acetate.

It is also possible to isolate salts directly from the reaction solution, for example by precipitation with suitable organic solvents or by lyophilization.

Compounds of the formula I in which $R_3$ represents an ester group, in particular a physiologically acceptable ester, can be obtained directly by using the appropriately esterified starting material of the formula II, or they can be obtained by subsequent esterification of compounds of the formula I in which the carboxyl group is present in the free form or as a salt, by processes which are known from the literature. Because it is easier to carry out, subsequent esterification can be advantageous for the manufacture of physiologically acceptable esters and a variation of the ester group.

For example, esters are obtained by subsequent reaction when the salts, preferably the triethylammonium salts or the alkali metal salts, preferably the sodium salts, are reacted with reactive halogenoalkyl compounds, such as, for example, chloroalkyl, bromoalkyl or iodoalkyl compounds, or trialkylammoniumalkyl compounds, in particular the corresponding chloromethyl, bromomethyl, iodoethyl or triethylammoniummethyl compounds. Examples of reactive halogenoalkyl compounds which can be used are halogenomethoxycarbonyl compounds, such as chloromethyl acetate, chloromethyl propionate or chloromethyl pivalate, or the $\omega$-halogenomethyl ketones, such as, for example, $\omega$-bromoacetophenone, chloroacetone or $\omega$-bromoacetophenone substituted in the aryl nucleus, such as, for example, in the phenyl nucleus, such as, for example, 5-sulfamyl-4-chloro -$\omega$-bromoacetophenone, but also halogenoalkyl-carboxylic acid derivatives, in particular the halogenomethyl-carboxylic acid derivatives, such as chloroacetic acid, bromoacetic acid and bromoacetic acid esters, such as, for example, the low-molecular alkyl esters and optionally the benzyl esters, such as the p-methoxybenzyl ester. Halogenomethyl ketones in which the 2-alkyl group is monosubstituted or polysubstituted by alkoxycarbonyl, oximino, oxido or alkoximino radicals, such as, for example, 1-chloro-(3-methoximino-3-carbethoxy)-acetone or 1-bromo-3-methoximino-3-carbethoxyacetone, but also bromo-3-oxido-3-carbethoxyacetone, have proved suitable reactive halogenomethyl derivatives.

Further reactive halogenoalkyl derivatives which may be mentioned are the alkyl iodides, such as, for example methyl iodide, ethyl iodide or isopropyl iodide, and the corresponding bromides.

The reaction with diazoalkanes, such as, for example, diazomethane or diazoethane, but also diarylmethyldiazomethane, such as, for example, diphenyldiazomethane, may furthermore be mentioned for the manufacture of optionally substituted esters.

A further esterification method consists in reacting the alkali metal salts, preferably in alcohol, such as, for example, methanol, with alkyl sulfochlorides, such as, for example, methyl sulfochloride.

The reaction of the salts of the cephem compounds of the formula I with alkyl halides is appropriately carried out in a solvent which does not interfere with the reaction, such as, for example, dimethylformamide or dimethylacetamide, or also dimethylsulfoxide. The reaction can be carried out within a wide temperature range, for example at 0° to 80° C., but preferably at 30°–50° C., depending on the activity of the halogenoalkane.

In order to achieve good yields, the halogenoalkane is employed in an at least equimolar amount. An excess of up to 5 equivalents has sometimes proved favorable.

On parental and oral administration, the physiologically acceptable esters obtained according to the invention exhibit surprising anti-bacterial activities in vivo and in vitro.

Compounds of the formula I in which $R_1$ represents acyl can be obtained by subsequent acylation of the free amino group of the corresponding cephem compound. The subsequent acylation is carried out with activated carboxylic acid derivatives in an organic solvent which does not hinder the reaction, such as, for example, halogenated hydrocarbons, such as, for example, methylene chloride or chloroform, in a temperature range which is limited by the solvents. Acid halides, such as, for example, acid chlorides or acid bromides, and symmetric or unsymmetric anhydrides have proved particularly suitable activated carboxylic acid derivatives. If acid halides are used, it is appropriate to add a base in order to achieve high yields.

The temperature range can be between about $-50°$ and the boiling point of the solvent, preferably between $-30°$ and $+40°$ C. The temperature range from 0° to 25° C. has proved particularly advantageous.

If cephem acids of the formula I in which $R_3$ represents hydrogen or an alkali metal cation are used, it is advisable to employ the anhydrides in a relatively large excess, for example an excess of about 1–5 moles, or even to employ them as the solvent. An alternative preparation method which has proved very suitable is to convert the acids or salts of the formula I into their silyl esters, then to acylate the esters and subsequently to split off the silyl group.

If acid halides are used, it is advisable to remove the moisture present by distilling it out azeotropically immediately before the reaction.

Examples which may be mentioned of carboxylic acids which are particularly suitable for the acylation are optionally substituted arylcarboxylic acids, such as, for example, benzoic acid, p-chlorobenzoic acid, p-sulfamoylbenzoic acid, m-sulfamoylbenzoic acid and 4-chloro-5-sulfamoylbenzoic acid, optionally substituted arylacetic acids, such as, for example, phenylacetic acid, p-nitrophenylacetic acid, 3-methoxyphenylacetic acid, 2,4-dichlorophenylacetic acid and p-amidinophenylacetic acid, optionally substituted aryloxyacetic acids, such as, for example, phenoxyacetic acid, p-hydroxyphenoxyacetic acid, p-methoxyphenoxyacetic acid, p-oxdiazolyl-phenoxyacetic acid or 3,5-dinitrophenoxyacetic acid, optionally substituted thiophenoxyacetic acids, such as, for example, thiophen-3-oxyacetic acid, as well as the corresponding S analogs, such as, for example, phenylthioacetic acids, optionally substituted alkylcarboxylic acids with 1 to 4 C atoms, such as, for example, acetic acid, propionic acid or butyric acid, chloroacetic acid, bromoacetic acid, α-bromopropionic acid, alkoxyacetic acids with 1 to 5 C atoms in the alkoxy part, such as, for example, methoxyacetic acid or butoxyacetic acid, and the analogous mercapto and amino compounds, such as, for example, alkylthioacetic acids or alkyl- or dialkyl-aminoacetic acids.

If α-halogenocarboxylic acids of the general formula

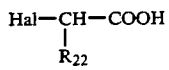

in which Hal represents a chlorine, bromine or iodine atom and $R_{22}$ denotes hydrogen, alkyl with 1 to 5 C atoms or aryl, in particular phenyl, are used, the halogen can subsequently be replaced, by reaction with a nucleophilic radical defined under Y, such as, for example, a nitrogen nucleophile or oxygen nucleophile, by the nucleophilic radical, but in particular, by reaction with mercapto compounds of the formula $HS-R_5$, by the S-nucleophilic radical $-SR_5$, wherein $R_5$ has the meanings indicated initially.

The replacement of halogen in the aliphatic acyl radical $R_1$ by the nucleophile can be carried out in organic or inorganic solvents, depending on the radical $R_3$. If $R_3$ represents hydrogen or a cation, the replacement reaction is advantageously carried out in an aqueous solution in the presence of organic or inorganic bases, such as, for example, triethylamine or alkali metal carbonates or bicarbonates, such as, for example, sodium bicarbonate. If $R_3$ represents an ester group, the reaction can also be carried out successfully in organic solvents, such as halogenated hydrocarbons, such as, for example, methylene chloride or chloroform, or in amides, such as, for example, dimethylformamide or dimethylacetamide, or sulfoxides, such as, for example, dimethylsulfoxide, in the presence of organic bases, such as, for example, trialkylamines, in particular triethylamine or N,N-dimethylaniline.

The reaction can be carried out within a wide temperature range; the range from about 10°–40° C., in particular from 15°–30° C., has proved advantageous.

Depending on the desired end product, the process steps α) to ε) which are possible according to the invention can be combined with one another, it frequently being possible to rearrange the sequence. Thus, for example, it is possible to first carry out a nucleophilic replacement reaction in the 3-position of the cephem ring, then an esterification of the carboxyl group, followed by a subsequent acylation of the aminothiazole group, or the acylation of the amino group in the thiazole ring is first carried out, and then the esterification. These rearrangement possibilities of the reaction steps, which are self-evident to any expert, also belong to the subject of the invention.

If $R_4$ is present in the form of one of the groups described above which can be converted into lower alkoxy, preferably methoxy, this conversion can be carried out in a manner which is known from the literature (compare, for example, German Offenlegungsschrift 2,440,790).

The compounds of the general formula I according to the invention are valuable chemotherapeutic agents which possess a surprisingly powerful antimicrobial action against Gram-positive and Gram-negative bacteria, have an unexpectedly good action against penicillinase-forming Staphylococci and in some cases also have a fungistatic activity.

The compounds of the general formula I are distinguished, for example, by a considerable antimicrobial activity against a number of bacteria against which the known cephalosporins are scarcely active.

Since the compounds of the formula I furthermore exhibit favorable toxicological and pharmacokinetic properties, they are valuable antimicrobial active compounds for the treatment of infectious diseases.

The invention thus also relates to medicinal formulations for the treatment of microbial infections, which are characterized in that they contain one or more of the compounds according to the invention.

The products according to the invention can also be used in combination with other active compounds, for example from the series of penicillins, aminoglycosides, cephalosporins or compounds which influence the systematics of bacterial infections, such as, for example, antipyretic agents, analgesic agents or antiphlogistic agents.

The compounds of the general formula I can be administered orally, intramuscularly or intravenously.

Medicinal formulations which contain one or more compounds of the general formula I as the active compound can be prepared by mixing the compound(s) of the general formula I with one or more pharmacologically acceptable excipients or diluents, such as, for example, fillers, emulsifiers, lubricants, flavor-correcting agents, dyestuffs or buffer substances, and converting the mixture into a suitable galenical formulation form, such as, for example, tablets, dragées, capsules or a solution or suspension suitable for parenteral administration. Examples of excipients or diluents which may be mentioned are tragacanth, lactose, talc, agar-agar, polyglycols, ethanol and water. Suspensions or solutions in water can preferably be used for parenteral administration. It is also possible to administer the active compounds as such, without excipients or diluents, in a suitable form, for example in capsules.

Suitable doses of the compounds of the general formula I are about 0.4 to 20 g/day, preferably 0.5 to 4 g/day, for an adult having a body weight of about 60 kg. Individual doses or, in general, multiple doses may be administered, it being possible for the individual dose to contain the active compound in an amount of about 50 to 1,000 mg, preferably 100 to 500 mg.

In addition to the compounds described in the embodiment examples, it is also possible, for example, to manufacture according to the invention the following compounds given in the table, the substituents $R_1$, $R_2$, $R_3$, $R_4$, X and A indicated for the particular compound relating to the basic structure of the general formula I

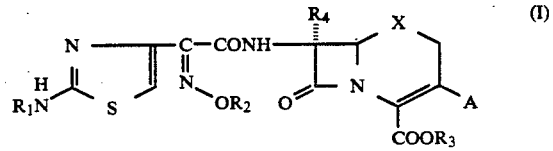

in which the group $-OR_2$ is in the syn-position.

| R₁ | R₂ | R₃ | R₄ | X | A |
|----|----|----|----|---|---|
| H | —CH₃ | H | H | S | ![thiazole with CH₂S, unsubstituted] |
| H | —CH₃ | H | H | S | ![thiazole with CH₃, CH₂S] |
| H | —CH₃ | H | H | S | ![thiazole with n-C₃H₇, CH₂S] |
| H | —CH₃ | CH₂OC(=O)—C(CH₃)₃ | H | S | ![thiazole with CH₃, CH₂S] |
| H | —CH₃ | H | H | S | ![thiazole with C₂H₅, CH₂S] |
| H | —CH₃ | H | H | S | ![thiazole with NH₂, CH₂S] |
| H | —C₂H₅ | H | H | S | ![thiazole with NH₂, CH₂S] |
| H | —CH₃ | H | H | S | ![thiazole with NHCOCH₃, CH₂—S] |

-continued
| R₁ | R₂ | R₃ | R₄ | X | A |
|---|---|---|---|---|---|
| H | —CH₃ | H | H | S | 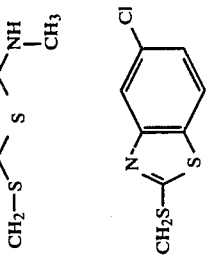 |
| H | —CH₃ | H | H | S | 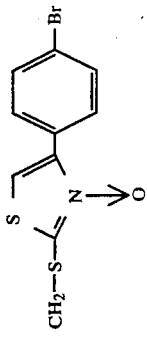 |
| H | —CH₃ | H | H | S | 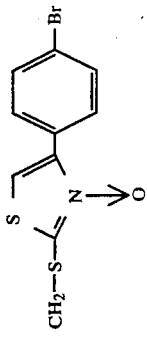 |
| H | —CH₂—CH₂—CH₃ | H | H | S | 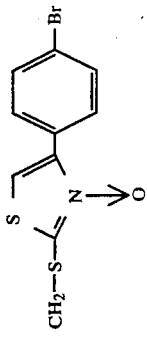 |
| H | —CH₃ | H | H | S | 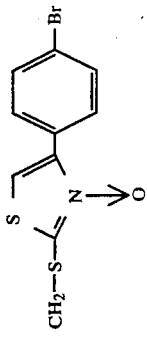 |
| H | —CH₃ | H | H | S | 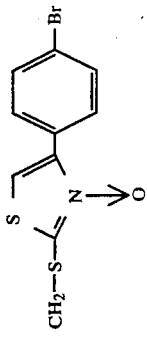 |

-continued
| R₁ | R₂ | R₃ | R₄ | X | A |
|---|---|---|---|---|---|
| H | —CH₃ | H | H | S | 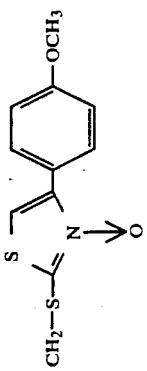 |
| H | —CH₃ | CH₂OC(O)—CH₃ | H | S | 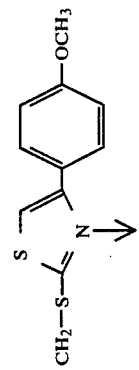 |
| H | —CH₃ | H | H | S | 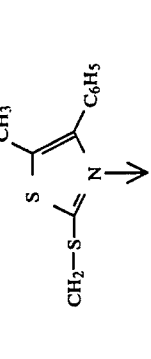 |
| H | —CH₃ | H | H | S | 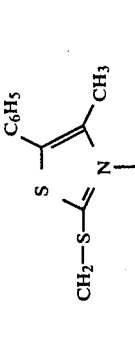 |
| H | n-C₄H₉ | H | H | S | 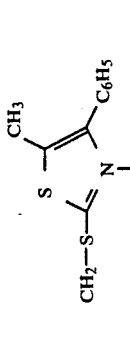 |
| H | —CH₃ | H | H | S | 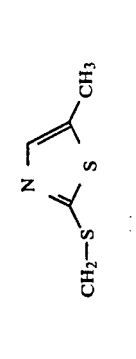 |

-continued
| R₁ | R₂ | R₃ | R₄ | X | A |
|---|---|---|---|---|---|
| H | —CH₃ | H | H | S |  |
| H | —C₂H₅ | H | H | S |  |
| H | —CH₃ | CH₂—O—C(=O)—C(CH₃)₃ | H | S |  |
| H | —CH₃ | CH₂—OCCH₃ (O=) | H | S |  |
| H | —CH₃ | H | H | S |  |
| H | —CH₃ | H | H | S |  |
| H | —CH₃ | H | H | S |  |
| H | —CH₃ | H | H | S |  |

-continued
| $R_1$ | $R_2$ | $R_3$ | $R_4$ | X | A |
|---|---|---|---|---|---|
| H | $-C_2H_5$ | H | H | S |  |
| H | $-CH_3$ | H | H | S |  |
| H | $-CH_3$ | $CH_2OC(=O)CH_3$ | H | S |  |
| H | $-CH_3$ | H | H | S |  |
| H | $-CH_3$ | H | H | S | 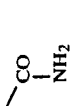 |
| H | $-CH_3$ | H | H | S | 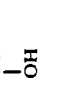 |
| H | $-CH_3$ | H | H | S |  |
| H | $-CH_3$ | H | H | S |  |

-continued
| R₁ | R₂ | R₃ | R₄ | X | A |
|---|---|---|---|---|---|
| H | —CH₃ | H | H | S | 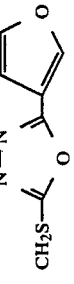 |
| H | —CH₃ | H | H | S | 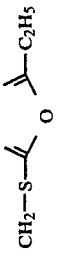 |
| H | —CH₃ | H | H | S | 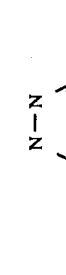 |
| H | —CH₃ | 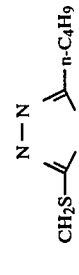 | H | S | 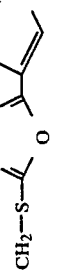 |
| H | —CH₃ | H | H | S | 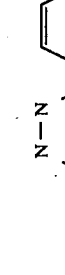 |
| H | —CH₃ | H | H | S |  |
| H | —C₂H₅ | H | H | S | 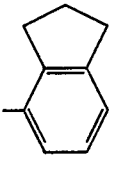 |
| H | —CH₃ |  | H | S |  |
| H | —CH₃ | H | H | S |  |

-continued
| R₁ | R₂ | R₃ | R₄ | X | A |
|---|---|---|---|---|---|
| H | —CH₃ | H | H | S | 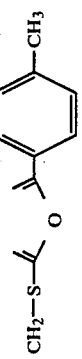 |
| H | —CH₃ | H | H | S | 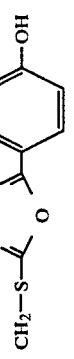 |
| H | —CH₃ | H | H | S | 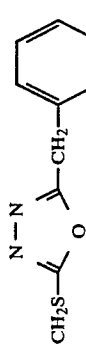 |
| H | —CH₃ | H | H | S | 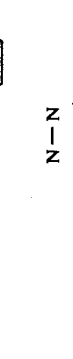 |
| H | —CH₃ | H | H | S | 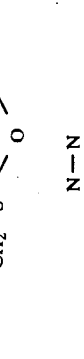 |
| H | —CH₃ | H | H | S | 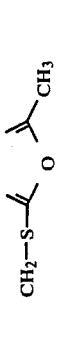 |
| H | —CH₃ | 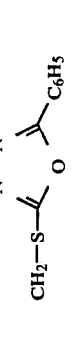 | H | S | 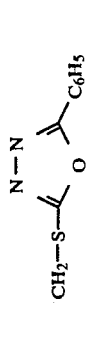 |
| H | —CH₃ | H | H | S |  |

-continued
| R1 | R2 | R3 | R4 | X | A |
|---|---|---|---|---|---|
| H | —CH₃ | H | H | S | 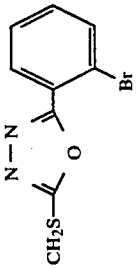 |
| H | -n-C₄H₉ | H | H | S | 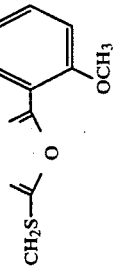 |
| H | —CH₃ | H | H | S | 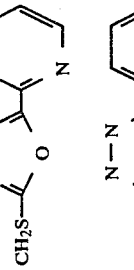 |
| H | —CH₃ | H | H | S | 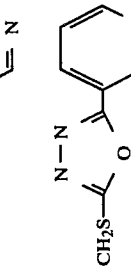 |
| H | —CH₃ | $\overset{O}{\underset{\|}{CH_2OC-CH_3}}$ | H | S | 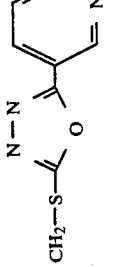 |
| H | —C₂H₅ | H | H | S | 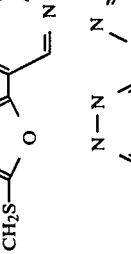 |
| H | —CH₃ | $\overset{O}{\underset{\|}{CH_2OC-C(CH_3)_3}}$ | H | S | 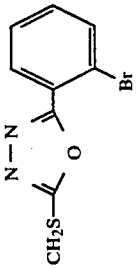 |
| H | —CH₃ | H | H | S | 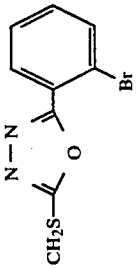 |

-continued

| R₁ | R₂ | R₃ | R₄ | X | A |
|---|---|---|---|---|---|
| H | —CH₃ | H | H | S | (thiadiazole-oxadiazole with CH₂S— and imidazole group) |
| H | —CH₃ | H | H | S | (thiadiazole-oxadiazole with CH₂S— and CH₂OCH₂—CO₂C₂H₅) |
| H | —CH₃ | CH₂OC(=O)—CH₃ | H | S | (thiadiazole-oxadiazole with CH₂S— and CH₂OCH₂—CO₂C₂H₅) |
| H | —CH₃ | H | H | S | (thiadiazole-oxadiazole with CH₂S— and CH₂OCH₂—CO₂H) |
| H | —CH₃ | H | H | S | (thiadiazole-oxadiazole with CH₃S— and CH₂OCH₂—CONH₂) |
| H | -n-C₃H₇ | H | H | S | (thiadiazole-oxadiazole with CH₃S— and CH₂OCH₂—CO₂NH₂) |
| H | —CH₃ | H | H | S | (thiadiazole-oxadiazole with CH₃S— and CH₂CO₂C₂H₅) |
| H | —CH₃ | H | H | S | (thiadiazole-oxadiazole with CH₃S— and CH₂CO₂H) |

-continued
| R₁ | R₂ | R₃ | R₄ | X | A |
|----|----|----|----|---|---|
| H | —CH₃ | H | H | S | 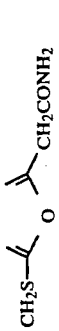 |
| H | —CH₃ | H | H | S | 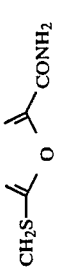 |
| H | —CH₃ | H | H | S | 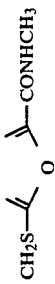 |
| H | —CH₃ | H | H | S | 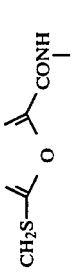 |
| H | —CH₃ | H | H | S | 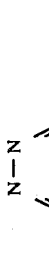 |
| H | —CH₃ | H | H | S | 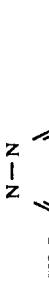 |
| H | —CH₃ | H | H | S | 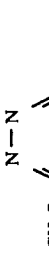 |
| H | —CH₃ | H | H | S | 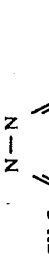 |
| H | —CH₃ | H | H | S | 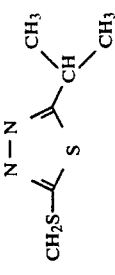 |

-continued

| $R_1$ | $R_2$ | $R_3$ | $R_4$ | X | A |
|---|---|---|---|---|---|
| H | —CH$_3$ | H | H | S | CH$_2$S—C(=N-N=)—S—C(n-C$_4$H$_9$)= |
| H | —CH$_3$ | H | H | S | CH$_2$S—C(=N-N=)—S—C(C$_6$H$_5$)= |
| H | —CH$_3$ | CH$_2$OCCH$_3$ (C=O) | H | S | CH$_2$S—C(=N-N=)—S—C(C$_6$H$_5$)= |
| H | —C$_3$H$_7$ | H | H | S | CH$_2$S—C(=N-N=)—S—C(C$_6$H$_5$)= |
| H | —CH$_3$ | H | H | S | CH$_2$S—C(=N-N=)—S—C(NHCOCH$_3$)= |
| H | —CH$_3$ | (indane ring) | H | S | CH$_2$S—C(=N-N=)—S—C(NHCOCH$_3$)= |
| H | —CH$_3$ | H | H | S | CH$_2$S—C(=N-N=)—S—C(NHCH$_3$)= |
| H | —CH$_3$ | H | H | S | CH$_2$S—C(=N-N=)—S—C(N(CH$_3$)$_2$)= |
| H | —CH$_3$ | H | H | S | CH$_2$S—C(=N-N=)—S—C(CH$_2$NH$_2$)= |

-continued
| R₁ | R₂ | R₃ | R₄ | X | A |
|---|---|---|---|---|---|
| H | —CH₃ | CH₂OC(=O)—C(CH₃)₃ | H | S |  |
| H | —CH₃ | H | H | S |  |
| H | —CH₃ | H | H | S |  |
| H | -n-C₄H₉ | H | H | S |  |
| H | —CH₃ | H | H | S |  |
| H | —CH₃ | H | H | S |  |
| H | —CH₃ | H | H | S |  |
| H | -n-C₃H₇ | H | H | S |  |
| H | —CH₃ | H | H | S |  |

-continued

| R₁ | R₂ | R₃ | R₄ | X | A |
|---|---|---|---|---|---|
| H | —CH₃ | ![3-methylphthalide] | H | S | CH₂S-C(=N-N=)-S-(2-thienyl) |
| H | —CH₃ | H | H | S | CH₂S-C(=N-N=)-S-(2-furyl) |
| H | —CH₃ | H | H | S | CH₂S-C(=N-N=)-S-(3-furyl) |
| H | —CH₃ | CH₂OCOCH₃ | H | S | CH₂S-C(=N-N=)-S-(2-furyl) |
| H | —CH₃ | H | H | S | CH₂S-C(=N-N=)-S-(4-OCH₃-C₆H₄) |
| H | —CH₃ | H | H | S | CH₂S-C(=N-N=)-S-(4-Cl-C₆H₄) |
| H | —CH₃ | H | H | S | CH₂S-C(=N-N=)-S-NHCOCH₂CH₂CO₂CH₃ |
| H | —CH₃ | H | H | S | CH₂S-C(=N-N=)-S-NHCOCH₂CH₂CO₂H |

-continued

| R₁ | R₂ | R₃ | R₄ | X | A |
|---|---|---|---|---|---|
| H | —CH₃ | H | H | S | thiadiazole with CH₂S– and –CH₂OCH₂CO₂C₂H₅ |
| H | —CH₃ | H | H | S | thiadiazole with CH₂S– and –CH₂OCH₂CO₂H |
| H | —CH₃ | H | H | S | thiadiazole with CH₂S– and –CH₂OCH₂CONH₂ |
| H | —CH₃ | CH₂OC(=O)—C(CH₃)₃ | H | S | thiadiazole with CH₂S– and –CH₂OCH₂CONH₂ |
| H | —CH₃ | H | H | S | thiadiazole with CH₂S– and –CH₂CO₂C₂H₅ |
| H | —CH₃ | H | H | S | thiadiazole with CH₂S– and –CH₂CO₂H |
| H | —CH₃ | H | H | S | thiadiazole with CH₂S– and –CH₂OH |
| H | —CH₃ | CH₂OC(=O)CH₃ | H | S | thiadiazole with CH₂S– and –CH₂OH |
| H | —CH₃ | H | H | S | thiadiazole with CH₂S– and –NHCOCH₂CO₂H |

-continued

| R₁ | R₂ | R₃ | R₄ | X | A |
|---|---|---|---|---|---|
| H | —CH₃ | H | H | S | CH₃S—⟨N—N/S⟩—NHCOCH₂—CO₂CH₃ |
| H | —CH₃ | H | H | S | CH₃S—⟨N—N/S⟩—NHCOCH₂—CN |
| H | —CH₃ | H | H | S | CH₃S—⟨N—N/S⟩—NHCOCH₂—CON(CH₃)₂ |
| H | —CH₃ | H | H | S | CH₃S—⟨N—N/S⟩—CH₂CH₂NH—COCH₃ |
| H | —CH₃ | H | H | S | CH₃S—⟨N—N/S⟩—CH₂CH₂NH₂ |
| H | —CH₃ | H | H | S | CH₃S—⟨N—N/S⟩—CH₂CH₂OH |
| H | —C₂H₅ | H | H | S | CH₃S—⟨N—N/S⟩—CH₂CH₂OH |
| H | —CH₃ | H | H | S | CH₂S—⟨N—N/S⟩—CH₂—CH₂—CO₂H |

-continued

| R₁ | R₂ | R₃ | R₄ | X | A |
|---|---|---|---|---|---|
| H | —CH₃ | H | H | S | CH₂S—⟨N-N/S⟩—S—CH₂—CH₂—CO₂H |
| H | —CH₃ | H | H | S | CH₂S—⟨N-N/S⟩—S—CH₂CO₂H |
| H | —CH₃ | CH₂OCCH₃ (O=) | H | S | CH₂S—⟨N-N/S⟩—S—CH₂—CONH₂ |
| H | —CH₃ | H | H | S | CH₂S—⟨N-N/S⟩—S—CH(CH₃)CO₂H |
| H | —CH₃ | H | H | S | CH₂S—⟨N-N/S⟩—SCH₂—SO₃H |
| H | -n-C₄H₉ | H | H | S | CH₂S—⟨N-N/S⟩—SCH₂—SO₃H |
| H | —CH₃ | H | H | S | CH₂S—⟨N-N/S⟩—CO₂H |
| H | —C₂H₅ | H | H | S | CH₂S—⟨N-N/S⟩—CO₂H |
| H | -nC₃H₇ | H | H | S | CH₂S—⟨N-N/S⟩—CO₂H |

-continued
| R₁ | R₂ | R₃ | R₄ | X | A |
|---|---|---|---|---|---|
| H | —CH₃ | | H | S |  |
| H | —CH₃ | $CH_2OC-C(CH_3)_3$ with C=O | H | S |  |
| H | —CH₃ | H | H | S |  |
| H | —CH₃ | H | H | S |  |
| H | —CH₃ | H | H | S |  |
| H | —CH₃ | H | H | S |  |
| H | —CH₃ | H | H | S |  |
| H | —CH₃ | —CH₂—O—C(=O)—C(CH₃)₃ | H | S |  |

-continued
| R₁ | R₂ | R₃ | R₄ | X | A |
|---|---|---|---|---|---|
| H | —C₂H₅ | H | H | S | 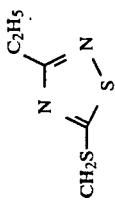 |
| H | —CH₃ | H | H | S | 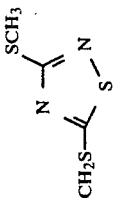 |
| H | —CH₃ | H | H | S | 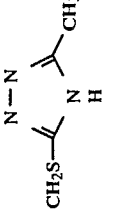 |
| H | —CH₃ | H | H | S | 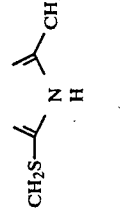 |
| H | —CH₃ | $CH_2OCCH_3$ with C=O | H | S | 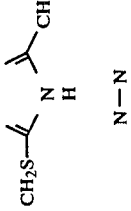 |
| H | -nC₃H₇ | H | H | S | 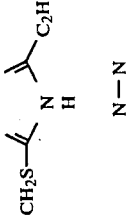 |
| H | —CH₃ | H | H | S | 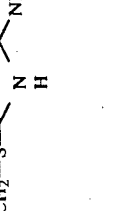 |
| H | —CH₃ | H | H | S |  |

| R₁ | R₂ | R₃ | R₄ | X | A |
|---|---|---|---|---|---|
| H | —CH₃ | H | H | S | CH₂S-C(=N-N=)-NH- pyridin-2-yl |
| H | —CH₃ | (indane) | H | S | CH₂S-C(=N-N=)-NH- pyridin-2-yl |
| H | —CH₃ | H | H | S | CH₂S-C(=N-N=)-NH-C(OH) |
| H | —CH₃ | H | H | S | CH₂S-C(=N-N=)-NH- furan-3-yl |
| H | —C₂H₅ | H | H | S | CH₂S-C(=N-N=)-NH-CH₂OCH₃ |
| H | —CH₃ | H | H | S | CH₂S-C(=N-N=)-NH-(4-SO₂NH-C₆H₄) |
| H | —CH₃ | H | H | S | CH₂S-C(=N-N=)-NH-C(C₆H₅) |
| H | —CH₃ | H | H | S | CH₂S-C(=N-N=)-NH-(4-OCH₃-C₆H₄) |

-continued

| R₁ | R₂ | R₃ | R₄ | X | A |
|---|---|---|---|---|---|
| H | —CH₃ | H | H | S | CH₃S–C(=N–N=)–NH (pyrazole), substituent = 4-chlorophenyl |
| H | —CH₃ | H | H | S | CH₃S–C(=N–N=)–NH (pyrazole), substituent = 2-methylpyridin-4-yl |
| H | —CH₃ | H | H | S | CH₃S–C(=N–N=)–NH (pyrazole), substituent = CH₂OC₆H₅ |
| H | —CH₃ | H | H | S | CH₃S–C(=N–N=)–NH (pyrazole), substituent = CH₂OC₂H₅ |
| H | —CH₃ | H | H | S | CH₃S–C(=N–N=)–NH (pyrazole), substituent = CH₂NHCOCH₃ |
| H | —CH₃ | CH₂OCCH₃ (=O) | H | S | CH₃S–C(=N–N=)–NH (pyrazole), substituent = CH₂NHCOCH₃ |
| H | —CH₃ | H | H | S | CH₃S–C(=N–N=)–NH (pyrazole), substituent = CH₂CH₂NH₂ |
| H | —CH₃ | H | H | S | CH₃S–C(=N–N=)–NH (pyrazole), substituent = CH₂CO₂C₂H₅ |

-continued

| R₁ | R₂ | R₃ | R₄ | X | A |
|---|---|---|---|---|---|
| H | -n-C₄H₉ | H | H | S | CH₃S—⟨pyrazole N-N/NH⟩—C(CH₂CO₂C₂H₅)=N-N |
| H | —CH₃ | H | H | S | CH₂(CH₃S—pyrazole)—C(NHCOCH₂CH₂CO₂CH₃)= |
| H | —CH₃ | H | H | S | CH₃S—⟨pyrazole⟩—C(CH₂CO₂H)= |
| H | —C₂H₅ | H | H | S | CH₃S—⟨pyrazole⟩—C(CH₂CO₂H)= |
| H | -nC₄H₉ | H | H | S | CH₃S—⟨pyrazole⟩—C(CH₂CO₂H)= |
| H | —CH₃ | H | H | S | CH₃S—⟨pyrazole⟩—C(CH₂OCH₂CO₂C₂H₅)= |
| H | —CH₃ | H | H | S | CH₃S—⟨pyrazole⟩—C(CH₂OCH₂CO₂H)= |
| H | —CH₃ | H | H | S | CH₃S—⟨pyrazole⟩—C(CH₂OCH₂CONH₂)= |

-continued
| $R_1$ | $R_2$ | $R_3$ | $R_4$ | X | A |
|---|---|---|---|---|---|
| H | —CH$_3$ | H | H | S | 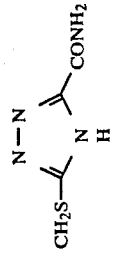 |
| H | —CH$_3$ | CH$_2$OC(=O)—CH$_3$ | H | S | 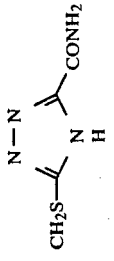 |
| H | —CH$_3$ | H | H | S | 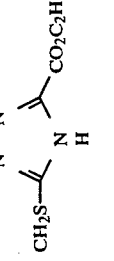 |
| H | —CH$_3$ | H | H | S | 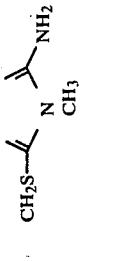 |
| H | —C$_2$H$_5$ | H | H | S | 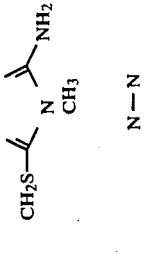 |
| H | —CH$_3$ | H | H | S | 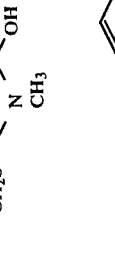 |
| H | —CH$_3$ | H | H | S | 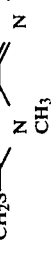 |

-continued

| R₁ | R₂ | R₃ | R₄ | X | A |
|---|---|---|---|---|---|
| H | —CH₃ | H | H | S | (furan-substituted pyrazole with CH₂S and N-CH₃) |
| H | —CH₃ | H | H | S | (pyrazole with CH₂S, N-CH₃, C₆H₅) |
| H | —CH₃ | CH₂OC(=O)—C(CH₃)₃ | H | S | (pyrazole with CH₂S, N-CH₃, C₆H₅) |
| H | —CH₃ | H | H | S | (pyrazole with CH₂S, N-C₂H₅) |
| H | —CH₃ | H | H | S | (pyridyl-pyrazole with CH₂S, N-C₂H₅) |
| H | —CH₃ | H | H | S | (pyridyl-pyrazole with CH₂S, N-C₂H₅) |
| H | —CH₃ | CH₂OCCH₃ (O=) | H | S | (pyridyl-pyrazole with CH₂S, N-C₂H₅) |

| R₁ | R₂ | R₃ | R₄ | X | A |
|---|---|---|---|---|---|
| H | —CH₃ | H | H | S | pyridin-2-yl pyrazole with CH₂S and N—C₂H₅ |
| H | —CH₃ | H | H | S | furan-3-yl pyrazole with CH₂S and N—C₂H₅ |
| H | —C₂H₅ | H | H | S | furan-3-yl pyrazole with CH₂S and N—C₂H₅ |
| H | —CH₃ | H | H | S | furan-2-yl pyrazole with CH₂S and N—C₂H₅ |
| H | —CH₃ | H | H | S | thien-2-yl pyrazole with CH₂S and N—C₂H₅ |
| H | —CH₃ | H | H | S | pyrazole with CH₂S, =N—C₂H₅ and N—C₂H₅ |

| R₁ | R₂ | R₃ | R₄ | X | A |
|---|---|---|---|---|---|
| H | —CH₃ | ![3-methylphthalide] | H | S | CH₃S—C(=N-N)—N(C₂H₅), 2-thienyl |
| H | —C₂H₅ | H | H | S | CH₃S—C(=N-N)—N(C₂H₅), 2-thienyl |
| H | —CH₃ | H | H | S | CH₃S—C(=N-N)—N(CH₂—CH₂—CH₃) |
| H | —CH₃ | H | H | S | CH₃S—C(=N-N)—N(CH₂—CH₂—CH₃), 2-pyridyl |
| H | —CH₃ | H | H | S | CH₃S—C(=N-N)—N(CH₂—CH₂—CH₃), 2-furyl |
| H | —CH₃ | CH₂OC(=O)—C(CH₃)₃ | H | S | CH₃S—C(=N-N)—N(CH₂—CH₂—CH₃), 2-furyl |
| H | —CH₃ | H | H | S | CH₃S—C(=N-N)—N(CH₂—CH=CH₂) |

-continued
| R₁ | R₂ | R₃ | R₄ | X | A |
|---|---|---|---|---|---|
| H | —CH₃ | H | H | S | 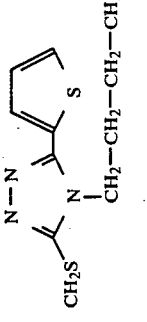 |
| H | —CH₃ | H | H | S | 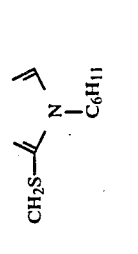 |
| H | —CH₃ | H | H | S | 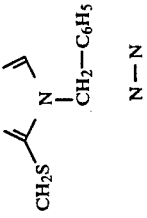 |
| H | —CH₃ | H | H | S | 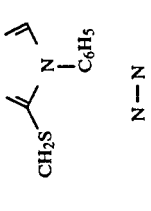 |
| H | —CH₃ | H | H | S | 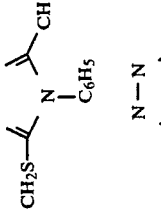 |
| H | —CH₃ | H | H | S | 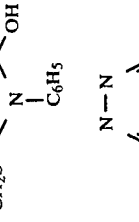 |
| H | —CH₃ | H | H | S | 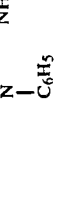 |

-continued
| R₁ | R₂ | R₃ | R₄ | X | A |
|---|---|---|---|---|---|
| H | —CH₃ | H | H | S | 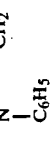 |
| H | —CH₃ | H | H | S |  |
| H | —CH₃ |  | H | S | 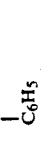 |
| H | —CH₃ | H | H | S | 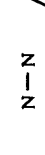 |
| H | —CH₃ | H | H | S | 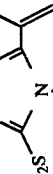 |
| H | —CH₃ | H | H | S | 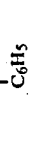 |

-continued

| R₁ | R₂ | R₃ | R₄ | X | A |
|---|---|---|---|---|---|
| H | -n-C₃H₇ | H | H | S | triazole-CH₂S, N-(2-pyridyl) |
| H | —CH₃ | H | H | S | triazole-CH₂S, N-(4-pyridyl) |
| H | —CH₃ | H | H | S | triazole-CH₂S, N-(2-pyridyl), COOH |
| H | —C₃H₇ | H | H | S | triazole-CH₂S, N-(2-pyridyl), COOH |

-continued

| R₁ | R₂ | R₃ | R₄ | X | A |
|---|---|---|---|---|---|
| H | —CH₃ | H | H | S | pyrazole with N—N, CH₂S, N-(4-OC₂H₅-phenyl), C(=O)OH |
| H | —CH₃ | H | H | S | pyrazole with N—N, CH₂S, N-(4-Cl-phenyl), C-OH |
| H | —CH₃ | H | H | S | pyrazole with N—N, CH₂S, N-NH₂, C-C₆H₅ |
| H | —CH₃ | H | H | S | pyrazole with N—N, CH₂S, N-NH₂, C-(4-F-phenyl) |
| H | —CH₃ | H | H | S | pyrazole with N—N, CH₂S, N-NH₂, C-(2-Br-phenyl) |

-continued
| R₁ | R₂ | R₃ | R₄ | X | A |
|----|----|----|----|---|---|
| H | —CH₃ | H | H | S | 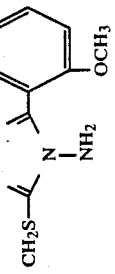 |
| H | —CH₃ | H | H | S | 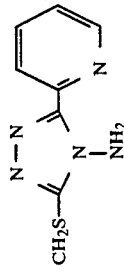 |
| H | —CH₃ | H | H | S | 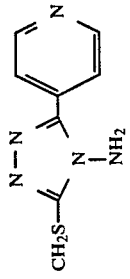 |
| H | -n-C₃H₇ | H | H | S | 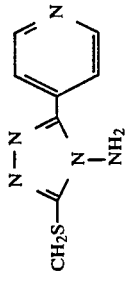 |
| H | —CH₃ | H | H | S | 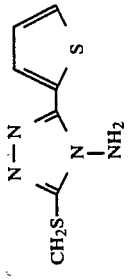 |
| H | —CH₃ | H | H | S | 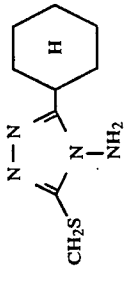 |
| H | —CH₃ | | | | 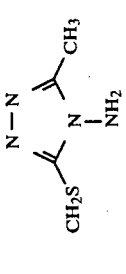 |

-continued

| R₁ | R₂ | R₃ | R₄ | X | A |
|---|---|---|---|---|---|
| H | —CH₃ | H | H | S | 3-CH₃S-5-C₂H₅-4-NH₂-1,2,4-triazole |
| H | —CH₃ | 4-methylindan-4-yl | H | S | 3-CH₃S-5-C₂H₅-4-NH₂-1,2,4-triazole |
| H | —CH₃ | H | H | S | 3-CH₃S-4-NH₂-1,2,4-triazole (SCH₃ at 5) |
| H | —CH₃ | H | H | S | 3-CH₃S-5-SCH₃-4-NH₂-1,2,4-triazole |
| H | —CH₃ | H | H | S | 3-CH₃S-5-SH-4-NH₂-1,2,4-triazole |
| H | —CH₃ | CH(CH₃)—O—C(O)OC₂H₅ | H | S | 3-CH₃S-5-CH₂C₆H₅-4-NH₂-1,2,4-triazole |
| H | —CH₃ | H | H | S | 3-CH₃S-5-CH₂C₆H₅-4-NH₂-1,2,4-triazole |

-continued

| R₁ | R₂ | R₃ | R₄ | X | A |
|---|---|---|---|---|---|
| H | —CH₃ | H | H | S | pyrazole ring with N—N, C₂H₅, NHCOCH₃, CH₃S |
| H | —C₆H₅ | H | H | S | pyrazole ring with N—N, C₆H₅, HNC₆H₅, CH₃S |
| H | —CH₃ | H | H | S | pyrazole ring with N—N, C₂H₅, HNC₂H₅, CH₃S |
| H | —CH₃ | H | H | S | 4-SO₂NH₂-C₆H₄ attached to pyrazole with CH₃, CH₃S |
| H | —CH₃ | H | H | S | 4-SO₂NH₂-C₆H₄ attached to pyrazole with CH₂CH=CH₂, CH₃S |
| H | —CH₃ | H | H | S | 4-SO₂NH₂-C₆H₄ attached to pyrazole with C₆H₅, CH₃S |

| $R_1$ | $R_2$ | $R_3$ | $R_4$ | X | A |
|---|---|---|---|---|---|
| H | —CH$_3$ | H | H | S | 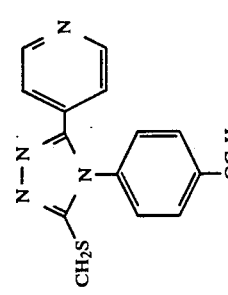 |
| H | —CH$_3$ | H | H | S | 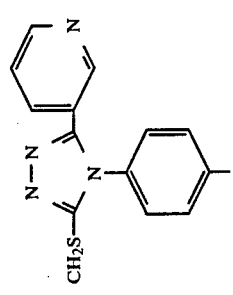 |
| H | —CH$_3$ | H | H | S | 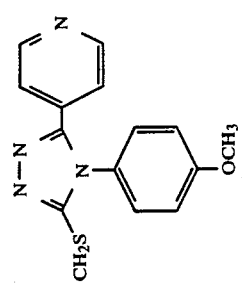 |
| H | —CH$_3$ | H | H | S | 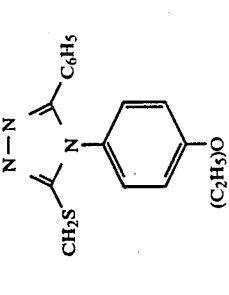 |

-continued

| $R_1$ | $R_2$ | $R_3$ | $R_4$ | X | A |
|---|---|---|---|---|---|
| H | $-CH_3$ | H | H | S | 1-(4-ethoxyphenyl)-5-(4-aminophenyl)-3-methylthio-1,2,4-triazole |
| H | $-CH_3$ | H | H | S | 1,3-diphenyl-5-methylthio-1,2,4-triazole |
| H | $-C_2H_5$ | H | H | S | 1-allyl-3-methylthio-5-phenyl-1,2,4-triazole (with $CH_2CH=CH_2$) |
| H | $-CH_3$ | H | H | S | 1-amino-3-methylthio-5-(carboxymethyl)-1,2,4-triazole ($CH_2CO_2H$, $NH_2$) |
| H | $-CH_3$ | H | H | S | 1-methyl-3-methylthio-5-(carboxymethyl)-1,2,4-triazole ($CH_2CO_2H$, $CH_3$) |
| H | $-CH_3$ | H | H | S | 1-methyl-3-methylthio-5-(methoxymethyl, carboxyl)-1,2,4-triazole ($CH_2OCH_2CO_2H$, $CH_3$) |

| R₁ | R₂ | R₃ | R₄ | X | A |
|---|---|---|---|---|---|
| H | —CH₃ | H | H | S | 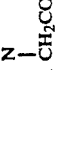 |
| H | —CH₂—CH₂—CH₃ | H | H | S | 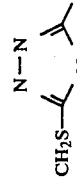 |
| H | —CH₃ | H | H | S | 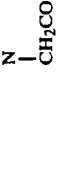 |
| H | —CH₃ | CH₂—OC—CH₃ (O=) | H | S | 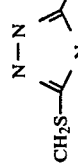 |
| H | —CH₃ | H | H | S | 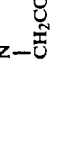 |
| H | —CH₃ | CH₂CO₂H | H | S | 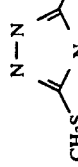 |
| H | —CH₃ | H | H | S | 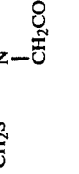 |

-continued

| R₁ | R₂ | R₃ | R₄ | X | A |
|---|---|---|---|---|---|
| H | —CH₃ | H | H | S | pyrazole: CH₂S-, N—N, N-CH₃, with -C(CONH₂)= |
| H | —CH₃ | H | H | S | pyrazole: CH₂S-, N—N, N-CH₃, with -C(CH₂-O-CH₂CONH₂)= |
| H | —CH₃ | (3-methyl-phthalide) | H | S | pyrazole: CH₂S-, N—N, N-CH₃, with -C(CH₂-O-CH₂CONH₂)= |
| H | —CH₃ | H | H | S | pyrazole: CH₂S-, N—N, N-NH₂, with -C(S-CH₂CO₂H)= |
| H | —CH₃ | CH₂CO₂H | H | S | pyrazole: CH₂S-, N—N, N-NH₂, with -C(S-CH₂CO₂H)= |
| H | —C₂H₅ | H | H | S | pyrazole: CH₂S-, N—N, N-NH₂, with -C(S-CH₂CO₂H)= |
| H | —CH₃ | H | H | S | pyrazole: CH₂S-, N—N, N-CH₂-C₆H₅, with -C(CO₂C₂H₅)= |

-continued

| R₁ | R₂ | R₃ | R₄ | X | A |
|---|---|---|---|---|---|
| H | —CH₃ | H | H | S | imidazole with CH₂S and N—CH₃ |
| H | —CH₃ | H | H | S | imidazole with CH₂S and N—CH₂—CH₂—CH₂—CH₃ |
| H | —CH₃ | H | H | S | imidazole with CH₂S and N—C₆H₅ |
| H | —CH₃ | CH₂OC(=O)—C(CH₃)₃ | H | S | imidazole with CH₂S and N—CH₂OCH₃ |
| H | —CH₃ | H | H | S | imidazole with CH₂S, =CH₃ and N—CH₃ |
| H | —CH₃ | H | H | S | imidazole with CH₂S and N—CH₂CH=CH₂ |
| H | —CH₃ | H | H | S | imidazole with OH, CH₂S and N—CH₃ |

-continued

| R₁ | R₂ | R₃ | R₄ | X | A |
|---|---|---|---|---|---|
| H | —CH₃ | H | H | S | ![structure with CH₂S, N, N-CH(CH₃)-CH₃, OH] |
| H | —CH₃ | H | H | S | ![structure with CH₂S, N, N-CH₂C₆H₅, OH] |
| H | —CH₃ | H | H | S | ![structure with CH₂S, N, N-CH₃, C₂H₅] |
| H | —CH₃ | H | H | S | ![structure with CH₂S, N, N-CH₂C₆H₅, CH₃] |
| H | —CH₃ | H | H | S | ![structure with CH₂S, N, N-CH₂OCH₃] |
| H | —CH₃ | H | H | S | ![structure with -CH₂-S-, N, N-CH₂-, CH₂COOH] |
| H | —CH₃ | H | H | S | ![structure —CH₂—S— triazole N=N, N—H] |

-continued
| R₁ | R₂ | R₃ | R₄ | X | A |
|---|---|---|---|---|---|
| H | —CH₃ | H | H | S | 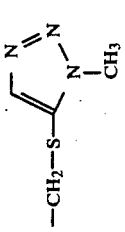 |
| H | —CH₃ | H | H | S | 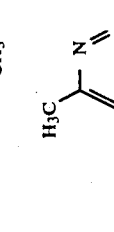 |
| H | —CH₃ | H | H | S | 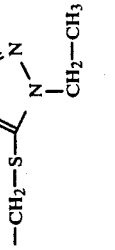 |
| H | —CH₃ | H | H | S | 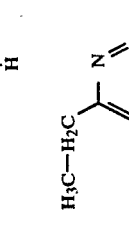 |
| H | —CH₃ | H | H | S |  |
| H | —CH₂—CH₃ | H | H | S | 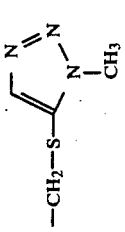 |

-continued

| R₁ | R₂ | R₃ | R₄ | X | A |
|---|---|---|---|---|---|
| H | —CH₃ | H | H | S | HOOC—H₂C—H₂C— attached to triazole-CH₂—S— |
| H | —CH₃ | H | H | S | HOOC—H₂C—H₂C—H₂C— attached to triazole-CH₂—S— |
| H | —CH₃ | H | H | S | (H₃C)(CH₃)(HOOC)C— attached to triazole-CH₂—S— |
| H | —CH₃ | H | H | S | (H₃C)(CH₃)(HOOC)C—H₂C— attached to triazole-CH₂—S— |
| H | —CH₃ | H | H | S | H₃C—HNOC— attached to triazole-CH₂—S— |

-continued
| $R_1$ | $R_2$ | $R_3$ | $R_4$ | X | A |
|---|---|---|---|---|---|
| H | —CH$_3$ | H | H | S | 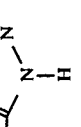 |
| H | —CH$_3$ | H | H | S | 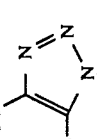 |
| H | —CH$_3$ | H | H | S | 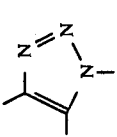 |
| H | —CH$_3$ | —CH$_2$—O—C(=O)—CH$_3$ | H | S | 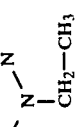 |
| H | —CH$_3$ | 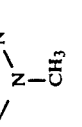 | H | S |  |
| H | —CH$_3$ | —CH$_2$—COOH | H | S |  |

-continued
| R₁ | R₂ | R₃ | R₄ | X | A |
|---|---|---|---|---|---|
| H | 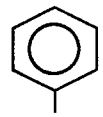 | H | H | S | 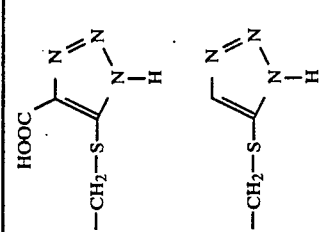 |
| H | —CH₂—CH₂—CH₃ | H | H | S | 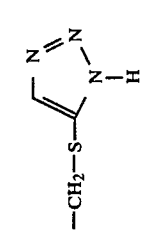 |
| H | —CH₃ | H | OCH₃ | S | 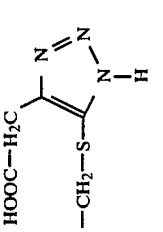 |
| H | —CH₃ | H | OCH₃ | S | 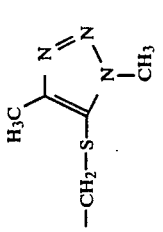 |
| H | —CH₃ | H | H | S | 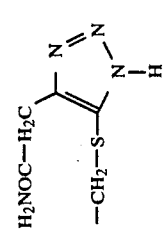 |
| H | —CH₃ | H | H | S | 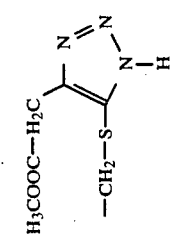 |

-continued
| R$_1$ | R$_2$ | R$_3$ | R$_4$ | X | A |
|---|---|---|---|---|---|
| H | —CH$_3$ | H | H | S | —CH$_2$—S—P(=S)(CH$_3$)(OCH$_3$) |
| H | —CH$_3$ | H | H | S | —CH$_2$—S—P(=S)(CH$_3$)(OC$_2$H$_5$) |
| H | —CH$_3$ | H | H | S | —CH$_2$—S—P(=S)(CH$_3$)(CH—CH$_2$—CH$_3$)(CH$_2$) |
| H | —CH$_3$ | H | H | S | —CH$_2$—S—P(=S)(C$_2$H$_5$)(OC$_2$H$_5$) |
| H | —CH$_3$ | H | H | S | —CH$_2$—S—P(=S)(CH$_2$—CH$_2$—CH$_3$)(OC$_2$H$_5$) |
| H | —CH$_3$ | H | OCH$_3$ | S | —CH$_2$—S—P(=S)(C$_2$H$_5$)(OC$_2$H$_5$) |
| H | 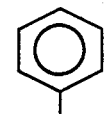 | H | H | S | —CH$_2$—S—P(=S)(C$_2$H$_5$)(OCH$_2$) |
| H | —CH$_2$—CH$_2$—CH$_3$ | H | H | S | —CH$_2$—S—P(=S)(CH$_3$)(OCH$_3$) |

-continued

| R₁ | R₂ | R₃ | R₄ | X | A |
|---|---|---|---|---|---|
| ![phenoxy-CH2-CO-] C₆H₅—O—CH₂—CO— | —CH₃ | H | H | S | —CH₂—S—P(=S)(CH₃)(CH₃) |
| H | —CH₃ | H | OCH₃ | S | 1,2,4-triazol-1-yl-SCH₂— with CH₂—CH₂—SO₃H on N |
| H | —CH₂—CH₃ | H | OCH₃ | S | 1,2,4-triazol-1-yl-SCH₂— with CH₂—CH₂—CH₂—CH₃ on N |
| H | —CH₂—CH=CH₂ | H | H | S | 1,2,4-triazol-1-yl-SCH₂— with 2,4-dichlorophenyl on N |
| H | —CH₃ | H | H | S | tetrazol-SCH₂— with N—H |
| H | —CH₃ | H | H | S | tetrazol-SCH₂— with N—C₂H₅ |

| R₁ | R₂ | R₃ | R₄ | X | A |
|---|---|---|---|---|---|
| H | —CH₃ | H | H | S | 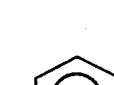 |
| H | —CH₃ | H | H | S |  |
| H | —CH₃ | H | H | S |  |
| H | —CH₃ | H | H | S |  |
| H | —CH₃ | H | H | S |  |
| H | —CH₃ | H | H | S | 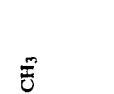 |

-continued

| R₁ | R₂ | R₃ | R₄ | X | A |
|---|---|---|---|---|---|
| H | —CH₃ | H | H | S | —CH₂—S— [1-CH₃-1,2,4-triazol-3-yl with CH attached] |
| H | —CH₃ | H | H | S | —CH₂—S— [1-(4-fluorophenyl)-1,2,4-triazol-3-yl] |
| H | —CH₃ | [4-methylindanyl] | H | S | —CH₂—S— [1-(CH₂—CH=CH₂)-1,2,4-triazol-3-yl] |
| H | —CH₃ | —CH₂—O—C(=O)—CH₃ | H | S | —CH₂—S— [1-CH₃-1,2,4-triazol-3-yl] |
| H | —CH₃ | H | H | S | —CH₂—S— [1-(4-chlorophenyl)-1,2,4-triazol-3-yl] |

-continued

| R₁ | R₂ | R₃ | R₄ | X | A |
|---|---|---|---|---|---|
| H | —CH₃ | H | H | S | —CH₂—S—[triazole]—CH₂—CH₂—CH₂—O—CH |
| H | —CH₃ | H | H | S | —CH₂—S—[triazole N-CH₃] |
| H | —CH₃ | H | H | S | —CH₂—S—[triazole N-(2,4-dichlorophenyl)] |
| H | —CH₃ | H | H | S | —CH₂—S—[triazole]—CH₂—CH₂—CH₃ |
| H | —CH₃ | H | H | S | —CH₂—S—[triazole N-phenyl] |
| H | —CH₃ | H | H | S | —CH₂—S—[triazole]—CH₂—CH₂—NH—C(O)—CH=CH₂ |

-continued
| $R_1$ | $R_2$ | $R_3$ | $R_4$ | X | A |
|---|---|---|---|---|---|
| H | —CH$_3$ | H | H | S | 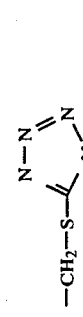 |
| H | —CH$_3$ | H | H | S | 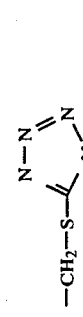 |
| H | —CH$_3$ | H | H | S | 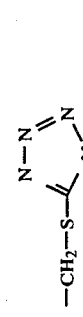 |
| H | —CH$_3$ | H | H | S | 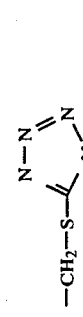 |
| H | —CH$_3$ | H | H | S | 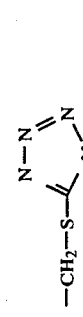 |

| R₁ | R₂ | R₃ | R₄ | X | A |
|---|---|---|---|---|---|
| Ph-O-CH₂-CO- | -CH₃ | H | H | S | -CH₂-S-(5-methyl-1,3,4-thiadiazol-2-yl) (N—N, N-CH₃) |
| (2-methyl-1,3,4-thiadiazol-5-yl)-S-CH₂-CO- | -CH₃ | H | H | S | -CH₂-S-(1-propyl-tetrazol-5-yl) |
| H | -CH₃ | H | H | S | -CH₂-S-(1-(CH₂-COOC₂H₅)-tetrazol-5-yl) |
| H | -CH₃ | -CH₂-COOH | H | S | -CH₂-S-(1-CH₂-COOH-tetrazol-5-yl) |
| H | -CH₃ | H | H | S | -CH₂-S-(1-allyl-tetrazol-5-yl) (-CH₂-CH=CH₂) |
| H | -CH₃ | H | H | S | -CH₂-S-(1-(CH₂-CH₂-CONH₂)-tetrazol-5-yl) |
| H | -CH₃ | -CH₂-O-CO-C(CH₃)₂-CONH₂ | H | S | -CH₂-S-(5-methyl-1,3,4-thiadiazol-2-yl) |
| H | -C₆H₅ | H | H | S | -CH₂-S-(5-methyl-1,3,4-thiadiazol-2-yl) (N—N, N-CH₃) |

-continued

| R₁ | R₂ | R₃ | R₄ | X | A |
|---|---|---|---|---|---|
| H | —CH₃ | H | H | S | —CH₂—S—[tetrazole-N-CH₂—CH₂—COOH] |
| H | —CH₃ | H | H | S | —CH₂—S—[triazole-N-CH₂—CH₂—CH₂—COOH] |
| H | —CH₃ | H | H | S | —CH₂—S—[H₃C-thiadiazole-N-CH₂—CH₂—COOH] |
| H | —CH₃ | H | H | S | —CH₂—S—[triazole-N-CH₂—CN] |
| H | —CH₃ | H | H | S | —CH₂—S—[tetrazole-N-CH₂—CON(CH₃)₂] |
| H | —CH₃ | H | H | S | —CH₂—S—[tetrazole-N-CH₂—CONH—CH₃] |
| H | —CH₃ | H | H | S | —CH₂—S—[tetrazole-N-CH₂—CH₂—SO₂NH₂] |

-continued

| R₁ | R₂ | R₃ | R₄ | X | A |
|---|---|---|---|---|---|
| H | —CH₃ | H | H | S | —CH₂—S—(tetrazole)—CH₂—SO₂NH₂ |
| H | —CH₃ | H | H | S | —CH₂—S—(tetrazole)—CH₂—CH₂—CH₂—SO₂H |
| H | —CH₃ | H | H | S | —CH₂—S—(tetrazole)—CH₂—CH₂—SO₃H |
| H | —CH₃ | H | H | S | —CH₂—S—(tetrazole with CH₂SO₃H)—CH₂—CH₂—CH₂ |
| H | —CH₃ | H | H | S | —CH₂—S—(tetrazole)—CH₂—SO₃H |
| H | —CH₃ | H | H | S | —CH₂—S—(tetrazole, H₃C—)—CH₂—CH₂—SO₃H |
| H | —CH₃ | H | H | S | —CH₂—S—(tetrazole)—CH₂—CH₂—CH₂—SO₃H |

-continued
| R₁ | R₂ | R₃ | R₄ | X | A |
|---|---|---|---|---|---|
| H | —CH₃ | H | H | S | 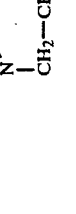 |
| H | —CH₃ | —CH₂—O—C(=O)—C(CH₃)₂—CH₃ | H | S | 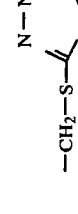 |
| H | —CH₃ | H | H | S |  |
| H | —CH₃ | (indane) | H | S | 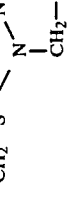 |
| H | —CH₃ | H | H | S |  |
| H | —CH₂—CH=CH₂ | H | H | S |  |

-continued
| $R_1$ | $R_2$ | $R_3$ | $R_4$ | X | A |
|---|---|---|---|---|---|
| H | —CH$_3$ | —CH$_2$—O—C(=O)—CH$_3$ | H | S | 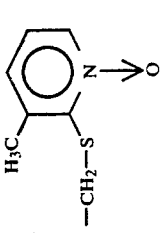 |
| H | —CH$_3$ | H | H | S | 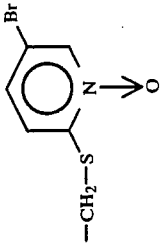 |
| H | —CH$_3$ | H | H | S | 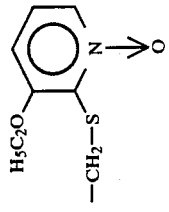 |
| H | —CH$_2$—CH$_2$—CH$_3$ | H | H | S | 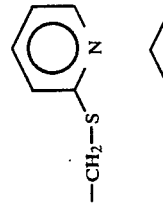 |
| H | —CH$_3$ | H | H | S | 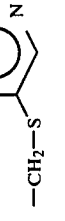 |
| H | —CH$_3$ | H | H | S | 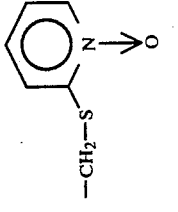 |

-continued
| $R_1$ | $R_2$ | $R_3$ | $R_4$ | X | A |
|---|---|---|---|---|---|
| H | —CH$_3$ | H | H | S | 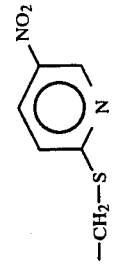 |
| H | —CH$_3$ | H | H | S | 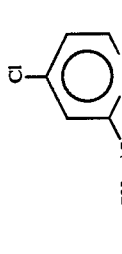 |
| H | —CH$_3$ | H | H | S | 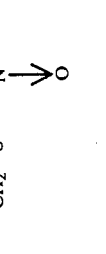 |
| H | —CH$_3$ | H | H | S | 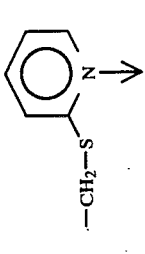 |
| H | —CH$_3$ | H | H | S | 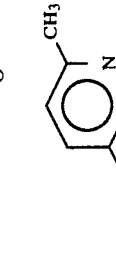 |
| H | —CH$_3$ | H | OCH$_3$ | S | 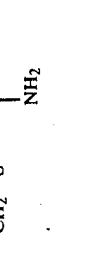 |
| H | —CH$_3$ | H | H | S |  |

| R₁ | R₂ | R₃ | R₄ | X | A |
|---|---|---|---|---|---|
| H | —CH₃ | H | H | S | ![pyridine with CH₂S at 4, COOH at 2] —CH₂—S-(pyridin-4-yl with 2-COOH) |
| H | —CH₃ | H | H | S | ![pyridine with CH₂S at 3, COOH at 2] —CH₂—S-(pyridin-3-yl with 2-COOH) |
| H | —CH₃ | H | H | S | ![pyridine with CH₂S at 3, COOH at 4] —CH₂—S-(pyridin-3-yl with 4-COOH) |
| H | —CH₂—CH=CH₂ | H | H | S | ![pyridine with CH₂S at 2, OH at 3] —CH₂—S-(3-hydroxypyridin-2-yl) |
| H | —CH₃ | —CH₂—O—C(=O)—C(CH₃)₂—CH₃ | H | S | ![pyridine with CH₂S at 2, NO₂ at 5] —CH₂—S-(5-nitropyridin-2-yl) |
| H | —CH₃ | —CH₂—COOH | H | S | ![pyridine N-oxide with CH₃ at 4, CH₂S at 2] —CH₂—S-(4-methylpyridin-2-yl N-oxide) |
| ![phenyl—O—CH₂—CO—] | —CH₃ | H | H | S | ![pyridine N-oxide with CH₂S at 2] —CH₂—S-(pyridin-2-yl N-oxide) |

-continued
| R₁ | R₂ | R₃ | R₄ | X | A |
|---|---|---|---|---|---|
| H | —CH₃ | H | OCH₃ | S | 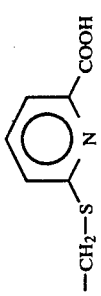 |
| H | —CH₃ | H | H | S | 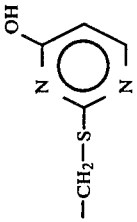 |
| H | —CH₃ | H | H | S | -CH₂-S-⟨pyridine⟩ |
| H | —CH₃ | H | H | S | 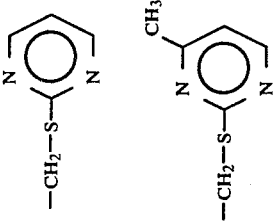 |
| H | —CH₃ | H | H | S | 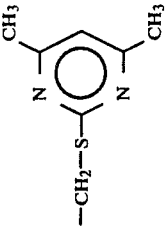 |
| H | —CH₃ | H | H | S | 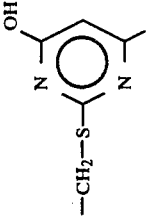 |

-continued

| R₁ | R₂ | R₃ | R₄ | X | A |
|---|---|---|---|---|---|
| H | —CH₃ | H | H | S | —CH₂—S—⟨pyrimidine: 4-NH₂, 6-OH⟩ |
| H | —CH₃ | H | H | S | —CH₂—S—⟨pyrimidine: 4-NH₂, 5-NH₂⟩ |
| H | —CH₃ | H | H | S | —CH₂—S—⟨pyrimidine: 4-NH₂, 6-NH₂⟩ |
| H | —CH₃ | H | H | S | —CH₂—S—⟨pyrimidine: 4-NH₂, 5-OH⟩ |
| H | —CH₃ | H | H | S | —CH₂—S—⟨pyrimidine: 4-SH⟩ |
| H | —CH₃ | H | H | S | —CH₂—S—⟨pyrimidine: 4-SCH₃⟩ |

-continued
| R₁ | R₂ | R₃ | R₄ | X | A |
|---|---|---|---|---|---|
| H | —CH₃ | H | H | S | 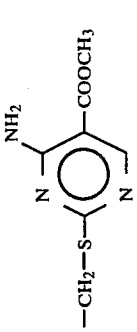 |
| H | —CH₃ | H | H | S | 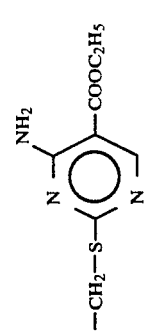 |
| H | —CH₃ | H | H | S | 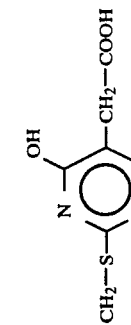 |
| H | —CH₃ | H | H | S | 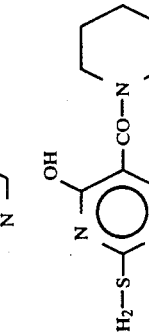 |
| H | —CH₃ | H | H | S | 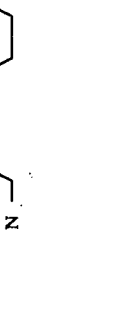 |
| H | —CH₃ | H | H | S |  |
| H | —CH₃ | H | H | S | (piperidine-N-CO- pyridine with OH, CH₂-S—) |

| R₁ | R₂ | R₃ | R₄ | X | A |
|---|---|---|---|---|---|
| H | —CH₃ | H | H | S |  |
| H | —CH₃ | H | H | S | 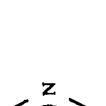 |
| H | —CH₃ | H | H | S | 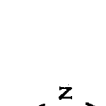 |
| H | —CH₃ | H | H | S | 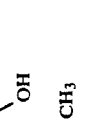 |
| H | —CH₃ | H | H | S | 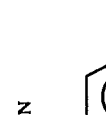 |
| H | —CH₃ | H | H | S | 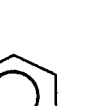 |

| R₁ | R₂ | R₃ | R₄ | X | A |
|---|---|---|---|---|---|
| H | —CH₃ | H | H | S | —CH₂—S— pyrimidine with H₅C₂OOC, OC₂H₅, phenyl substituents |
| H | —CH₃ | H | H | S | —CH₂—S— pyrimidine with H₅C₂OOC, NH₂, phenyl substituents |
| H | —CH₃ | H | H | S | —CH₂—S— pyrimidine with CH₃, NC, OH substituents |
| H | —CH₃ | H | H | S | —CH₂—S— pyrimidine with CH₃, H₃COC, CH₃ substituents |
| H | —CH₃ | H | H | S | —CH₂—S— pyrimidine with CH₃, H₅C₂OOC, CH₃ substituents |

-continued
| R₁ | R₂ | R₃ | R₄ | X | A |
|---|---|---|---|---|---|
| H | —CH₃ | H | H | S | 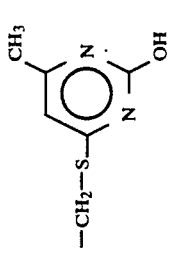 |
| H | —CH₃ | H | H | S | 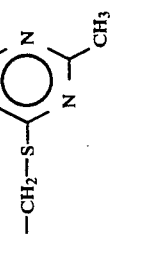 |
| H | —CH₃ | H | H | S | 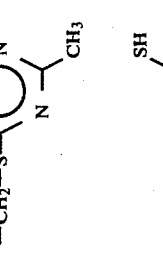 |
| H | —CH₃ | H | H | S | 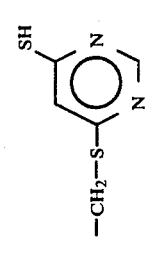 |
| H | —CH₃ | H | H | S | 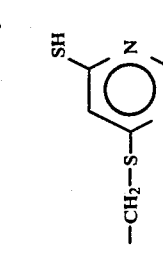 |

-continued
| R₁ | R₂ | R₃ | R₄ | X | A |
|---|---|---|---|---|---|
| H | —CH₃ | H | H | S | 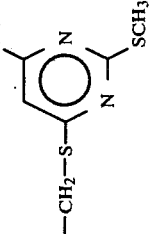 |
| H | —CH₃ | H | H | S | 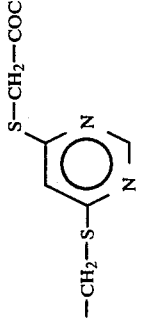 |
| H | —CH₃ | H | H | S | 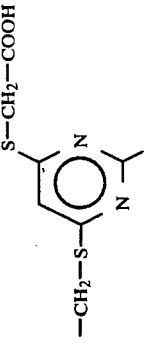 |
| H | —CH₃ | H | H | S | 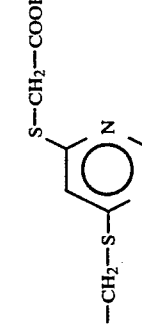 |
| H | —CH₃ |  | H | S | 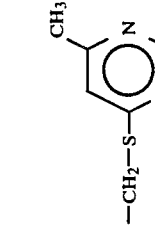 |

-continued

| R₁ | R₂ | R₃ | R₄ | X | A |
|---|---|---|---|---|---|
| H | —CH₃ | —CH₂—O—C(=O)—CH₃ | H | S | pyrimidine ring with 4,6-di-CH₃ and 2-(-CH₂-S-) substituent |
| H | —CH₃ | —CH₂—O—C(=O)—C(CH₃)₃ | H | S | pyridine ring with 4-(S—C₂H₅) and 2-(-CH₂-S-) substituent |
| H | —CH₂—CH₂—CH₃ | H | H | S | pyrimidine ring with 4-OH, 5-CH₂—COOH, 6-CH₃ and 2-(-CH₂-S-) substituent |
| H | —C₆H₅ (phenyl) | H | H | S | pyrimidine ring with 4-NH₂, 5-COOC₂H₅ and 2-(-CH₂-S-) substituent |
| H | —CH₂—CH₃ | H | H | S | pyridine ring with 5-CH₂—COOH, 2-CH₃ and 3-(-CH₂-S-) substituent |
| H | —CH₃ | H | OCH₃ | S | pyridine ring with 3-Cl, 4-COOH and 6-(-CH₂-S-) substituent |

-continued

| R$_1$ | R$_2$ | R$_3$ | R$_4$ | X | A |
|---|---|---|---|---|---|
| ![phenoxy-CH2-CO-] Ph-O-CH$_2$-CO- | -CH$_3$ | H | H | S | pyrazine with -CH$_2$-S- and -S-CH$_3$ substituents |
| H$_3$C-(N=N)-S-CH$_2$-CO- (thiadiazole) | -CH$_3$ | H | H | S | pyridine with CH$_3$, H$_3$C-O, -CH$_2$-S-, and -CH$_3$ substituents |
| H | -CH$_3$ | -CH$_2$-COOH | H | S | pyrazine with -CH$_2$-S-CH$_2$-COOH |
| H | -CH$_3$ | H | H | S | pyridine N-oxide with OCH$_3$ and -CH$_2$-S- |
| H | -CH$_3$ | H | H | S | pyridine N-oxide with OC$_2$H$_5$ and -CH$_2$-S- |
| H | -CH$_3$ | H | H | S | pyridine N-oxide with O-n-C$_4$H$_9$ and -CH$_2$-S- |

-continued
| $R_1$ | $R_2$ | $R_3$ | $R_4$ | X | A |
|---|---|---|---|---|---|
| H | —CH$_3$ | 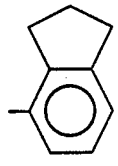 | H | S | 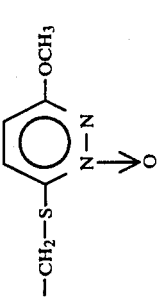 |
| H | —CH$_3$ | H | H | S | 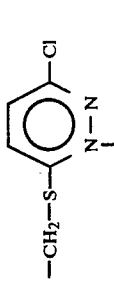 |
| H | —CH$_3$ | H | H | S | 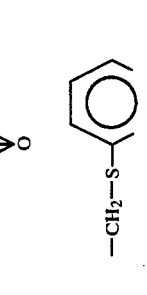 |
| H | —CH$_2$—CH$_3$ | H | H | S | 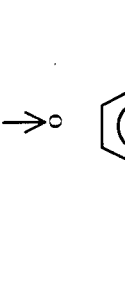 |
| H | —CH$_3$ | H | H | S | 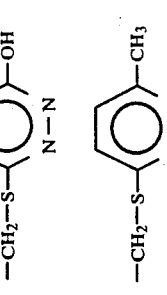 |
| H | —CH$_3$ | H | H | S | 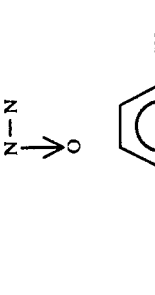 |

-continued
| $R_1$ | $R_2$ | $R_3$ | $R_4$ | X | A |
|---|---|---|---|---|---|
| H | —CH$_3$ | H | H | S | 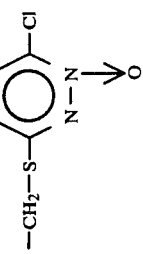 |
| H | —CH$_3$ | H | H | S | 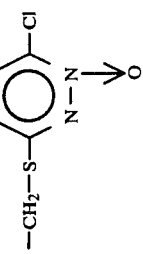 |
| H | —CH$_3$ | H | H | S | 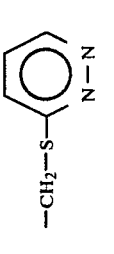 |
| H | —CH$_2$—CH$_2$—CH$_3$ | H | H | S | 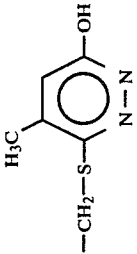 |
| H | —CH$_3$ | H | H | S | 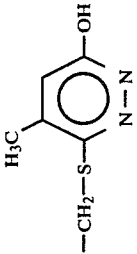 |
| H | —CH$_3$ | H | H | S | 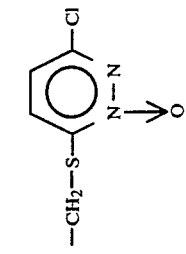 |

-continued

| R₁ | R₂ | R₃ | R₄ | X | A |
|---|---|---|---|---|---|
| H | —CH₃ | H | H | S | 4-hydroxy-2-(ethoxycarbonyl)-5-(thiomethyl-)phenylazo group (—CH₂—S— linkage to ring bearing H₅C₂OOC and OH, with N=N) |
| H | —CH₃ | H | H | S | 2-hydroxy-3-(ethoxycarbonyl)-5-methyl-6-(thiomethyl-)phenylazo (H₃C, COOC₂H₅, OH, —CH₂—S—, N=N) |
| H | —CH₃ | H | H | S | 2-hydroxy-3-ethyl-5-(ethoxycarbonyl)-6-(thiomethyl-)phenylazo (C₂H₅, OH, H₅C₂OOC, —CH₂—S—, N=N) |
| H | —CH₃ | H | H | S | 2-hydroxy-3-methyl-5-(ethoxycarbonyl)-6-(thiomethyl-)phenylazo (CH₃, OH, H₅C₂OOC, —CH₂—S—, N=N) |
| H | —CH₃ | H | H | S | 2-mercapto-5-(thiomethyl-)pyridylazo (SH, —CH₂—S—, N=N) |
| H | —CH₃ | —CH₂—O—C(=O)—CH₃ | H | S | 2-chloro-5-(thiomethyl-)pyridylazo N-oxide (Cl, —CH₂—S—, N→O, N=N) |
| H | —CH₃ | —CH₂—O—C(=O)—C(CH₃)₃ | H | S | 3-(thiomethyl-)pyridylazo (—CH₂—S—, N=N) |

-continued
| R₁ | R₂ | R₃ | R₄ | X | A |
|---|---|---|---|---|---|
| H | —CH₃ | H | OCH₃ | S | 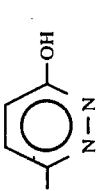 |
|  | —CH₃ | H | H | S |  |
|  | —CH₃ | H | H | S |  |
| H | —CH₃ | H | H | S |  |
| H | CH₃ | CH₂CO₂H | H | S | (see figure) |
|  | CH₃ | H | H | S | (see figure) |
|  | CH₃ | CH₂OCCH₃ (O=) | H | S | (see figure) |
| H | CH₃ | CH₂-C.C.CO₂C₂H₅ / O N—OCH₃ | H | S | (see figure) |

-continued

| R$_1$ | R$_2$ | R$_3$ | R$_4$ | X | A |
|---|---|---|---|---|---|
| C$_6$H$_5$-O-CH$_2$-CO- | CH$_3$ | H | OCH$_3$ | S | CH$_3$S-(thiazole)-N=N-C(CH$_3$)=CH- |
| H$_2$N-(thiazole,N=N)-C-SCH$_2$CO- | CH$_3$ | H | H | S | CH$_3$S-(thiazole)-N=N-C(NH$_2$)=CH- |
| H | CH$_3$ | H | OCH$_3$ | S | CH$_3$S-(thiazole)-N=CH-C(NH$_2$)=CH- |
| H | CH$_3$ | H | OCH$_3$ | S | CH$_3$S-(thiazole)-CH=CH-(pyridyl) |
| H | CH$_3$ | H | OCH$_3$ | S | CH$_3$S-(thiazole)-N=C(CH$_2$CO$_2$H)-CH= |
| H | CH$_3$ | H | OCH$_3$ | S | CH$_3$S-(thiazole)-N=C(CH$_3$)-C(CO$_2$H)= |
| H | CH$_3$ | H | OCH$_3$ | S | CH$_3$S-(oxazole)-N=N-(thienyl) |
| H | CH$_3$ | H | OCH$_3$ | S | CH$_3$S-(oxazole)-N=N-C(CH$_3$)(CH$_2$CONH)-CH$_2$CONH- |
| H | CH$_3$ | H | OCH$_3$ | S | CH$_3$S-(oxazole)-N=N-C(CH$_2$CO$_2$H)= |

-continued
| R₁ | R₂ | R₃ | R₄ | X | A |
|---|---|---|---|---|---|
| H | CH₃ | H | OCH₃ | S |  |
| H | CH₃ | H | OCH₃ | S |  |
| H | CH₃ | H | OCH₃ | S |  |
| H | CH₃ | H | OCH₃ | S |  |
| H | CH₃ | H | OCH₃ | S |  |
| H | CH₃ | H | OCH₃ | S |  |
| H | CH₃ | H | OCH₃ | S |  |
| H | CH₃ | H | OCH₃ | S |  |
| H | CH₃ | H | H | O | CH₂OCOCH₃ |

-continued

| R₁ | R₂ | R₃ | R₄ | X | A |
|---|---|---|---|---|---|
| H | CH₃ | H | H | O | ![]N=N with CH₃S and S, NH₂ substituted thiadiazole |
| H | CH₃ | H | H | NH | CH₂OCOCH₃ |
| H | CH₃ | H | H | NH | CH₃S-C(N-N=N-CH₃)= (methyl triazole-thio) |
| H | CH₃ | H | H | CH₂ | CH₂OCOCH₃ |
| H | —CH₃ | H | —OCH₃ | S | —CH₂—O—C(=O)—CH₃ |
| H | (phenyl) | H | H | S | —CH₂—O—C(=O)—CH₃ |
| —O—CH₂—CO— (phenoxyacetyl) | (4-Cl-phenyl) | —CH₂O—C(=O)—C(CH₃)₃ | H | S | —CH₂—O—C(=O)—CH₃ |
| H | (phenyl) | H | H | S | —CH₂—O—C(=O)—CH₃ |
| H | (phenyl) | H | H | S | —CH₂—O—C(=O)—CH₃ |
| H₃C-C(=N-N)-S-CH₂-CO— | —CH₃ | H | H | S | —CH₂—O—C(=O)—CH₃ |

-continued

| R₁ | R₂ | R₃ | R₄ | X | A |
|---|---|---|---|---|---|
| H | -C₆H₄-OCH₃ (p) | H | H | S | -CH₃ |
| -S-CH₂-CO- phenyl | -CH₃ | H | H | S | -CH₂-O-C(=O)-CH₃ |
| -S-CH₂-CO- (1-methyl-1,2,4-triazol-3-yl) | -CH₃ | H | H | S | -CH₂-O-C(=O)-CH₃ |
| H | -CH₃ | -CH₂-O-C(=O)-C(CH₃)₂-CH₃ | OCH₃ | S | -CH₃ |
| H | -CH₃ | -CH₂-COOH | OCH₃ | S | -CH₂-O-C(=O)-CH₃ |
| H | -CH₃ | -CH₂-O-C(=O)-C(CH₃)₂-CH₃ | H | S | -CH₂-O-C(=O)-CH₃ |
| H | -CH₂-CH₃ | H | H | S | -Cl |
| H | -CH₂-CH₃ | H | H | S | -Cl |
| H | -CH₃ | -CH₂-O-C(=O)-C(CH₃)₂-CH₃ | H | S | -OCH₃ |
| H | -C₂H₅ | -CH₂-COOH | H | S | -OCH₃ |
| H | -C₃H₇ | -CH₂-COOH | H | S | -CH₂-O-C(=O)-CH₃ |
| H | | | | | -CH₂-O-C(=O)-CH₃ |

-continued
| R₁ | R₂ | R₃ | R₄ | X | A |
|---|---|---|---|---|---|
| H | —CH₂—CH=CH₂ | —CH₂—COOH | H | S | —CH₂—O—C(=O)—CH₃ |
| H | —C₆H₅ | —CH₂—COOH | H | S | —CH₂—O—C(=O)—CH₃ |
| H | —CH₃ | —CH₂—COOH | H | S | —CH₂—S—C(=O)—CH₃ |
| H | —CH₃ | —CH₂—O—C(CH₃)₂—C(=O)—CH₃ | H | S | —CH₂—S—C(=O)—CH₃ |
| H | —CH₃ | —CH₂—COOH | H | S | —CH₂—S—C₃H₇ |
| H | —CH₃ | —CH₂—O—C(=O)—CH₃ | H | S | —CH₂—O—C(=O)—CH₃ |
| H | —CH₃ |  | H | S | —CH₂—O—C(=O)—CH₃ |
| H | —CH₃ | 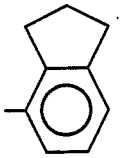 | H | S | —CH₂—O—C(=O)—CH₃ |
| H | —CH₃ | —CH₂—C(=O)—C(=N—OCH₃)—COC₂H₅ | H | S | —CH₂—O—C(=O)—CH₃ |

-continued

| R₁ | R₂ | R₃ | R₄ | X | A |
|---|---|---|---|---|---|
| H | —CH₃ | —CH₂—C(=O)—C(=N—OCH₂COOH)—COC₂H₅ | H | S | —CH₂—O—C(=O)—CH₃ |
| H | —CH₃ | —CH₂—C(=O)—C(=N—OC₃H₇)—OC₂H₅ | H | S | —CH₂—O—C(=O)—CH₃ |
| H | —CH₂—COOCH₃ | —CH₂—C(=O)—C(=N—OCH₂—CH(COOCH₃))—OC₂H₅ | H | S | —CH₂—O—C(=O)—CH₃ |
| H | —CH₃ | —CH₂—COOH | H | S | —CH₂—O—C(=O)—NH₂ |
| H | —CH₃ | —CH₂—C(=O)—O—C(CH₃)₂—CH₃ | H | S | —CH₂—O—C(=O)—NH₂ |
| H | —C₆H₅ | —CH₂—COOH | H | S | —CH₂—O—C(=O)—NH₂ |
| H | —CH₂—COOH | —CH₃ | H | S | —CH₂—O—C(=O)—NH₂ |
| H | —CH₃ | —CH(CH₃)—O—C(=O)—O—C₂H₅ | H | S | —CH₂—O—C(=O)—CH₃ |

-continued

| R₁ | R₂ | R₃ | R₄ | X | A |
|---|---|---|---|---|---|
| H | —CH₃ |  | H | S | —CH₂—O—C(=O)—CH₃ |
| H | —CH₃ | —CH₂—O—CH₃ | OCH₃ | S | —CH₂—O—C(=O)—CH₃ |
| H | —C₂H₅ | —CH(CH₃)—O—C(=O)—O—C₂H₅ | OCH₃ | S | —CH₂—O—C(=O)—CH₃ |
| H | —CH₃ | —CH(CH₃)—O—C(=O)—O—C₂H₅ | H | S | —CH₂—O—C(=O)—CH₃ |
| H | —CH₃ | —CH₂—C(=O)—C(=O)—CH₃ | H | S | —CH₂—O—C(=O)—CH₃ |
| H |  | —CH₂—C(=O)—C(=O)—CO₂C₆H₃ | H | S | —CH₂—O—C(=O)—CH₃ |
| H |  | H |  |  | —CH₂—O—C(=O)—CH₃ |
| H | —CH₂—COOH | —C(CH₃)₂—C(=O)—O—CH₂—C(CH₃)₃ | H | S | —CH₂—O—C(=O)—CH₃ |
| H | H | —C(CH₃)₂—C(=O)—O—CH₂—C(CH₃)₃ | H | S | —CH₂—O—C(=O)—CH₃ |

-continued

| R₁ | R₂ | R₃ | R₄ | X | A |
|---|---|---|---|---|---|
| H | H | (phthalide structure) | H | S | —CH₂—O—C(=O)—CH₃ |
| H | H | | OCH₃ | S | —CH₂—O—C(=O)—CH₃ |
| H | —CH—COOH (cyclopentyl) | | H | S | —CH₂—O—C(=O)—CH₃ |
| H | —CH—COOH (cyclohexyl) | | H | S | —CH₂—O—C(=O)—CH₃ |
| H | —CH₂—SO₃H | | H | S | —CH₂—O—C(=O)—CH₃ |
| H | —CH₂—SO₂NH₂ | | H | S | —CH₂—O—C(=O)—CH₃ |
| H | —CH—COOH (cyclopentyl) | | H | S | —CH₂—O—C(=O)—CH₂ |
| H | —CH—COOH (cyclopentyl) | | H | S | —CH₂—S—C(=O)—CH₃ |
| H | —CH₂—COOC₂H₅ | | OCH₃ | S | —CH₂—O—C(=O)—NH₂ |

-continued

| R₁ | R₂ | R₃ | R₄ | X | A |
|---|---|---|---|---|---|
| N₃—CH₂—C(=O)— | —CH₃ | H | H | S | —CH₂—O—C(=O)—CH₃ |
| (1-methyl-1H-tetrazol-5-yl)-S—CH₂—C(=O)— | —CH₃ | H | H | S | (1-methyl-1H-tetrazol-5-yl)-S—CH₂— |
| NCS—CH₂—C(=O)— | —CH₃ | | H | S | —CH₂—O—C(=O)—CH₃ |
| (2-amino-1,3-thiazol-4-yl)-S—CH₂—C(=O)— | —CH₃ | H | H | S | (2-methyl-1,3-thiazol-5-yl)-S—CH₂— |
| H | —CH₃ | —CH(O—CH₃)—O—C(=O)—OC₂H₅ | H | S | (3-methyl-1,3-thiazol-2-yl)-S—CH₂— |
| H | —CH₃ | phthalide | H | S | (2-methyl-1,3-thiazol-5-yl)-S—CH₂— |
| H | —CH₃ | phthalide | H | S | (1-methyl-1H-tetrazol-5-yl)-S—CH₂— |
| H | H | phthalide | H | S | (2-methyl-1,3-thiazol-2-yl)-S—CH₂— |

-continued

| R₁ | R₂ | R₃ | R₄ | X | A |
|---|---|---|---|---|---|
| H | H | ![phthalide] | H | S | −CH₂−S−C(=O)−CH₃ |
| H | H | ![phthalide] | H | S | −CH₂−S−C(=N−N=N−N(CH₃)) |
| H | H | ![phthalide] | H | S | −CH₂−S−C(=O)−CH₃ |
| H₅C₂O−C₆H₄−C(=O)− | −CH₃ | H | H | S | −CH₂−O−C(=O)−CH₃ |
| C₆H₅−O−CH₂−C(=O)− | −CH₃ | ![phthalide] | H | S | −CH₂−O−C(=O)−CH₃ |
| C₆H₅−S−CH₂−C(=O)− | −CH₃ | ![phthalide] | H | S | −CH₂−S−C(=N−N=N−N(CH₃)) |

| R$_1$ | R$_2$ | R$_3$ | R$_4$ | X | A |
|---|---|---|---|---|---|
| H$_2$N–⟨N=N/S⟩–S–CH$_2$–C(=O)– | –CH$_3$ | ⟨phthalide⟩ | H | S | –CH$_2$–O–C(=O)–CH$_3$ |
| H$_2$N–⟨N=N/S⟩–S–CH$_2$–C(=O)– | –CH$_3$ | –CH$_2$–O–C(=O)–C(CH$_3$)$_3$ | H | S | –CH$_2$–O–C(=O)–CH$_3$ |
| H$_2$N–⟨N=N/S⟩–S–CH$_2$–C(=O)– | –CH$_3$ | –CH$_2$–COOH | H | S | –CH$_2$O–C(=O)–CH$_3$ |
| H$_2$N–⟨N=N/S⟩–S–CH(CH$_3$)–C(=O)– | –CH$_3$ | H | H | S | –CH$_2$O–C(=O)–CH$_3$ |
| H$_2$N–⟨N=N/S⟩–S–CH(C$_6$H$_5$)–C(=O)– | –CH$_3$ | H | H | S | –CH$_2$–O–C(=O)–CH$_3$ |
| H$_3$C–⟨N=N/S⟩–S–CH(C$_6$H$_5$)–C(=O)– | –CH$_3$ | H | H | S | –CH$_2$–O–C(=O)–CH$_3$ |
| ⟨N=N/N–N(CH$_3$)⟩–S–CH(CH$_3$)–C(=O)– | –CH$_3$ | H | H | S | –CH$_2$–O–C(=O)–CH$_3$ |

-continued

| R₁ | R₂ | R₃ | R₄ | X | A |
|---|---|---|---|---|---|
| H | −CH₂−C₆H₅ | H | H | S | −CH₂−O−C(=O)−CH₃ |
| H | −CH₂−C₆H₅ | H | H | S | −CH₂−S−C(=O)−CH₃ |
| H | −CH₂−C₆H₅ | H | H | S | −CH₂−S-(2-pyridyl N-oxide) |
| H | −CH₂−C₆H₅ | 3-methylphthalide | H | S | −CH₂−S−(1-methyl-1,2,3,4-tetrazol-5-yl) |
| H | −CH₂−C₆H₄−NO₂ | H | H | S | −CH₂−O−C(=O)−CH₃ |
| H | −CH₂−C₆H₄−NO₂ | H | H | S | −CH₂−S−(2-methyl-1,3,4-thiadiazol-5-yl) |
| H | −CH₂−C₆H₄−NO₂ | −CH₂O−C(=O)−C(CH₃)₂−CH₃ | H | S | −CH₂−S−C(=O)−CH₃ |

-continued
| $R_1$ | $R_2$ | $R_3$ | $R_4$ | X | A |
|---|---|---|---|---|---|
| H | $-CH_2-C_6H_4-Cl$ (p) | H | H | S | $-CH_2-O-C(=O)-CH_3$ |
| H | $-CH_2-C_6H_4-Cl$ (p) | H | H | S | 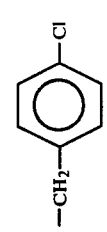 |
| H | $-CH_2-C_6H_4-CH_3$ (p) | H | H | S | $-CH_2-O-C(=O)-CH_3$ |
| H | $-CH_2-C_6H_4-CH_3$ (m) | H | H | S | $-CH_2-O-C(=O)-CH_3$ |
| H | $-CH(COOH)-C_6H_5$ | H | H | S | $-CH_2-O-C(=O)-CH_3$ |
| H | $-CH(COOH)-C_6H_5$ | H | H | S | 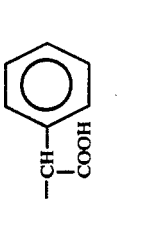 |
| H | $-CH(CH_3)-C_6H_5$ | H | H | S | $-CH_2-O-C(=O)-CH_3$ |
| H | $-CH(CH_3)-C_6H_5$ | $-CH_2-COOH$ | H | S | $-CH_2-O-C(=O)-CH_3$ |

-continued

| R₁ | R₂ | R₃ | R₄ | X | A |
|---|---|---|---|---|---|
| H | —CH(C₆H₅)CH₃ | H | H | S | —CH₂—S—C(=O)—CH₃ |
| H | cyclopropyl-COOH | H | H | S | —CH₂—O—C(=O)—CH₃ |
| H | cyclopentyl-COOH | H | H | S | —CH₂—O—C(=O)—CH₃ |
| H | cyclohexyl-COOH | H | H | S | —CH₂—O—C(=O)—CH₃ |
| H | —CH₂-cyclopropyl-COOH | H | H | S | —CH₂—O—C(=O)—CH₃ |
| H | —CH₂-cyclohexyl-COOH | H | H | S | —CH₂—O—C(=O)—CH₃ |
| H | —CH₂-cyclopentyl-COOH | H | H | S | —CH₂—O—C(=O)—CH₃ |
| Cl—CH₂—C(=O)— | —CH₂—C₆H₄—Cl | H | H | S | —CH₂—O—C(=O)—CH₃ |
| Cl—CH₂—C(=O)— | —CH₂—C₆H₄—NO₂ | —CH₂O—C(=O)—CH₃ | H | S | —CH₂—O—C(=O)—CH₃ |

-continued

| R₁ | R₂ | R₃ | R₄ | X | A |
|---|---|---|---|---|---|
| Cl—CH₂—C(=O)— | 4-CH₃-C₆H₄-CH₂— | H | H | S | —CH₂—S—C(=O)—CH₃ |
| C₆H₅—O—CH₂—C(=O)— | C₆H₅—CH₂— | H | H | S | —CH₂—O—C(=O)—CH₃ |
| C₆H₅—O—CH₂—C(=O)— | 4-Cl-C₆H₄-CH₂— | H | H | S | (thiophene-N=N-N(CH₃)-C-S-CH₂—) |
| C₆H₅—O—CH₂—C(=O)— | C₆H₅—CH(COOH)— | H | H | S | —CH₂—O—C(=O)—CH₃ |
| C₆H₅—O—CH₂—C(=O)— | 1-COOH-cyclopropyl-CH₂— | H | H | S | —CH₂—O—C(=O)—CH₃ |
| C₆H₅—O—CH₂—C(=O)— | 1-COOH-cyclopentyl-CH₂— | H | H | S | —CH₂—O—C(=O)—CH₃ |
| C₆H₅—C(CH₃)₃— | C₆H₅—CH(CH₃)— | C(CH₃)₃ | H | S | —CH₂—O—C(=O)—CH₃ |
| C₆H₅—C(CH₃)₃— | 4-CH₃-C₆H₄-CH₂— | H | H | S | —CH₂—S—C(=O)—CH₃ |

-continued
| R₁ | R₂ | R₃ | R₄ | X | A |
|---|---|---|---|---|---|
| 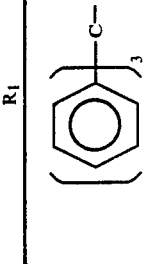 | —CH₂—⟨△⟩—COOH | H | H | S | —CH₂—S—C(=O)—CH₃ |
| H |  | H | H | S | —CH₂—O—C(=O)—CH₃ |
| H |  | —CH(OCH₃)—CO₂CH₃ | H | S | —CH₂—O—C(=O)—CH₃ |
| H | 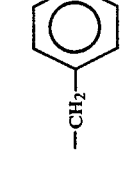 | —CH₂—COOH | H | S | —CH₂—O—C(=O)—CH₃ |
| H |  | —CH₂—CCl₃ | H | S | —CH₂—O—C(=O)—CH₃ |
| H | 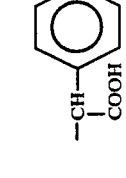 | —CH₂—COOH | H | S | —CH₂—O—C(=O)—CH₃ |
| H |  | —CH₂—⟨C₆H₄-NO₂⟩ | H | S | —CH₂—O—C(=O)—CH₃ |
| H | 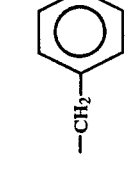 | —CH₂—C(CH₃)₃ | H | S | —CH₂—O—C(=O)—CH₃ |

-continued

| R₁ | R₂ | R₃ | R₄ | X | A |
|---|---|---|---|---|---|
| H | —CH₂—C₆H₁₀—COOH (1-carboxycyclohexyl) | —CH₂—O—C(CH₃)₃ with C=O | H | S | —CH₂—O—C(=O)—CH₃ |
| H | —CH₃ | —C(CH₃)₃ | H | S | —CH₂—S—(1,2,3-thiadiazol-5-yl) |
| Cl—CH₂—C(=O)— | —CH₂—CH=CH₂ | H | H | S | —CH₂—S—(1,2,3-thiadiazol-5-yl) |
| H | —CH₂—COOH | H | H | S | —CH₂—S—(1,3-thiazol-2-yl) |
| H | —CH(CH₃)₂ | H | H | S | —CH₂—S—(1,3-thiazol-2-yl) |
| H | H | —CH₂—O—C(=O)—CH₃ | H | S | —CH₂—S—(1,2,4-thiadiazol-3-yl) |
| H | —CH₂—COOC₂H₅ | —CH₂—COOC₂H₅ | H | S | —CH₂—S—(1,2,4-thiadiazol-3-yl) |
| H | —CH₂—C₆H₄—NO₂ | H | H | S | —CH₂—S—(isoxazol-3-yl) |
| —C(C₆H₅)₃ | —CH₂—CH₃ | H | H | S | —CH₂—S—(isoxazol-5-yl) |

-continued

| R₁ | R₂ | R₃ | R₄ | X | A |
|---|---|---|---|---|---|
| -CH₂-C₆H₅ (phenyl-CH₂-CH₂-) | -CH(C₂H₅)-COOH | H | H | S | -CH₂-S-C(=N-)-O-C(CH₃)=C(CH₃)- (5-membered oxazole with two CH₃) |
| H | -CH₃ | -CH₂-O-C(=O)-C₆H₅ | H | S | -CH₂-S-C(=N-)-O-C(CH₃)=C(CH₃)- |
| Br-CH₂-C(=O)- | -CH₂-CH₂-CH₂-CH₃ | H | H | S | -CH₂-S-C(=N-)-O-CH=C(C₆H₅)- |
| H | cyclopentane-1-COOH (1,1-disubstituted cyclopentane with COOH) | -CH₂-CH(CH₃)₂ (isobutyl: -CH(CH₃)CH₃ via CH₂) | H | S | -CH₂-S-(benzoxazol-2-yl) |
| H | -CH₂-C₆H₁₁ (cyclohexylmethyl) | H | H | S | -CH₂-S-(benzoxazol-2-yl) |
| C₆H₅-CH₂-O-C(=O)- | -CH₃ | H | H | S | -CH₂-S-(benzoxazol-2-yl) |
| H | -CH₃ | -CH₂-O-C(=O)-C(CH₃)₃ | H | S | -CH₂-S-C(=N-CH₂-CH₂-O-) (oxazoline) |
| Cl-CH₂-C(=O)- | -CH₂-CH₂-CH₃ | H | H | S | -CH₂-S-C(=N-CH=CH-NH-) (imidazole) |

-continued
| R₁ | R₂ | R₃ | R₄ | X | A |
|---|---|---|---|---|---|
| H | —CH₃ | H | H | S | 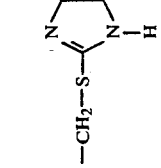 |
| H | —CH₂—CH=CH₂ | H | H | S | 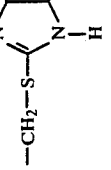 |
| H | $\begin{array}{c}\text{CH}_3\\ \text{—CH}\\ \text{CH}_3\end{array}$ | $\begin{array}{c}\text{CH}_3\\ \text{—C—CH}_3\\ \text{CH}_3\end{array}$ | H | S |  |
| H | $\begin{array}{c}\text{—CH—COOH}\\ \text{CH}_3\end{array}$ | —CH₂—O—C—CH₃<br>‖<br>O | H | S | 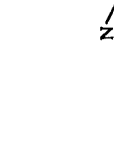 |
| H | —CH₂—CO₂C(CH₃)₃ | H | H | S |  |
| H |  | H | H | S | 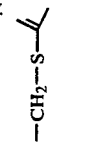 |
|  | —CH₃ | H | H | S |  |

-continued

| R₁ | R₂ | R₃ | R₄ | X | A |
|---|---|---|---|---|---|
| H | —CH₂—CH=CH₂ | H | H | S | —CH₂—S—(furan) |
| H | H | H | H | S | —CH₂—S—(thiophene) |
| H | ![cyclohexyl-COOH-CH₂] | H | H | S | —CH₂—S—(thiophene) |
| Cl—CH₂—C(=O)— | —CH₃ | H | H | S | —CH₂—S—(pyrrole N-H) |
| H | —CH₂—CH₃ | H | H | S | —CH₂—S—(thiazoline) |
| H | (CH₃)₃C— | (CH₃)₃C— | H | S | —CH₂—S—(thiazoline) |
| H | —CH₂—CH=CH₂ | —CH(CO₂CH₃)OCH₃ | H | S | —CH₂—S—(isothiazole) |
| H | —CH₂—CH=CH—CO₂H | H | H | S | —CH₂—S—(isothiazole) |
| H | —CH₃ | —CH₂—O—C(=O)—CH₃ | H | S | —CH₂—S—(pyrazole N-N-H) |

-continued

| R₁ | R₂ | R₃ | R₄ | X | A |
|---|---|---|---|---|---|
| H | —CH₃ | | H | S | —CH₂—S—(1,3,4-thiadiazole) |
| H | —CH—COOH, C₃H₇ | —CH₂—O—C(=O)—C(CH₃)₃ | H | S | —CH₂—S—(1,3,4-thiadiazole) |
| H | —CH₂—CH₃ | H | H | S | —CH₂—S—(pyridine) |
| H | H | —CH(CH₃)₂ | H | S | —CH₂—S—(pyridine) |
| Cl—CH₂—C(=O)— | —CH₂—CH=CH₂ | H | H | S | —CH₂—S—(pyridine) |
| H | —CH₃ | H | H | S | —CH₂—S—(pyridine) |
| H | —CH₃ | H | H | S | —CH₂—S—(4-OH, 5-CH₃-pyrimidine) |
| H | —CH(CH₃)₂ | —CH₂—O—C(=O)—C(CH₃)₃ | H | S | —CH₂—S—(4-OH, 5-CH₃-pyrimidine) |

-continued
| R₁ | R₂ | R₃ | R₄ | X | A |
|---|---|---|---|---|---|
| H | —CH₃ | H | H | S | 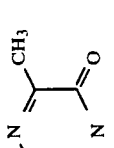 |
| H | —CH₃ | H | H | S | 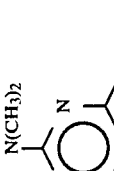 |
| H | —CH₃ | H | H | S | 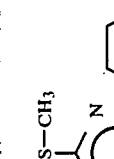 |
| H | —CH₃ | H | H | S | 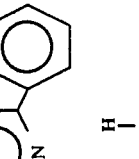 |
| H | —CH₃ | H | H | S | 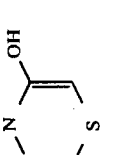 |
| H | —CH₂—COOH | H | H | S |  |
| H | —CH₃ | H | H | S |  |

-continued
| $R_1$ | $R_2$ | $R_3$ | $R_4$ | X | A |
|---|---|---|---|---|---|
| H | -CH(C$_6$H$_5$)CH$_3$ | -CH$_2$-COOH | H | S | 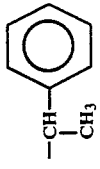 |
| H | -CH$_3$ | H | H | S | 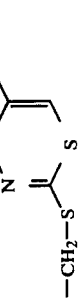 |
| H-C(=O)- | -CH$_2$-CH=CH$_2$ | H | H | S | 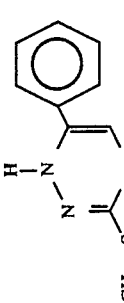 |
| H | -CH$_3$ | H | H | S | 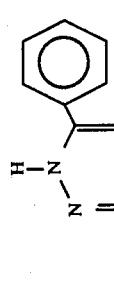 |
| H | -CH$_2$-CH$_2$-CH$_3$ | -CH$_2$-O-C(=O)-O-CH$_3$ | H | S | 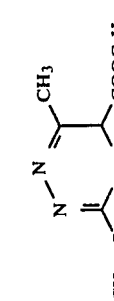 |
| H | -CH$_3$ | -C(CH$_3$)$_3$ | H | S | 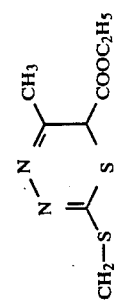 |
| H | -CH$_2$-(cyclopropyl)-COOH | H | H | S | 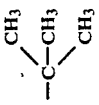 |

-continued

| R₁ | R₂ | R₃ | R₄ | X | A |
|---|---|---|---|---|---|
| H | —CH₃ | —CH₂O—C(=O)—C(CH₃)₃ | H | S | —CH₂—S— (imidazo[4,5]pyrazine, NH) |
| H | —CH₂—C₆H₅ | H | H | S | —CH₂—S— (imidazo[4,5]pyrazine, NH) |
| H | —CH₂—CH₃ | —CH(C₆H₅)₂ | H | S | —CH₂—S— (imidazole-pyrimidine, NH) |
| H | —C(CH₃)₂CH₃ | H | H | S | —CH₂—S— (imidazole-pyrimidine, NH) |

In the above table, in addition to denoting S, X can also represent, in each case, —O—, —CH$_2$— or —NH—. A repetition of the table containing these variations of X was dispensed with for reasons of saving space.

Compounds of the general formula I in which R$_1$ represents hydrogen, acyl, preferably R$_5$-S-acetyl, phenoxyacetyl or phenylthioacetyl, R$_2$ represents alkyl with 1-4 C atoms, preferably methyl, R$_3$ represents hydrogen, a cation, preferably an alkali metal, in particular sodium, or an ester group, preferably acyloxymethyl, carboxyalkyl or phthalide, R$_4$ represents hydrogen, X represents sulfur and A represents acetoxymethyl or the group —SR$_5$, wherein R$_5$ can have the preferred meanings indicated above, are of particular interest according to the invention.

The following embodiment examples serve to further illustrate the invention, but do not limit it thereto. Unless otherwise indicated, all the part, % and ratio data relate to the weight.

The Rf values indicated in the examples were determined by thin layer chromatography on silica gel finished plates 60 F 254 from Messrs. Merck, Darmstadt.

EXAMPLE 1

7-Beta-[alpha-syn-methoximino-alpha-(2-amino-thiazol-4-yl)-acetamido]-3-(4-methyl-3-oxy-1,3-thiazol-2-yl-thiomethyl)-3-cephem-4-carboxylic acid 2.5 g (5 mmoles) of the formate of 7-beta-[alpha-syn-methoximino-(2-amino-thiazol-4-yl)-acetamido]-cephalosporanic acid and 0.8 g (6 mmoles) of 2-mercapto-4-methyl-3-oxy-1,3-thiazole are dissolved in 50 ml of water with the required amount of sodium bicarbonate. After adding 50 ml of acetone, the reaction solution is warmed to 64° for 4 hours, the pH value being kept between 6.5 and 7.0. Thereafter, the reaction mixture is cooled to 20°, the acetone is removed in vacuo at 40° C. and the aqueous solution which remains is adjusted to a pH value of 3.2 with 2N hydrochloric acid. The solution is extracted 3 times with 30 ml of ethyl acetate each time. The aqueous phase is freed from ethyl acetate residues in vacuo, diluted to 100 ml with water and adjusted to the pH value of 2.5 at 0° C. with 2N hydrochloric acid. The precipitate is filtered off, washed with water and dried at room temperature over phosphorus pentoxide.

1.3 g of the title compound are obtained:
R$_f$: 0.16 (acetone:glacial acetic acid = 10:1).
IR (KBr): 1,765 cm$^{-1}$ ($\beta$-lactam band).
NMR (d$_6$-dimethylsulfoxide, 60 MHz): $\delta$ = 6.8 ppm (singlet, 1H,

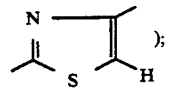

$\delta$ = 7.7 ppm (doublet, 1H,

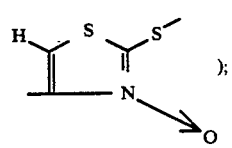

and $\delta$ = 9.6 ppm (doublet, 1H,

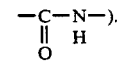

EXAMPLE 2

7-Beta-[alpha-syn-methoximino-alpha-(2-amino-thiazol-4-yl)-acetamido]-3-(3-oxy-4-phenyl-1,3-thiazol-2-yl-thiomethyl)-3-cephem-4-carboxylic acid 2.6 g (5 mmoles) of an (1:1:1)-adduct of 7-beta-[alpha-syn-methoximino-alpha-(2-amino-thiazol-4-yl)-acetamido]-cephalosporanic acid, water and ethanol are dissolved in 50 ml of water with 1.5 g (7.5 mmoles) of 2-mercapto-3-oxy-4-phenyl-1,3-thiazole and with the required amount of sodium bicarbonate and the reaction solution is warmed to 64° C. for 12 hours, the pH value being kept between 6.0 and 7.0. The reaction product is worked up and isolated according to Example 1.

0.9 g of the title compound is obtained; R$_f$ = 0.45 (acetone:glacial acetic acid = 10:1).
IR (KBr): 1,765 cm$^{-1}$ ($\beta$-lactam band).
NMR (d$_6$-dimethylsulfoxide, 60 MHz): $\delta$ = 6.8 ppm (singlet, 1H,

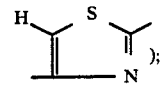

$\delta$ = 8.13 ppm (singlet, 1H,

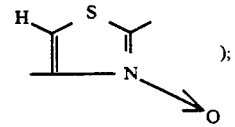

and $\delta$ = 9.6 ppm (doublet, 1H,

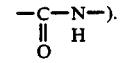

EXAMPLE 3

7-Beta-[alpha-syn-methoximino-alpha-(2-amino-thiazol-4-yl)-acetamido]-3-[4-(4-chlorophenyl)-3-oxy-1,3-thiazol-2-yl-thiomethyl]-3-cephem-4-carboxylic acid The procedure is as according to Example 1, using 1.86 g (8 mmoles) of 4-(4-chlorophenyl)-2-mercapto-3-oxy-1,3-thiazole. The reaction solution is warmed to 64° C. for 24 hours. 0.75 g of the title compound is obtained.
R$_f$: 0.50 (acetone:glacial acetic acid = 10:1).
IR (KBr): 1,755 cm$^{-1}$ ($\beta$-lactam band).
NMR (d$_6$-dimethylsulfoxide, 60 MHz): $\delta$ = 6.8 ppm (singlet, 1H,

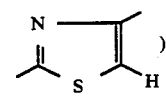

$\delta$ = 8.3 ppm (singlet, 1H,

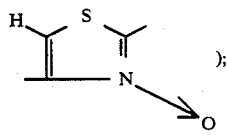

and δ=9.65 ppm (doublet, 1H,

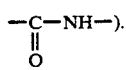).

EXAMPLE 4

7-Beta-[alpha-syn-methoximino-alpha-(2-amino-thiazol-4-yl)-acetamido]-3-(4-tert.-butyl-1,3-thiazol-2-yl-thiomethyl)-3-cephem-4-carboxylic acid 2.0 g (4 mmoles) of the formate of 7-beta-[alpha-syn-methoximino-alpha-(2-amino-thiazol-4-yl)-acetamido]-cephalosporanic acid are suspended in 30 ml of a water-/acetone (2:1) mixture. 0.7 g (4 mmoles) of 4-tert.-butyl-2-mercapto-1,3-thiazole is added, and 2N sodium bicarbonate solution is added until a homogeneous solution is formed. The reaction solution is then adjusted to a pH value of 7.0 with solid sodium bicarbonate and warmed to 50° to 60° C. for 5 hours, the pH value being kept constant. The acetone is distilled off in vacuo at 40° C., the aqueous solution is filtered and the filtrate is adjusted to a pH value of 2.0 with 2N hydrochloric acid, whilst cooling with ice. The precipitate is filtered off, washed with water and dissolved again in 2N sodium bicarbonate solution. The aqueous solution is clarified with active charcoal and, after acidifying to a pH value of 2 with 2N hydrochloric acid, 0.9 g of the title compound is obtained.

$R_f$: 0.55 (n-butanol:water:ethanol:glacial acetic acid=5:2:1.5:1.5).

IR (KBr): 1,770 cm$^{-1}$ (β-lactam band).

NMR (d$_6$-dimethylsulfoxide, 60 MHz): δ=1.2 ppm (singlet, 9H, —C(CH$_3$)$_3$); δ=3.8 ppm (singlet, 3H, =N—OCH$_3$); δ=6.43 ppm (singlet, 1H,

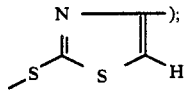

δ=6.67 ppm (singlet, 1H,

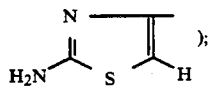

and δ=7.16 ppm (2H, —NH$_2$).

EXAMPLE 5

7-Beta-[alpha-syn-methoximino-alpha-(2-amino-thiazol-4-yl)-acetamido]-3-(1-oxy-pyrid-2-yl-thiomethyl)-3-cephem-4-carboxylic acid 1.5 g (3.3 mmoles) of 7-beta-[α-syn-methoximino-alpha-(2-amino-thiazol-4-yl)-acetamido]-cephalosporanic acid are dissolved in 50 ml of water with the equimolar amount of sodium bicarbonate. A solution of 457 mg (3.6 mmoles) of the N-oxide of 2-mercapto-pyridine and 303 mg (3.6 mmoles) of sodium bicarbonate in 30 ml of water is added and, if necessary, the reaction solution is adjusted to a pH value of 6.8–7.2 by adding 1N sodium bicarbonate solution. The solution is warmed to 50° for 4 hours, whilst stirring and keeping the pH value constant. After cooling to 20° C., it is adjusted to pH 5 with 2N hydrochloric acid and extracted with ethyl acetate and the aqueous phase is then acidified to the pH value of 2.0 with 2N hydrochloric acid. The precipitate is filtered off, washed with water and dried in vacuo at 37° C. over potassium hydroxide.

385 mg of the title compound are obtained.

$R_f$: 0.11 (acetone:glacial acetic acid=10:1).

IR (KBr): 1,768 cm$^{-1}$ (β-lactam band).

NMR (d$_6$-dimethylsulfoxide, 60 MHz): δ=3.92 ppm (singlet, 3H, =N—OCH$_3$); δ=5.20 ppm (doublet, 1H, 6—CH—); δ=5.81 ppm (quartet, 1H, 7—CH—); δ=3.70 ppm (2—CH$_2$—); δ=4.07 ppm (C3—CH$_2$—S—); δ=6.79 ppm (singlet, 1H,

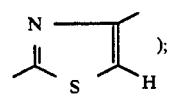

δ=7.24 ppm (2H, —NH$_2$); δ=7.42 ppm (multiplet, 3H,

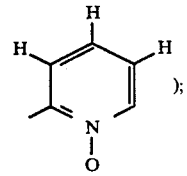

δ=8.35 ppm (multiplet, 1H,

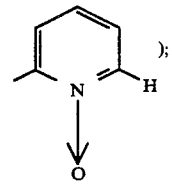

and δ=9.64 ppm (doublet, 1H, —CO—NH—).

EXAMPLE 6

7-Beta-[alpha-syn-methoximino-alpha-(2-amino-thiazol-4-yl)-acetamido]-3-(3-methyl-1-oxy-pyrid-2-yl-thiomethyl)-3-cephem-4-carboxylic acid The procedure is as according to Example 5, using 508 mg (3.6 mmoles) of the N-oxide of 2-mercapto-3-methyl-pyridine. The reaction solution is warmed to 60° C. for 7 hours. The isolated crude product is purified by dissolving in 1N sodium bicarbonate solution, extracting the aqueous solution with ethyl acetate at pH 8 and precipitating the product again with 2N hydrochloric acid.

496 mg of the title compound are obtained.

$R_f$=0.13 (acetone/glacial acetic acid=10:1).

IR (KBr): 1,759 cm$^{-1}$ (β-lactam band).

NMR (d$_6$-dimethylsulfoxide, 60 MHz): δ=2.37 ppm (singlet, 3H, CH$_3$—puridine); δ=3.83 ppm (singlet, 3H, =N—OCH$_3$); δ=5.05 ppm (doublet, 1H, 6—CH—);

δ=5.70 ppm (quartet, 1H, 7—CH—); δ=6.72 ppm (singlet, 1H,

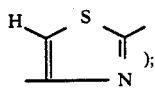

and δ=9.56 ppm (doublet, 1H, —CO—NH—).

EXAMPLE 7

7-Beta-[alpha-syn-methoximino-alpha-(2-amino-thiazol-4-yl)-acetamido]-3-(4-methyl-1-oxy-pyrid-2-yl-thiomethyl)-3-cephem-4-carboxylic acid The procedure is as according to Example 5, using 508 mg (3.6 mmoles) of the N-oxide of 2-mercapto-4-methyl-pyridine. The reaction solution is warmed to 60° C. for 4 hours. 512 mg of the title compound are isolated.

$R_f$: 0.12 (acetone:glacial acetic acid=10:1).

IR (KBr): 1,766 cm$^{-1}$ ($\beta$-lactam band).

NMR (d$_6$-dimethylsulfoxide, 60 MHz): δ=2.32 ppm (singlet, 3H, CH$_3$-pyridine); δ=3.87 ppm (singlet, 3H, =N—OCH$_3$); δ=5.19 ppm (doublet, 1H, 6—CH—); δ=5.76 ppm (quartet, 1H, 7—CH—); δ=6.76 ppm (singlet, 1H,

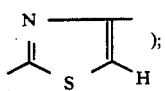

δ=7.04 ppm (multiplet, 1H,

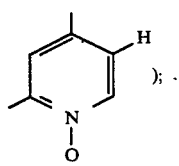

δ=7.23 ppm (2H, —NH$_2$); δ=7.46 ppm (singlet, 1H,

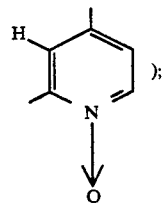

δ=8.16 ppm (doublet, 1H,

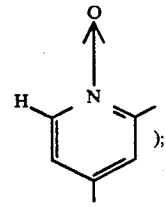

and δ=9.57 ppm (doublet, 1H, —CO—NH—).

EXAMPLE 8

7-Beta-[alpha-syn-methoximino-alpha-(2-amino-thiazol-4-yl)-acetamido]-3-[2-(4-pyridyl)-1,3,4-oxadiazol-5-yl-thiomethyl]-3-cephem-4-carboxylic acid The procedure is as according to Example 5, using 644 mg (3.6 mmoles) of 5-mercapto-2-(4-pyridyl)-1,3,4-oxadiazole. The reaction solution is warmed to 60° C. for 6.5 hours. 478 mg of the title compound are isolated.

$R_f$: 0.59 (ethyl acetate:methanol:glacial acetic acid=20:10:1).

IR (KBr): 1,767 cm$^{-1}$ ($\beta$-lactam band).

NMR (d$_6$-dimethylsulfoxide, 60 MHz): δ=3.84 ppm (singlet, 3H, =N—OCH$_3$); δ=6.76 ppm (singlet, 1H,

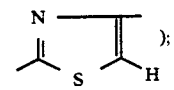

δ=7.87 ppm (multiplet, 2H,

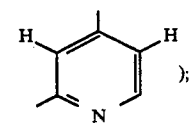

δ=8.82 ppm (multiplet, 2H,

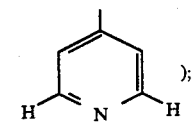

and δ=9.60 ppm (doublet, 1H, —CO—NH—).

EXAMPLE 9

7-Beta-[alpha-syn-methoximino-alpha-(2-amino-thiazol-4-yl)-acetamido]-3-[2-(2-thienyl)-1,3,4-oxadiazol-5-yl-thiomethyl]-3-cephem-4-carboxylic acid The procedure is as according to Example 5, using 663 mg (3.6 mmoles) of 5-mercapto-2-(2-thienyl)-1,3,4-oxadiazole. The reaction solution is warmed to 80° C. for 7.5 hours.

609 mg of the title compound are obtained.

$R_f$: 0.19 (acetone:glacial acetic acid=10:1).

IR (KBr): 1,767 cm$^{-1}$ ($\beta$-lactam band).

NMR (d$_6$-dimethylsulfoxide, 60 MHz): δ=3.89 ppm (singlet, 3H, =N—OCH$_3$); δ=5.17 ppm (doublet, 1H, 6—CH—); δ=5.78 ppm (quartet, 1H, 7—CH—); δ=6.76 ppm (singlet, 1H,

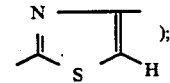

δ=7.18 ppm (2H, —NH$_2$); δ=7.30 ppm (multiplet, 1H,

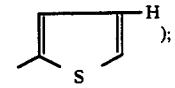

δ=7.88 ppm (multiplet, 2H,

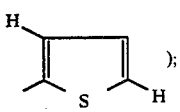

);

and δ=9.62 ppm (doublet, 1H, —CO—NH—).

EXAMPLE 10

7-Beta-[alpha-syn-methoximino-alpha-(2-amino-thiazol-4-yl)-acetamido]-3-(2-amino-1,3,4-thiadiazol-5-yl-thiomethyl)-3-cephem-4-carboxylic acid The procedure is as according to Example 5, using 479 mg (3.6 mmoles) of 2-amino-5-mercapto-1,3,4-thiadiazole. The reaction solution is warmed to 70° C. for 10 hours.

804 mg of the title compound are obtained.

$R_f$: 0.21 (acetone:glacial acetic acid=10:1).

IR (KBr): 1,758 cm$^{-1}$ (β-lactam band).

NMR (d$_6$-dimethylsulfoxide, 60 MHz): δ=3.82 ppm (singlet, 3H, =N—OCH$_3$); δ=5.09 ppm (doublet, 1H, 6—CH—); δ=5.73 ppm (quartet, 1H, 7—CH—); δ=6.73 ppm (singlet, 1H,

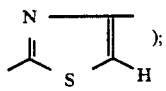

);

δ=6.9 ppm–7.5 ppm (4H, —NH$_2$); and δ=9.53 ppm (doublet, 1H, —CO—NH—).

EXAMPLE 11

7-Beta-[alpha-syn-methoximino-alpha-(2-amino-thiazol-4-yl)-acetamido]-3-[2-(4-pyridyl)-1,3,4-thiadiazol-5-yl-thiomethyl]-3-cephem-4-carboxylic acid 2 g (4 mmoles) of the formate of 7-beta-[alpha-syn-methoximino-alpha-(2-amino-thiazol-4-yl)-acetamido]-cephalosporanic acid are dissolved in 20 ml of water, the equimolar amount of sodium bicarbonate being added. A solution of 1 g (5.2 mmoles) of 5-mercapto-2-(4-pyridyl)-1,3,4-thiadiazole in 20 ml of a water/acetone (1:1) mixture is added and the reaction solution is warmed to 50° C. for 24 hours, the pH value of the solution being kept at 7.5. The acetone is distilled off in vacuo at 40° C., the aqueous solution is filtered and the filtrate is adjusted to the pH value of 2.8 with 1N hydrochloric acid. The precipitate is filtered off, washed with water and dried in vacuo over phosphorus pentoxide: 880 mg of the title compound are obtained:

$R_f$: 0.44 (n-butanol:water:ethanol:glacial acetic acid=5:2:1.5:1.5).

IR (KBr): 1,760 cm$^{-1}$ (β-lactam band).

NMR (d$_6$-dimethylsulfoxide, 60 MHz): δ=3.86 ppm (singlet, 3H, =N—OCH$_3$); δ=6.75 ppm (singlet, 1H,

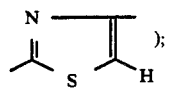

);

δ=7.8 ppm (multiplet, 2H,

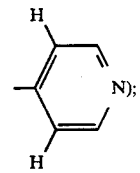

);

and δ=8.77 ppm (multiplet, 2H,

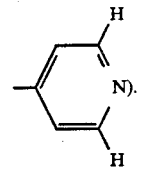

).

EXAMPLE 12

7-Beta-[alpha-syn-methoximino-alpha-(2-amino-thiazol-4-yl)-acetamido]-3-[2-(3-pyridyl)-1,3,4-thiadiazol-5-yl-thiomethyl]-3-cephem-4-carboxylic acid The procedure is as according to Example 11, using 1.0 g (5.2 mmoles) of 5-mercapto-2-(3-pyridyl)-1,3,4-thiadiazole. 400 mg of the title compound are isolated:

$R_f$: 0.44 (n-butanol:water:ethanol:glacial acetic acid=5:2:1.5:1.5).

IR (KBr): 1,760 cm$^{-1}$ (β-lactam band).

NMR (d$_6$-dimethylsulfoxide, 60 MHz): δ=3.9 ppm (singlet, 3H, =N—OCH$_3$); δ=6.75 ppm (singlet, 1H,

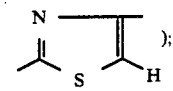

);

δ=8.5–9.1 ppm (multiplet, 4H,

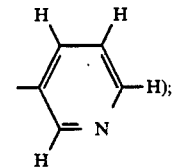

);

and δ=9.6 ppm (doublet, 1H, —CO—NH—).

EXAMPLE 13

7-Beta-[alpha-syn-methoximino-alpha-(2-amino-thiazol-4-yl)-acetamido]-3-(1H-1,3,4-triazol-2-yl-thiomethyl)-3-cephem-4-carboxylic acid 17.2 g (40 mmoles) of 7-beta-[alpha-syn-methoximino-alpha-(2-amino-thiazol-4-yl)-acetamido]-cephalosporanic acid are dissolved in 500 ml of water with the equimolar amount of sodium bicarbonate. A solution of 4.5 g (40 mmoles) of 2-mercapto-1H-1,3,4-triazole and the calculated amount of sodium bicarbonate in 70 ml of water is added and the reaction solution is warmed to 60° C. for 6.5 hours, the pH value of the solution being kept at 6–7 by adding sodium bicarbonate. The reaction solution is lyophilized, the residue is taken up with a little water and the reaction mixture is adjusted to a pH value of 2 with 2N hydrochloric acid. The precipitate is filtered off, washed with water and purified by dissolving in 1N sodium bicarbonate solution and precipitating again with 2N hydrochloric acid. After drying the precipitate over potassium hydroxide at 37° C. in vacuo, 6.58 g of the title compound are isolated:

R<sub>f</sub>: 0.30 (acetone:glacial acetic acid=10:1).

IR (KBr): 1,754 cm$^{-1}$ (β-lactam band).

NMR (d<sub>6</sub>-dimethylsulfoxide, 60 MHz): δ=3.59 ppm (2H, 2—CH<sub>2</sub>—); δ=3.83 ppm (singlet, 3H, =N—OCH<sub>3</sub>); δ=4.03 ppm (AB spectrum, 2H, C3—CH<sub>2</sub>—S—); δ=5.06 ppm (doublet, 1H, 6—CH—); δ=5.68 ppm (quartet, 1H, 7—CH—); δ=6.74 ppm (singlet, 1H,

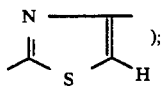

δ=7.14 ppm (2H, —NH<sub>2</sub>); δ=8.30 ppm (singlet, 1H,

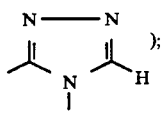

and δ=9.50 ppm (doublet, 1H, —CO—NH—).

EXAMPLE 14

7-Beta-[alpha-syn-methoximino-alpha-(2-amino-thiazol-4-yl)-acetamido]-3-(2-trifluoromethyl-1H-1,3,4-triazol-5-yl-thiomethyl)-3-cephem-4-carboxylic acid The procedure is as according to Example 5, using 493 mg (3.6 mmoles) of 5-mercapto-2-trifluoromethyl-1H-1,3,4-triazole. The reaction solution is warmed to 60° C. for 6.5 hours. 275 mg of the title compound are isolated.

R<sub>f</sub>: 0.58 (ethyl acetate:methanol:glacial acetic acid=20:10:1).

IR (KBr): 1,764 cm$^{-1}$ (β-lactam band).

NMR (d<sub>6</sub>-dimethylsulfoxide, 60 MHz): δ=3.88 ppm (singlet, 3H, =N—OCH<sub>3</sub>); δ=5.14 ppm (doublet, 1H, 6—CH—); δ=5.77 ppm (quartet, 1H, 7—CH—); δ=6.77 ppm (singlet, 1H,

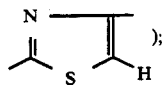

δ=9.59 ppm (doublet, 1H, —CO—NH—).

EXAMPLE 15

7-Beta-[alpha-syn-methoximino-alpha-(2-amino-thiazol-4-yl)-acetamido]-3-(2-acetamido-1H-1,3,4-triazol-5-yl-thiomethyl)-3-cephem-4-carboxylic acid The procedure is as according to Example 6, using 569 mg (3.6 mmoles) of 2-acetamido-5-mercapto-1H-1,3,4-triazole, the reaction solution being warmed to 60° for 9 hours.

459 mg of the title compound are obtained: R<sub>f</sub>: 0.25 (ethyl acetate:methanol:glacial acetic acid=20:10:1)

IR (KBr): 1,763 cm$^{-1}$ (β-lactam band).

NMR (d<sub>6</sub>-dimethylsulfoxide, 60 MHz): δ=2.08 (singlet, 3H, —CO—CH<sub>3</sub>); δ=3.64 (2 —CH<sub>2</sub>—); δ=3.85 ppm (singlet, 3H, =N—OCH<sub>3</sub>); δ=4.05 ppm (2H, —C-3—CH<sub>2</sub>—S—); δ=5.13 ppm (doublet, 1H, 6—CH—);

δ=5.75 ppm (quartet, 1H, 7—CH—); δ=6.77 ppm (singlet, 1H,

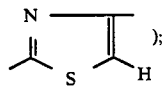

δ=9.60 ppm (doublet, 1H, —CO—NH—); and δ=11.46 ppm (singlet, 1H,

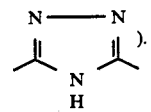

EXAMPLE 16

7-Beta-[alpha-syn-methoximino-alpha-(2-amino-thiazol-4-yl)-acetamido]-3-[2-(2-furyl)-1H-1,3,4-triazol-5-yl-thiomethyl]-3-cephem-4-carboxylic acid The procedure is as according to Example 5, using 603 mg (3.6 mmoles) of 2-(2-furyl)-5-mercapto-1H-1,3,4-triazole. After adding 10 ml of acetone, the reaction solution is warmed to 60° C. for 8 hours. The isolated crude product is purified by trituration in an acetone/water (1:1) mixture.

268 mg of the title compound are obtained:

R<sub>f</sub>: 0.27 (acetone:glacial acetic acid=10:1).

IR (KBr): 1,758 cm$^{-1}$ (β-lactam band).

NMR (d<sub>6</sub>-dimethylsulfoxide, 60 MHz): δ=3.79 ppm (singlet, 3H =N—OCH<sub>3</sub>); δ=4.21 ppm (AB spectrum, 2H, —C3—CH<sub>2</sub>—S—); δ=5.12 ppm (doublet, 1H, 6—CH—); δ=5.73 ppm (quartet, 1H, 7—CH—); δ=6.65 ppm (multiplet, 1H,

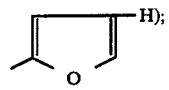

δ=6.72 ppm (singlet, 1H,

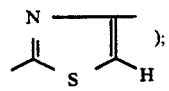

δ=7.10 ppm (multiplet, 3H, —NH<sub>2</sub> and

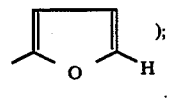

δ=6.84 ppm (multiplet, 1H,

and δ=9.55 ppm (doublet, 1H, —NH—CO—).

EXAMPLE 17

7-Beta-[alpha-syn-methoximino-alpha-(2-amino-thiazol-4-yl)-acetamido]-3-[2-(3-pyridyl)-1H-1,3,4-triazol-5-yl-thiomethyl]-3-cephem-4-carboxylic acid Following the procedure of Example 5, 9.1 g (18.2 mmoles) of 7-beta-[alpha-syn-methoximino-alpha-(2-amino-thiazol-4-yl)-acetamido] cephalosporanic acid and 4.2 g (23.6 mmoles) of 5-mercapto-2-(3-pyridyl)-1H-1,3,4-triazole are dissolved in 300 ml of water with the calculated amount of sodium bicarbonate and the solution is warmed to 55° C. for 2.5 hours. The isolated crude product is purified by trituration in 200 ml of ethyl acetate.

7.0 g of the title compound are obtained.

$R_f$: 0.35 (acetone:glacial acetic acid=10:1).

IR (KBr): 1,758 cm$^{-1}$ ($\beta$-lactam band).

NMR (d$_6$-dimethylsulfoxide, 60 MHz): $\delta$=3.60 ppm (2H, 2—CH$_2$—); $\delta$=3.76 ppm (singlet, 3H, =N—OCH$_3$); $\delta$=4.21 ppm (AB spectrum, 2H, —C-3—CH$_2$—S—); $\delta$=5.05 ppm (doublet, 1H, 6—CH—); $\delta$=5.65 ppm (quartet, 1H, 7—CH—); $\delta$=6.67 ppm (singlet, 1H,

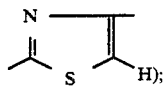

);

$\delta$=7.12 ppm (2H, —NH$_2$); $\delta$=7.46 ppm (multiplet, 1H,

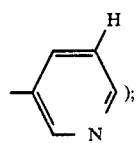

);

$\delta$=8.28 ppm (multiplet, 1H,

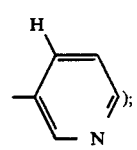

);

$\delta$=8.64 ppm (multiplet, 1H,

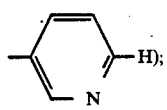

);

$\delta$=9.13 ppm (singlet, 1H,

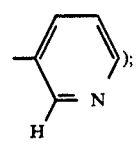

);

and $\delta$=9.54 ppm (doublet, 1H, —CO—NH—).

EXAMPLE 18

7-Beta-[alpha-syn-methoximino-alpha-(2-amino-thiazol-4-yl)-acetamido]-3-[2-(4-pyridyl)-1H-1,3,4-triazol-5-yl-thiomethyl]-3-cephem-4-carboxylic acid The procedure is as according to Example 5, using 641 mg (3.6 mmoles) of 5-mercapto-2-(4-pyridyl)-1H-1,3,4-triazole, the reaction solution being warmed to 60° for 7 hours.

903 mg of the title compound are obtained.

$R_f$: 0.33 (acetone:glacial acetic acid=10:1).

IR (KBr): 1,759 cm$^{-1}$ ($\beta$-lactam band).

NMR (d$_6$-dimethylsulfoxide, 60 MHz): $\delta$=3.71 ppm (2—CH$_2$—); $\delta$=3.87 ppm (singlet, 3H, =N—OCH$_3$); $\delta$=4.33 ppm (AB spectrum, 2H, —C3—CH$_2$—S—); $\delta$=5.13 ppm (doublet, 1H, 6—CH—); $\delta$=5.76 ppm (quartet, 1H, 7—CH—); $\delta$=6.74 ppm (singlet, 1H,

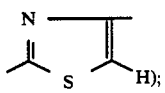

$\delta$=7.19 ppm (2H, —NH$_2$); $\delta$=7.92 ppm (multiplet, 2H,

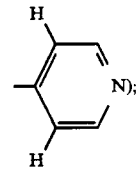

$\delta$=8.71 ppm (multiplet, 2H,

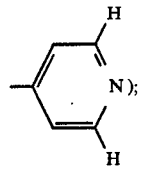

and $\delta$=9.57 ppm (doublet, 1H, —CO—NH—).

EXAMPLE 19

7-Beta-[alpha-syn-methoximino-alpha-(2-amino-thiazol-4-yl)-acetamido]-3-(2-tert.-butyl-1H-1,3,4-triazol-5-yl-thiomethyl)-3-cephem-4-carboxylic acid The procedure is as according to Example 4, using 630 mg (4 mmoles) of 2-tert.-butyl-5-mercapto-1H-1,3,4-triazole. The reaction solution is warmed to 50°-60° C. for 12 hours. 600 mg of the title compound are isolated.

$R_f$: 0.50 (n-butanol:water:ethanol:glacial acetic acid=4:2:1.5:1.5).

IR (KBr): 1,765 cm$^{-1}$ ($\beta$-lactam band).

NMR (d$_6$-dimethylsulfoxide, 60 MHz): $\delta$=1.2 ppm (singlet, 9H, —C(CH$_3$)$_3$); $\delta$=3.8 ppm (singlet, 3H, =N—OCH$_3$); and $\delta$=6.7 ppm (singlet, 1H,

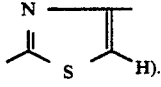

EXAMPLE 20

7-Beta-[alpha-syn-methoximino-alpha-(2-amino-thiazol-4-yl)-acetamido]-3-(1-amino-2-trifluoromethyl-1,3,4-triazol-5-yl-thiomethyl)-3-cephem-4-carboxylic acid 2.5 g (5 mmoles) of a (1:1:1)-adduct of 7-beta-[alpha-syn-methoximino-alpha-(2-amino-thiazol-4-yl)-acetamido]-cephalosporanic acid, water and ethanol and 1.1 g (6 mmoles) of 1-amino-5-mercapto-2-trifluoromethyl-1,3,4-triazole are suspended in 50 ml of water and dissolved by adding the calculated amount of sodium bicarbonate. The reaction solution is warmed to 70° for 8.5 hours, whilst keeping the pH value constant at 6.8-7.0. The solution is allowed to cool to room temperature, covered with a layer of 50 ml of ethyl acetate and adjusted to a pH value of 5.7 with 2N hydrochloric acid. The organic phase is separated off and the aqueous phase is extracted twice more with 30 ml of ethyl acetate each time. The aqueous phase is freed from residual ethyl acetate in vacuo and adjusted to a pH value of 2 at 0° C. with 2N hydrochloric acid. The precipitate is filtered off, washed with water and dried in vacuo over phosphorus pentoxide. 1.1 g of the title compound are obtained.

$R_f$: 0.35 (n-butanol:glacial acetic acid:water=6:2:2).
IR (KBr): 1,765 cm$^{-1}$ ($\beta$-lactam band).
NMR (d$_6$-dimethylsulfoxide, 60 MHz): $\delta$=6.25 ppm (2H, —N—NH$_2$); $\delta$=6.8 ppm (singlet, 1H

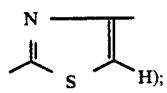

and $\delta$=9.55 ppm (doublet, 1H, —CO—NH—).

EXAMPLE 21

7-Beta-[alpha-syn-methoximino-alpha-(2-amino-thiazol-4-yl)-acetamido]-3-[1-amino-2-(2-hydroxyphenyl)-1,3,4-triazol-5-yl-thiomethyl]-3-cephem-4-carboxylic acid The procedure is as according to Example 20, using 1.25 g (6 mmoles) of 1-amino-2-(2-hydroxyphenyl)-5-mercapto-1,3,4-triazole. The reaction solution is warmed to 70° for 4.5 hours and extracted with ethyl acetate at a pH value of 6.2 and the reaction mixture is adjusted to a pH value of 1.5 with 2N hydrochloric acid. 2.4 g of the title compound are isolated.

$R_f$: 0.28 (n-butanol:glacial acetic acid:water=6:2:2).
IR (KBr): 1,770 cm$^{-1}$ ($\beta$-lactam band).
NMR (d$_6$-dimethylsulfoxide, 60 MHz): $\delta$=6.8 ppm (singlet, 1H,

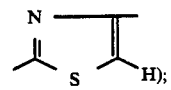

$\delta$=6.9-8.0 ppm (multiplet, 4H,

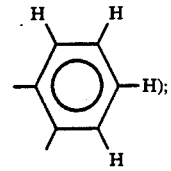

and $\delta$=9.65 ppm (doublet, 1H, —CO—NH—).

EXAMPLE 22

7-Beta-[alpha-syn-methoximino-alpha-(2-amino-thiazol-4-yl)-acetamido]-3-[2-ethyl-1-(1-pyrrolyl)-1,3,4-triazol-5-yl-thiomethyl]-3-cephem-4-carboxylic acid The procedure is as according to Example 20, using 1.15 g (6 mmoles) of 2-ethyl-5-mercapto-1-(1-pyrrolyl)-1,3,4-triazole.

1.2 g of the title compound are obtained.
$R_f$: 0.37 (n-butanol:glacial acetic acid:water=6:2:2).
IR (KBr): 1,770 cm$^{-1}$ ($\beta$-lactam band).
NMR (d$_6$-dimethylsulfoxide, 60 MHz): $\delta$=6.25 ppm (triplet, 2H,

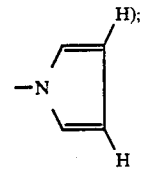

$\delta$=6.7 ppm (singlet, 1H,

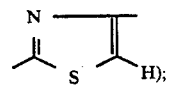

$\delta$=7.1 ppm (triplet, 2H,

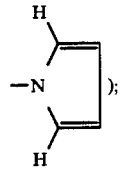

and $\delta$=9.55 ppm (doublet, 1H, —CO—NH—).

EXAMPLE 23

7-Beta-[alpha-syn-methoximino-alpha-(2-amino-thiazol-4-yl)-acetamido]-3-[2-ethyl-1-(2,5-dimethyl-pyrrol-1-yl)-1,3,4-triazol-5-yl-thiomethyl]-3-cephem-4-carboxylic acid The procedure is as according to Example 20, using 1.34 g (6 mmoles) of 2-ethyl-1-(2,5-dimethyl-pyrrol-1-yl)-5-mercapto-1,3,4-triazole.

1.8 g of the title compound are obtained.
$R_f$: 0.43 (n-butanol:glacial acetic acid:water=6:2:2).
IR (KBr): 1,770 cm$^{-1}$ ($\beta$-lactam band).
NMR (d$_6$-dimethylsulfoxide, 60 MHz): $\delta$=5.95 ppm (singlet, 2H,

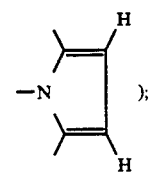

$\delta$=6.75 ppm (singlet, 1H,

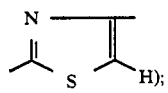

and δ=9.6 ppm (doublet, 1H, —CO—NH—).

EXAMPLE 24

7-Beta-[alpha-syn-methoximino-alpha-(2-amino-thiazol-4-yl)-acetamido]-3-[2-(2-hydroxyphenyl)-1,3,4-oxadiazol-5-yl-thiomethyl]-3-cephem-4-carboxylic acid The procedure is as according to Example 20, using 970 mg (6 mmoles) of 2-(2-hydroxyphenyl)-5-mercapto-1,3,4-oxadiazole.

740 mg of the title compound are obtained.

$R_f$: 0.56 (n-butanol:glacial acetic acid:water=6:2:2).

IR (KBr): 1,760 cm$^{-1}$ (β-lactam band).

NMR (d$_6$-dimethylsulfoxide, 60 MHz): δ=6.8 ppm (singlet, 1H,

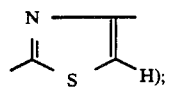

δ=6.8–7.8 ppm (multiplet, 4H, H,

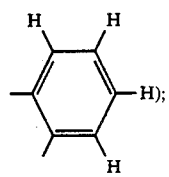

and δ=9.6 ppm (doublet, 1H, —CO—NH—).

EXAMPLE 25

7-Beta-[alpha-syn-methoximino-alpha-(2-amino-thiazol-4-yl)-acetamido]-3-(1-methyl-1,3,4-triazol-5-yl-thiomethyl)-3-cephem-4-carboxylic acid The procedure is as according to Example 5, using 529 mg (4.6 mmoles) of 5-mercapto-1-methyl-1,3,4-triazole. The reaction solution is heated to 50°–60° C. for 5 hours and the isolated crude material is purified by trituration with ethyl acetate.

395 mg of the title compound are obtained.

$R_f$: 0.07 (acetone:glacial acetic acid=10:1).

IR (KBr): 1,752 cm$^{-1}$ (β-lactam band).

NMR (d$_6$-dimethylsulfoxide, 60 MHz): δ=3.54 ppm (singlet, 3H, —N—CH$_3$); δ=3.83 ppm (singlet, 3H, =N—OCH$_3$); δ=5.10 ppm (doublet, 1H, 6—CH—); δ=5.72 ppm (quartet, 1H, 7—CH—); δ=6.72 ppm (singlet, 1H,

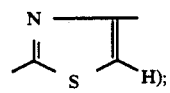

δ=7.16 ppm (2H, —NH$_2$); δ=8.55 ppm (singlet, 1H,

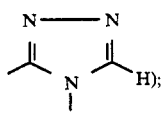

and δ=9.55 ppm (doublet, 1H, —CO—NH—).

EXAMPLE 26

7-Beta-[alpha-syn-methoximino-alpha-(2-amino-thiazol-4-yl)-acetamido]-3-(1-methyl-2-trifluoromethyl-1,3,4-triazol-5-yl-thiomethyl)-3-cephem-4-carboxylic acid The procedure is as according to Example 5, using 732 mg (4 mmoles) of 5-mercapto-1-methyl-2-trifluoromethyl-1,3,4-triazole. The reaction solution is heated to 60° C. for 6.5 hours. 556 mg of the title compound are isolated.

$R_f$: 0.42 (ethyl acetate:isopropanol:water=4:3:2).

IR (KBr): 1,766 cm$^{-1}$ (β-lactam band).

NMR (d$_6$-dimethylsulfoxide, 60 MHz): δ=3.52 ppm (2—CH$_2$—); δ=3.64 ppm (singlet, —N—CH$_3$); δ=3.80 ppm (singlet, =N—OCH$_3$); δ=4.04 ppm (AB spectrum, 2H, —C3—CH$_2$—S—); δ=5.07 ppm (doublet, 1H, 6—CH—); δ=5.72 ppm (quartet, 1H, 7—CH—); δ=6.69 ppm (singlet, 1H,

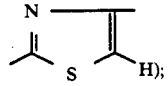

δ=7.13 ppm (2H, —NH$_2$); and δ=9.51 ppm (doublet, 1H, —CO—NH—).

EXAMPLE 27

7-Beta-[alpha-syn-methoximino-alpha-(2-amino-thiazol-4-yl)-acetamido]-3-[1-methyl-2-(3-pyridyl)-1,3,4-triazol-5-yl)-thiomethyl]-3-cephem-4-carboxylic acid The procedure is as according to Example 5, using 663 mg (3.6 mmoles) of 5-mercapto-1-methyl-2-(3-pyridyl)-1,3,4-triazole. The reaction solution is warmed to 60° C. for 9 hours and the isolated crude material is purified by dissolving again in 1N sodium bicarbonate solution and precipitating with 2N hydrochloric acid. 201 mg of the title compound are obtained.

$R_f$: 0.02 (ethyl acetate:methanol:glacial acetic acid=20:10:1).

IR (KBr): 1,762 cm$^{-1}$ (β-lactam band).

NMR (d$_6$-dimethylsulfoxide, 60 MHz): δ=3.61 ppm (singlet, 3H, —N—CH$_3$); δ=3.85 ppm (singlet, 3H, =N—OCH$_3$); δ=5.13 ppm (doublet, 1H, 6—CH—); δ=5.76 ppm (quartet, 1H, 7—CH—); δ=6.76 ppm (singlet, 1H,

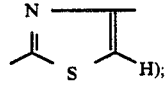

δ=7.57 ppm (multiplet, 1H,

δ=8.14 ppm (multiplet, 1H,

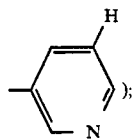

δ=8.80 ppm (multiplet, 2H,

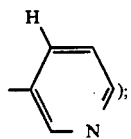

and δ=9.58 ppm (doublet, 1H, —CO—NH—).

EXAMPLE 28

7-Beta-[alpha-syn-methoximino-alpha-(2-amino-thiazol-4-yl)-acetamido]-3-[1-methyl-2-(4-pyridyl)-1,3,4-triazol-5-yl-thio-methyl]-3-cephem-4-carboxylic acid The procedure is as according to Example 5, using 691 mg (3.6 mmoles) of 5-mercapto-1-methyl-2-(4-pyridyl)-1,3,4-triazole. The reaction solution is warmed to 65° C. for 2 hours and the isolated crude material is purified by redissolving in 1N sodium bicarbonate solution and precipitating again with 2N hydrochloric acid.

349 mg of the title compound are obtained.

R$_f$: 0.11 (acetone:glacial acetic acid=10:1).

IR (KBr): 1,766 cm$^{-1}$ (β-lactam band).

NMR (d$_6$-dimethylsulfoxide, 60 MHz): δ=3.66 ppm (singlet, —NCH$_3$); δ=3.87 ppm (singlet, =N—OCH$_3$); δ=5.12 ppm (doublet, 1H, 6—CH—); δ=5.74 ppm (quartet, 1H, 7—CH—); δ=6.74 ppm (singlet, 1H,

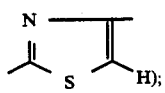

δ=7.18 ppm (2H, —NH$_2$); δ=7.73 ppm (multiplet, 2H,

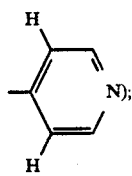

δ=8.77 ppm (multiplet, 2H,

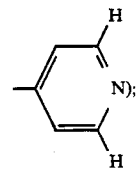

δ=9.61 ppm (doublet, 1H, —CO—NH—).

EXAMPLE 29

7-Beta-[alpha-syn-methoximino-alpha-(2-amino-thiazol-4-yl)-acetamido]-3-[2-(2-furyl)-1-methyl-1,3,4-triazol-5-yl-thio-methyl]-3-cephem-4-carboxylic acid The procedure is as according to Example 5, using 652 mg (3.6 mmoles) of 2-(2-furyl)-5-mercapto-1-methyl-1,3,4-triazole. The reaction solution is warmed to 60°–65° C. for 3.5 hours and the isolated crude product is purified by dissolving in 1N sodium bicarbonate solution, extracting the solution with ethyl acetate and precipitating the product again from the aqueous phase with 2N hydrochloric acid.

486 mg of the title compound are obtained.

R$_f$: 0.29 (aceton:glacial acetic acid=10:1).

IR (KBr): 1,760 cm$^{-1}$ (β-lactam band).

NMR (d$_6$-dimethylsulfoxide, 60 MHz); δ=3.64 ppm (singlet, 3H, —NCH$_3$); δ=3.78 ppm (singlet, 3H, =N—OCH$_3$); δ=5.05 ppm (doublet, 1H, 6—CH—); δ=5.69 ppm (quartet, 1H, 7—CH—); δ=6.68 ppm (singlet, 2H,

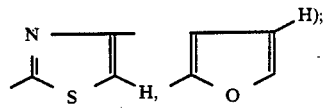

δ=7.08 ppm (multiplet, 3H, —NH$_2$+

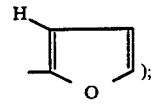

δ=7.86 ppm (multiplet, 1H,

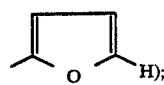

and δ=9.51 ppm (doublet, 1H, —CO—NH—).

EXAMPLE 30

7-Beta-[alpha-syn-methoximino-alpha-(2-amino-thiazol-4-yl)-acetamido]-3-[1-methyl-2-(2-thienyl)-1,3,4-triazol-5-yl-thiomethyl]-3-cephem-4-carboxylic acid The procedure followed is as according to Example 29, using 709 mg (3.6 mmoles) of 5-mercapto-1-methyl-2-(2-thienyl)-1,3,4-triazole.

799 mg of the title compound are obtained.

R$_f$: 0.38 (acetone:glacial acetic acid=10:1).

IR (KBr): 1,763 cm$^{-1}$ (β-lactam band).

NMR (d$_6$-dimethylsulfoxide, 60 MHz): δ=3.69 ppm (singlet, 3H, —NCH$_3$); δ=3.82 ppm (singlet, 3H, =N—OCH$_3$); δ=4.32 ppm (AB spectrum, 2H, —C-3—CH$_2$—S—); δ=5.12 ppm (doublet, 1H, 6—CH—);

δ=5.73 ppm (quartet, 1H, 7—CH—); δ=6.72 ppm (singlet, 1H,

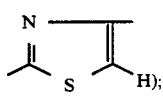

δ=7.19 ppm (multiplet, 3H, —NH₂+

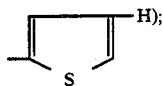

δ=7.63 ppm (multiplet, 1H,

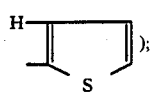

δ=7.78 ppm (multiplet, 1H,

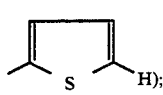

and δ=9.56 ppm (doublet, 1H, —CO—NH—).

EXAMPLE 31

7-Beta-[alpha-syn-methoximino-alpha-(2-amino-thiazol-4-yl)-acetamido]-3-(1,3-dimethyl-1,2,4-triazol-5-yl-thiomethyl)-3-cephem-4-carboxylic acid The procedure followed is as according to Example 5, using 584 mg (4.6 mmoles) of 1,3-dimethyl-5-mercapto-1,2,4-triazole. The reaction solution is warmed to 50°-55° C. for 5.5 hours and the isolated crude product is purified by trituration with ethyl acetate. 542 mg of the title compound are obtained.

R_f: 0.27 (acetone:glacial acetic acid=10:1).
IR (KBr): 1,758 cm⁻¹ (β-lactam band).
NMR (d₆-dimethylsulfoxide, 60 MHz): δ=2.20 ppm (singlet, 3H,

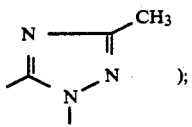

δ=3.66 ppm (singlet, 3H, —NCH₃); δ=3.85 ppm (singlet, 3H, =N—OCH₃); δ=5.10 ppm (doublet, 1H, 6—CH—); δ=5.76 ppm (quartet, 1H, 7—CH—); δ=6.73 ppm (singlet, 1H,

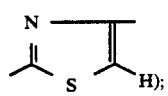

δ=7.17 ppm (2H, —NH₂); and δ=9.53 ppm (doublet, 1H, —CO—NH—).

EXAMPLE 32

7-Beta-[alpha-syn-methoximino-alpha-(2-amino-thiazol-4-yl)-acetamido]-3-[2-(pyrid-2-yl-amino)-1,3,4-thiadiazol-5-yl-thiomethyl]-3-cephem-4-carboxylic acid The procedure followed is as according to Example 2, using 1.05 g (5 mmoles) of 5-mercapto-2-(pyrid-2-yl-amino)-1,3,4-thiadiazole. The reaction solution is warmed to 70° C. for 7 hours and the isolated crude product is extracted with ethanol in a Soxhlet apparatus. 0.63 g of the title compound is obtained as the residue.

R_f: 0.35 (n-butanol:glacial acetic acid:water=6:2:2).
IR (KBr): 1,760 cm⁻¹ (β-lactam band).
NMR (d₆-dimethylsulfoxide, 60 MHz): δ=6.8 ppm (singlet, 1H,

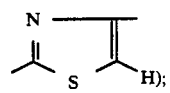

δ=7.75 ppm (triplet, 1H,

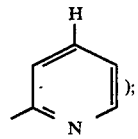

δ=8.3 ppm (doublet, 1H,

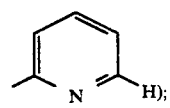

and δ=9.5 ppm (doublet, 1H, —CO—NH—).

EXAMPLE 33

7-Beta-[alpha-syn-methoximino-alpha-(2-amino-thiazol-4-yl)-acetamido]-3-[2-(2-thienyl)-1H-1,3,4-triazol-5-yl-thiomethyl]-3-cephem-4-carboxylic acid The procedure is as according to Example 5, the reaction solution being warmed to 70° C. for 4.5 hours. The resulting crude material is purified by trituration with ethyl acetate.

1.24 g of the title compound are obtained.

R_f: 0.37 (ethyl acetate:methanol:glacial acetic acid=20:10:1).
IR (KBr): 1,761 cm⁻¹ (β-lactam band).
NMR (d₆-dimethylsulfoxide, 60 MHz): δ=3.63 ppm (2—CH₂—); δ=3.81 ppm (singlet, 3H, =N—OCH₃); δ=4.19 ppm (AB spectrum, 2H, —C3—CH₂—S—); δ=5.06 ppm (doublet, 1H, 6—CH—); δ=5.70 ppm (quartet, 1H, 7—CH—); δ=6.68 ppm (singlet, 1H,

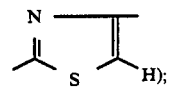

δ=7.14 ppm (triplet, 3H, —NH₂+

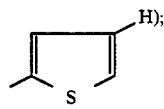

δ=7.62 ppm (doublet, 2H,

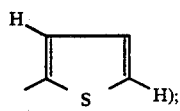

and δ=9.50 ppm (doublet, 1H, —NH—CO—).

EXAMPLE 34

7-Beta-[alpha-syn-methoximino-alpha-(2-amino-thiazol-4-yl)-acetamido]-3-[2-(2-furyl)-1,3,4-oxadiazol-5-yl-thiomethyl]-3-cephem-4-carboxylic acid According to example 5, 1.5 g (3.14 mmoles) of sodium 7-beta-[alpha-syn-methox-imino-alpha-(2-amino-thiazol-4-yl)-acetamido]-cephalosporanate, 1.7 g (10 mmoles) of 2-(2-furyl)-5-mercapto-1,3,4-oxadiazole and the equivalent amount of sodium bicarbonate are dissolved in 50 ml of water and the solution is warmed to 65° C. for 4.5 hours. The resulting crude product is purified by trituration in ethyl acetate and dried at 37° C. in vacuo over potassium hydroxide.

698 mg of the title compound are obtained.

R$_f$: 0.45 (acetone:glacial acetic acid=10:1).

IR (KBr): 1,770 cm$^{-1}$ (β-lactam band).

NMR (d$_6$-dimethylsulfoxide; 60 MHz): δ=3.83 ppm (singlet, 3H, =N—OCH$_3$); δ=5.12 ppm (doublet, 1H, 6—CH—); δ=5.75 ppm (quartet, 1H, 7—CH—); δ=6.73 ppm (singlet, 1H,

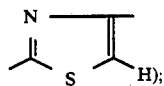

δ=6.78 ppm (triplet, 1H,

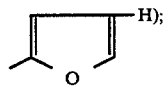

δ=7.16 ppm (2H, —NH$_2$).

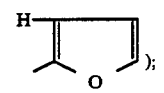

δ=7.28 ppm (doublet, 1H,

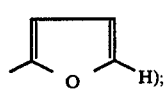

and
δ=8.04 ppm (doublet, 1H, δ=9.56 ppm (doublet, 1H, —NH—CO—).

EXAMPLE 35

7-Beta-[alpha-syn-methoximino-alpha-(2-amino-thiazol-4-yl)-acetamido]-3-(1-ethyl-2-trifluoromethyl-1,3,4-triazol-5-yl-thiomethyl)-3-cephem-4-carboxylic acid According to example 5, 1.5 g (3.14 mmoles) of sodium-7-beta-[alpha-syn-methox-imino-(2-amino-thiazol-4-yl)-acetamido]-cephalosporanate, 709 mg (3.6 mmoles) of 1-ethyl-5-mercapto-2-trifluoromethyl-1,3,4-triazole and the equivalent amount of sodium bicarbonate are dissolved in 50 ml of water and the solution is warmed to 67° C. at a pH value of 7 for 1.5 hours. The resulting crude product is purified by trituration with ethyl acetate and dried at 37° C. in vacuo over potassium hydroxide.

387 mg of the title compound are obtained.

R$_f$: 0.50 (acetone:glacial acetic acid=10:1).

IR (KBr): 1,764 cm$^{-1}$ (β-lactam band).

NMR (d$_6$-dimethylsulfoxide, 60 MHz): δ=1.29 ppm (triplet, 3H, —N—C—CH$_3$); δ=3.85 ppm (singlet, 3H, =N—OCH$_3$); δ=4.14 ppm (quartet, 2H, —N—CH$_2$—C); δ=5.14 ppm (doublet, 1H, 6—CH—); δ=5.76 ppm (quartet, 1H, 7—CH—); δ=6.74 ppm (singlet, 1H,

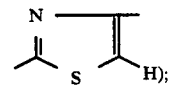

δ=7.18 ppm (2H, —NH$_2$); and δ=9.56 ppm (doublet, 1H, —NH—CO—).

EXAMPLE 36

7-Beta-[alpha-syn-methoximino-alpha-(2-amino-thiazol-4-yl)-acetamido]-3-(2-acetamidomethyl-1,3,4-thiadiazol-5-yl-thio-methyl)-3-cephem-4-carboxylic acid According to example 5, 1.5 g (3.14 mmoles) of sodium-7-beta-[alpha-syn-methoxy-imino-alpha-(2-amino-thiazol-4-yl)-acetamido]-cephalosporanate, 699 mg (3.7 mmoles) of 2-acetamido-methyl-5-mercapto-1,3,4-thiadiazole and the equivalent amount of sodium bicarbonate are dissolved in 50 ml of water and the solution is warmed to 65° C. for 6 hours. The crude product is purified by trituration with ethyl acetate.

0.67 g of the title compound is obtained.

R$_f$: 0.32 (acetone:glacial acetic acid=10:1).

IR (KBr): 1,760 cm$^{-1}$ (β-lactam band).

NMR (d$_6$-dimethylsulfoxide, 60 MHz): δ=1.88 ppm (singlet, 3H, CH$_3$—CO—N); δ=3.86 ppm (singlet, 3H, =N—OCH$_3$); δ=4.56 ppm (doublet, 2H,

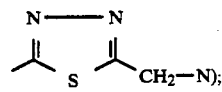

δ=5.12 ppm (doublet, 1H, 6—CH—); δ=5.77 ppm (quartet, 1H, 7—CH—); δ=6.74 ppm (singlet, 1H,

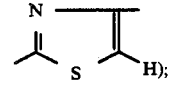

δ=7.12 ppm (2H, —NH$_2$); δ=8.73 ppm (triplet, 1H,

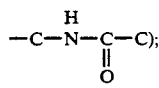

δ=9.56 ppm (doublet, 1H,

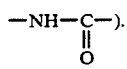

EXAMPLE 37

7-Beta-[alpha-syn-methoximino-alpha-(2-amino-thiazol-4-yl-thio-methyl)-acetamido]-3-[1-ethyl-2-(3-pyridyl)-1,3,4-triazol-5-yl-thiomethyl]-3-cephem-4-carboxylic acid The procedure is as according to Example 5, using 742 mg (3.6 mmoles) of 1-ethyl-5-mercapto-2-(3-pyridyl)-1,3,4-triazole. The reaction solution is warmed to 63° C. for 4.5 hours. 675 mg of the title compound are obtained.

$R_f$: 0.19 (ethyl acetate:methanol:glacial acetic acid=20:10:1).

IR (KBr): 1,765 cm$^{-1}$ ($\beta$-lactam band).

NMR (d$_6$-dimethylsulfoxide; 60 MHz): δ=1.16 ppm (triplet, 3H, N—C—CH$_3$); δ=3.81 ppm (singlet, 3H, =N—O—CH$_3$); δ=3.92 ppm (quartet, 2H, —N—CH$_2$—C); δ=4.14 ppm (AB spectrum, 2H, —C3—CH$_2$—S—); δ=5.12 ppm (doublet, 1H, 6—CH—); δ=5.75 ppm (quartet, 1H, 7—CH—); δ=6.73 ppm (singlet, 1H,

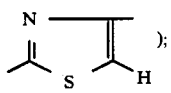

δ=7.16 ppm (singlet, 2H, —NH$_2$); δ=7.57 ppm (multiplet, 1H,

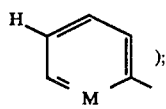

δ=8.08 ppm (multiplet, 1H,

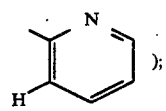

δ=8.76 ppm (multiplet, 2H,

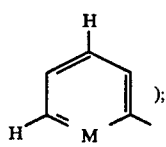

and δ=9.54 ppm (doublet, 1H,

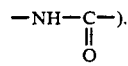

EXAMPLE 38

7-Beta-[alpha-syn-methoximino-alpha-(2-amino-thiazol-4-yl)-acetamido]-3-[1-methyl-2-(4-sulfamoylphenyl)-1,3,4-triazol-5-yl-thiomethyl]-3-cephem-4-carboxylic acid 1.82 g (4 mmoles) of 7-beta-[alpha-syn-methoximino-alpha-(2-amino-thiazol-4-yl)-acetamido]-cephalosporanic acid are dissolved in 30 ml of water, the calculated amount of sodium bicarbonate being added. 1.35 g (5 mmoles) of 1-methyl-5-mercapto-2-(4-sulfamoylphenyl)-1,3,4-triazole and the calculated amount of sodium bicarbonate in 30 ml of water are added and the reaction solution is adjusted to a pH value of 7.0–7.3, if necessary, and warmed to 65° C. for 8 hours. After cooling, it is adjusted to the pH value of 2 with 2N hydrochloric acid and the precipitate is filtered off and washed with ethyl acetate and water. The crude product is purified by trituration with ethanol. 650 mg of the title compound are obtained.

$R_f$: 0.32 (n-butanol:water:ethanol:glacial acetic acid=5:2:1.5:1.5).

IR (KBr): 1,760 cm$^{-1}$ ($\beta$-lactam band).

NMR (d$_6$-dimethylsulfoxide, 60 MHz): δ=3.5 ppm (singlet, 3H, —N—CH$_3$); δ=3.8 ppm (singlet, 3H, =N—OCH$_3$); δ=5.1 ppm (doublet, 1H, 6—CH—); δ=5.7 ppm (quartet, 1H, 7—CH—); δ=6.7 ppm (singlet, 1H,

δ=7.2 ppm (2H, —NH$_2$); δ=7.47 ppm (2H, —SO$_2$NH$_2$); δ=7.93 ppm (multiplet, 4H,

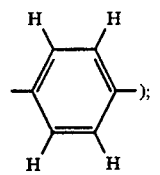

and δ=9.5 ppm (doublet, 1H,

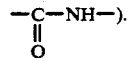

EXAMPLE 39

7-Beta-[alpha-syn-methoximino-alpha-(2-amino-thiazol-4-yl)-acetamido]-3-[1-allyl-2-(4-sulfamoylphenyl)-1,3,4-triazol-5-yl-thiomethyl]-3-cephem-4-carboxylic acid The procedure is as according to Example 38, using 1.48 g (5 mmoles) of 1-allyl-5-mercapto-2-(4-sulfamoylphenyl)-1,3,4-triazole. The reaction solution is warmed to 60° C. for 10 hours. 0.78 g of the title compound is obtained.

R<sub>f</sub>: 0.42 (n-butanol:water:ethanol:glacial acetic acid=5:2:1.5:1.5).

NMR (d<sub>6</sub>-dimethylsulfoxide, 60 MHz): δ=3.83 ppm (singlet, 3H, =N—OCH<sub>3</sub>); δ=4.7–5.2 and 5.5–6.1 ppm (multiplet, 5H, —CH<sub>2</sub>—CH=CH<sub>2</sub>); δ=6.67 ppm (singlet, 1H,

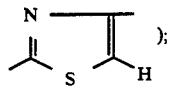

);

δ=7.41 ppm (singlet, 2H, —SO<sub>2</sub>NH<sub>2</sub>); and δ=7.87 ppm (multiplet, 4H,

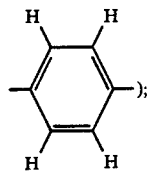

);

EXAMPLE 40

7-Beta-[alpha-syn-methoximino-alpha-(2-amino-thiazol-4-yl)-acetamido]-3-[2-(4-sulfamoylphenyl)-1,3,4-thiadiazol-5-yl-thiomethyl]-3-cephem-4-carboxylic acid The procedure is as according to Example 38, using 1.39 g (5 mmoles) of 5-mercapto-2-(4-sulfamoylphenyl)-1,3,4-thiadiazole. The reaction solution is warmed to 55°–60° C. for 8 hours. The isolated crude product is purified by redissolving in 1N sodium bicarbonate solution and precipitating again with 2N hydrochloric acid. 400 mg of the title compound are obtained.

R<sub>f</sub>: 0.45 (n-butanol:water:ethanol:glacial acetic acid=5:2:1.5:1.5).

IR (KBr): 1,755 cm<sup>−1</sup> (β-lactam band).

NMR (d<sub>6</sub>-dimethylsulfoxide, 60 MHz): δ=3.87 ppm (singlet, 3H, =N—OCH<sub>3</sub>); δ=6.8 ppm (singlet, 1H,

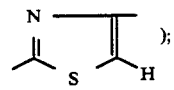

);

δ=7.5 ppm (2H, —SO<sub>2</sub>NH<sub>2</sub>); δ=8.0 ppm (multiplet, 4H,

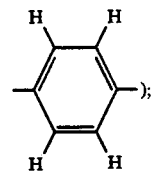

);

and δ=9.5 ppm (doublet, 1H,

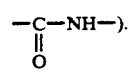

).

EXAMPLE 41

7-Beta-[alpha-syn-methoximino-alpha-(2-amino-thiazol-4-yl)-acetamido]-3-[2-(4-sulfamoylphenyl)-1,3,4-oxadiazol-5-yl-thiomethyl]-3-cephem-4-carboxylic acid The procedure is as according to Example 40, using 1.3 g (5 mmoles) of 5-mercapto-2-(4-sulfamoylphenyl)-1,3,4-oxadiazole. 450 mg of the title compound are obtained.

R<sub>f</sub>: 0.40 (n-butanol:water:ethanol:glacial acetic acid=5:2:1.5:1.5).

IR (KBr): 1,758 cm<sup>−1</sup> (β-lactam band).

NMR (d<sub>6</sub>-dimethylsulfoxide, 60 MHz): δ=3.85 ppm (singlet, 3H, =N—OCH<sub>3</sub>): δ=6.75 ppm (singlet, 1H,

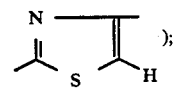

);

δ=7.48 ppm (2H, —SO<sub>2</sub>NH<sub>2</sub>): δ=8.0 ppm (multiplet, 4H,

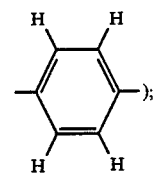

);

and δ=9.45 ppm (doublet, 1H,

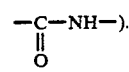

).

EXAMPLE 42

7-β-[α-syn-Methoximino-α-(2-amino-thiazol-4-yl)-acetamido]-3-[4-(3-pyridyl)-thiazol-2-yl-thiomethyl]-3-cephem-4-carboxylic acid 1.82 g (4 mmoles) of 7-β-[α-syn-methoximino-α-(2-amino-thiazol-4-yl)-acetamido]-cephalosporanic acid are dissolved in 50 ml of water together with the equivalent amount of sodium bicarbonate. After adding 0.97 g (5 mmoles) of 4-(3-pyridyl)-2-mercapto-thiazole and the equivalent amount of sodium bicarbonate, the mixture is heated to 65° C. for 6 hours. After cooling, it is filtered and the filtrate is adjusted to pH 3.2 with 2N HCl. The precipitate which has separated is washed with ethyl acetate and with water and dried. After trituration with alcohol, 0.8 g of the title compound remains.

R<sub>f</sub>: 0.49 (n-butanol:water:ethanol:glacial acetic acid=5:2:1.5:1.5).

Melting point: >250°, decomposition.

IR (KBr): 1,768 cm<sup>−1</sup> (β-lactam band).

NMR (d<sub>6</sub>-dimethylsulfoxide): δ=3.83 ppm (N—OCH<sub>3</sub>); 6.67 ppm singlet, thiazole ring proton); 7.25–9.15 ppm (4H, several multiplets, pyridyl ring protons); 8.2 ppm (1H, singlet, mercaptothiazole proton); and 9.5 ppm (doublet, 1H, —CONH—).

EXAMPLE 43

7-β-[α-syn-Methoximino-α-(2-amino-thiazol-4-yl)-acetamido]-3-(5-ethoxycarbonyl-methyl-4-hydroxy-6-methyl-pyrimidin-2-yl-thio-methyl)-3-cephem-4-carboxylic acid 1.82 g (4 mmoles) of 7-β-[α-syn-methoximino-α-(2-amino-thiazol-4-yl)-acetamido]-cephalosporanic acid are dissolved in about 50 ml of water and the solution is neutralized with NaHCO$_3$.

1.15 g (5 mmoles) of ethyl 4-hydroxy-2-mercapto-6-methyl-pyrimidin-5-yl-acetate are dissolved in 50 ml of H$_2$O together with 0.5 g of NaHCO$_3$, a little acetone being added, and the solution is added to the solution of the cephalosporin. The mixture is stirred at 55°-60° for 10 hours. After cooling, it is filtered and the filtrate is subjected to fractional precipitation with 1N HCl. 1.1 g of the product precipitate in the range of pH 5–3.5. 0.85 g of the pure product could be obtained by taking the precipitate up in alcohol and filtering off undissolved substances.

R$_f$: 0.50 (n-butanol:water:ethanol:glacial acetic acid=5:2:1.5:1.5).

Melting point: >220° decomposition.

IR (KBr): 1,765 cm$^{-1}$ (β-lactam band) and 1,720 cm$^{-1}$ (—COOC$_2$H$_5$).

NMR (d$_6$-dimethylsulfoxide): δ=9.6 ppm (1H, doublet, —CONH—), δ=6.76 ppm (1H, singlet, thiazole ring proton); δ=4.1 ppm (2H, quartet, —COO—CH$_2$—); δ=3.9 ppm (3H, singlet, =NOCH$_3$), δ=3.5 ppm (2H, singlet, —CH$_2$—COO—); and β=1.2 ppm (3H, triplet, —COO—CH$_2$—CH$_3$).

EXAMPLE 44

7-β-[α-syn-Methoximino-α-(2-amino-thiazol-4-yl)-acetamido]-3-(4-hydroxy-5-carboxymethyl-6-methyl-pyrimidin-2-yl-thiomethyl)-3-cephem-4-carboxylic acid 1.82 g (4 mmoles) of 7-β-[α-syn-methoximino-α-(2-amino-thiazol-4-yl)-acetamido]-cephalosporanic acid are dissolved in 20 ml of water, the calculated amount of NaHCO$_3$ being added. A solution of 1.1 g (6 mmoles) of [2-mercapto-4-hydroxy-6-methyl-pyrimid-5-yl]-acetic acid and 0.5 g of NaOH in 10 ml of water is added to this solution. The mixture is stirred at 50°-60° C. for 20 hours, the pH being kept at 7–7.5. After cooling, the mixture is filtered and the filtrate is subject to fractional precipitation by acidifying with 1N HCl. 0.7 g of the pure product precipitates out between pH 4.3 and 2.8.

Melting point: 230° (decomposition).

IR (KBr): 1,765 cm$^{-1}$ (β-lactam).

NMR (d$_6$-dimethylsulfoxide): δ=2.2 ppm (3H, singlet, —CH$_3$); δ=3.4 (2H, singlet, —CH$_2$—COO—); δ=3.86 ppm (3H, singlet, =NOCH$_3$); and δ=6.76 ppm (1H, singlet, thiazole ring proton).

EXAMPLE 45

7-β-[α-Methoximino-α-(2-amino-thiazol-4-yl)-acetamido]-3-(4-carboxymethyl-1,3-thiazol-4-yl-thiomethyl)-3-cephem-4-carboxylic acid 2.3 g (5 mmoles) of 7-β-[α-methoximino-α-(2-amino-thiazol-4-yl)-acetamido]-cephalosporanic acid are dissolved in 50 ml of water together with the equivalent amount of sodium bicarbonate. 0.9 g (5 mmoles) of 2-mercapto-1,3-thiazol-4-yl-acetic acid is dissolved in water, 2 equivalents of sodium bicarbonate being added, and the solution is added to the solution of the cephalosporin. After stirring the mixture at pH 7–7.2 and 60° for 7 hours, it is allowed to cool and then acidified to pH 2.5 with 2N hydrochloric acid. The precipitate is filtered off, washed with ethyl acetate and water and dried. 1.39 g of the title compound are obtained.

R$_f$: 0.34 (n-butanol:water:ethanol:glacial acetic acid=5:2:1.5:1.5).

IR (KBr): 1,762 cm$^{-1}$ (β-lactam band).

NMR (d$_6$-dimethylsulfoxide): δ=3.7 ppm (2H, singlet, —CH$_2$—COO—); δ=3.83 ppm (3H, singlet, =NOCH$_3$); δ=5.1 ppm (1H, doublet, 6—CH—); δ=5.73 ppm (1H, quartet, 7—CH—); δ=6.7 ppm (1H, singlet, aminothiazole ring proton); δ=7.17 ppm (2H, —NH$_2$); and δ=7.4 ppm (1H, singlet, mercaptothiazole ring proton); and δ=9.55 ppm (1H, doublet, —NH—CO—).

EXAMPLE 46

7-β-[α-Methoximino-α-(2-amino-thiazol-4-yl)-acetamido]-3-[2-(β-methoxycarbonyl-propionylamido)-thiadiazol-5-yl-thiomethyl]-3-cephem-4-carboxylic acid 1.5 g (3.3 mmoles) of 7-β-[α-syn-methoximino-α-(2-amino-thiazol-4-yl)-acetamido]-cephalosporanic acid are dissolved in 50 ml of water with the equimolar amount of sodium bicarbonate. A solution of 889 mg (3.6 mmoles) of 2-(β-methoxycarbonyl-propionylamido)-5-mercapto-thiadiazole and 303 mg (3.6 mmoles) of sodium bicarbonate in 30 ml of water is added and, if necessary, the pH is adjusted to 6.8 to 7.2 with 1N sodium bicarbonate solution. The reaction solution is heated to 65° C. for 5 hours. After cooling, the solution is covered with a layer of ethyl acetate and acidified to pH 4 with 2N hydrochloric acid. The precipitate is filtered off, washed with little ethyl acetate and thereafter with water and dried at 37° C. in vacuo over potassium hydroxide. 1.1 g of 7-β-[α-methoximino-α-(2-amino-thiazol-4-yl)-acetamido]-3-[2-(β-methoxycarbonyl-propionylamido)-thiadiazol-5-yl-thiomethyl]-3-cephem-4-carboxylic acid are obtained. The substance decomposes at about 100° C.

R$_f$: 0.34 and 0.15 (ethyl acetate:methanol:glacial acetic acid=20:10:1).

The substance is a mixture of the syn-isomer and the anti-isomer in the ratio 2:1.

IR (KBr): 1,762 cm$^{-1}$ (β-lactam band).

NMR (d$_6$-dimethylsulfoxide): δ=2.68 ppm (—CO—CH$_2$—CH$_2$—COOC—); δ=3.44 ppm (2—CH$_2$—); δ=3.62 ppm (—CO—OCH$_3$, singlet); δ=3.81 and 3.95 ppm (singlet, =N—OCH$_3$); δ=4.32 ppm (AB spectrum, 2H, C3—CH$_2$—S—); δ=5.12 ppm (doublet, 1H, 6—CH—); δ=5.74 ppm (quartet, 1H, 7—CH—); δ=6.73 ppm (singlet, syn=CH—thiazole); δ=7.17 ppm (2H, —NH$_2$); δ=7.44 ppm (singlet, anti-=CH—thiazole); and δ=9.56 ppm (doublet, 1H, —CO—NH—).

EXAMPLE 47

7-β-[α-syn-Methoximino-α-(2-amino-thiazol-4-yl)-acetamido]-3-[2-(β-carboxy-propionylamido)-1,3,4-thiadiazol-5-yl-thiomethyl]-3-cephem-4-carboxylic acid 1.5 g (3.3 mmoles) of 7-β-[α-syn-methoximino-α-(2-amino-thiazol-4-yl)-acetamido]-cephalosporanic acid are dissolved in 50 ml of water with the equimolar amount of sodium bicarbonate. A solution of 839 mg (3.6 mmoles) of 5-mercapto-2-(β-carboxypropionylamido)-1,3,4-thiadiazole and 303 mg (3.6 mmoles) of sodium bicarbonate in 30 ml of water is added and, if necessary, the solution is adjusted to pH 6.8 to 7.2 with 1N sodium bicarbonate solution. The reaction solution is heated to 60° C. for 4 hours, whilst stirring and keeping the pH value constant. After cooling, the pH is adjusted to 5 with 2N hydrochloric acid, the mixture is extracted with ethyl acetate and the aqueous phase is acidified to pH 2 with 2N hydrochloric acid. The precipitate is filtered off, washed with water and purified by redissolving in 1N sodium bicarbonate solution and precipitating again with 2N hydrochloric acid. The reaction product is dried at 37° C. in vacuo over potassium hydroxide. 550 mg of 7-β-[α-syn-methoximino-α-(2-amino-thiazol-4-yl)-acetamido]-3-[2-(β-carboxy-propionylamido)-1,3,4-thiadiazol-5-yl-thiomethyl]-3-cephem-4-carboxylic acid are obtained.

R$_f$: 0.37 (acetone:glacial acetic acid=10:1), 0.35 (ethyl acetate:isopropanol:water=20:15:10).

(The substance is still not molten at >290° C.).

IR (KBr): 1,761 cm$^{-1}$ (β-lactam band).

NMR (d$_6$-dimethylsulfoxide): δ=3.82 ppm (singlet, 4H, —N—CO—CH$_2$—CO—); δ=5.08 ppm (doublet, 1H, C—6—H); δ=5.71 ppm (quartet, 1H, C—); δ=6.75 ppm (singlet, 1H, =CH—thiazole); and δ=9.56 ppm (doublet, 1H, —CO—NH—C—7).

EXAMPLE 48

7-δ-[α-syn-Methoximino-α-(2-amino-thiazol-4-yl)-acetamido]-3-[2-(β-carbomethoxypropionylamido)-1H-1,3,4-triazol-5-yl-thiomethyl]-3-cephem-4-carboxylic acid 500 mg (1 mmole) of 7-β-[α-syn-methoximino-α-(2-amino-thiazol-4-yl)-acetamido]-cephalosporanic acid are dissolved in water (20 ml) with the equivalent amount of sodium bicarbonate. After adding 296 mg (1.3 mmoles) of 2-(β-carbomethoxypropionyl-amido)-5-mercapto-1H-1,3,4-triazole and the equivalent amount of sodium bicarbonate, the reaction solution is warmed to 60° C. for 7 hours at a pH value close to the neutral point. The solution is allowed to cool and extracted 2× with 20 ml of ethyl acetate and the aqueous solution is acidified to pH 2 with 2N hydrochloric acid. The precipitate is filtered off, washed with water and dried at 37° C. in vacuo over potassium hydroxide. 150 mg of the title compound are obtained.

R$_f$: 0.39 (acetone:glacial acetic acid=10:1).

IR (KBr): 1,760 cm$^{-1}$ (β-lactam band).

NMR (d$_6$-dimethylsulfoxide; 60 MHz): δ=2.59 ppm (singlet, 4H, —CO—CH$_2$—CO); δ=3.56 ppm (singlet, 3H,

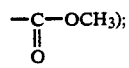

δ=3.88 ppm (singlet, 3H, =N—OCH$_3$); δ=5.13 ppm (doublet, 1H, 6—CH—); δ=5.72 ppm (quartet, 1H, 7—CH—); δ=6.77 ppm (singlet, 1H,

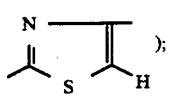

δ=9.57 ppm (doublet, 1H, —CO—NH—); and δ=11.47 ppm (singlet, 1H,

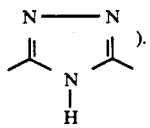

EXAMPLE 49

7-β-[α-syn-Methoximino-α-(2-amino-thiazol-4-yl)-acetamido]-3-(dimethyl-thiophosphothiomethyl)-3-cephem-4-carboxylic acid 1.5 g (3.3 mmoles) of 7-β-[α-syn-methoximino-α-(2-amino-thiazol-4-yl)-acetamido]-cephalosporanic acid are dissolved in 50 ml of water with the equimolar amount of sodium bicarbonate. 598 mg (3.6 mmoles) of sodium dimethyldithiophosphinate monohydrate in 30 ml of water are added and the reaction solution is adjusted to a pH value of 6.8 to 7.2 with 1N sodium bicarbonate solution. The solution is warmed to 60° C. for 4 hours, whilst keeping the pH value constant. After cooling, the pH value is adjusted to 2 with 2N hydrochloric acid and the precipitate is filtered off and washed with water until free from chloride. After drying the precipitate at 37° C. in vacuo over potassium hydroxide, 520 mg of the title compound are obtained.

R$_f$: 0.59 (acetone:glacial acetic acid=10:1).

IR (KBr): 1,769 cm$^{-1}$ (β-lactam band).

NMR (d$_6$-dimethylsulfoxide; 60 MHz): δ=1.97 ppm and 2.18 ppm (doublet, 6H, —P(CH$_3$)$_2$); δ=3.64 ppm (2—CH$_2$—); δ=3.84 ppm (singlet, 3H, =N—OCH$_3$); δ=4.03 ppm (—C3—CH$_2$—S—); δ=5.20 ppm (doublet, 1H, 6—CH—); δ=5.81 ppm (quartet, 1H, 7—CH—); δ=6.79 ppm (singlet, 1H,

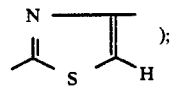

δ=7.25 ppm (2H, —NH$_2$); and δ=9.58 ppm (doublet, 1H, —NH—CO—).

EXAMPLE 50

7-β-[α-syn-Methoximino-α-(2-amino-thiazol-4-yl)-acetamido]-3-[1-carboxymethyl-tetrazol-5-yl-thiomethyl]-3-cephem-4-carboxylic acid The procedure is as according to Example 45, using 0.8 g (5 mmoles) of 1-carboxymethyl-5-mercapto-tetrazole. The reaction solution is heated to 60° C. for 5 hours. 0.95 g of the title compound is isolated.

R$_f$: 0.47 (n-butanol:water:ethanol:glacial acetic acid=5:2:1.5:1.5).

IR (KBr): 1,765 cm$^{-1}$ (β-lactam band).

NMR (d$_6$-dimethylsulfoxide): δ=3.86 ppm (3H, singlet, =NOCH$_3$); δ=5.33 ppm (2H, singlet, —CH$_2$—COO—); δ=6.75 ppm (1H, singlet, thiazole ring proton); δ=7.22 ppm (2H, —NH$_2$); and 9.55 (1H, doublet, —NH—CO—).

EXAMPLE 51

7-β-[α-syn-Ethoximino-(2-aminothiazol-4-yl)-acetamido]-cephalosporanic acid

Stage 1

36.6 g (0.08 mole) of α-syn-ethoximino-α-(2-tritylaminothiazol-4-yl)-acetic acid in 120 ccs of chloroform are added dropwise to a solution, cooled to +5° C., of 9.7 g (0.047 mole) of dicyclohexylcarbodiimide in 70 ccs of chloroform, whilst stirring. After stirring at room temperature for two hours, the dicyclohexylurea which has precipitated is separated off. A solution of 10.9 g (0.04 mole) of 7-aminocephalosporanic acid and 13.8 ccs (0.1 mole) of triethylamine in 160 ccs of methylene chloride is added dropwise to the filtrate, which has been cooled to −10° C., whilst stirring. After stirring the mixture at room temperature for three hours, it is carefully acidified with 100 ccs of 1N hydrochloric acid, unreacted 7-aminocephalosporanic acid is filtered off and the filtrate is washed with water until neutral, dried and concentrated. The residue is dissolved in 100 ccs of dioxan, the solution is filtered with a little charcoal, and 100 ccs of ether and 12.3 ml of diethylamine are then added to the filtrate. On cooling in ice, 18 g of the diethylamine salt of α-syn-ethoximino-α-(2-tritylaminothiazol-4-yl)-acetic acid precipitate in the crystalline form. The diethylamine salt is filtered off, the filtrate is concentrated and the residue is triturated with ether. After filtering off and drying the solid, 24 g of the crude diethylamine salt of the coupling product are obtained. The salt is dissociated in methylene chloride by adding the equivalent amount of 1N hydrochloric acid, the methylene chloride solution is separated off, washed with water until neutral, dried and filtered with charcoal and the filtrate is concentrated. When triturated with ether and dried, the residue gives 14.9 g of 7-β-[α-syn-ethoximino-α-(2-tritylaminothiazol-4-yl)-acetamido]-cephalosporanic acid.

Stage 2

3.56 g (0.005 mole) of 7-β-[α-syn-ethoximino-α-(2-tritylaminothiazol-4-yl)-acetamino]-cephalosporanic acid are dissolved in 20 ccs of 80% strength aqueous formic acid and the solution is stirred at room temperature for 2 hours. After adding 20 ccs of water, the triphenylcarbinol is filtered off, the filtrate is concentrated and the residue is triturated with ether and dried in vacuo over phosphorus pentoxide. 2.0 g of the title compound, which decomposes above 250° C., are obtained.

NMR (ppm, $d_6$-dimethylsulfoxide): 1.23 (3H, t, C—CH$_3$); 2.05 (3H, s, COCH$_3$); 3.55 (2H, s, 2—CH$_2$); 4.10 (2H, q, O—CH$_2$—); 4.83 (2H, q, 3—C—CH$_2$—O); 5.15 (1H, d, 6—H); 5.78 (1H, q, 7—H); 6.72 (1H, s, aromatic H); 7.18 (2H, s, —NH$_2$) and 9.53 (1H, d, —CONH—).

EXAMPLE 52

7-β-[α-Aminothiazol-4-yl)-α-syn-propoximino-acetamido]-cephalosporanic acid

Stage 1

37.7 g (0.08 mole) of α-syn-propoximino-2-(2-tritylaminothiazol-4-yl)-acetic acid were coupled with 10.9 g (0.04 mole) of 7-aminocephalosporanic acid analogously to Example 51, stage 1. 19.8 g of 7-β-[α-syn-propoximino-α-(2-tritylaminothiazol-4-yl)-acetamido]-cephalosporanic acid are obtained.

Stage 2

4.4 g (0.006 mole) of 7-β-[α-syn-propoximino-α-(2-tritylaminothiazol-4-yl)-acetamido]-cephalosporanic acid were detritylated analogously to Example 51, stage 2. 2.3 g of the title compound, which decomposes above 120° C., were obtained.

NMR (ppm, $d_6$-dimethylsulfoxide): 0.9 (3H, t, —CH$_2$—CH$_3$); 1.63 (2H, m, —CH$_2$—CH$_3$); 2.05 (3H, s, CO—CH$_3$); 3.55 (2H, s, 2—CH$_2$); 4.0 (2H, t, O—CH$_2$—CH$_2$—); 4.83 (2H, q, 3—C—CH$_2$—O—); 5.13 (1H, d, 6—H); 5.77 (1H, q, 7—H); 6.70 (1H, aromatic H); 7.17 (2H, s, —NH$_2$); and 9.50 (1H, d, CONH—).

EXAMPLE 53

7-β-[α-(2-Aminothiazol-4-yl)-α-syn-butoximino-acetamido]cephalosporanic acid

Stage 1

31.6 g (0.065 mole) of α-syn-n-2-butoximino-α-(2-tritylamino-thiazol-4-yl)-acetic acid are coupled with 7-aminocephalosporanic acid analogously to Example 51, stage 1. The crude diethylamine salt of the coupling product was dissolved in 500 ccs of water, the solution was filtered with charcoal and the filtrate was acidified with 1N hydrochloric acid and extracted with chloroform. The extract was dried and concentrated and the residue was triturated with ether. 10.5 g of 7-β-[α-syn-butoximino-α-(2-tritylaminothiazol-4-yl)-acetamido]-cephalosporanic acid are obtained.

Stage 2

3.7 g (0.005 mole) of 7-β-[α-syn-n-butoximino-α-(2-tritylamino-thiazol-4-yl)-acetamido]-cephalosporanic acid were detritylated analogously to Example 51, stage 2, to give 1 g of the crystalline title compound, decomposition point >250° C.

NMR (ppm, $d_6$-dimethylsulfoxide): 0.7–1.8 (7H, m, —CH$_2$—CH$_2$—CH$_3$) 2.07 (3H, s, CO—CH$_3$); 3.58 (2H, s, 2—CH$_2$); 4.08 (2H, t, —O—CH$_2$—CH$_2$); 4.88 (2H, q, 3—C—CH$_2$—O—); 5.2 (1H, d, 6—H); 5.83 (1H, q, 7—H); 6.75 (1H, s, aromatic H); 7.23 (2H, s, —NH$_2$); and 9.60 (1H, d, CONH—).

EXAMPLE 54 a)

7β-(2-(2-Chloroacetylamido-thiazol-4-yl)-2-syn-methoximinoacetamido)-cephalosporanic acid 9.6 g of the sodium salt of 7-(2-(2-amino-thiazol-4-yl)-2-methoximino-acetamido)-cephalosporanic acid are suspended in 400 ml of absolute CH$_2$Cl$_2$, the suspension is heated under reflux for 15 minutes and 200 ml of CH$_2$Cl$_2$ are then distilled off under normal pressure.

5 ml of N,O-bis-trimethylsilylacetamide are added to the residue, the mixture is stirred at room temperature for 1½ hours and then cooled to 10° and a solution of 2.5 g of chloroacetyl chloride in 15 ml of CH$_2$Cl$_2$ is added dropwise. On subsequent stirring, a completely clear solution is formed from which, on standing overnight, a solid separates out. The reaction mixture is concentrated, 200 ml of water and 200 ml of diisopropyl ether are added and the pH is adjusted to 1 with 2N HCl. The cephem acid thereby precipitates as a colorless solid.

The residue is dried at 50° under a high vacuum.

Melting point 210°, decomposition.

IR: lactam-carbonyl: 1,772 cm$^{-1}$.

b)

7β-[2-(2-(5-methyl-1,3,4-thiadiazol-2-yl-mercaptoacetamido)-thiazol-4-yl)-2-syn-methoximino-acetamido]-cephalosporanic acid 400 mg of 2-mercapto-5-methyl-1,3,4-thiadiazole and 1.6 g of 7-(2-(2-chloroacetylamido-thiazol-4-yl)-2-syn-methoximino-acetamido)-cephalosporanic acid are added to a solution of 645 mg of NaHCO$_3$ in 8 ml of water and 2 ml of acetone, whereupon a clear solution forms. After some time, a solid begins to separate out. After 3 hours at room temperature, the mixture is acidified to pH 1 with 2N HCl and the solid which has precipitated is isolated. The solid is rinsed with water and finally with ether and the colorless crystals are dried under a high vacuum for 2 hours. The title compound of melting point 196°–201°, decomposition, is isolated.

IR: lactam CO: 1,774 cm$^{-1}$.

EXAMPLE 55

Example 54 b is repeated, with the difference that 3-hydroxy-6-mercapto-pyridazine is employed instead of the thiadiazole.

After the working up described in Example 54 b, 7β-[2-(2-(3-hydroxy-pyridazin-6-yl-thioacetamido)-thiazol-4-yl)-2-syn-methoximinoacetamido]-cephalosporanic acid is obtained as a cream-colored solid of melting point 228°–234°.

IR: lactam CO: 1,780 cm$^{-1}$.

The compounds which follow are prepared and isolated in the manner described in Example 54 b.

| Example No. | R$^1$ | Melting point | IR: LACTAM CO cm$^{-1}$ |
|---|---|---|---|
| 56 | C$_2$H$_5$—(thiadiazole) | 188–194°, decomposition | 1,775 |
| 57 | n-C$_3$H$_7$—(thiadiazole) | 169–173°, decomposition | 1,770 |
| 58 | benzothiazole | 190–194°, decomposition | 1,773 |
| 59 | C$_6$H$_5$—(thiadiazole) | 158–161°, decomposition | 1,778 |
| 60 | N-methyl tetrazole | 110–116°, decomposition | 1,775 |
| 61 | CH$_3$—(thiazole) | 153–157°, decomposition | 1,775 |
| 62 | H—(thiadiazole) | 159–163°, decomposition | 1,768 |
| 63 | H$_2$N—(thiadiazole) | >250°, decomposition | 1,768 |

EXAMPLE 64

4.55 g of 7β-[2-(2-aminothiazol-4-yl)-2-syn-methoximinoacetamido]-cephalosporanic acid are introduced into 35 ml of acetic anhydride and the mixture is stirred at 40°–45° for 3 hours. The reaction mixture is then poured onto ice and the acylated compound which has precipitated is isolated and washed with water, then with ethanol and finally with ether.

7β-[2-(2-Acetamido-thiazol-4-yl)-2-syn-methoximino-acetamido]-cephalosporanic acid is isolated as a colorless solid of melting point 205° (decomposition).

IR: lactam CO: 1,775 cm$^{-1}$.

EXAMPLE 65

9.12 g of phenoxyacetic acid are dissolved in 75 ml of CH$_2$Cl$_2$, 6.18 g of dicyclohexylcarbodiimide are added to the solution, the mixture is stirred for 1 hour and the urea which has formed is filtered off.

4.55 g of 7β-[2-(2-amino-thiazol-4-yl)-2-syn-methox-iminoacetamido]-cephalosporanic acid are added to the phenoxyacetic anhydride solution and the mixture is stirred at 40° for 4 hours and then cooled. The product which has precipitated is stirred thoroughly with 50 ml of methanol in order to remove traces of unreacted material.

The residue is washed with ether and dried. 7β-[2-(2-Phenoxyacetamidothiazol-4-yl)-2-syn-methoximino-acetamido]-cephalosporanic acid is obtained as colorless crystals of melting point 170°-171° (decomposition).

IR: lactam CO at 1,780 cm$^{-1}$.

EXAMPLE 66

464 mg of N-methyl-2-mercapto-tetrazole and 1.18 g of 7β-[2-(2-phenoxyacetamido-thiazol-4-yl)-2-syn-methoximinoacetamido]-cephalosporanic acid are added to a solution of 504 mg of NaHCO$_3$ in 25 ml of water and 5 ml of acetone at room temperature, the solution is warmed to 70° for 5 hours and then filtered and, after cooling, the filtrate is acidified to pH 1 with 2N HCl. 7β-[2-(2-Phenoxyacetamido-thiazol-4-yl)-2-syn-methoximino-acetamido]-3-(1-methyltetrazol-2-yl-thiomethyl)-3-cephem-4-carboxylic acid is thereby obtained as a cream-colored solid of melting point 175°-180° (decomposition).

IR: lactam CO: 1,770 cm$^{-1}$.

EXAMPLE 67

By a procedure analogous to that indicated in the above example, when 3-hydroxy-6-mercaptopyridazine is employed, 7β-[2-(2-phenoxyacetamido-thiazol-4-yl)-2-syn-methoximino-acetamido]-3-(3-hydroxy-pyridazin-6-yl-thiomethyl)-3-cephem-4-carboxylic acid is obtained as a cream-colored solid of melting point 160°-165°.

IR: lactam CO: 1,770 cm$^{-1}$.

EXAMPLE 68

By a procedure analogous to that indicated in Example 66, when 4 methyl-2-mercapto-1,3-thiazole is employed instead of N-methyl-2-mercaptotetrazole, 7β-[2-(2-phenoxyacetamidothiazol-4-yl)-2-syn-methoximino-acetamido]-3-(4-methyl-1,3-thiazol-2-yl-thiomethyl)-3-cephem-4-carboxylic acid is obtained as a beige-colored solid of melting point 180°-185° (decomposition).

EXAMPLE 69

By a procedure analogous to that indicated in Example 66, when 2-mercapto-5-methyl-1,3,4-thiadiazole is employed, 7β-[2-(2-phenoxyacetamido-thiazol-4-yl)-2-syn-methoximino-acetamido]-3-(5-methyl-1,3,4-thiadiazol-2-yl-thiomethyl)-3-cephem-4-carboxylic acid is obtained as a cream-colored solid of melting point 163°-165°.

IR: lactam CO: 1,771 cm$^{-1}$.

EXAMPLE 70

Benzhydryl
7β[2-(2-aminothiazol-4-yl)-2-syn-methoximino-acetamido]-cephalosporanate A freshly prepared solution of 2.00 g of diphenyldiazomethane (prepared from benzophenone hydrazone by oxidation with HgO in the presence of Na$_2$SO$_4$ and saturated methanolic KOH) in 10 ml of ethyl acetate is added to a solution of 2.27 g of 7β[2-(2-aminothiazol-4-yl)-2-syn-methoximino-acetamido]-cephalosporanic acid in a mixture of 50 ml of methanol and 15 ml of tetrahydrofuran, at 10°, whilst stirring. The reaction solution slowly decolorizes. After the decolorization, the reaction mixture is concentrated to dryness, the residue is stirred with aqueous bicarbonate, filtered off and taken up in ethyl acetate, the ethyl acetate solution is dried and substantially concentrated and the residue is triturated with ether.

The title compound is isolated as a colorless solid of melting point 135°-142° (decomposition).

EXAMPLE 71

Pivaloyloxymethyl
7β[2-(2-aminothiazol-4-yl)-2-syn-methoximinoacetamido]-cephalosporanate 100 ml of absolute methylene chloride are poured over 4.8 g of the sodium salt of 7β[2-(2-aminothiazol-4-yl)-2-syn-methoximino-acetamido]-cephalosporanic acid in order to remove adhering traces of water and the methylene chloride is substantially distilled off under normal pressure. The residue is dissolved in 40 ml of dimethylformamide, 2.3 g of chloromethyl pivalate are added and the mixture is heated to 45°. After 4 hours, the solvent was substantially removed, the residue was introduced into water, the solid which had precipitated was dissolved in ethyl acetate, the ethyl acetate solution was dried over sodium sulfate, active charcoal was added and the mixture was filtered. After evaporating off ethyl acetate from the filtrate, the residue was triturated with hexane. A cream-colored solid of melting point 105°-108° (decomposition) is isolated.

EXAMPLE 72

Carboxymethyl
7β[2-(2-aminothiazol-4-yl)-2-syn-methoximinoacetamido]-cephalosporanate 0.67 g of triethylamine and 0.71 g of trimethylchlorosilane are added to 0.9 g of bromoacetic acid in 10 ml of absolute dimethylformamide at 0°. The reaction mixture was subsequently stirred for 1 hour and 2.4 g of freshly dried sodium 7β[2-(2-amino-thiazol-4-yl)-2-methoximinoacetamido]-cephalosporanate were then added. After 6 hours at 50°, the reaction mixture was filtered, the sodium bromide which had precipitated was removed and the filtrate was concentrated to dryness.

Water was added to the residue and the residue was dissolved with bicarbonate, the solution was filtered, with the addition of active charcoal, and the filtrate was carefully acidified to pH 1.5 with 2N HCl. The title compound is obtained as colorless crystals of melting point 163°-166° (decomposition).

EXAMPLE 73

Ethoxycarbonylmethyl
7β[2-(2-aminothiazol-4-yl)-2-syn-methoximinoacetamido]-cephalosporanate 1.67 g of ethyl bromoacetate are added to a solution of 2.4 g of sodium 7β[2-(2-aminothiazol-4-yl)-2-syn-methoximinoacetamido]-cephalosporanate in 40 ml of dimethylformamide and the mixture is stirred at 55° for 4 hours. The volatile constituents are then removed in vacuo and the oil which remains is dissolved in ethyl acetate. The solution is washed twice with dilute NaHCO$_3$ solution and then three times with water and dried with Na$_2$SO$_4$, active charcoal is added, the solution is filtered and the residue is concentrated. Ether is poured over the oil which remains, whereupon the title compound separates out as a cream-colored solid. Melting point 98°–102° (decomposition).

EXAMPLE 74

(bis-Ethoxycarbonyl)-methyl 7β[2-(2-aminothiazol-4-yl)-2-syn-methoximinoacetamido]-cephalosporanate If diethyl bromomalonate is used instead of the ethyl bromoacetate in Example 73 indicated above, a completely analogous working up of the reaction mixture gives the title compound as a cream-colored solid of melting point 90°–95°, decomposition.

EXAMPLE 75

(3-Sulfamoyl-4-chlorobenzoyl)-methyl 7β[2-(2-aminothiazol-4-yl)-2-syn-methoximinoacetamido]-cephalosporanate 1.45 g of 3-sulfamoyl-4-chloro-ω-bromoacetophenone were added to a solution of 2.4 g of the sodium salt of 7β[2-(2-aminothiazol-4-yl)-2-syn-methoximinoacetamido]-cephalosporanate in 45 ml of dimethylformamide and the reaction mixture was stirred at 50° for 4½ hours. The solvent was then removed, the residue was stirred with dilute NaHCO$_3$ solution for ½ hour and the cream-colored powder which remained was isolated. The solid was washed with water, ether and then with hot isopropanol. The title compound is obtained as a cream-colored solid of melting point 147°–151°, decomposition.

EXAMPLE 76

Tert.-butyl 7-β-[2-aminothiazol-4-yl)-2-syn-methoximinoacetamido]-cephalosporanate a) 21.5 g of 2-syn-methoximino-2-(2-tritylaminothiazol-4-yl)-acetic acid (82% pure) are dried azeotropically with toluene at 40°–50° C. The dry residue is dissolved in 100 ml of methylene chloride, and a solution of 4.12 g of dicyclohexylcarbodiimide in 50 ml of methylene chloride is added dropwise at 0°–5° C. The mixture is subsequently stirred at 5° C. for 40 minutes and at room temperature for 20 minutes and the dicyclohexylurea which has precipitated is separated off. A solution of 6.54 g of tert.-butyl 7-aminocephalosporanate in 20 ml of methylene chloride is added dropwise to the clear filtrate. The mixture is further stirred overnight at room temperature and concentrated in vacuo, the residue is taken up in a little chloroform and the chloroform solution is washed with NaHCO$_3$ solution and water and, after drying, is again concentrated. The residue is dissolved in acetone, the solution is filtered with charcoal and, after substantially concentrating the filtrate, the product is precipitated with diisopropyl ether. Tert.-butyl 7-β-[2-syn-methoximino-2-(2-tritylaminothiazol-4-yl)-acetamido]-cephalosporanate of melting point 145°–148° C. is obtained.

IR (KBr): 1,780 cm$^{-1}$ (β-lactam band).

NMR (ppm, CDCl$_3$): 1.55 (9H, s, C(CH$_3$)$_3$); 4.06 (3H, s, =NOCH$_3$) and 6.73 ppm (1H, s, thiazole ring proton).

b) 7.25 g of tert.-butyl 7-β-[2-syn-methoximino-2-(2-trithylaminothiazol-4-yl)-acetamido]-cephalosporanate are stirred in 145 ml of 80% strength formic acid at 30° C. for 2 hours. Thereafter, 85 ml of H$_2$O are added, the triphenylcarbinol is filtered off and the filtrate is adjusted to pH 6 and extracted with chloroform. After drying, the chloroform solution is concentrated and the residue is triturated with diisopropyl ether and filtered off. The title compound, of melting point 154°–156° C., is obtained as an almost colorless solid.

IR (KBr): 1,775 cm$^{-1}$ (β-lactam band).

NMR (ppm, CDCl$_3$): 1.56 (9H, s, C(CH$_3$)$_3$); 4.06 (3H, s, =NOCH$_3$) and 6.86 ppm (1H, s, thiazole ring proton).

EXAMPLE 77

Isopropyl 7β[2-(2-aminothiazol-4-yl)-2-syn-methoximinoacetamido]-cephalosporanate 1.23 g of isopropyl bromide are added to a solution of 2.4 g of the sodium salt of 7β[2-(2-aminothiazol-4-yl)-2-syn-methoximino-acetamido]-cephalosporanate in 45 ml of dimethylformamide at 50°, the mixture is stirred at 50° for 5 hours under nitrogen and the volatile constituents are then removed in vacuo. Water is added to the residue, the pH is brought to 7.5 with triethylamine and the solid which remains is filtered off, extracted by stirring with water and then with diisopropyl ether and dried. The title compound is obtained as a beige-colored solid of melting point 142°–146° (decomposition).

EXAMPLE 78

(2-Oxo-3-syn-methoximino-3-carboxyethyl)-propyl 7β[2-(2-aminothiazol-4-yl)-2-syn-methoximinoacetamido]-cephalosporanate A solution of 1.40 g of 3-syn-methoximino-3-carboxyethyl-1-bromoacetone in 7 ml of dimethylformamide is added to a solution of 2.4 g of the sodium salt of 7β[2-(2-aminothiazol-4-yl)-2-syn-methoximinoacetamido]-cephalosporanate in 45 ml of dimethylformamide at 10°, the mixture is stirred at 15° for 3 hours, the volatile constituents are then removed in vacuo, the oily residue is taken up in ethyl acetate, the organic phase is washed with aqueous NaHCO$_3$, dried over Na$_2$SO$_4$ and substantially concentrated and the oily product is allowed to run into diisopropyl ether.

The title compound is formed as a cream-colored solid of melting point 112°–116°, decomposition.

EXAMPLE 79

Methyl 7β[2-(2-aminothiazol-4-yl)-2-syn-methoximinoacetamido]-cephalosporanate 210 mg of sodium acetate are added to a suspension of 1.14 g of 7β[2-(2-aminothiazol-4-yl)-2-syn-methoximinoacetamido]-cephalosporanate in 5 ml of methanol, a clear solution being formed. 300 mg of methanesulfonyl chloride are added to this solution, crystals separating out on subsequent stirring of the mixture.

After 2 hours, the reaction mixture was filtered, the filtrate was concentrated to dryness and water was added to the oil which remained. After a short time, the solid which had separated out became crystalline. The title compound is isolated as colorless crystals of melting point 160°–163°.

EXAMPLE 80

Benzhydryl 7β[2-(2-methylsulfonylamido-thiazol-4-yl)-2-syn-methoximinoacetamido]-cephalosporanate a) 11 g of triethylamine and a solution of 12.6 g of methanesulfonyl chloride in 50 ml of methylene chloride are added to a solution of 22.9 g of ethyl 2-(2-amino-thiazol-4-yl)-2-syn-methoximinoacetate in 400 ml of methylene chloride and the mixture is heated to the boil for 1 hour. It is then washed with water, the organic phase is concentrated, the residue is triturated with ether and the resulting solid product is recrystallized from methanol. Ethyl 2-(2-methylsulfonylamido-thiazol-4-yl)-2-syn-methoximinoacetate of melting point 200°-202° is obtained.

b) 10.35 g of ethyl 2-(2-methylsulfonylamido-thiazol-4-yl)-2-syn-methoximino-acetate are heated in 100 ml of 1N sodium hydroxide solution on a steam bath for 30 minutes. The resulting clear solution is cooled and acidified to pH 1 with concentrated hydrochloric acid. The 2-(2-methylsulfonylamido-thiazol-4-yl)-2-syn-methoximinoacetic acid which has precipitated is isolated and dried. Melting point 177°, decomposition.

c) 4.53 g of dicyclohexylcarbodiimide and then 8.76 g of benzhydryl 7-amino-cephalosporanate are added to a solution of 5.58 g of 2-(2-methylsulfonylamido-thiazol-4-yl)-2-syn-methoximinoacetic acid in 100 ml of dimethylformamide. The mixture is stirred at room temperature for 6 hours, the urea which has precipitated is then filtered off, the filtrate is concentrated and 500 ml of water are added to the residue. A solid thereby precipitates, which is washed with water and then taken up in methylene chloride. The organic phase is dried over Na₂SO₄ and concentrated and the residue is triturated with ether. Benzhydryl 7-[2-(2-methyl-sulfonylamido-thiazol-4-yl)-2-syn-methoximino-acetamido]-cephalosporanate is isolated as an amorphous solid of melting point 160°-165°, decomposition.

EXAMPLE 81

7β-[2-(2-Methylsulfonylamido-thiazol-4-yl)-2-syn-methoximinoacetamido]-cephalosporanic acid 15 g of the benzhydryl ester prepared by the above process are suspended in 45 ml of anisole, 30 ml of CF₃COOH are added and the mixture is stirred for 2 hours.

The volatile constituents are then removed in vacuo and the residue is taken up in ethyl acetate, and reconcentrated, several times.

Finally, ether is added to the oil which remains, whereupon the oil slowly crystallizes. The title compound is isolated as almost colorless crystals of melting point 155°-158°, decomposition.

The free acid can be converted in methanol to the sodium salt of melting point 205°, decomposition, using sodium acetate.

EXAMPLE 82

7-β-[2-(2-Amino-thiazol-4-yl)-2-syn-methoximino-acetamido]-3-[2-(pyrid-3-yl)-1,3,4-oxadiazol-5-yl-thiomethyl]-ceph-3-em-4-carboxylic acid The procedure is as according to Example 5, using 644 mg (3.6 mmoles) of 5-mercapto-2-(pyrid-3-yl)-1,3,4-oxadiazole. The reaction solution is warmed to 60° C. for 4 hours. 784 mg of the title compound are isolated.

$R_f$: 0.33 (acetone:glacial acetic acid=10:1).
IR (KBr): 1,764 cm⁻¹ (β-lactam band).
NMR (d₆-DMSO, 60 MHz): δ=3.81 ppm (s, 3H, =N—OCH₃), δ=4.33 ppm (AB, 2H, 3—CH₂—S—), δ=5.11 ppm (d, 1H, 6—CH—), δ=5.74 ppm (q, 1H, 7—CH—), δ=6.72 ppm (s, 1H,

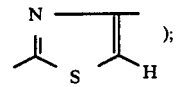

);

δ=7.14 ppm (s, 2H, —NH₂), δ=7.59 ppm (m, 1H,

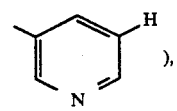

),

δ=8.23 ppm (m, 1H,

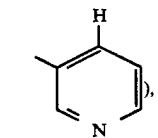

),

δ=8.74 ppm (m, 1H,

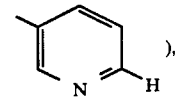

),

δ=9.04 ppm (m, 1H,

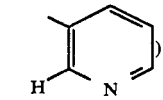

)

and δ=9.54 ppm (d, 1H,

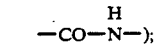

);

EXAMPLE 83

7-β-[2-(2-Amino-thiazol-4-yl)-2-syn-methoximino-acetamido]-3-[2-(pyrid-2-yl)-1,3,4-oxadiazol-5-yl-thiomethyl]-ceph-3-em-4-carboxylic acid The procedure is as according to Example 5, using 644 mg (3.6 mmoles) of 5-mercapto-2-(pyrid-2-yl)-1,3,4-oxa-diazole. The reaction solution is warmed to 55° C. for 3 hours. The crude product isolated is purified by trituration with ethyl acetate. 384 mg of the title compound are obtained.

$R_f$: 0.44 (acetone:glacial acetic acid=10:1).
IR (KBr): 1,760 cm⁻¹ (β-lactam band).
NMR (d₆-DMSO, 60 MHz) δ=3.52 ppm (AB, 2—CH₂—), δ=3.76 ppm (s, 3H, =N—OCH₃), δ=4.36 ppm (AB, 3—CH₂—S), δ=5.12 ppm (d, 1H, 6—CH—), δ=5.76 ppm (q, 1H, 7—CH—), δ=6.73 ppm (s, 1H,

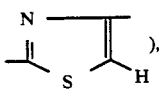

δ=7.16 ppm (s, 2H, —NH₂), δ=7.63 ppm (m, 1H,

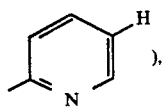

δ=8.04 ppm (m, 2H,

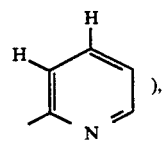

δ=8.74 ppm (m, 1H,

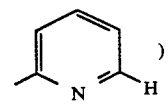

and δ=9.58 ppm (d, 1H, —CO—NH—).

EXAMPLE 84

7-β-[2-(2-Amino-thiazol-4-yl)-2-syn-methoximino-acetamido]-3-(2-amino-1H-1,3,4-triazol-5-yl-thiomethyl)-ceph-3-em-4-carboxylic acid The procedure is as according to Example 5, using 418 mg (3.6 mmoles) of 2-amino-5-mercapto-1H-1,3,4-triazole. The reaction solution is warmed to 60° C. for 4 hours. The crude product isolated is purified by trituration with ethyl acetate. 430 mg of the title compound are obtained.

R_f: 0.41 (acetone:glacial acetic acid=10:1).

IR (KBr): 1,756 cm⁻¹ (β-lactam band).

NMR (d₆-DMSO, 60 MHz): δ=3.63 ppm (AB, 2—CH₂—), δ=3.83 ppm (s, 3H, =N—OCH₃), δ=4.00 ppm (AB, 3—CH₂—S—), δ=5.09 ppm (d, 1H, 6—CH—), δ=5.73 ppm (q, 1H, 7—CH—), δ=6.73 ppm (s, 1H,

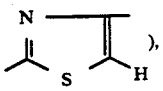

δ=7.17 ppm (s, 2H,

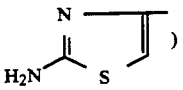

and δ=9.56 ppm (d, 1H, —CO—NH—).

EXAMPLE 85

7-β-[2-(2-Amino-thiazol-4-yl)-2-syn-methoximino-acetamido]-3-(4,6-diamino-pyrimidin-2-yl-thiomethyl)-ceph-3-em-4-carboxylic acid The procedure is as according to Example 5, using 511 mg (3.6 mmoles) of 4,6-diamino-2-mercapto-pyrimidine. The reaction solution is warmed to 65° C. for 2 hours and the crude product isolated is purified by trituration with ethyl acetate. 1.14 g of the title compound are obtained.

R_f: 0.43 (acetone:glacial acetic acid=10:1).

IR (KBr): 1,754 cm⁻¹ (β-lactam band).

NMR (d₆-DMSO, 60 MHz): δ=3.56 ppm (AB, 2—CH₂—), δ=3.79 ppm (s, 3H, =N—OCH₃), δ=4.15 ppm (AB, 2H, 3—CH₂—S—), δ=5.07 ppm (m, 2H, 6—CH—+

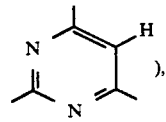

δ=5.65 ppm (q, 1H, 7—CH—), δ=6.06+6.67 ppm (2 s, 4H,

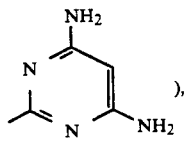

δ=6.79 ppm (s, 1H,

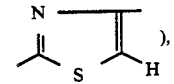

δ=7.12 ppm (s, 2H,

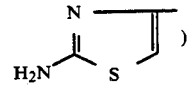

and δ=9.48 ppm (d, 1H, —CO—NH—).

EXAMPLE 86

Sodium 7-β-[2-(2-amino-thiazol-4-yl)-2-syn-methoximino-acetamido]-3-(4,6-diamino-pyrimidin-2-yl-thiomethyl)-ceph-3-em-4-carboxylate dihydrate 1 g of the compound obtained according to Example 85 is suspended in a little water. The mixture is rapidly adjusted to a pH value of 7 with 1N sodium hydroxide solution, whilst stirring and cooling with ice, and filtered and the filtrate is freeze-dried. 678 mg of the title compound are obtained.

Elementary analysis for C₁₈H₁₈N₉O₅S₃Na.2H₂O Calculated: C 36.3; H 3.7; N 21.2; O 18.8; S 16.1; Na 3.9. Found: C 34.4; H 3.7; N 20.8; O 16.8; S 11.6; Na 3.6.

EXAMPLE 87

7-β-[2-(2-Amino-thiazol-4-yl)-2-syn-methoximino-acetamido]-3-[1-(β-carboxyethyl)-tetrazol-5-yl-thiomethyl]-ceph-3-em-4-carboxylic acid The procedure is as according to Example 5, using 625 mg (3.6 mmoles) of 1-(β-carboxyethyl)-5-mercapto-tetrazole. The reaction solution is warmed to 60° C. for 3.5 hours and the crude product isolated is purified by trituration with ethyl acetate. 421 mg of the title compound are obtained.

$R_f$: 0.43 (acetone:glacial acetic acid = 10:1).

IR (KBr): 1,760 cm$^{-1}$ (β-lactam band).

NMR (d$_6$-DMSO, 60 MHz): δ=2.89 ppm (t, 2H, —C—CH$_2$—COO—), δ=3.64 ppm (AB, 2—CH$_2$—), δ=3.82 ppm (s, 3H, =N—OCH$_3$), δ=4.23 ppm (AB, 3—CH$_2$—S—), δ=4.38 ppm (t, N—CH$_2$—C—COO—), δ=5.06 ppm (d, 1H, 6—CH—), δ=5.72 ppm (q, 1H, 7—CH—), δ=6.70 ppm (s, 1H,

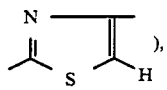),

δ=7.12 ppm (s, 2H, —NH$_2$) and δ=9.52 ppm (d, 1H, —CO—NH—).

EXAMPLE 88

7-β-[2-(2-Amino-thiazol-4-yl)-2-syn-methoximino-acetamido]-3-[1-ethyl-2-(pyrid-4-yl)-1,3,4-triazol-5-yl-thiomethyl]-ceph-em-4-carboxylic acid The procedure is as according to Example 5, using 742 mg (3.6 mmoles) of 1-ethyl-5-mercapto-2-(pyrid-4-yl)-1,3,4-triazole. The reaction solution is warmed to 60° C. for 2 hours and the crude product isolated is purified by trituration with ethyl acetate. 226 mg of the title compound are obtained.

$R_f$: 0.20 (acetone:glacial acetic acid = 10:1).

IR (KBr): 1,767 cm$^{-1}$ (β-lactam band).

NMR (d$_6$-DMSO, 60 MHz): δ=1.22 ppm (t, 3H, N—C—CH$_3$), δ=3.81 ppm (s, 3H, =N—OCH$_3$), δ=5.09 ppm (d, 1H, 6—CH—), δ=5.72 ppm (q, 1H, 7—CH—), δ=6.71 ppm (s, 1H,

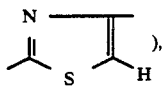),

δ=7.12 ppm (s, 2H, —NH$_2$), δ=7.67 ppm (m, 2H,

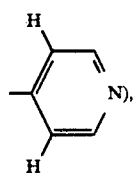),

δ=8.75 ppm (m, 2H,

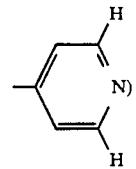)

and δ=9.55 ppm (d, 1H, —CO—NH—

EXAMPLE 89

7-β-[2-(2-Amino-thiazol-4-yl)-2-syn-methoximino-acetamido]-3-(5,6-diamino-4-hydroxy-pyrimidin-2-yl-thiomethyl)-ceph-3-em-4-carboxylic acid The procedure is as according to Example 5, using 568 mg (3.6 mmoles) of 5,6-diamino-4-hydroxy-2-mercaptopyrimidine. The reaction solution is warmed to 55° C. for 7.5 hours and the crude product isolated is purified by trituration with ethyl acetate. 857 mg of the title compound are obtained.

$R_f$: 0.06 (acetone:glacial acetic acid = 10:1).

IR (KBr): 1,752 cm$^{-1}$ (β-lactam band).

NMR (d$_6$-DMSO, 60 MHz): δ=3.80 ppm (s, 3H, =N—OCH$_3$), δ=5.09 ppm (d, 1H, 6—CH—), δ=5.68 ppm (q, 1H, 7—CH—), δ=6.71 ppm (s, 1H,

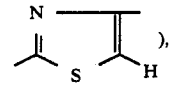),

δ=7.15 ppm (s, 2H,

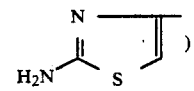)

and δ=9.53 ppm (q, 1H, —CO—NH—).

EXAMPLE 90

7-β-[2-(2-Amino-thiazol-4-yl)-2-syn-methoximino-acetamido]-3-(4-amino-6-hydroxy-pyrimidin-2-yl-thiomethyl)-ceph-3-em-4-carboxylic acid The procedure is as according to Example 5, using 580 mg (3.6 mmoles) of 4-amino-6-hydroxy-2-mercaptopyrimidine. The reaction solution is warmed to 60° C. for 5 hours and the crude product isolated is purified by trituration with ethyl acetate. 907 mg of the title compound are obtained.

$R_f$: 0.23 (acetone:glacial acetic acid = 10:1).

IR (KBr): 1,759 cm$^{-1}$ (β-lactam band).

NMR (d$_6$-DMSO, 60 MHz): δ=3.82 ppm (s, 3H, =N—OCH$_3$), δ=4.97 ppm (s, 1H,

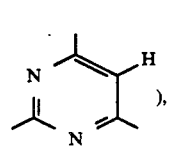),

δ=5.11 ppm (d, 1H, 6—CH—δ=5.67 ppm (q, 1H, 7—CH—), δ=6.38 ppm (s, 2H,

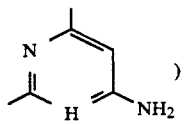

δ=6.71 ppm (s, 1H,

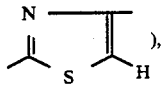

δ=7.15 ppm (s, 2H,

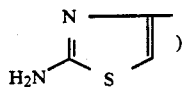

and δ=9.50 ppm (d, 1H, —CO—NH—).

EXAMPLE 91

7-β-[2-(2-Amino-thiazol-4-yl)-2-syn-methoximino-acetamido](benzimidazol-2-yl-thiomethyl)-ceph-3-em-4-carboxylic acid The procedure is as according to Example 5, using 540 mg (3.6 mmoles) of 2-mercapto-benzimidazole. The reaction solution is warmed to 60° C. for 5 hours and the crude product isolated is purified by trituration with ethyl acetate. 517 mg of the title compound are obtained.

$R_f$: 0.42 (acetone:glacial acetic acid=10:1).

IR (KBr): 1,760 cm$^{-1}$ (β-lactam band).

NMR (d$_6$-DMSO, 60 MHz): δ=3.81 ppm (s, 3H, =N—OCH$_3$—), δ=4.32 ppm (AB, 3—CH$_2$—S—), δ=5.09 ppm (d, 1H, 6—CH—), δ=5.69 ppm (q, 1H, 7—CH—), δ=6.68 ppm (s, 1H,

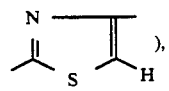

δ=7.0–7.6 ppm (m, 6H,

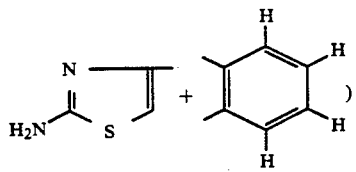

and δ=9.49 ppm (d, 1H, —CO—NH—).

EXAMPLE 92

7-β-[2-(2-Amino-thiazol-4-yl)-2-syn-methoximino-acetamido]-3-(1-allyl-2-trifluoromethyl-1,3,4-triazol-5-yl-thiomethyl)-ceph-3-em-4-carboxylic acid.

The procedure is as according to Example 5, using 627 mg (3 mmoles) of 1-allyl-5-mercapto-2-trifluoromethyl-1,3,4-triazole. The reaction solution is warmed to 60° C. for 6 hours and the crude product isolated is purified by trituration with ethyl acetate. 321 mg of the title compound are obtained.

$R_f$: 0.24 (acetone:glacial acetic acid=10:1).

IR (KBr): 1,765 cm$^{-1}$ (β-lactam band).

NMR (d$_6$-DMSO, 60 MHz): δ=3.82 ppm (s, 3H, =N—OCH$_3$), δ=4.21 ppm (AB, 3—CH$_2$—S—), δ=5.06 ppm (d, 1H, 6—CH—), δ=5.21 ppm (d, 2H, N—CH$_2$—C=), δ=5.65 ppm (q, 1H, 7—CH—), δ=6.70 ppm (s, 1H,

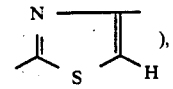

δ=7.12 ppm (s, 2H, —NH$_2$) and δ=9.51 ppm (d, 1H, —CO—NH—).

EXAMPLE 93

7-β-[2-(2-Amino-thiazol-4-yl)-2-syn-methoximino-acetamido]-3-(1-n-butyl-2-trifluoromethyl-1,3,4-triazol-5-yl-thiomethyl)-ceph-3-em-4-carboxylic acid The procedure is as according to Example 5, using 810 mg (3.6 mmoles) of 1-n-butyl-5-mercapto-2-trifluoromethyl-1,3,4-triazole. The reaction solution is warmed to 65° C. for 4.5 hours. 433 mg of the title compound are isolated.

$R_f$: 0.30 (acetone:glacial acetic acid=10:1).

IR (KBr): 1,768 cm$^{-1}$ (β-lactam band).

NMR (d$_6$-DMSO, 60 MHz): δ=0.87 ppm (t, 3H, N—C—C—C—CH$_3$), δ=1.48 ppm (m, 4H, N—C—CH$_2$—CH$_2$—C), δ=3.63 ppm (AB, 2H, 2—CH$_2$—), δ=3.80 ppm (s, 3H, =N—OCH$_3$), δ=4.01 ppm (t, 2H, —N—CH$_2$—C—C—C), δ=4.25 ppm (AB, 2H, 3—CH$_2$—S—), δ=5.08 ppm (d, 1H, 6—CH—), δ=5.72 ppm (q, 1H, 7—CH—), δ=6.70 ppm (s, 1H,

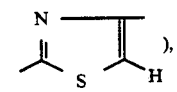

δ=7.12 ppm (s, 2H, —NH$_2$) and δ=9.53 ppm (d, 1H, —CO—NH—).

EXAMPLE 94

7-β-[2-(2-Amino-thiazol-4-yl)-2-syn-methoximino-acetamido]-3-[1-ethyl-2-(thien-2-yl)-1,3,4-triazol-5-yl-thiomethyl]-ceph-3-em-4-carboxylic acid The procedure is as according to Example 5, using 760 mg (3.6 mmoles) of 1-ethyl-5-mercapto-2-(thien-2-yl)-1,3,4-triazole. The reaction solution is warmed to 60° C. for 4 hours. 670 mg of the title compound are isolated.

$R_f$: 0.53 (acetone:glacial acetic acid=10:1).

IR (KBr): 1,768 cm$^{-1}$ (β-lactam band).

NMR (d$_6$-DMSO, 60 MHz): δ=1.24 ppm (t, 3H, N—C—CH$_3$), δ=3.83 ppm (s, 3H, =N—OCH$_3$), δ=4.19 ppm (m, 4H, 3—CH$_2$—S—+—N—CH$_2$—C), δ=5.09 ppm (d, 1H, 6—CH—), δ=5.71 ppm (q, 1H, 7—CH—), δ=6.70 ppm (s, 1H,

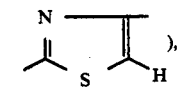

δ=7.16 ppm (m, 3H, H$_2$N—+

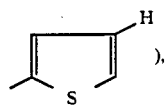

δ=7.54 ppm (m, 1H,

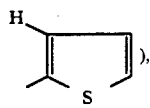

δ=7.79 ppm (m, 1H,

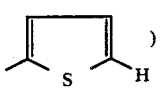

and δ=9.51 ppm (d, 1H, —CO—NH—).

EXAMPLE 95

7-β-[2-(2-Amino-thiazol-4-yl)-2-syn-methoximino-acetamido]-3-(2-aminomethyl-1,3,4-thiadiazol-5-yl-thiomethyl)-ceph-3-em-4-carboxylic acid The procedure is as according to Example 5, using 551 mg (3.6 mmoles) of 2-aminomethyl-5-mercapto-1,3,4-thiadiazole hydrochloride. The reaction solution is warmed to 60° C. for 2.5 hours and the crude product isolated is purified by trituration with ethyl acetate. 914 mg of the title compound are obtained.

$R_f$: 0.40 (acetone:glacial acetic acid=10:1).
IR (KBr): 1,753 cm$^{-1}$ (β-lactam band).
NMR (d$_6$-DMSO, 60 MHz): δ=3.81 ppm (s, 3H, =N—OCH$_3$), δ=4.22 ppm (s, 2H, —CH$_2$—N), δ=5.06 ppm (d, 1H, 6—CH—), δ=5.71 ppm (q, 1H, 7—CH—), δ=6.69 ppm (s, 1H,

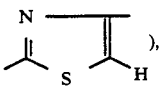

δ=7.11 ppm (s, 2H, —NH$_2$) and δ=9.53 ppm (d, 1H, —CO—NH—).

EXAMPLE 96

7-β-[2-(2-Amino-thiazol-4-yl)-2-syn-methoximino-acetamido]-3-[2-(5-methyl-thien-2-yl)-1H-1,3,4-triazol-5-yl-thiomethyl]-ceph-3-em-4-carboxylic acid The procedure is as according to Example 5, using 847 mg (3.6 mmoles) of 5-mercapto-2-(5-methyl-thien-2-yl)-1H-1,3,4-triazole. The reaction solution is heated to 60° C. for 1 hour and the crude product isolated is purified by trituration with ethyl acetate. 1.14 g of the title compound are obtained.

$R_f$: 0.51 (acetone:glacial acetic acid=10:1).
IR (KBr): 1,760 cm$^{-1}$ (δ-lactam band).
NMR (d$_6$-DMSO, 60 MHz): δ=2.51 ppm (s,

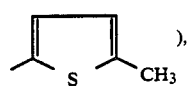

δ=3.80 ppm (s, 3H, =N—OCH$_3$), δ=5.06 ppm (d, 1H, 6—CH—), δ=5.69 ppm (q, 1H, 7—CH—), δ=6.67 ppm (s, 1H,

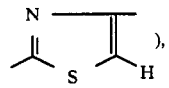

δ=6.81 ppm (d, 1H,

δ=7.10 ppm (s, 2H, —NH$_2$), δ=7.40 ppm (d, 1H,

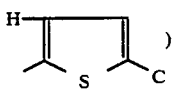

and δ=9.50 ppm (d, 1H, —CO—NH—).

EXAMPLE 97

7-β-[2-(2-Amino-thiazol-4-yl)-2-syn-methoximino-acetamido]-3-(2-hydroxy-1-phenyl-1,3,4-triazol-5-yl-thiomethyl)-ceph-3-em-4-carboxylic acid The procedure is as according to Example 5, using 695 mg (3.6 mmoles) of 2-hydroxy-5-mercapto-1-phenyl-1,3,4-triazole. The reaction solution is warmed to 55°–65° C. for 5 hours and the crude product isolated is purified by trituration with ethyl acetate. 857 mg of the title compound are obtained.

$R_f$=0.41 (acetone:glacial acetic acid=10:1).
IR (KBr): 1,770 cm$^{-1}$ (β-lactam band).
NMR (d$_6$-DMSO, 60 MHz): δ=3.82 ppm (s, 3H, =N—OCH$_3$), δ=5.01 ppm (d, 1H, 6—CH—), δ=5.67 ppm (q, 1H, 7—CH—), δ=6.67 ppm (s, 1H,

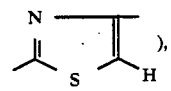

δ=7.13 ppm (s, 2H, —NH$_2$), δ=7.40 ppm (m, 5H,

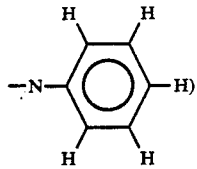

and δ=9.49 ppm (d, 1H, —CO—NH—).

EXAMPLE 98

7-β-[2-(2-Amino-thiazol-4-yl)-2-syn-methoximino-acetamido]-3-(3-hydroxy-1-methyl-1,2,4-triazol-5-yl-thiomethyl)-ceph-3-em-4-carboxylic acid The procedure is as according to Example 5, using 472 mg (3.6 mmoles) of 3-hydroxy-5-mercapto-1-methyl-1,2,4-triazole. The reaction solution is warmed to 55°–60° C. for 5 hours and the crude product isolated is purified by trituration with ethyl acetate. 308 mg of the title compound are obtained.

R$_f$: 0.16 (acetone:glacial acetic acid=10:1).
IR (KBr): 1,751 cm$^{-1}$ ($\beta$-lactam band).
NMR (d$_6$-DMSO, 60 MHz): $\delta$=3.54 ppm (s, 3H, —N—CH$_3$), $\delta$=3.83 ppm (s, 3H, =N—OCH$_3$), $\delta$=5.10 ppm (d, 1H, 6—CH—), $\delta$=5.69 ppm (q, 1H, 7—CH—), $\delta$=6.70 ppm (s, 1H,

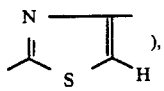

$\delta$=7.12 ppm (s, 2H, —NH$_2$) and $\delta$=9.51 ppm (d, 1H, —CO—NH—).

EXAMPLE 99

7-$\beta$-[2-(2-Amino-thiazol-4-yl)-2-syn-methoximino-acetamido]-3-[2-(3-furyl)-1,3,4-oxadiazol-5-yl-thiomethyl]-ceph-3-em-4-carboxylic acid The procedure is as according to Example 5, using 605 mg (3.6 mmoles) of 2-(3-furyl)-5-mercapto-1,3,4-oxadiazole. The reaction solution is warmed to 60° C. for 5.5 hours and the crude product isolated is purified by triturating with ethyl acetate. 449 mg of the title compound are obtained.

R$_f$=0.52 (acetone:glacial acetic acid=10:1).
IR (KBr): 1,754 cm$^{-1}$ ($\beta$-lactam band).
NMR (d$_6$-DMSO, 60 MHz): $\delta$=3.82 ppm (s, 3H, =N—OCH$_3$), $\delta$=4.26 ppm (AB, 2H, 3—CH$_2$—S—), $\delta$=5.10 ppm (d, 1H, 6—CH—), $\delta$=5.65 ppm (q, 1H, 7—CH—), $\delta$=6.69 ppm (s, 1H,

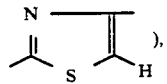

$\delta$=6.88 ppm (d, 1H,

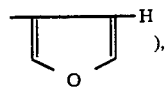

$\delta$=7.10 ppm (s, broad, 1H, —NH$_2$), $\delta$=7.85 ppm (d, 1H,

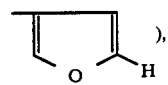

$\delta$=8.45 ppm (s, 1H,

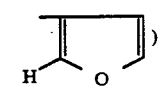

and $\delta$=9.52 ppm (d, 1H, —CO—NH—).

EXAMPLE 100

7-$\beta$-[2-(2-Amino-thiazol-4-yl)-2-syn-methoximino-acetamido]-3-[2-(3-furyl)-1-methyl-1,3,4-triazol-5-yl-thiomethyl]-ceph-3-em-4-carboxylic acid The procedure is as according to Example 5, using 653 mg (3.6 mmoles) of 2-(3-furyl)-5-mercapto-1-methyl-1,3,4-triazole. The reaction solution is warmed to 60° C. for 5.5 hours and the crude product isolated is purified by trituration with ethyl acetate. 500 mg of the title compound are obtained.

R$_f$: 0.33 (acetone:glacial acetic acid=10:1).
IR (KBr): 1,761 cm$^{-1}$ ($\beta$-lactam band).
NMR (d$_6$-DMSO, 60 MHz): $\delta$=3.61 ppm (s, 3H, —N—CH$_3$), $\delta$=3.81 ppm (s, 3H, =N—OCH$_3$), $\delta$=4.08 ppm (AB, 2H, 3—CH$_2$—S—), $\delta$=5.06 ppm (d, 1H, 6—CH—), $\delta$=5.69 ppm (q, 1H, 7—CH—), $\delta$=6.68 ppm (s, 1H,

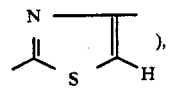

$\delta$=6.85 ppm (m, 1H,

$\delta$=7.10 ppm (s, broad, 2H, —NH$_2$), $\delta$=7.81 ppm (m, 1H,

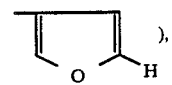

$\delta$=8.38 ppm (m, 1H,

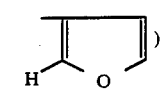

and $\delta$=9.50 ppm (d, 1H, —CO—NH—).

EXAMPLE 101

7-$\beta$-[2-(2-Amino-thiazol-4-yl)-2-syn-methoximino-acetamido]-3-(2,6-diamino-pyrimidin-4-yl-thiomethyl)-ceph-3-em-4-carboxylic acid The procedure is as according to Example 5, using 688 mg of 2,6-diamino-4-mercapto-pyrimidine. The reaction solution is heated to 65° C. for 3 hours. 861 mg of the title compound are isolated.

R$_f$: 0.18 (acetone:glacial acetic acid=10:1).
IR (KBr): 1,753 cm$^{-1}$ ($\beta$-lactam band).
NMR (d$_6$-DMSO, 60 MHz): $\delta$=3.51 ppm (AB, 2—CH$_2$—), $\delta$=3.79 ppm (s, =N—OCH$_3$), $\delta$=5.07 ppm (d, 1H, 6—CH—), $\delta$=5.58 ppm (s, 1H,

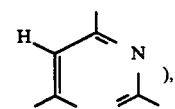

$\delta$=5.65 ppm (q, 1H, 7—CH—), $\delta$=6.00+6.31 ppm (2s, broad, 4H,

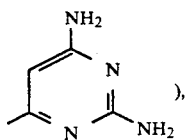

δ=6.65 ppm (s, 1H,

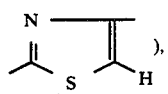

δ=7.12 ppm (s, broad, 2H,

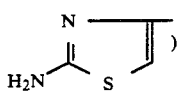

and δ=9.50 ppm (d, 1H, —CO—NH—).

EXAMPLE 102

7-β-[2-(2-Amino-thiazol-4-yl)-2-syn-methoximino-acetamido]-3-(1H-imidazol-2-yl-thiomethyl)-ceph-3-em-4-carboxylic acid The procedure is as according to Example 5, using 360 mg (3.6 mmoles) of 2-mercapto-1H-imidazole. The reaction solution is warmed to 64° C. for 3 hours. 492 mg of the title compound are isolated.

$R_f$: 0.28 (ethyl acetate:methanol:glacial acetic acid=20:10:1).

IR (KBr): 1,762 cm$^{-1}$ (β-lactam band).

NMR (d$_6$-DMSO, 60 MHz): δ=3.55 ppm (AB, 2—CH$_2$—), δ=3.77 ppm (s, =N—OCH$_3$), δ=5.03 ppm (d, 1H, 6—CH—), δ=5.64 ppm (q, 1H, 7—CH—), δ=6.67 ppm (s, 1H,

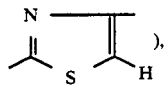

δ=7.10 ppm (m, 4H,

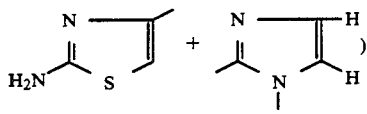

and δ=9.50 ppm (d, 1H, —CO—NH—).

EXAMPLE 103

7-β-[2-(2-Amino-thiazol-4-yl)-2-syn-methoximino-acetamido]-3-[2-(thien-3-yl)-1H-1,3,4-triazol-5-yl-thiomethyl]-ceph-3-em-4-carboxylic acid The procedure is as according to Example 5, using 659 mg (3.6 mmoles) of 5-mercapto-2-(thien-3-yl)-1H-1,3,4-triazole. The reaction solution is warmed to 65° C. for 5 hours. 1.37 g of the title compound are isolated.

$R_f$: 0.45 (ethyl acetate:methanol:glacial acetic acid=20:10:1).

IR (KBr): 1,761 cm$^{-1}$ (β-lactam band)

NMR (d$_6$-DMSO, 60 MHz): δ=3.54 ppm (AB, 2—CH$_2$—), δ=3.73 ppm (s, =N—OCH$_3$), δ=4.17 ppm (AB, 3—CH$_2$—S—), δ=5.02 ppm (d, 1H, 6—CH—), δ=5.64 ppm (q, 1H, 7—CH—), δ=6.63 ppm (s, 1H,

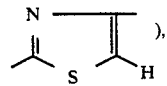

δ=7.09 ppm (s, broad, 2H, —NH$_2$), δ=7.52 ppm (m, 2H,

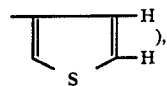

δ=7.97 ppm (m, 1H,

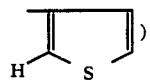

and δ=9.47 ppm (d, 1H, —CO—NH—).

EXAMPLE 104

7-β-[2-(2-Amino-thiazol-4-yl)-2-syn-methoximino-acetamido]-3-(pyrimidin-2-yl-thiomethyl)-ceph-3-em-4-carboxylic acid The procedure is as according to Example 5, using 403 mg (3.6 mmoles) of 2-mercapto-pyrimidine. The reaction solution is warmed to 60° C. for 2.5 hours and the crude product isolated is purified by trituration with ethyl acetate. 496 mg of the title compound are obtained.

$R_f$: 0.31 (ethyl acetate:methanol:glacial acetic acid=20:10:1).

IR (KBr): 1,765 cm$^{-1}$ (β-lactam band).

NMR (d$_6$-DMSO, 60 MHz): δ=3.50 ppm (AB, 2—CH$_2$—), δ=3.74 ppm (s, =N—OCH$_3$), δ=4.53 ppm (AB, 2H, 3—CH$_2$—S—), δ=5.04 ppm (d, 1H, 6—CH—), δ=5.66 ppm (q, 1H, 7—CH—), δ=6.64 ppm (s, 1H, δ=7.11 ppm (m, 3H, δ=8.53 ppm (m, 2H, and δ=9.48 ppm (d, 1H, —CO—NH—).

EXAMPLE 105

7-β-[2-(2-Amino-thiazol-4-yl)-2-syn-methoximino-acetamido]-3-[2-(5-bromo-thien-2-yl)-1-methyl-1,3,4-triazol-5-yl-thiomethyl]-ceph-3-em-4-carboxylic acid The procedure is as according to Example 5, using 994 mg (3.6 mmoles) of 2-(5-bromo-thien-2-yl)-5-mercapto-1-methyl-1,3,4-triazole. The reaction solution is heated to 60° C. for 3.5 hours and the crude product isolated is purified by trituration with ethyl acetate. 754 mg of the title compound are obtained.

$R_f$: 0.57 (acetone:glacial acetic acid = 10:1).

IR (KBr): 1,764 cm$^{-1}$ (β-lactam band).

NMR (d$_6$-DMSO, 60 MHz): δ=3.70 ppm (s, —N—CH$_3$), δ=3.83 ppm (s, =N—OCH$_3$), δ=5.10 ppm (d, 1H, 6—CH—), δ=5.70 ppm (q, 1H, 7—CH—), δ=6.70 ppm (s, 1H,

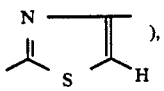),

δ=7.14 ppm (s, broad, 2H, —NH$_2$), δ=7.88 ppm (m, 2H,

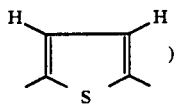)

and δ=9.55 ppm (d, 1H, —CO—NH—).

EXAMPLE 106

7-β-[2-(2-Amino-thiazol-4-yl)-2-syn-methoximino-acetamido]-3-[2-(5-bromo-thien-2-yl)-1,3,4-oxadiazol-5-yl-thiomethyl]-ceph-3-em-4-carboxylic acid The procedure is as according to Example 5, using 945 mg (3.6 mmoles) of 2-(5-bromo-thien-2-yl)-5-mercapto-1,3,4-oxadiazole. The reaction solution is warmed to 60° C. for 3 hours and the crude product isolated is purified by trituration with ethyl acetate. 947 mg of the title compound are obtained.

$R_f$: 0.35 (acetone:glacial acetic acid = 10:1).

IR (KBr): 1,759 cm$^{-1}$ (β-lactam band).

NMR (d$_6$-DMSO, 60 MHz): δ=3.84 ppm (s, =N—OCH$_3$), δ=4.32 ppm (AB, 3—CH$_2$—S—), δ=5.08 ppm (d, 1H, 6—CH—), δ=5.70 ppm (q, 1H, 7—CH—), δ=6.69 ppm (s, 1H,

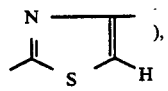),

δ=7.13 ppm (s, broad, 2H, —NH$_2$), δ=7.38 ppm (d, 1H,

),

δ=7.68 ppm (d, 1H,

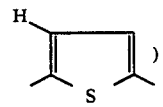)

and δ=9.53 ppm (d, 1H, —CO—NH—).

EXAMPLE 107

7-β-[2-(2-Amino-thiazol-4-yl)-2-syn-methoximino-acetamido]-3-[2-(3-methoxy-thien-2-yl)-1-methyl-1,3,4-triazol-5-yl-thiomethyl]-ceph-3-em-4-carboxylic acid The procedure is as according to Example 5, using 814 mg (3.6 mmoles) of 5-mercapto-2-(3-methoxy-thien-2-yl)-1-methyl-1,3,4-triazole. The reaction solution is heated to 60° C. for 4.3 hours. 791 mg of the title compound are obtained.

$R_f$: 0.29 (acetone:glacial acetic acid = 10:1).

IR (KBr): 1,765 cm$^{-1}$ (β-lactam band).

NMR (d$_6$-DMSO, 60 MHz): δ=3.48 ppm (s, —N—CH$_3$), δ=3.67 ppm (AB, 2—CH$_2$—), δ=3.84 ppm (s, =N—OCH$_3$), δ=3.89 ppm (s, =C—OCH$_3$), δ=4.17 ppm (AB, 3—CH$_2$—S—), δ=5.11 ppm (d, 1H, 6—CH—), δ=5.73 ppm (q, 1H, 7—CH—), δ=6.72 ppm (s, 1H,

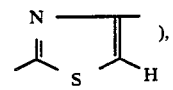),

δ=7.13 ppm (m, 3H,

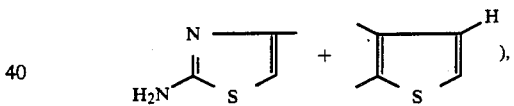),

δ=7.74 ppm (d, 1H,

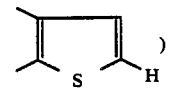)

and δ=9.53 ppm (d, 1H, —CO—NH—).

EXAMPLE 108

7-β-[2-(2-Amino-thiazol-4-yl)-2-syn-methoximino-acetamido]-3-(pyrid-4-yl-thiomethyl)-ceph-3-em-4-carboxylic acid The procedure is as according to Example 5, using 328 mg (3.6 mmoles) of 4-mercapto-pyridine. The reaction solution is heated to 60°–75° C. for 5 hours. 780 mg of the title compound are isolated.

$R_f$: 0.22 (acetone:glacial acetic acid = 10:1).

IR (KBr): 1,757 cm$^{-1}$ (β-lactam band).

NMR (d$_6$-DMSO, 60 MHz): δ=3.54 ppm (AB, 2—CH$_2$—), δ=3.84 ppm (s, =N—OCH$_3$), δ=4.15 ppm (AB, 3—CH$_2$—S—), δ=5.13 ppm (d, 1H, 6—CH—), δ=5.70 ppm (q, 1H, 7—CH—), δ=6.70 ppm (s, 1H,

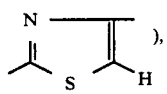

δ=7.14 ppm (s, broad, 2H, —NH₂), δ=7.28 ppm (d, 2H,

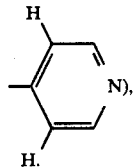

δ=8.31 ppm (d, 2H,

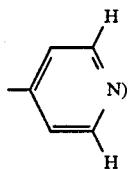

and δ=9.53 ppm (d, 1H, —CO—NH—).

EXAMPLE 109

7-β-[2-(2-Amino-thiazol-4-yl)-2-syn-methoximino-acetamido]-3-(2-carboxymethylthio-1,3,4-thiadiazol-5-yl-thiomethyl)-ceph-3-em-4-carboxylic acid The procedure is as according to Example 5, using 749 mg (3.6 mmoles) of 2-carboxymethylthio-5-mercapto-1,3,4-thiadiazole. The reaction solution is warmed to 55° C. for 1 hour. 469 mg of the title compound are isolated.

R_f: 0.12 (acetone:glacial acetic acid=10:1).

IR (KBr): 1,763 cm⁻¹ (β-lactam band).

NMR (d₆-DMSO, 60 MHz): δ=3.62 ppm (AB, 2—CH₂—), δ=3.83 ppm (s, =N—OCH₃), δ=4.13 ppm (s, —S—CH₂—COO—), δ=4.33 ppm (AB, 3—CH₂—S—), δ=5.11 ppm (d, 1H, 6—CH—), δ=5.71 ppm (q, 1H, 7—CH—), δ=6.71 ppm (s, 1H,

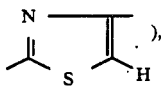

δ=7.15 ppm (s, broad, 2H, —NH₂) and δ=9.54 ppm (d, 1H, —CO—NH—).

EXAMPLE 110

7-β-[2-(2-Amino-thiazol-4-yl)-2-syn-methoximino-acetamido]-3-[2-(5-methyl-thien-2-yl)-1,3,4-oxadiazol-5-yl-thiomethyl]-ceph-3-em-4-carboxylic acid The procedure is as according to Example 5, using 713 mg (3.6 mmoles) of 5-mercapto-2-(5-methyl-thien-2-yl)-1,3,4-oxadiazole. The reaction solution is heated to 60° C. for 6 hours. 1.09 g of the title compound are isolated.

R_f: 0.56 (acetone:glacial acetic acid=10:1).

IR (KBr): 1,765 cm⁻¹ (β-lactam band).

NMR (d₆-DMSO, 60 MHz): δ=2.51 ppm (s, =C—CH₃), δ=3.66 ppm (AB, 2—CH₂—), δ=3.82 ppm (s, =N—OCH₃), δ=4.32 ppm (AB, 3—CH₂—S—), δ=5.10 ppm (d, 1H, 6—CH—), δ=5.74 ppm (q, 1H, 7—CH—), δ=6.70 ppm (s, 1H,

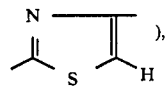

δ=6.96 ppm (m, 1H,

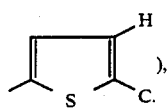

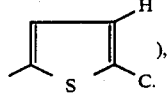

δ=7.15 ppm (s, broad, 2H, —NH₂), δ=7.52 ppm (m, 1H,

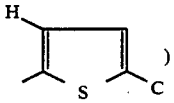

and δ=9.53 ppm (d, 1H, —CO—NH—).

EXAMPLE 111

7-β-[2-(2-Amino-thiazol-4-yl)-2-syn-methoximino-acetamido]-3-(2-methyl-1H-1,3,4-triazol-5-yl-thiomethyl)-ceph-3-em-4-carboxylic acid The procedure is as according to Example 5, using 414 mg (3.6 mmoles) of 5-mercapto-2-methyl-1H-1,3,4-triazole. The reaction solution is heated to 60° C. for 5 hours. 730 mg of the title compound are isolated.

R_f: 0.34 (acetone:glacial acetic acid=10:1).

IR (KBr): 1,754 cm⁻¹ (β-lactam band).

NMR (d₆-DMSO, 60 MHz): δ=2.29 ppm (s, 3H, =C—CH₃), δ=3.57 ppm (AB, 2—CH₂), δ=3.84 ppm (s, =N—OCH₃), δ=4.12 ppm (AB, 3—CH₂—S—), δ=5.06 ppm (d, 1H, 6—CH—), δ=5.73 ppm (q, 1H, 7—CH—), δ=6.71 ppm (s, 1H,

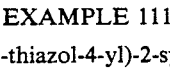

δ=7.15 ppm (s, broad, 2H, —NH₂) and δ=9.52 ppm (d, 1H, —CO—NH—).

EXAMPLE 112

7-β-[2-(2-Amino-thiazol-4-yl)-2-syn-methoximino-acetamido]-3-(2-amino-purin-6-yl-thiomethyl)-ceph-3-em-4-carboxylic acid The procedure is as according to Example 5, using 602 mg (3.6 mmoles) of 2-amino-6-mercapto-purine. The reaction solution is warmed to 60° C. for 4.2 hours and the crude product isolated is purified by trituration with ethyl acetate 681 mg of the title compound are obtained.

R_f: 0.25 (acetone:glacial acetic acid=10:1).

IR (KBr): 1,758 cm⁻¹ (β-lactam band).

NMR (d₆-DMSO, 60 MHz): δ=3.55 ppm (AB, 2—CH₂—), δ=3.84 ppm (s, =N—OCH₃), δ=4.12 ppm (AB, 3—CH₂—S—), δ=5.10 ppm (d, 1H, 6—CH—), δ=5.69 ppm (q, 1H, 7—CH—), δ=6.70 ppm (s, 1H,

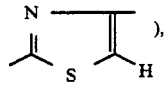

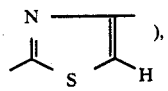

δ=7.15 ppm (s, broad, 2H, —NH₂), δ=7.87 ppm (s, 1H,

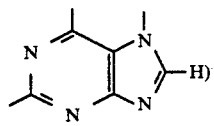

and δ=9.53 ppm (d, 1H, —CO—NH—).

EXAMPLE 113

7-β-[2-(2-Amino-thiazol-4-yl)-2-syn-methoximino-acetamido]-3-(purin-6-yl-thiomethyl)-ceph-3-em-4-carboxylic acid The procedure is as according to Example 5, using 613 mg (3.6 mmoles) of 6-mercapto-purine. The reaction solution is warmed to 60° C. for 4 hours and the crude product isolated is purified by trituration with ethyl acetate. 809 mg of the title compound are obtained.

R$_f$: 0.29 (acetone:glacial acetic acid=10:1).
IR (KBr): 1,760 cm⁻¹ (β-lactam band).
NMR (d₆-DMSO, 60 MHz): δ=3.58 ppm (AB, 2—CH₂—), δ=3.80 ppm (s, =N—OCH₃), δ=4.08 ppm (AB, 3—CH₂—S—), δ=5.10 ppm (d, 6—CH—), δ=5.71 ppm (q, 1H, 7—CH—), δ=6.70 ppm (s, 1H,

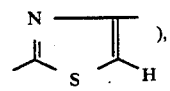

δ=7.16 ppm (s, broad, 2H, —NH₂), δ=8.41 ppm (s, 1H,

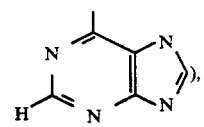

δ=8.65 ppm (s, 1H,

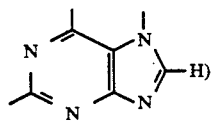

and δ=9.52 ppm (d, 1H, —CO—NH—).

EXAMPLE 114

7-β-[2-(2-Amino-thiazol-4-yl)-2-syn-methoximino-acetamido]-3-(1-methyl-imidazol-2-yl-thiomethyl)-ceph-3-em-4-carboxylic acid The procedure is as according to Example 5, using 465 mg (4 mmoles) of 2-mercapto-1-methyl-imidazole. The reaction solution is heated to 60° C. for 5.7 hours and the crude product isolated is purified by trituration with ethyl acetate. 508 mg of the title compound are obtained.

R$_f$: 0.10 (acetone:glacial acetic acid=10:1).
IR (KBr): 1,759 cm⁻¹ (β-lactam band).
NMR (d₆-DMSO, 60 MHz): δ=3.62 ppm (s, —N—CH₃), δ=3.81 ppm (s, =N—OCH₃), δ=4.07 ppm (AB, 3—CH₂—S—), δ=5.09 ppm (d, 1H, 6—CH—), δ=5.70 ppm (q, 1H, 7—CH—), δ=6.69 ppm (s, 1H,

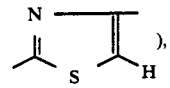

δ=7.02 ppm (d, 1H,

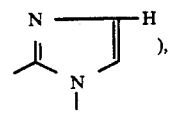

δ=7.15 ppm (s, broad, 2H, —NH₂), δ=7.28 ppm (d, 1H,

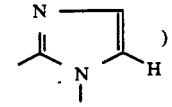

and δ=9.53 ppm (d, 1H, —CO—NH—).

EXAMPLE 115

7-β-[2-(2-Amino-thiazol-4-yl)-2-syn-methoximino-acetamido]-3-(2-methylamino-1,3,4-thiadiazol-5-yl-thiomethyl)-ceph-3-em-4-carboxylic acid The procedure is as according to Example 5, using 529 mg (3.6 mmoles) of 5-mercapto-2-methylamino-1,3,4-thiadiazole. The reaction solution is warmed to 60° C. for 4 hours. 713 mg of the title compound are isolated.

R$_f$: 0.34 (acetone: glacial acetic acid=10:1).
IR (KBr): 1,755 cm⁻¹ (β-lactam band).
NMR (d₆-DMSO, 60 MHz): δ=2.83 ppm (d, —N—CH₃), δ=3.63 ppm (AB, 2—CH₂—), δ=3.83 ppm (s, =N—OCH₃), δ=4.09 ppm (AB, 3—CH₂—S—), δ=5.09 ppm (d, 1H, 6—CH—), δ=5.72 ppm (q, 1H, 7—CH—), δ=6.70 ppm (s, 1H,

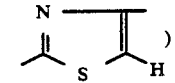

and δ=9.54 ppm (d, 1H, —CO—NH—).

EXAMPLE 116

7-β-[2-(2-Amino-thiazol-4-yl)-2-syn-methoximino-acetamido]-3-(2-N-methylacetamido-1,3,4-thiadiazol-5-yl-thiomethyl)-ceph-3-em-4-carboxylic acid The procedure is as according to Example 5, using 680 mg (3.6 mmoles) of 5-mercapto-2-N-methyl-acetamido-1,3,4-thiadiazole. The reaction solution is warmed to 60° C. for 6.5 hours. 897 mg of the title compound are isolated.

$R_f$: 0.40 (acetone:glacial acetic acid = 10:1).

IR (KBr): 1,763 cm$^{-1}$ ($\beta$-lactam band).

NMR (d$_6$-DMSO, 60 MHz): $\delta$=2.37 ppm (s, 3H, —N—CO—CH$_3$), $\delta$=3.40 ppm (AB, 2H, 2—CH$_2$—), $\delta$=3.63 ppm (s, 3H, —CO—N—CH$_3$), $\delta$=3.82 ppm (s, 3H, =N—OCH$_3$), $\delta$=4.28 ppm (AB, 2H, 3—CH$_2$—S—), $\delta$=5.09 ppm (d, 1H, 6—CH—), $\delta$=5.72 ppm (q, 1H, 7—CH—), $\delta$=6.72 ppm (s, 1H,

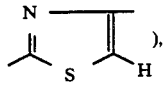

$\delta$=7.15 ppm (s, broad, 2H, —NH$_2$) and $\delta$=9.53 ppm (d, 1H, —CO—NH—).

EXAMPLE 117

7-$\beta$[2-(2-Amino-thiazol-4-yl)-2-syn-methoximino-acetamido]-3-[2-(3-methoxy-thien-2-yl)-1,3,4-oxadiazol-5-yl-thiomethyl]-ceph-3-em-4-carboxylic acid The procedure is as according to Example 5, using 1.07 g (5 mmoles) of 5-mercapto-2-(3-methoxy-thien-2-yl)-1,3,4-oxadiazole. The reaction solution is warmed to 65° C. for 4.5 hours and the crude product isolated is purified by trituration with ethyl acetate. 395 mg of the title compound are obtained.

$R_f$: 0.40 (acetone:glacial acetic acid = 10:1).

IR (KBr): 1,758 cm$^{-1}$ ($\beta$-lactam band).

NMR (d$_6$-DMSO, 60 MHz): $\delta$=3.82 ppm (s, =N—OCH$_3$), $\delta$=3.98 ppm (s, =C—OCH$_3$), $\delta$=4.26 ppm (AB, 3—CH$_2$—S—), $\delta$=5.03 ppm (d, 1H, 6—CH—), $\delta$=5.65 ppm (q, 1H, 7—CH—), $\delta$=6.72 ppm (s, 1H,

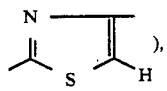

$\delta$=7.19 ppm (m, 3H,

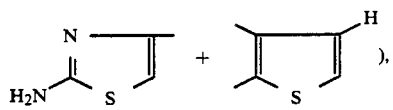

$\delta$=7.83 ppm (d, 1H,

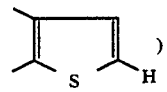

and $\delta$=9.51 ppm (d, 1H, —CO—NH—).

EXAMPLE 118

7-$\beta$-[2-(2-Amino-thiazol-4-yl)-2-syn-methoximino-acetamido]-3-[1-(2-morpholino-ethyl)-1,3,4-triazol-5-yl-thiomethyl]-ceph-3-em-4-carboxylic acid The procedure is as according to Example 5, using 770 mg (3.6 mmoles) of 5-mercapto-1-(2-morpholino-ethyl)-1,3,4-triazole. The reaction solution is heated to 60° C. for 3 hours. 330 mg of the title compound are isolated.

$R_f$: 0.52 (acetone:glacial acetic acid = 10:1).

IR (KBr): 1,758 cm$^{-1}$ ($\beta$-lactam band).

NMR (d$_6$-DMSO, 60 MHz): $\delta$=3.84 ppm (s, =N—OCH$_3$), $\delta$=5.08 ppm (d, 1H, 6—CH—), $\delta$=5.69 ppm (q, 1H, 7—CH—), $\delta$6.70 ppm (s, 1H,

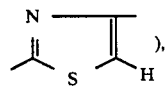

$\delta$=7.13 ppm (s, broad, 2H, —NH$_2$), $\delta$=8.57 ppm (s, 1H,

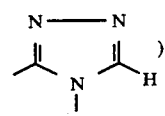

and $\delta$=9.53 ppm (d, 1H, —CO—NH—).

EXAMPLE 119

7-$\beta$-[2-(2-Amino-thiazol-4-yl)-2-syn-methoximino-acetamido]-3-(1,2-dimethyl-1,3,4-triazol-5-yl-thiomethyl)-ceph-3-em-4-carboxylic acid The procedure is as according to Example 5, using 645 mg (5 mmoles) of 1,2-dimethyl-5-mercapto-1,3,4-triazole. The reaction solution is warmed to 60°–70° C. for 4 hours. 800 mg of the title compound are isolated.

$R_f$: 0.21 (acetone:glacial acetic acid = 10:1).

IR (KBr): 1,762 cm$^{-1}$ ($\beta$-lactam band).

NMR (d$_6$-DMSO, 60 MHz): $\delta$=2.33 ppm (s, =C—CH$_3$), $\delta$=3.39 ppm (s, —N—CH$_3$), $\delta$=3.59 ppm (AB, 2—CH$_2$—), $\delta$=3.80 ppm (s, =N—OCH$_3$), $\delta$=4.04 ppm (AB, 3—CH$_2$—S—), $\delta$=5.09 ppm (d, 1H, 6—CH—), $\delta$=5.71 ppm (q, 1H, 7—CH—), $\delta$=6.71 ppm (s, 1H,

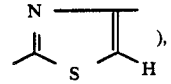

$\delta$=7.14 ppm (s, broad, 2H, —NH$_2$) and $\delta$=9.53 ppm (d, 1H, —CO—NH—).

EXAMPLE 120

7-$\beta$-[2-(2-Amino-thiazol-4-yl)-2-syn-methoximino-acetamido]-3-[1-methyl-2-(pyrid-2-yl)-1,3,4-triazol-5-yl-thiomethyl]-ceph-3-em-4-carboxylic acid The procedure is as according to Example 5, using 691 mg (3.6 mmoles) of 5-mercapto-1-methyl-2-(pyrid-2-yl)-1,3,4-triazole. The reaction solution is heated to 60° C. for 5 hours. 724 mg of the title compound are isolated.

$R_f$: 0.13 (acetone:glacial acetic acid = 10:1).

IR (KBr): 1,765 cm$^{-1}$ ($\beta$-lactam band).

NMR (d$_6$-DMSO, 60 MHz): $\delta$=3.69 ppm (AB, 2—CH$_2$—), $\delta$=3.80 ppm (s, 3H, =N—OCH$_3$), $\delta$=3.95 ppm (s, 3H, —N—CH$_3$), $\delta$=4.20 ppm (AB, 2H, 3—CH$_2$—S—), $\delta$=5.13 ppm (d, 1H, 6—CH—), $\delta$=5.73 ppm (q, 1H, 7—CH—), $\delta$=6.75 ppm (s, 1H,

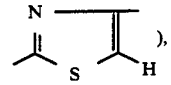

δ=7.16 ppm (s, broad, 2H, —NH₂), δ=7.48 ppm (m, 1H,

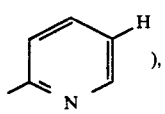

δ=7.93 ppm (m, 1H,

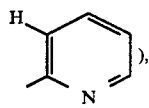

δ=8.08 ppm (m, 1H,

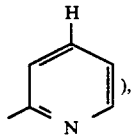

δ=8.70 ppm (m, 1H,

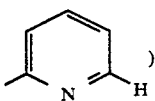

and δ=9.57 ppm (d, 1H, —CO—NH—).

EXAMPLE 121

7-β-[2-(2-Amino-thiazol-4-yl)-2-syn-methoximino-acetamido]-3-(1H-tetrazol-5-yl-thiomethyl)-ceph-3-em-4-carboxylic acid The procedure is as according to Example 5, using 367 mg (3.6 mmoles) of 5-mercapto-1H-tetrazole. The reaction solution is warmed to 60° C. for 1 hour. 593 mg of the title compound are obtained.

R/: 0.47 (acetone:glacial acetic acid=10:1).
IR (KBr): 1,760 cm⁻¹ (β-lactam band).
NMR (d₆-DMSO, 60 MHz): δ=3.62 ppm (AB, 2—CH₂—), δ=3.83 ppm (s, =N—OCH₃), δ=4.27 ppm (AB, 3—CH₂—S—), δ=5.09 ppm (d, 1H, 6—CH—), δ=5.72 ppm (q, 1H, 7—CH—), δ=6.72 ppm (s, 1H,

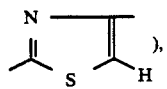

δ=7.17 ppm (broad, 2H, —NH₂) and δ=9.53 ppm (d, 1H, —CO—NH—).

EXAMPLE 122

7-β-[2-(2-Amino-thiazol-4-yl)-2-syn-methoximino-acetamido]-3-(4,5-dihydro-thiazol-2-yl-thiomethyl)-ceph-3-em-4-carboxylic acid The procedure is as according to Example 5, using 428 mg (3.6 mmoles) of 2-mercapto-4,5-dihydro-thiazole. The reaction solution is warmed to 60° C. for 4.5 hours. 388 mg of the title compound are isolated.

R/: 0.51 (acetone:glacial acetic acid=10:1)
IR (KBr): 1,762 cm⁻¹ (β-lactam band)
NMR (d₆-DMSO, 60 MHz): δ=3.82 ppm (s, =N—OCH₃), δ=5.09 ppm (d, 1H, 6—CH—), δ=5.71 ppm (q, 1H, 7—CH—), δ=6.70 ppm (s, 1H,

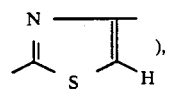

δ=7.12 ppm (s, broad, 2H, —NH₂) and δ=9.52 ppm (d, 1H, —CO—NH—).

EXAMPLE 123

7-β-[2-(2-Amino-thiazol-4-yl)-2-syn-methoximino-acetamido]-3-[1H-pyrazolo(3,4-d)pyrimidin-4-yl-thiomethyl]-ceph-3-em-4-carboxylic acid The procedure is as according to Example 5, using 580 mg (3.6 mmoles) of 4-mercapto-1H-pyrazolo(3,4-d)pyrimidine hemihydrate. The reaction solution is heated to 60°–75° C. for 64 hours. 529 mg of the title compound are isolated.

R/: 0.31 (acetone:glacial acetic acid=10:1).
IR (KBr): 1,757 cm⁻¹ (β-lactam band).
NMR (d₆-DMSO, 60 MHz): δ=3.57 ppm (AB, 2—CH₂—), δ=3.80 ppm (s, =N—OCH₃), δ=4.57 ppm (AB, 3—CH₂—S—), δ=5.09 ppm (d, 1H, 6—CH—), δ=5.69 ppm (q, 1H, 7—CH—), δ=6.72 ppm (s, 1H,

δ=7.11 ppm (s, broad, 2H, —NH₂), δ=8.13 ppm (s, 1H,

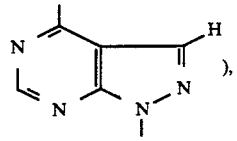

δ=8.63 ppm (s, 1H,

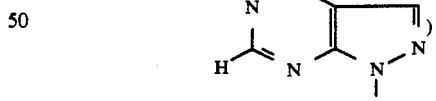

and δ=9.53 ppm (d, 1H, —CO—NH—).

EXAMPLE 124

7-β-[2-(2-Amino-thiazol-4-yl)-2-syn-methoximino-acetamido]-3-[1-methyl-2-(thien-3-yl)-1,3,4-triazol-5-yl-thiomethyl]-ceph-3-em-4-carboxylic acid The procedure is as according to Example 5, using 710 mg (3.6 mmoles) of 5-mercapto-1-methyl-2-(thien-3-yl)-1,3,4-triazole. The reaction solution is warmed to 60° C. for 2.5 hours. 574 mg of the title compound are isolated.

R/: 0.40 (acetone:glacial acetic acid=10:1).
IR (KBr): 1,772 cm⁻¹ (β-lactam band).

NMR (d6-DMSO, 60 MHz): δ=3.31 ppm (AB, 2—CH2—), δ=3.66 ppm (s, —N—CH3), δ=3.79 ppm (s, =N—OCH3), δ=4.12 ppm (AB, 3—CH2—S—), δ=5.09 ppm (d, 1H, 6—CH—), δ=5.70 ppm (q, 1H, 7—CH—), δ=6.71 ppm (s, 1H,

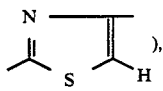

δ=7.15 ppm (s, broad, 2H, —NH2), δ=7.48 ppm (m, 1H,

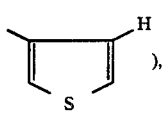

δ=7.73 ppm (m, 1H,

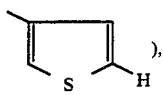

δ=8.00 ppm (m, 1H,

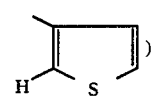

and δ=9.55 ppm (d, 1H, —CO—NH—).

EXAMPLE 125

7-β-[2-(2-Amino-thiazol-4-yl)-2-syn-methoximino-acetamido]-3-[2-(thien-3-yl)-1,3,4-oxadiazol-5-yl-thiomethyl]-ceph-3-em-4-carboxylic acid The procedure is as according to Example 5, using 663 mg (3.6 mmoles) of 5-mercapto-2-(thien-3-yl)-1,3,4-oxadiazole. The reaction solution is warmed to 60° C. for 4 hours. 530 mg of the title compound are isolated.

R_f: 0.32 (acetone:glacial acetic acid=10:1).

IR (KBr): 1,757 cm$^{-1}$ (β-lactam band).

NMR (d6-DMSO, 60 MHz): δ=3.65 ppm (AB, 2—CH2—), δ=3.85 ppm (s, =N—OCH3), δ=4.36 ppm (AB, 2H, 3—CH2—S—), δ=5.08 ppm (d, 1H, 6—CH—), δ=5.71 ppm (s, 1H, 7—CH—), δ=6.74 ppm (s, 1H,

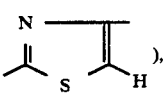

δ=7.17 ppm (s, broad, 2H, —NH2), δ=7.55 ppm (m, 1H,

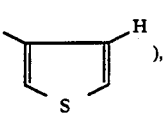

δ=7.68 ppm (m, 1H,

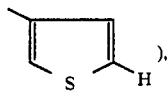

δ=8.32 ppm (m, 1H,

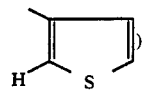

and δ=9.55 ppm (d, 1H, —CO—NH—).

EXAMPLE 126

7-β-[2-(2-Amino-thiazol-4-yl)-2-syn-methoximino-acetamido]-3-[1-ethyl-2-(2-furyl)-1,3,4-triazol-5-yl-thiomethyl]-ceph-3-em-4-carboxylic acid The procedure is as according to Example 5, using 702 mg (3.6 mmoles) of 1-ethyl-2-(2-furyl)-5-mercapto-1,3,4-triazole. The reaction solution is warmed to 60° C. for 4 hours. 525 mg of the title compound are isolated.

R_f: 0.32 (acetone:glacial acetic acid=10:1).

IR (KBr): 1,770 cm$^{-1}$ (β-lactam band).

NMR (d6-DMSO, 60 MHz): δ=1.23 ppm (t, 3H, —N—C—CH3), δ=3.67 ppm (AB, 2H, 2—CH2—), δ=3.80 ppm (s, 3H, =N—OCH3), δ=4.02 ppm (q, 2H, —N—CH2—C), δ=4.19 ppm (AB, 2H, 3—CH2—S—) δ=5.09 ppm (d, 1H, 6—CH—), δ=5.72 ppm (q, 1H, 7—CH—), δ=6.69 ppm (m, 2H,

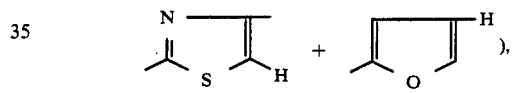

δ=7.08 ppm (m, 3H,

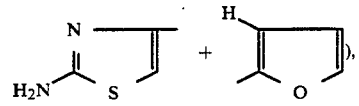

δ=7.92 ppm (d, 1H,

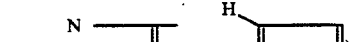

and δ=9.53 ppm (d, 1H, —CO—NH—).

EXAMPLE 127

7-β-[2-(2-Methylamino-thiazol-4-yl)-2-syn-methoximino-acetamido]-cephalosporanic acid Stage 1:
2-(2-Methylamino-thiazol-4-yl)-2-syn-methoximino-acetohydrazide 2.43 g of ethyl 2-(2-methylamino-thiazol-4-yl)-2-syn-methoximino-acetate are dissolved hot in 5 ml of methanol, 20 ml of 80% strength hydrazine hydrate are added and the mixture is stirred at room temperature for 20 hours. On passing a weak stream of air over the stirred solution, 1.44 g of the acid hydrazide of melting point 166°–8° C. separate out.

Stage 2

1.15 g of the hydrazide prepared in stage 1 are dissolved in 25 ml of DMF, the solution is cooled to −20° and 3.3 ml of 4.51N HCl in dioxan and then 0.6 ml of tert.-butyl nitrite in 2 ml of DMF are added. The mixture is stirred at room temperature for 1 hour, 1.5 g of triethylamine are added and a solution of 1.36 g of 7-amino-cephalosporanic acid and 1.0 g of triethylamine in 10 ml of DMF is added dropwise to the suspension formed. The mixture is stirred at −20° for 3 hours, poured into 120 ml of ice-water and extracted three times with 50 ml of ethyl acetate each time. The extract is then acidified to pH 4.0 with 2N HCl, unreacted 7-amino-cephalosporanic acid is filtered off and the filtrate is concentrated under reduced pressure to ⅓ of the original volume. After further acidifying to pH 1.5, the reaction mixture is extracted with ethyl acetate, the ethyl acetate phases are dried over $Na_2SO_4$ and filtered and the solution is concentrated in vacuo. The oil formed is triturated with ether. 0.85 g of the title compound is obtained as a beige powder of melting point 130°-5° C. (decomposition).

$R_f$: 0.56 (ethyl acetate:iso-propanol:$H_2O$=20:15:10).
IR (KBr): 1,770 cm$^{-1}$ ($\beta$-lactam band) and 1,720 cm$^{-1}$ ($OCOCH_3$).
NMR (DMSO-$d_6$): $\delta$=9.6 ppm (d, 1H, —CONH—), $\delta$=6.7 ppm (s, 1H,

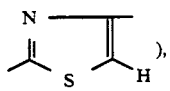

$\delta$=5.6 ppm (q, 1H, 7—CH—), $\delta$=5.1 ppm (d, 1H, 6—CH—), $\delta$=4.9 ppm (AB, 2H, 3—$CH_2$—S—), $\delta$=3.9 ppm (s, 3H, $CH_3O$—N=), $\delta$=3.6 ppm (AB, broad, 2—$CH_2$—), $\delta$=2.7 ppm (d, 3H, $CH_3$—N—) and $\delta$=2.1 ppm (s, 3H, —$OCOCH_3$).

EXAMPLE 128

7-$\beta$-[2-(2-Amino-thiazol-4-yl)-2-syn-methoximino-acetamido]-3-[2-(carboxy-methoxy-methyl)-1H-1,3,4-triazol-5-yl-thiomethyl]-ceph-3-em-4-carboxylic acid 4.55 g of 7-$\beta$-[2-(2-amino-thiazol-4-yl)-2-syn-methoximino-acetamido]-cephalosporanic acid are dissolved in 100 ml of $H_2O$ at pH 7.5 using a saturated $NaHCO_3$ solution. After adding 2.8 g of 2-(carboxy-methoxy-methyl)-5-mercapto-1,3,4-triazole, the mixture is stirred at 60°-65° C. in a pH range from 6.8 to 7.5 for 4 hours. After again adding 1.4 g of the mercaptotriazole, the mixture is stirred at 60°-65° C. and at a pH of 6.8 to 7.5 for a further 2 hours.

The cooled solution is adjusted to pH 5.0 with 2N HCl, 50 ml of ethyl acetate and 4 g of active charcoal are added, the mixture is stirred for 10 minutes and filtered and the layers of the filtrate are separated. The aqueous phase is extracted a further two times with 50 ml of ethyl acetate each time and acidified to pH 2.0 with 2N HCl, whilst cooling in an icebath. The reaction mixture is stirred for ½ hour and the precipitate is filtered off and dried. 3.0 g of the title compound are obtained as a beige powder of melting point 160° (decomposition).

$R_f$: 0.08 (glacial acetic acid:acetone=1:10).
IR (KBr): 1,765 cm$^{-1}$ ($\beta$-lactam band).
NMR (DMSO-$d_6$, 60 MHz): $\delta$=6.7 ppm (s, 1H,

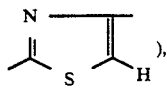

$\delta$=5.5-5.9 ppm (q, 1H, 7—CH—), $\delta$=4.65 ppm (s, broad, 2H, 3—$CH_2$—S—), $\delta$=4.4-4.5 ppm (s, 2H, —$CH_2$—O—$CO_2$—), $\delta$=4.0-4.1 ppm (s, 2H, —C—O—$CH_2$—$CO_2$—) and $\delta$=3.8 ppm (s, 3H, =N—O—$CH_3$).

EXAMPLE 129

7-$\beta$-[2-(2-Amino-thiazol-4-yl)-2-syn-methoximino-acetamido]-3-[2-(carboxy-methoxy-methyl)-1,3,4-thiadiazol-5-yl-thiomethyl]-ceph-3-em-4-carboxylic acid The procedure is as according to Example 128, using 4.5 g of 2-(carboxy-methoxy-methyl)-5-mercapto-1,3,4-thiadiazole. 3.6 g of the title compound are isolated.
Melting point <200° (decomposition).
IR (KBr): 1,770 cm$^{-1}$ ($\beta$-lactam band).
NMR (DMSO-$d_6$, 60 MHz): $\delta$=9.5 ppm (d, 1H, —NHCO—), $\delta$=6.7 ppm (s, 1H,

$\delta$=5.6 ppm (q, 1H, 7—CH—), $\delta$=5.0 ppm (s, 2H, —$CH_2$—O—$CO_2$—), $\delta$=4.05 ppm (s, 2H, —C—O—$CH_2$—$CO_2$—) and $\delta$=3.85 ppm (s, 3H, =N—O—$CH_3$).

EXAMPLE 130

7-$\beta$-[2-(2-Aminothiazol-4-yl)-2-syn-methoximino-acetamido]3-[2-(carboxy-methoxy-methyl)-1,3,4-oxadiazol-5-yl-thiomethyl]-ceph-3-em-4-carboxylic acid The procedure is as according to Example 128, using 4.2 g of 2-(carboxy-methoxy-methyl)-5-mercapto-1,3,4-oxadiazole. 1.9 g of the title compound are isolated.
Melting point=140°-50° (decomposition).
IR (KBr): 1,760 cm$^{-1}$ ($\beta$-lactam band).
NMR (DMSO-$d_6$, 60 MHz): $\delta$=9.6 ppm (d, 1H, —NHCO—), $\delta$=6.7 ppm (s, 1H,

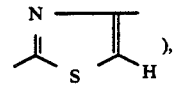

$\delta$=5.6 ppm (q, 1H, 6—CH—), $\delta$=5.1 ppm (AB, 1H, 7—CH—), $\delta$=4.7 ppm (s, 2H, $CH_2$—O—$CO_2$—), $\delta$=4.1 ppm (s, 2H, —O—$CH_2CO_2$—) and $\delta$=3.85 ppm (s, 2H, =N—$OCH_3$).

EXAMPLE 131

7-$\beta$-[2-(2-Amino-thiazol-4-yl)-2-syn-methoximino-acetamido]-3-(4-carboxy-1,3-thiazol-2-yl-thiomethyl)-ceph-3-em-4-carboxylic acid The procedure is as according to Example 5, using 2.3 g (5 mmoles) of 7-$\beta$-[2-(2-amino-thiazol-4-yl)-2-syn-methoximino-acetamido]-cephalosporanic acid and 800 mg (5 mmoles) of 4-carboxy-2-mercapto-1,3-thiazole in 70 ml of water. The reaction solution is heated to 60° C. for 6 hours. 1.0 g of the title compound is isolated.

R$_f$: 0.13 (n-butanol:water:ethanol:glacial acetic acid = 10:4:3:3).

IR (KBr): 1,760 cm$^{-1}$ ($\beta$-lactam band).

NMR (d$_6$-DMSO, 60 MHz): δ=3.83 ppm (s, 3H, =N—OCH$_3$), δ=6.73 ppm (s, 1H,

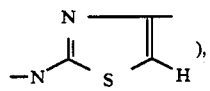

δ=8.37 ppm (s, 1H,

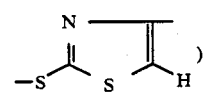

and δ=9.57 ppm (d, 1H, —CO—NH—).

EXAMPLE 132

7-β-[2-(2-Amino-thiazol-4-yl)-2-syn-methoxyimino-acetamido]-3-(4-methyl-coumarin-7-yl-thiomethyl)-ceph-3-em-4-carboxylic acid The procedure is as according to Example 5, using 691 mg (3.6 mmoles) of 7-mercapto-4-methyl-coumarin. The reaction solution is heated to 60° C. for 3 hours. 719 mg of the title compound are isolated.

R$_f$: 0.47 (ethyl acetate:isopropanol:water=4:3:2).

IR (KBr): 1,764 cm$^{-1}$ ($\beta$-lactam band).

NMR (d$_6$-DMSO, 60 MHz): δ=3.83 ppm (s, =N—OCH$_3$), δ=4.23 ppm (AB, 3—CH$_2$—S—), δ=5.12 ppm (d, 1H, 6—CH—), δ=5.71 ppm (q, 1H, 7—CH—), δ=6.33 ppm (m, 1H,

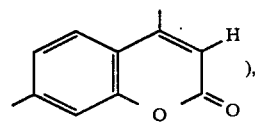

δ=6.72 ppm (s, 1H,

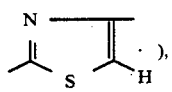

δ=7.2–7.8 ppm (m, 5H,

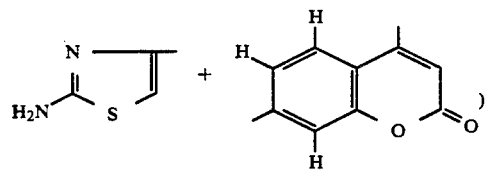

and δ=9.53 ppm (d, 1H, —CO—NH—).

EXAMPLE 133

7-β-[2-(2-Amino-thiazol-4-yl)-2-syn-methoxyimino-acetamido]-3-[4(3H)-quinazolinon-2-yl-thiomethyl]-ceph-3-em-4-carboxylic acid The procedure is as according to Example 5, using 641 mg (3.6 mmoles) of 2-mercapto-4(3H)-quinazoli-none. The reaction solution is heated to 65° C. for 1.5 hours. 666 mg of the title compound are obtained.

R$_f$: 0.52 (ethyl acetate:isopropanol:water=4:3:2).

IR (KBr): 1,758 cm$^{-1}$ ($\beta$-lactam band).

NMR (d$_6$-DMSO, 60 MHz): δ=3.81 ppm (s, =N—OCH$_3$), δ=5.08 ppm (d, 1H, 6—CH—), δ=5.71 ppm (q, 1H, 7—CH—), δ=6.72 ppm (s, 1H,

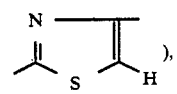

δ=7.0–8.1 ppm (m, 6H,

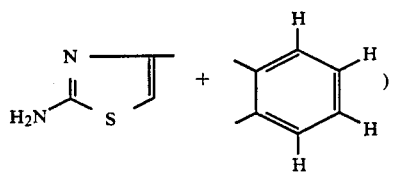

and δ=9.55 ppm (d, 1H, —CO—NH—).

EXAMPLE 134

7-β-[2-(2-Amino-thiazol-4-yl)-2-syn-methoxyimino-acetamido]-3-[2-(pyrrol-2-yl)-1H-1,3,4-triazol-5-yl-thiomethyl]-ceph-3-em-4-carboxylic acid The procedure is as according to Example 5, using 600 mg (3.43 mmoles) of 5-mercapto-2-(pyrrol-2-yl)-1H-1,3,4-triazole. The reaction solution is heated to 65° C. for 1.5 hours and the crude product isolated is purified by trituration with ethyl acetate. 802 mg of the title compound are obtained.

R$_f$: 0.38 (ethyl acetate:isopropanol:water=4:3:2).

IR (KBr): 1,758 cm$^{-1}$ ($\beta$-lactam band).

NMR (d$_6$-DMSO, 60 MHz): δ=3.85 ppm (s, =N—OCH$_3$), δ=4.19 ppm (AB, 3—CH$_2$—S—), δ=5.09 ppm (d, 1H, 6—CH—), δ=5.70 ppm (q, 1H, 7—CH—), δ=6.12 ppm (m, 1H,

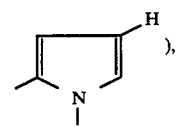

δ=6.71 ppm (s, 1H,

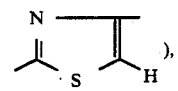

δ=6.88 ppm (m, 1H,

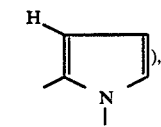

δ=7.10 ppm (m, 3H,

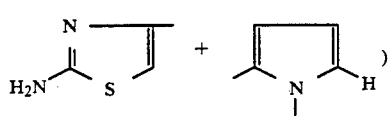

and δ=9.53 ppm (d, 1H, —CO—NH—).

EXAMPLE 135

7-β-[2-(2-amino-thiazol-4-yl)-2-syn-methoximino-acetamido]-3-(3-hydroxy-pyrid-2-yl-thiomethyl)-ceph-3-em-4-carboxylic acid The procedure is as according to Example 5, using 457 mg (3.6 mmoles) of 3-hydroxy-2-mercapto-pyridine. The reaction solution is heated to 60°–75° C. for 2 hours and the crude product isolated is purified by trituration with ethyl acetate. 940 mg of the title compound are obtained.

$R_f$: 0.10 (ethyl acetate:isopropanol:glacial acetic acid=4:3:2).

IR (KBr): 1,751 cm$^{-1}$ (β-lactam band).

NMR (d$_6$-DMSO, 60 MHz): δ=3.81 ppm (s, =N—OCH$_3$), δ=4.81 ppm (d, 1H, 6—CH—), δ=5.51 ppm (q, 1H, 7—CH—), δ=6.71 ppm (s, 1H,

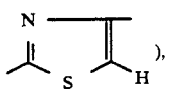

δ=7.14 ppm (m, 4H,

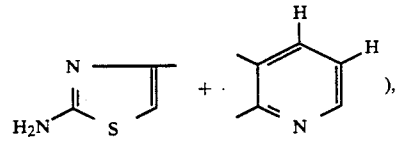

δ=8.12 ppm (m, 1H,

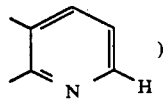

and δ=9.58 ppm (d, 1H, —CO—NH—).

EXAMPLE 136

7-β-[2-(2-Amino-thiazol-4-yl)-2-syn-methoximino-acetamido]-3-[2-(pyrrol-2-yl)-1,3,4-oxadiazol-5-yl-thiomethyl]-ceph-3-em-4-carboxylic acid The procedure is as according to Example 5, using 601 mg (3.6 mmoles) of 5-mercapto-2-(pyrrol-2-yl)-1,3,4-oxadiazole. The reaction solution is heated to 60° C. for 3 hours and the crude product isolated is purified by trituration with ethyl acetate. 1.08 g of the title compound are obtained.

$R_f$: 0.63 (ethyl acetate:isopropanol:water=4:3:2).

IR (KBr): 1,760 cm$^{-1}$ (β-lactam band).

NMR (d$_6$-DMSO, 60 MHz): δ=3.64 ppm (AB, 2—CH$_2$—), δ=3.81 ppm (s, =N—OCH$_3$), δ=4.30 ppm (AB, 3—CH$_2$—S—), δ=5.11 ppm (d, 1H, 6—CH—), δ=5.71 ppm (q, 1H, 7—CH—), δ=6.20 ppm (m, 1H,

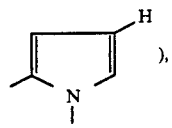

δ=6.70 ppm (s, 1H,

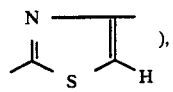

δ=6.74 ppm (m, 1H,

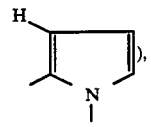

δ=7.07 ppm (m, 3H,

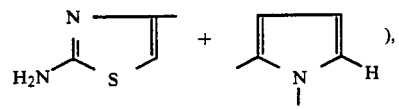

δ=9.52 ppm (d, 1H, —CO—NH—) and δ=12.10 ppm (broad, 1H,

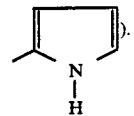

EXAMPLE 137

7-β-[2-(2-Amino-thiazol-4-yl)-2-syn-methoximino-acetamido]-3-(1-ethyl-1,3,4-triazol-5-yl-thiomethyl)-ceph-3-em-4-carboxylic acid The procedure is as according to Example 5, using 3.0 g (6 mmoles) of 7-β-[2-(2-amino-thiazol-4-yl)-2-syn-methoximino-acetamido]-cephalosporanic acid and 1.0 g (7.2 mmoles) of 1-ethyl-5-mercapto-1,3,4-triazole in 100 ml of water. The reaction solution is heated to 60° C. for 5 hours and the crude product isolated is purified by trituration with ethyl acetate. 2.1 g of the title compound are obtained.

$R_f$: 0.15 (acetone:glacial acetic acid=10:1).

IR (KBr): 1,764 cm$^{-1}$ (β-lactam band).

NMR (d$_6$-DMSO, 60 MHz): δ=1.31 ppm (t, 3H, —N—C—CH$_3$), δ=3.84 ppm (s, 3H, =N—O—CH$_3$), δ=5.09 ppm (d, 1H, 6—CH—), δ=5.73 ppm (q, 1H, 7—CH—), δ=6.71 ppm (s, 1H,

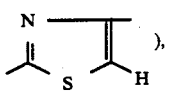

δ=7.18 ppm (s, broad, 2H, —NH$_2$), δ=8.60 ppm (s, 1H,

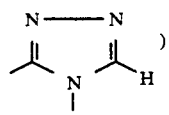

and δ=9.53 ppm (d, 1H, —CO—NH—).

EXAMPLE 138*

7-β-[2-(2-Amino-thiazol-4-yl)-2-syn-methoximino-acetamido]-3-(2-phenyl-1H-1,3,4-triazol-5-yl-thiomethyl)-ceph-3-em-4-carboxylic acid The procedure is as according to Example 5, using 3.0 g (6 mmoles) of 7-β-[2-(2-amino-thiazol-4-yl)-2-syn-methoximino-acetamido]-cephalosporanic acid and 1.73 g (9.6 mmoles) of 5-mercapto-2-phenyl-1H-1,3,4-triazole in 60 ml of water. The reaction solution is heated to 60°–70° C. for 5 hours. 1.98 g of the title compound are isolated.

$R_f$: 0.47 (acetone:glacial acetic acid=10:1).
IR (KBr): 1,759 cm$^{-1}$ (β-lactam band).
NMR (d$_6$-DMSO, 60 MHz): δ=3.81 ppm (s, =N—OCH$_3$), δ=4.09 ppm (AB, 3—CH$_2$—S—), δ=5.09 ppm (d, 1H, 6—CH—), δ=5.69 ppm (q, 1H, 7—CH—), δ=6.70 ppm (s, 1H,

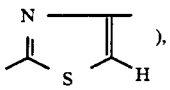

δ=7.10 ppm (s, broad, 2H, —NH$_2$), δ=7.4–7.9 ppm (m, 5H,

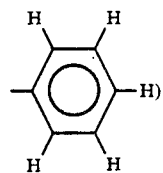

and δ=6.49 ppm (d, 1H, —CO—NH—).

EXAMPLE 139

7-β-[2-(2-Amino-thiazol-4-yl)-2-syn-methoximino-acetamido]-3-(1-phenyl-1,3,4-triazol-5-yl-thiomethyl)-ceph-3-em-4-carboxylic acid The procedure is as according to Example 5, using 3.0 (6 mmoles) of 7-β-[2-(2-amino-thiazol-4-yl)-2-syn-methoximino-acetamido]-cephalosporanic acid and 1.49 g (8.4 mmoles) of 5-mercapto-1-phenyl-1,3,4-triazole in 120 ml of water. The reaction solution is heated to 60° C. for 5 hours. 1.31 g of the title compound are isolated.

$R_f$: 0.23 (acetone:glacial acetic acid=10:1).
IR (KBr): 1,758 cm$^{-1}$ (β-lactam band).
NMR (d$_6$-DMSO, 60 MHz): δ=3.55 ppm (AB, 2—CH$_2$—), δ=3.84 ppm (s, =N—OCH$_3$), δ=4.15 ppm (AB, 3—CH$_2$—S—), δ=5.01 ppm (d, 1H, 6—CH—), δ=6.70 ppm (s, 1H,

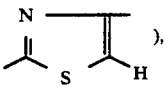

δ=7.15 ppm (s, broad, 2H, —NH$_2$), δ=7.56 ppm (m, 5H,

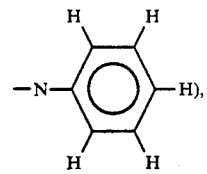

δ=8.84 ppm (s, 1H,

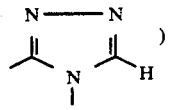

and δ=9.53 ppm (d, 1H, —CO—NH—).

EXAMPLE 140

7-β-[2-(2-Amino-thiazol-4-yl)-2-syn-methoximino-acetamido]-3-(1-phenyl-tetrazol-5-yl-thiomethyl)-ceph-3-em-4-carboxylic acid The procedure is as according to Example 5, using 3.0 g (6 mmoles) of 7-β-[2-(2-amino-thiazol-4-yl)-2-syn-methoximino-acetamido]-cephalosporanic acid and 1.92 g (9.6 mmoles) of 5-mercapto-1-phenyl-tetrazole in 120 ml of water. The reaction solution is heated to 60° for 8 hours and the crude product isolated after concentrating the solution is purified by trituration with ethyl acetate. 992 mg of the title compound are obtained.

$R_f$: 0.43 (ethyl acetate:isopropanol:water=4:3:2).
IR (KBr): 1,764 cm$^{-1}$ (β-lactam band).
NMR (d$_6$-DMSO, 60 MHz): δ=3.58 ppm (AB, 2—CH$_2$—), δ=3.79 ppm (s, =N—OCH$_3$), δ=4.37 ppm (AB, 3—CH$_2$—S—), δ=5.06 ppm (d, 1H, 6—CH—), δ=5.73 ppm (q, 1H, 7—CH—), δ=6.71 ppm (s, 1H,

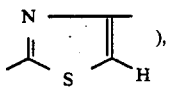

δ=7.14 ppm (s, broad, 2H, —NH$_2$), δ=7.62 ppm (m, 5H,

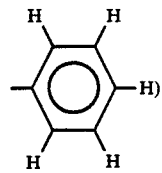

and δ=9.52 ppm (d, 1H, —CO—NH—).

EXAMPLE 141

7-β-[2-(2-Amino-thiazol-4-yl)-2-syn-methoximino-acetamido]-3-(2-methylthio-1,3,4-thiadiazol-5-yl-thiomethyl)-ceph-3-em-4-carboxylic acid The procedure is as according to Example 5, using 1.6 g (3.2 mmoles) of 7-β-[2-(2-amino-thiazol-4-yl)-2-syn-methoximino-acetamido]-cephalosporanic acid and 700 mg (4.2 mmoles) of 5-mercapto-2-methylthio-1,3,4-thiadiazole in 60 ml of water. The reaction solution is heated to 30° to 70° C. for 70 hours and the crude product isolated is purified by trituration with ethyl acetate. 507 mg of the title compound are obtained.

R$_f$: 0.37 (acetone:glacial acetic acid = 10:1).

IR (KBr): 1,756 cm$^{-1}$ (β-lactam band).

NMR (d$_6$-DMSO, 60 MHz): δ=2.63 ppm (s, —S—CH$_3$), δ=3.62 ppm (AB, 2—CH$_2$—), δ=3.80 ppm (s, =N—OCH$_3$), δ=4.34 ppm (AB, 3—CH$_2$—S—), δ=5.12 ppm (d, 1H, 6—CH—), δ=5.74 ppm (q, 1H, 7—CH—), δ=6.70 ppm (s, 1H,

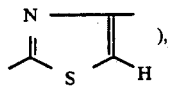

δ=7.15 ppm (s, broad, 2H, —NH$_2$) and δ=9.53 ppm (d, 1H, —CO—NH—).

EXAMPLE 142

7-β-[2-(2-Amino-thiazol-4-yl)-2-syn-methoximino-acetamido]-3-[2-(3-furyl)-1H-1,3,4-triazol-5-yl-thiomethyl]-ceph-3-em-4-carboxylic acid The procedure is as according to Example 5, using 1.6 g (3.2 mmoles) of 7-β-[2-(2-amino-thiazol-4-yl)-2-syn-methoximino-acetamido]-cephalosporanic acid and 602 mg (3.6 mmoles) of 2-(3-furyl)-5-mercapto-1H-1,3,4-triazole in 65 ml of water. The reaction solution is heated to 63°–70° C. for 3 hours. 829 mg of the title compound are isolated.

R$_f$: 0.41 (acetone:glacial acetic acid = 10:1).

IR (KBr): 1,759 cm$^{-1}$ (β-lactam band).

NMR (d$_6$-DMSO, 60 MHz): δ=3.62 ppm (AB, 2—CH$_2$—), δ=3.82 ppm (s, =N—OCH$_3$), δ=4.20 ppm (AB, 3—CH$_2$—S—), δ=5.07 ppm (d, 1H, 6—CH—), δ=5.71 ppm (q, 1H, 7—CH—), δ=6.71 ppm (s, 1H,

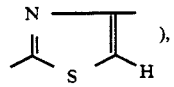

δ=6.86 ppm (d, 1H,

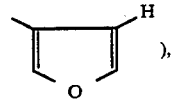

δ=7.15 ppm (s, broad, 2H, —NH$_2$), δ=7.78 ppm (m, 1H,

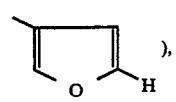

δ=8.17 ppm (m, 1H,

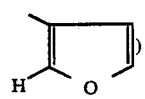

and δ=9.53 ppm (d, 1H, —CO—NH—).

EXAMPLE 143

7-β-[2-(2-Amino-thiazol-4-yl)-2-syn-methoximino-acetamido]-3-(5-amino-1,3-thiazol-2-yl-thiomethyl)-ceph-3-em-4-carboxylic acid The procedure is as according to Example 5, using 1.1 g (2.2 mmoles) of 7-β-[2-(2-amino-thiazol-4-yl)-2-syn-methoximino-acetamido]-cephalosporanic acid and 358 mg (2.7 mmoles) of 5-amino-2-mercapto-1,3-thiazole in 70 ml of water. The reaction solution is warmed to 60° C. for 4.5 hours and the crude product isolated is purified by trituration with ethyl acetate. 705 mg of the title compound are obtained.

R$_f$: 0.30 (acetone:glacial acetic acid = 10:1).

IR (KBr): 1,761 cm$^{-1}$ (β-lactam band).

NMR (d$_6$-DMSO, 60 MHz): δ=3.81 ppm (s, 3H, =N—OCH$_3$), δ=5.09 ppm (d, 1H, 6—CH—), δ=5.67 ppm (q, 1H, 7—CH—), δ=6.71 ppm (s, 1H,

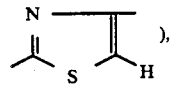

δ=7.16 ppm (s, 2H,

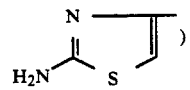

and δ=9.51 ppm (d, 1H, —CO—NH—).

EXAMPLE 144

7-β-[2-(2-Amino-thiazol-4-yl)-2-syn-methoximino-acetamido]-3-(3-carboxy-pyrid-6-yl-thiomethyl)-ceph-3-em-4-carboxylic acid The procedure is as according to Example 5, using 1.0 g (2 mmoles) of 7-β-[2-(2-amino-thiazol-4-yl)-2-syn-methoximino-acetamido]-cephalosporanic acid and 400 mg (2.6 mmoles) of 6-mercapto-nicotinic acid in 60 ml of water. The reaction solution is warmed to 60°–70° for 3 hours. 390 mg of the title compound are isolated.

R$_f$: 0.31 (ethyl acetate:methanol:glacial acetic acid = 20:10:1).

NMR (d$_6$-DMSO, 60 MHz): δ=3.58 ppm (AB, 2—CH$_2$), δ=3.84 ppm (s, =N—OCH$_3$), δ=4.43 ppm (AB, 3—CH$_2$—S—), δ=5.09 ppm (d, 1H, 6—CH—), δ=5.70 ppm (q, 1H, 7—CH—), δ=6.72 ppm (s, 1H,

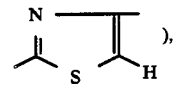

δ=7.17 ppm (s, broad, 2H, —NH$_2$), δ=7.38 ppm (d, 1H,

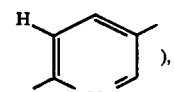

δ=8.03 ppm (q, 1H,

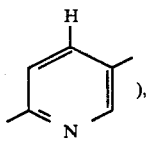

δ=8.86 ppm (d, 1H,

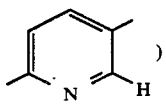

and δ=9.52 ppm (d, 1H, —CO—NH—).

EXAMPLE 145

7-β-[2-(2-Amino-thiazol-4-yl)-2-syn-methoximino-acetamido]-3-(4,5-dimethyl-1,3-oxazol-2-yl-thiomethyl)-ceph-3-em-4-carboxylic acid The procedure is as according to Example 5, using 464 mg (3.6 mmoles) of 4,5-dimethyl-2-mercapto-1,3-oxazole. The reaction solution is heated to 60° C. for 4 hours. 502 mg of the title compound are isolated.

$R_f$: 0.30 (ethyl acetate:isopropanol:water=4:3:2).
IR (KBr): 1,766 $cm^{-1}$ (β-lactam band).
NMR (d$_6$-DMSO, 60 MHz): δ=1.94 ppm (s, 3H,

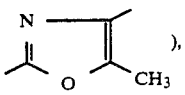

δ=2.17 ppm (s, 3H,

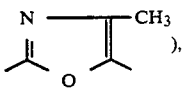

δ=3.57 ppm (AB, 2—CH$_2$—), δ=3.81 ppm (s, =N—OCH$_3$), δ=4.17 ppm (AB, 2H, 3—CH$_2$—S—), δ=5.07 ppm (d, 1H, 6—CH—), δ=5.73 ppm (q, 1H, 7—CH—), δ=6.71 ppm (s, 1H,

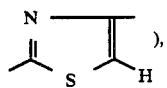

δ=7.17 ppm (s, broad, 2H, —NH$_2$) and δ=9.55 ppm (d, 1H, —CO—NH—).

EXAMPLE 146

7-β-[2-(2-Amino-thiazol-4-yl)-2-syn-methoximino-acetamido]-3-[2-(2-hydroxy-phenyl)-1-methyl-1,3,4-triazol-5-yl-thiomethyl]-ceph-3-em-4-carboxylic acid The procedure is as according to Example 5, using 745 mg (3.6 mmoles) of 2-(2-hydroxy-phenyl)-5-mercapto-1-methyl-1,3,4-triazole. The reaction solution is warmed to 60° C. for 4.5 hours and the crude product isolated is purified by trituration with ethyl acetate. 702 mg of the title compound are obtained.

$R_f$: 0.12 (acetone:glacial acetic acid=10:1).
IR (KBr): 1,751 $cm^{-1}$ (β-lactam band).
NMR (d$_6$-DMSO, 60 MHz): δ=3.25 ppm (s, 3H, —N—CH$_3$), δ=3.76 ppm (s, =N—OCH$_3$), δ=4.29 ppm (AB, 3—CH$_2$—S—), δ=5.07 ppm (d, 1H, 6—CH—), δ=5.67 ppm (q, 1H, 7—CH—), δ=6.6-7.6 ppm (m, 7H,

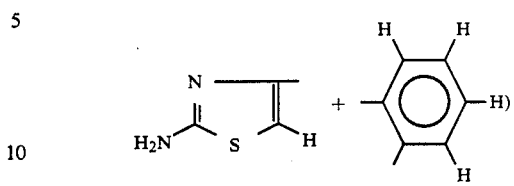

and δ=9.56 ppm (d, 1H, —CO—NH—).

EXAMPLE 147

7-β-[2-(2-Amino-thiazol-4-yl)-2-syn-methoximino-acetamido]-3-(2-hydroxy-1-methyl-1,3,4-triazol-5-yl-thiomethyl)-ceph-3-em-4-carboxylic acid The procedure is as according to Example 5, using 472 mg (3.6 mmoles) of 2-hydroxy-5-mercapto-1-methyl-1,3,4-triazole. The reaction solution is heated to 65° C. for 4.5 hours. 881 mg of the title compound are obtained.

$R_f$: 0.19 (acetone:glacial acetic acid=10:1).
IR (KBr): 1,760 $cm^{-1}$ (β-lactam band).
NMR (d$_6$-DMSO, 60 MHz) (syn): δ=3.07 ppm (s, 3H, —N—CH$_3$), δ=3.62 ppm (AB, 2—CH$_2$—), δ=3.80 ppm (s, =N—OCH$_3$), δ=5.06 ppm (d, 1H, 6—CH—), δ=5.72 ppm (q, 1H, 7—CH—), δ=6.71 ppm (s, 1H,

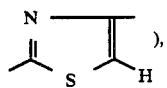

δ=7.14 ppm (s, broad, 2H, —NH$_2$) and δ=9.50 ppm (d, 1H, —CO—NH—).

By concentrating and working up the mother liquor, a further 206 mg of reaction product are isolated which are a mixture of the syn-oxime ether and the anti-oxime ether in the ratio 1:2.

NMR (d$_6$-DMSO, 60 MHz) (anti): δ=3.94 ppm (s, =N—OCH$_3$), δ=7.42 ppm (s,

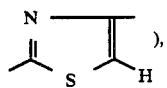

and δ=9.40 ppm (d, —CO—NH—).

EXAMPLE 148

7-β-[2-(2-Amino-thiazol-4-yl)-2-syn-methoximino-acetamido]-3-(2-carboxy-1,3,4-oxadiazol-5-yl-thiomethyl)-ceph-3-em-4-carboxylic acid The procedure is as according to Example 5, using 799 mg (3.6 mmoles) of 5-mercapto-1,3,4-oxadiazole-2-carboxylic acid. The reaction solution is heated to 60° C. for 4 hours. 811 mg of the title compound are isolated.

$R_f$: 0.26 (acetone:glacial acetic acid=10:1).
IR (KBr): 1,763 $cm^{-1}$ (β-lactam band).
NMR (d$_6$-DMSO, 60 MHz): δ=3.63 ppm (AB, 2—CH$_2$—), δ=3.83 ppm (s, =N—OCH$_3$), δ=4.30 ppm (AB, 3—CH$_2$—S—), δ=5.08 ppm (d, 1H, 6—CH—), δ=5.73 ppm (q, 1H, 7—CH—), δ=6.71 ppm (s, 1H,

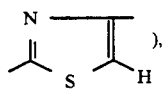

δ=7.16 ppm (s, broad, 2H, —NH₂) and δ=9.52 ppm (d, 1H, —CO—NH—).

EXAMPLE 149

7-β-[2-(2-Amino-thiazol-4-yl)-2-syn-methoximino-acetamido]-3-(1,4,5,6-tetrahydro-pyrimidin-2-yl-thiomethyl)-ceph-3-em-4-carboxylic acid trihydrate The procedure is as according to Example 5, using 928 mg (8 mmoles) of 2-mercapto-1,4,5,6-tetrahydro-pyrimidine. The reaction solution is heated to 60° C. for 4 hours. 200 mg of the thiol are again added and the reaction solution is heated to 65° C. for a further 5.5 hours. The reaction product is isolated as described in Example 5. 818 mg of the title compound are obtained.

$R_f$: 0.13 (ethyl acetate:isopropanol:water=4:3:2).

IR (KBr): 1,761 cm⁻¹ (β-lactam band).

NMR (d₆-DMSO, 60 MHz): δ=3.86 ppm (s, =N—OCH₃), δ=5.09 ppm (d, 1H, 6—CH—), δ=5.44 ppm (q, 1H, 7—CH—), δ=6.73 ppm (s, 1H,

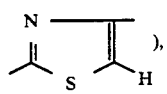

δ=7.14 ppm (broad, 2H, —NH₂) and δ=9.52 ppm (d, 1H, —CO—NH—).

Elementary analysis for C₂₀H₂₁N₇O₅S₃.3H₂O Calculated: C 38.2% H 4.8% N 17.4% O 22.7% S 17.0%. Found: C 36.7% H 4.2% N 15.3% O 20.6% S 14.9%.

EXAMPLE 150

7-β-[2-(2-Amino-thiazol-4-yl)-2-syn-methoximino-acetamido]-3-(4-ethyl-6-hydroxy-5-oxo-1,2,4-triazin-3-yl-thiomethyl)-ceph-3-em-4-carboxylic acid The procedure is as according to Example 5, using 623 mg (3.6 mmoles) of 4-ethyl-6-hydroxy-3-mercapto-5-oxo-1,2,4-triazine. The reaction solution is heated to 60° C. for 4 hours. 602 mg of the title compound are isolated.

$R_f$: 0.18 (ethyl acetate:methanol:glacial acetic acid=20:10:1).

IR (KBr): 1,766 cm⁻¹ (β-lactam band).

NMR (d₆-DMSO, 60 MHz): δ=1.14 ppm (t, 3H, —N—C—CH₃), δ=3.77 ppm (s, =N—OCH₃), δ=4.07 ppm (q, —N—CH₂—C), δ=5.07 ppm (d, 1H, 6—CH—), δ=5.74 ppm (q, 1H, 7—CH—), δ=6.69 ppm (s, 1H,

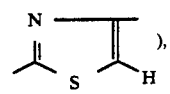

δ=7.14 ppm (s, broad, 2H, —NH₂) and δ=9.53 ppm (d, 1H, —CO—NH—).

EXAMPLE 151

7-β-[2-(2-Amino-thiazol-4-yl)-2-syn-methoximino-acetamido]-3-(6-hydroxy-4-methyl-5-oxo-1,2,4-triazin-3-yl-thiomethyl)-ceph-3-em-4-carboxylic acid The procedure is as according to Example 5, using 572 mg (3.6 mmoles) of 6-hydroxy-3-mercapto-4-methyl-5-oxo-1,2,4-triazine. The reaction solution is heated to 60° C. for 4 hours. 200 mg (1.26 mmoles) of the thiol are then again added and the mixture is heated to 65° C. for a further 6 hours. The reaction product is isolated as described in Example 5. 818 mg of the title compound are obtained.

$R_f$: 0.19 (ethyl acetate:methanol:glacial acetic acid=20:10:1).

IR (KBr): 1,760 cm⁻¹ (β-lactam band).

NMR (d₆-DMSO, 60 MHz): δ=3.28 ppm (s, —N—CH₃), δ=3.82 ppm (s, =N—OCH₃), δ=5.10 ppm (d, 1H, 6—CH—), δ=5.73 ppm (q, 1H, 7—CH—), δ=6.72 ppm (s, 1H,

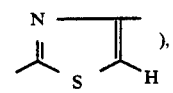

δ=7.16 ppm (broad, 2H, —NH₂) and δ=9.54 ppm (d, 1H, —CO—NH—).

EXAMPLE 152

7-β-[2-(2-Amino-thiazol-4-yl)-2-syn-methoximino-acetamido]-3-(4-hydroxy-pyrimidin-2-yl-thiomethyl)-ceph-3-em-4-carboxylic acid The procedure is as according to Example 5, using 461 mg (3.6 mmoles) of 4-hydroxy-2-mercapto-pyrimidine. The reaction solution is heated to 60° C. for 2.5 hours. 771 mg of the title compound are isolated.

$R_f$: 0.11 (ethyl acetate:methanol:glacial acetic acid=20:10:1).

IR (KBr): 1,752 cm⁻¹ (β-lactam band).

NMR (d₆-DMSO, 60 MHz): δ=3.85 ppm (s, =N—OCH₃), δ=4.20 ppm (AB, 3—CH₂—S—), δ=5.31 ppm (d, 1H, 6—CH—), δ=5.53 ppm (q, 1H, 7—CH—), δ=5.83 ppm (d, 1H,

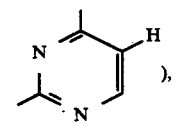

δ=6.71 ppm (s, 1H,

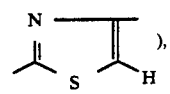

δ=7.15 ppm (broad, 2H, —NH₂), δ=7.73 ppm (d, 1H,

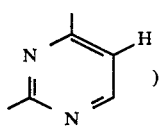

and δ=9.58 ppm (d, 1H, —CO—NH—).

EXAMPLE 153

7-β-[2-(2-Amino-thiazol-4-yl)-2-syn-methoximino-acetamido]-3-(4,5-diamino-pyrimidin-2-yl-thiomethyl)-ceph-3-em-4-carboxylic acid The procedure is as according to Example 5, using 511 mg (3.6 mmoles) of 4,5-diamino-2-mercapto-pyrimidine. The reaction solution is heated to 60° C. for 3 hours. 720 mg of the title compound are obtained.

$R_f$ 0.43 (acetone:glacial acetic acid=10:1).

IR (KBr): 1,756 cm$^{-1}$ (β-lactam band).

NMR (d$_6$-DMSO, 60 MHz): δ=3.54 ppm (AB, 2—CH$_2$—), δ=3.80 ppm (s, =N—OCH$_3$), δ=4.23 ppm (AB, 3—CH$_2$—S—), δ=5.08 ppm (d, 1H, 6—CH—), δ=5.66 ppm (q, 1H, 7—CH—), δ=6.71 ppm (s, 1H,

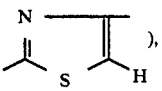

δ=7.15 ppm (s, broad, 2H,

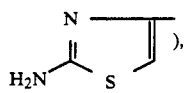

δ=7.38 ppm (s, 1H,

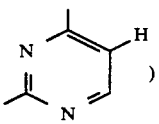

and δ=9.50 ppm (d, 1H, —CO—NH—).

EXAMPLE 154

7-β-[2-(2-Amino-thiazol-4-yl)-2-syn-methoximino-acetamido]-3-[2-(pyrid-2-yl)-1H-1,3,4-triazol-5-yl-thiomethyl]-ceph-3-em-4-carboxylic acid The procedure is as according to Example 5, using 641 mg (3.6 mmoles) of 5-mercapto-2-(pyrid-2-yl)-1H-1,3,4-triazole. The reaction solution is heated to 60° C. for 1.5 hours. 677 mg of the title compound are isolated.

$R_f$ 0.25 (acetone:glacial acetic acid).

IR (KBr): 1,761 cm$^{-1}$ (β-lactam band).

NMR (d$_6$-DMSO, 60 MHz): δ=3.59 ppm (AB, 2—CH$_2$—), δ=3.76 ppm (s, =N—OCH$_3$), δ=4.18 ppm (AB, 3—CH$_2$—S—), δ=5.07 ppm (d, 1H, 6—CH—), δ=5.71 ppm (q, 1H, 7—CH—), δ=6.68 ppm (s, 1H,

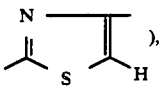

δ=7.14 ppm (broad, 2H, —NH$_2$), δ=7.46 ppm (m, 1H,

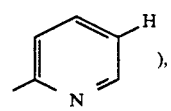

δ=7.96 ppm (m, 2H,

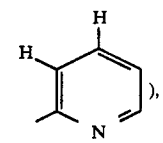

δ=8.63 ppm (m, 1H,

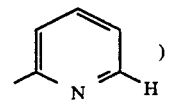

and δ=9.51 ppm (d, 1H, —CO—NH—).

EXAMPLE 155

7-[2-(2-Methoxycarbonylpropionylamido-thiazol-4-yl)-2-syn-methoximinoacetamido]-cephalosporanic acid 2.06 g of O,N-bis-trimethylsilylacetamide are added to a suspension of 4.77 g of the sodium salt of 7-(2-(2-aminothiazol-4-yl)-2-syn-methoximinoacetamido)-cephalosporanic acid (dried at 50° under a high vacuum for 2 hours) in 50 ml of absolute methylene chloride at 10°, the mixture is stirred at room temperature for 2 hours, a solution of 1.65 g of succinic acid ester-chloride in 10 ml of methylene chloride is then added at 10° and, after stirring for a short time, the mixture is left at room temperature for 16 hours.

After evaporating off the solvent, 100 ml of water are added to the residue, the mixture is acidified to pH 2 with 2N HCl and the resulting solid is isolated. The solid is stirred with ethanol and 7-[2-(2-methoxycarbonylpropionylamidothiazol-4-yl)-2-syn-methoximinoacetamido]-cephalosporanic acid is obtained as a cream-colored solid.

IR (KBr): lactam CO: 1,775 cm$^{-1}$.

Thin layer chromatogram: $R_f$ 0.44 (n-BuOH:-H$_2$O:EtOH:glacial acetic acid=10:4:3:3).

EXAMPLE 156

In a manner analogous to that in Example 157, using phenylacetyl chloride, 7-[2-(2-phenylacetamido-thiazol-4-yl)-2-syn-methoximino-acetamido]-cephalosporanic acid is obtained as a light beige powder.

IR (KBr): lactam CO: 1,775 cm$^{-1}$.

Thin layer chromatogram: $R_f$ 0.48 (n-BuOH:-H$_2$O:EtOH:glacial acetic acid=10:4:3:3).

EXAMPLE 157

7-[2-(2-Carboxyacetamido-thiazol-4-yl)-2-syn-methoximino-acetamido]-cephalosporanic acid In a manner analogous to that described in Example 155, 4.77 g of the sodium salt of 7-[2-(2-amino-thiazol-4-yl)-2-syn-methoximinoacetamido]-cephalosporanic acid in 50 ml of absolute methylene chloride are silylated with 2.35 ml of O,N-bis-trimethylsilylacetamide, and a solution of 1.35 g of malonic acid monochloride in 10 ml of chloroform is then added at 10°. After 4 hours, 100 ml of water are added to the reaction mixture, the pH is brought to 1.5 and the product which has precipitated is isolated and dried. 7-[2-(2-Carboxyacetamido-thiazol-4-yl)-2-syn-methoximinoacetamido]-cephalosporanic acid is obtained as almost colorless crystals.

IR (KBr): lactam CO: 1,767 cm$^{-1}$.

Thin layer chromatogram: $R_f$ 0.49 (running agent as in the preceding example).

EXAMPLE 158

7-[2-(2-α-Phenyl-α-chloroacetamido-thiazol-4-yl)-2-syn-methoximino-acetamido]-cephalosporanic acid 1.1 ml of O,N-bis-trimethylsilylacetamide are added to a suspension of 2.4 g of 7-[2-(2-aminothiazol-4-yl)-2-syn-methoximinoacetamido]-cephalosporanic acid (dried at 50° under a high vacuum for 2 hours) in 50 ml of absolute methylene chloride at room temperature and the mixture is stirred at room temperature for 2 hours. It is then cooled to 0° and a solution of 1 g of α-chloro-α-phenylacetyl chloride in 10 ml of methylene chloride is added dropwise. The reaction mixture is left at room temperature for 3 hours, the solvent is then removed and water is added to the residue. After acidifying, the cephem acid which has precipitated is isolated and dissolved in acetone/ethyl acetate 1:1 and the solution is treated with active charcoal and then concentrated to dryness. On digesting with ether, 7-[2-(2-α-phenyl-α-chloroacetamido-thiazol-4-yl)-2-syn-methoximino-acetamido]-cephalosporanic acid remains as a cream-colored solid substance.

IR (KBr): lactam CO: 1,772 cm$^{-1}$.

Thin layer chromatogram: $R_f$ 0.57 (n-BuOH:H$_2$O:glacial acetic acid:ethanol=20:4:3:3).

EXAMPLE 159

7-(2-(2-α-Phenyl-α-(1-methyl-tetrazol-5-yl-thio)-acetamido-thiazol-4-yl)-2-syn-methoximino-acetamido)-cephalosporanic acid 2.0 g of the α-phenyl-α-chloroacetamido compound of the preceding example are introduced in portions into a solution of 390 mg of 1-methyl-5-mercaptotetrazole in a mixture of 1.0 g of NaHCO$_3$, 24 ml of water and 6 ml of acetone at room temperature, the mixture is stirred at room temperature for 4 hours and then covered with a layer of ethyl acetate, and the aqueous phase is brought to pH 1 with 2N HCl and the ethyl acetate phase is isolated. The aqueous phase is again extracted with ethyl acetate, the combined ethyl acetate phases are then dried over Na$_2$SO$_4$ and the solvent is removed.

On digesting with ether, the residue gives 7-[2-<2-α-phenyl-α-(1-methyltetrazol-5-yl-thio)-acetamido-thiazol-4-yl>-2-syn-methoximinoacetamido]-cephalosporanic acid as a cream-colored solid.

IR (KBr): lactam CO: 1,776 cm$^{-1}$.

Thin layer chromatogram: $R_f$ 0.50 (n-BuOH:H$_2$O:glacial acetic acid:ethanol=20:4:3:3).

EXAMPLE 160

Using 2-mercapto-5-methyl-1,3,4-oxadiazole and following the procedure described in the preceding example, 7-[2-<2-α-phenyl-α-(5-methyl-1,3,4-oxadiazol-2-yl-thio)-acetamido-thiazol-4-yl>-2-syn-methoximinoacetamido]-cephalosporanic acid is obtained as a colorless solid.

IR (KBr): lactam CO: 1,779 cm$^{-1}$.

Thin layer chromatogram: $R_f$ 0.69 (n-BuOH:H$_2$O:glacial acetic acid:ethanol=10:4:3:3).

EXAMPLE 161

Using 3-hydroxy-6-mercaptopyridazine and following the procedure described in Example 159, 7-[2-<2-α-phenyl-α(3-hydroxy-pyridazin-6-yl-thio)-acetamido-thiazol-4-yl>-2-syn-methoximinoacetamido]-cephalosporanic acid is obtained as a beige-colored solid.

IR (KBr): lactam CO: 1,779 cm$^{-1}$.

Thin layer chromatogram: $R_f$ 0.69 (running agent as in the previous example).

EXAMPLE 162

7-[2-(2-Aminothiazol-4-yl)-2-syn-benzyloximinoacetamido]-3-(1-methyl-tetrazol-2-yl-thiomethyl)-Δ-3-cephem-4-carboxylic acid a) Acylation

A solution of 2.88 g of dicyclohexylcarbodiimide in 25 ml of absolute methylene chloride is added to a solution of 14.5 g of 2-(2-triphenylmethylaminothiazol-4-yl)-2-syn-benzyloximinoacetic acid in 110 ml of absolute methylene chloride, the mixture is subsequently stirred at room temperature for 2 hours and the dicyclohexylurea which has precipitated is filtered off.

A solution of 3.73 g of 7-amino-3-(1-methyl-tetrazol-2-yl-thiomethyl)-Δ-3-cephem-4-carboxylic acid in 50 ml of absolute methylene chloride and 7.1 g of triethylamine is added in portions to the filtrate, which has been cooled to 5°, the mixture is stirred at room temperature for 6 hours and 100 ml of water are then added at 0°. After acidifying to pH 1, the mixture is stirred for 10 minutes and filtered and the organic phase is separated off from the filtrate, dried and concentrated.

b) Detritylation and purification 18.0 g of the above residue are introduced into 70 ml of 50 per cent strength formic acid at 60°, the mixture is stirred for 2 hours and the triphenylcarbinol which has precipitated is then filtered off. Active charcoal is added to the filtrate, the mixture is filtered and the filtrate is concentrated. On triturating with water, the residue gives a cream-colored product. After drying, the substance is dissolved in 150 ml of acetone at 40°, the solution is filtered and a solution of 3.2 g of sodium acetate in 130 ml of water is added to the filtrate.

The sodium salt of 2-(2-aminothiazol-4-yl)-2-syn-benzyloximinoacetic acid is formed as a cream-colored solid and is filtered off and discarded. The filtrate is then acidified to pH 2 with 2N HCl and the cream-colored crystals of 7-[2-(2-aminothiazol-4-yl)-2-syn-benzyloximinoacetamido]-3-(1-methyl-tetrazol-2-yl-thiomethyl)-Δ-3-cephem-4-carboxylic acid are filtered off and dried.

IR: lactam CO 1,770 cm$^{-1}$.

Thin layer chromatogram: $R_f$ 0.35 (n-BuOH:H$_2$O:glacial acetic acid:ethanol=20:4:3:3).

EXAMPLE 163

7-[2-(2-Aminothiazol-4-yl)-2-syn-benzyloximinoacetamido]-cephalosporanic acid a) Acylation 5.45 g of dicyclohexylcarbodiimide in 50 ml of methylene chloride are added to a solution of 27.3 g of 2-(2-triphenylmethylaminothiazol-4-yl)-2-syn-benzyloximino-acetic acid in 250 ml of methylene chloride. After 2½ hours, the dicyclohexylurea which has precipitated is filtered off.

The filtrate, containing the symmetric anhydride, is cooled to 5°, with the exclusion of moisture, and a solution of 6.0 g of 7-aminocephalosporanic acid in 100 ml of methylene chloride and 8 g of triethylamine is added dropwise, whilst stirring. After the addition has ended, the mixture is stirred at room temperature for 4 hours, 80 ml of water are then added and the reaction mixture is acidified to pH 2.5 with 2N HCl. It is filtered and the organic phase is separated off from the filtrate, washed until neutral and, after drying over $Na_2SO_4$, concentrated. A solid consisting of 2-(2-triphenylmethylamino-thiazol-4-yl)-2-syn-benzyloximinoacetic acid and 7-[2-(2-triphenylmethylamino-thiazol-4-yl)-2-syn-benzyloximinoacetamido]-cephalosporanic acid is obtained.

b) Detritylation 23.6 g of the above mixture are dissolved in 60 ml of dioxan, the solution is diluted with 118 ml of ether in portions and 3.5 ml of diethylamine are then added. After 1 hour, the diethylamine salt of 2-(2-triphenylmethylamino-thiazol-4-yl)-2-syn-benzyloximinoacetic acid of melting point 188°-189° is filtered off.

The filtrate is concentrated to dryness, the residue is digested with ether and the resulting solid is introduced into 70 ml of 50% strength formic acid. After 1¾ hours at 60°, the triphenylcarbinol formed is filtered off, the filtrate is concentrated and the reaction product which remains is stirred with 200 ml of water. The resulting solid is isolated and dried and the residual triphenylcarbinol is removed with 250 ml of ether. After renewed filtration, 7-[2-(2-aminothiazol-4-yl)-2-syn-benzyloximinoacetamido]-cephalosporanic acid is obtained as a cream-colored solid, melting point 270°;

IR (KBr): lactam CO: 1,773 $cm^{-1}$.

Thin layer chromatogram-$R_f$ 0.35 (20 ml of n-butanol, 4 ml of $H_2O$, 3 ml of $C_2H_5OH$ and 3 ml of glacial acetic acid).

EXAMPLE 164

7-(2-(2-Amino-thiazol-4-yl)-2-syn-phenoximinoacetamido)-cephalosporanic acid a) Acylation 1 g of dicyclohexylcarbodiimide is added to a solution of 3.6 g of 2-(2-triphenylmethylamino-thiazol-4-yl)-2-syn-phenoximinoacetic acid in 40 ml of absolute methylene chloride at 0° and the mixture is subsequently stirred at room temperature for 3 hours, whereupon dicyclohexylthiourea separates out.

A solution of 950 mg of 7-aminocephalosporanic acid in 20 ml of methylene chloride and 1.1 ml of triethylamine is added dropwise to this suspension at 0°. The reaction mixture is stirred at 0° for 2 hours and is then left to stand at room temperature for 16 hours, before the dicyclohexylurea is filtered off. 200 ml of water are added to the filtrate, the mixture is acidified to pH 2 with 2N HCl and the organic phase is separated off. The aqueous phase is extracted a further 3 times with methylene chloride. The combined organic phases are dried, the solvent is stripped off and the residue is triturated with ether. A cream-colored solid of melting point 145°-150°, decomposition, remains, which is identified as 7-[2-(2-triphenylmethylamino-thiazol-4-yl)-2-syn-phenoximinoacetamido]-cephalosporanic acid.

b) Detritylation and purification 2.3 g of the tritylated compound are introduced into 10 ml of 50 per cent formic acid, the mixture is warmed to 60° for 1 hour and the triphenylcarbinol which has precipitated is then removed. The filtrate is concentrated to dryness and the residue is triturated with ether. A solid is isolated and is dissolved in aqueous bicarbonate, the solution is clarified with the addition of active charcoal and the solid is then reprecipitated with 2N HCl.

7-[2-(2-Aminothiazol-4-yl)-2-syn-phenoximinoacetamido]-cephalosporanic acid is isolated as beige-colored crystals of melting point >250°.

IR (KBr) lactam CO: 1,770 $cm^{-1}$.

Thin layer chromatogram: $R_f$ 0.54 (n-BuOH, $H_2O$:glacial acetic acid:ethanol=10:4:3:3).

Preparation of the Starting Compound for Examples 162 and 163 a) Ethyl 2-syn-benzyloximinoacetoacetate 30.5 g of potassium carbonate are introduced into a solution of 23.5 g of ethyl 2-syn-oximinoacetoacetate in 120 ml of acetone at 15°, whilst stirring, and 25.6 g of benzyl bromide are then added dropwise to the reaction mixture, the mixture is stirred at room temperature for 4 hours and then left for 16 hours without stirring. The solids are filtered off and the solution is concentrated to dryness. The oil which remains is warmed to 80° in vacuo (0.05 mm) in order to remove excess benzyl bromide and, after cooling, 5% strength sodium bicarbonate solution is added to the residue and the mixture is extracted with ether. The ether phase is washed twice with water, dried with $Na_2SO_4$ and then concentrated. Ethyl 2-syn-benzyloximino-acetoacetate remains as a pale yellow oil.

(Thin layer chromatogram in $CHCl_3$/ethyl acetate=20:1: $R_f$ 0.74).

b) Ethyl 2-syn-benzyloximino-4-bromoacetoacetate 150 mg of toluenesulfonic acid are added to a solution of 12.5 g of ethyl 2-syn-benzyloximino-acetoacetate in 80 ml of absolute methylene chloride, and about 2 g of the 8 g of bromine required are then added at room temperature. On subsequent stirring, the initially deep brown solution decolorizes. The rest of the bromine is then added dropwise. After the addition has ended, the reaction mixture is subsequently stirred for 1½ hours at room temperature, cooled to 0° and washed with 10 per cent strength sodium bicarbonate solution.

The organic phase is separated off, dried over $Na_2SO_4$ and concentrated and the oil which remains is recrystallized from cyclohexane. Ethyl 2-syn-benzyloximino-4-bromoacetoacetate is obtained as colorless crystals of melting point 66°-68°.

c) Ethyl 2-(2-amino-thiazol-4-yl)-2-syn-benzyloximino-acetate

A solution of 11.8 g of ethyl 2-syn-benzyloximino-4-bromoacetoacetate in 60 ml of ethanol (98% pure) and 40 ml of acetone is added dropwise to a solution of 2.66 g of thiourea in 50 ml of 40 per cent strength ethanol at room temperature in the course of 20 minutes. The reaction mixture is subsequently stirred at 25° for 2 hours and then concentrated in order to crystallize out the end product and the resulting crystals are isolated. The product is dissolved hot in 50% strength ethanol and the pH of the solution is then adjusted to 7 with aqueous ammonia. The cream-colored crystals which precipitate are isolated, washed with 40% strength ethanol and diisopropyl ether and dried. Ethyl 2-(2-aminothiazol-4-yl)-2-syn-benzyloximino-acetoacetate of melting point 135°–138° is obtained as almost colorless crystals.

d) Ethyl 2-(2-triphenylmethylamino-thiazol-4-yl)-2-syn-benzyloximinoacetate 6.7 g of triethylamine are added to a solution of 18.3 g of ethyl 2-(2-aminothiazol-4-yl)-2-syn-benzyloximinoacetate in 125 ml of absolute $CH_2Cl_2$ and 25 ml of dimethylformamide at −15°, the mixture is then cooled to −35°, 17.5 g of triphenylchloromethane are introduced in portions and the reaction mixture is subsequently stirred at −30° for 1 hour and then at room temperature for 3 hours.

The reaction solution is then cooled to 0° and washed several times with 2N HCl and finally with water, the organic phase is isolated and dried over $Na_2SO_4$ and the solvent is removed. Ethyl 2-(2-triphenylmethylamino-thiazol-4-yl)-2-syn-benzyloximino-acetate is obtained as a cream-colored solid, (thin layer chromatogram in $CHCl_3$/ethyl acetate 1:1=$R_f$0.98, compare the starting material, $R_f$0.63), which can be reacted further without further purification.

e) The sodium salt of 2-(2-triphenylmethylamino-thiazol-4-yl)-2-syn-benzyloximinoacetic acid The resulting ethyl 2-(2-triphenylmethylamino-thiazol-4-yl)-2-syn-benzyloximinoacetate is dissolved in a mixture of 230 ml of ethanol and 40 ml of dioxan at 60°, a solution of 3 g of NaOH in 45 ml of water is added and the mixture is heated under reflux for 2 hours. The reaction mixture is then substantially concentrated, 350 ml of water are added to the residue and the sodium salt of 2-(2-triphenylmethylamino-thiazol-4-yl)-2-syn-benzyloximinoacetic acid is isolated as a colorless solid of melting point 257°–258° (decomposition).

f) 2-(2-Triphenylmethylamino-thiazol-4-yl)-2-syn-benzyloximinoacetic acid

The resulting sodium salt of 2-(2-triphenylmethylamino-thiazol-4-yl)-2-syn-benzyloximinoacetic acid is suspended in 250 ml of methylene chloride and the suspension is stirred with 50 ml of 2N hydrochloric acid at 5°, whereupon the acid forms, which is readily soluble in $CH_2Cl_2$.

The organic phase is isolated and dried with sodium sulfate and the solvent is removed. Cyclohexane is added to the residue, whereupon an almost colorless solid forms, which is isolated and washed with diisopropyl ether. 2-(2-Triphenylmethylamino-thiazol-4-yl)-2-syn-benzyloximinoacetic acid is obtained as an amorphous solid which exhibits a $R_f$ value of 0.21 in a thin layer chromatogram in $CHCl_3/CH_3OH$ 6:1. Preparation of the starting compound for Example 164 a) Ethyl bromoacetoglyoxylate 120 g of ethyl acetoglyoxylate are dissolved in 700 ml of methylene chloride and reacted with a solution of 146 g of bromine in 200 ml of methylene chloride at 5° in the course of 1 hour.

After decolorizing the solution, the solvent is stripped off and the oil which remains is reacted without further purification.

b) Ethyl 2-amino-thiazol-4-yl-glyoxylate 195 g of ethyl bromoacetylglyoxylate are added dropwise to a solution of 66 g of thiourea in 450 ml of water and 450 ml of ethanol at 5° and after the addtion has ended, the mixture is stirred at room temperature for 30 minutes and at 50° for 30 minutes and, after adding active charcoal, the resulting reaction mixture is then filtered. The filtrate is brought to pH 7 by adding sodium bicarbonate solution, whereupon ethyl 2-amino-thiazol-4-ylglyoxylate crystallizes out in crystals of melting point 147°.

c) Ethyl 2-triphenylmethylamino-thiazol-4-yl-glyoxylate 27 g of triethylamine are added to a solution of 90 g of ethyl 2-aminothiazol-4-ylglyoxylate in 225 ml of dimethylformamide and 375 ml of $CH_2Cl_2$ at −15° and 75 g of triphenylchloromethane are then added at −30°. After 15 minutes at −30°, the mixture is stirred for 3 hours without a cooling bath and 500 ml of $CH_2Cl_2$ are added to the resulting reaction mixture, the mixture is washed with 300 ml of 1N HCl and then twice with 200 ml of water, the organic phase is dried over $Na_2SO_4$ and the solvent is evaporated off.

An oil remains, which is used for further reactions without purification beforehand.

d) 2-Triphenylmethylamino-thiazol-4-yl-glyoxylic acid

A solution of 14.8 g of NaOH in 370 ml of methanol is added to a solution of 156 g of crude ethyl 2-triphenylmethylamino-thiazol-4-yl-glyoxylate in 150 ml of methanol and the mixture is boiled under reflux for 5 minutes, whereupon the sodium salt of 2-triphenylmethylamino-thiazol-4-yl-glyoxylic acid crystallizes out.

The resulting sodium salt is suspended in 380 ml of water, and 76 ml of 2N HCl are added, whilst stirring vigorously. After 15 minutes, the precipitate is filtered off, washed with water and dried.

2-Triphenylmethylamino-thiazol-4-yl-glyoxylic acid are obtained as yellow crystals of melting point 163°–165° (decomposition).

e) 2-(2-Triphenylmethylamino-thiazol-4-yl)-2-syn-phenoximino-acetic acid 30 g of 2-triphenylmethylamino-thiazol-4-yl-glyoxylic acid are introduced into a solution of 450 ml of glacial acetic acid and 90 ml of water, and 8 g of O-phenyl-hydroxylamine are added at 15°. The reaction mixture initially becomes clear, then the crystallization of the oxime begins. After 15 minutes, 200 ml of water are added at 10°–15°, whilst stirring The crystals which have precipitated are filtered off, extracted by stirring with acetone and filtered off again. 2-(2-Triphenylmethylamino-thiazol-4-yl)-2-syn-phenoximino-acetic acid of melting point 141°–143° (decomposition) is isolated in the form of a colorless solid.

EXAMPLE 165

7-[2-(2-Propionamido-thiazol-4-yl)-2-syn-methoximino-acetamido]-cephalosporanic acid 4.0 g of 2-(2-propionylamido-thiazol-4-yl)-2-syn-methoximino-acetic acid (melting point 192° C.; prepared by reacting ethyl 2-(2-amino-thiazol-4-yl)-2-syn-methoximino-acetate with propionyl chloride and subsequently saponifying the product) are dissolved in 50 ml of methylene chloride and 5 ml of dimethylformamide and the solution is cooled to −5° C. After adding 3.2 g of dicyclohexylcarbodiimide, the mixture is stirred for 30 minutes, whilst cooling with ice, and for 30 minutes at room temperature. After filtering off the dicyclohexylurea, the filtrate is cooled to −5° C. and a solution of 4.3 g of 7-aminocephalosporanic acid and 2.2 ml of triethylamine in 50 ml of methylene chloride is added. The mixture is allowed to warm to room temperature and is subsequently stirred for 3 hours. The methylene chloride phase is extracted with water and the aqueous phase is separated off and acidified to pH 2.5 with 2N hydrochloric acid, whilst cooling. The precipitate formed is filtered off, stirred with ethanol and dried. The title compound thus obtained is colored slightly yellow.

$R_f$ value: 0.39 (n-BuOH: $H_2O$:ethanol:glacial acetic acid = 10:4:3:3).

IR (KBr): lactam CO: 1,770 $cm^{-1}$.

EXAMPLE 166

7-[2-(2-<2-Oxo-imidazolidin-1-yl>-carbonylamino-thiazol-4-yl)-2-methoximino-acetamido]-cephalosporanic acid In a manner analogous to that in Example 165, the title compound given above is obtained as a colorless substance from 2-(2-<2-oxo-imidazolidin-1-yl>-carbonylamino-thiazol-4-yl)-2-syn-methoximino-acetic acid.

$R_f$ value: 0.24 (n-BuOH: $H_2O$:ethanol:glacial acetic acid = 10:4:3:3).

IR (KBr) lactam CO: 1,770 $cm^{-1}$.

The starting substance required for Example 166 is prepared in the following manner:

a) Ethyl 2-(2-<3-acetyl-2-oxo-imidazolidin-1-yl>-carbonylamino-thiazol-4-yl)-2-methoximino-acetate 15.6 g of ethyl 2-(2-amino-thiazol-4-yl)-2-syn-methoximino-acetate are dissolved in 400 ml of methylene chloride, the solution is cooled to −10° C. and 10.8 ml of triethylamine are added. 12.2 g of 3-acetyl-2-oxo-imidazolidine-1-carbonyl chloride are then added dropwise in the course of 10 minutes and the mixture is subsequently stirred at room temperature for three hours. It is then extracted by shaking twice with water and twice with dilute hydrochloric acid and the extract is dried and concentrated in vacuo. The residue is solidified by adding diisopropyl ether and is recrystallized from ethanol.

Melting point 186°–188° C.

b) 2-(2-<2-Oxo-imidazolidin-1-yl>-carbonylamino-thiazol-4-yl)-2-syn-methoximino-acetic acid 7.6 g of the ester obtained according to a) are warmed to 40°–45° C. in 50 ml of ethanol and 50 ml of 1N sodium hydroxide solution for 4 hours, whilst stirring. After cooling, the mixture is acidified with acetic acid and evaporated to dryness in vacuo. The residue is boiled up with 500 ml of ethanol and filtered off.

Melting point > 280° C.

EXAMPLE 167

7-Amino-3-(4,6-diamino-pyrimidin-2-yl-thiomethyl)-ceph-3-em-4-carboxylic acid dihydrate 2.7 g (0.01 mole) of 7-aminocephalosporanic acid are dissolved in 50 ml of water with the required amount of sodium bicarbonate. 1.7 g (0.013 mole) of 4,6-diamino-2-mercapto-pyrimidine and the equivalent amount of sodium bicarbonate are added and the reaction solution is heated to 60° C. for 4 hours, whilst stirring and keeping the pH value constant (pH = 7). The mixture is allowed to cool, undissolved material is filtered off and the filtrate is concentrated in vacuo at 30° C. to half its volume. The aqueous solution which remains is extracted several times with ethyl acetate and the aqueous phase is adjusted to a pH of 2 with 2N hydrochloric acid. The precipitate is filtered off, washed with water until free from chloride and dried in vacuo at 37° C. over potassium hydroxide. 1.61 g of the title compound are obtained.

$R_f$: 0.27 (acetone:glacial acetic acid = 10:1).

IR (KBr): 1,745 $cm^{-1}$ (β-lactam band).

NMR (d6-DMSO, 60 MHz): δ = 3.53 ppm (AB, 2—$CH_2$—), δ = 4.7–5.0 ppm (m, 2H, 6—CH—+7—CH—), δ = 5.07 ppm (s, 1H,

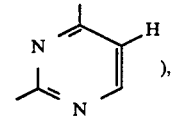),

δ = 6.08 ppm (broad, 2H, 7—$NH_2$) and δ = 6.68 ppm (s, broad, 4H,

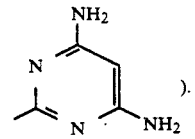).

Elementary analysis: for $C_{12}H_{14}N_6O_3S_2 \cdot 2H_2O$; calculated: C 36.9% H 4.7% N 21.5% O 20.5% S 16.4%. found: C 36.4% H 4.5% N 19.8% O 19.6% S 15.5%.

EXAMPLE 168

7-β-[2-(2-Amino-thiazol-4-yl)-2-syn-methoximino-acetamido]-3-(4,6-diamino-pyrimidin-2-yl-2-thiomethyl)-ceph-3-em-4-carboxylic acid 3.45 g (8 mmoles) of 2-syn-methoximino-2-(2-tritylamino-thiazol-4-yl)-acetic acid in 20 ml of chloroform are added dropwise to a solution, cooled to +5° C., of 1 g (4.7 mmoles) of dicyclohexylcarbodiimide in 10 ml of chloroform. After stirring for one and a half hours at room temperature, the dicyclohexylurea which has precipitated is separated off.

A solution of 1.56 g (4 mmoles) of 7-amino-3-(4,6-diamino-pyrimidin-2-yl-thiomethyl)-ceph-3-em-4-carboxylic acid and 1.4 ml (10 mmoles) of triethylamine in 20 ml of methylene chloride is added dropwise to the filtrate, cooled to −10° C., whilst stirring. After stirring at room temperature for three hours, the solution is washed with 10 ml of 1N HCl and then with 10 ml of water, dried and filtered and the solvent is evaporated off to dryness. The crude product (4.7 g) is purified by column chromatography on 500 g of silica gel. 10% strength aqueous acetone is used as the running agent. 1.42 g of 7-β-[2-syn-methoximino-2-(2-tritylamino-thiazol-4-yl]-3-(4,6-diamino-pyrimidin-2-thiomethyl)-ceph-3-em-4-carboxylic acid are isolated.

This compound is dissolved in 10 ml of 80% strength formic acid and the solution is heated to 55° C. for 30 minutes. It is allowed to cool and is diluted with 10 ml of water and the triphenylcarbinol is filtered off. The filtrate is concentrated to dryness and the residue is triturated with ethyl acetate. 615 mg of the title compound are isolated. The product is identical to the compound described in Example 85.

EXAMPLE 169

7-Amino-3-[2-(thien-2-yl)-1H-1,3,4-triazol-5-yl-thiomethyl]-ceph-3-em-4-carboxylic acid 5.4 g (0.02 mole) of 7-aminocephalosporanic acid are dissolved in 100 ml of water with the required amount of sodium bicarbonate. 4.76 g (0.026 mole) of 5-mercapto-2-(thien-2-yl)-1H-1,3,4-triazole and the equivalent amount of sodium bicarbonate are added and the reaction solution is heated to 55°-60° C. for 3 hours. The reaction solution is allowed to cool and is extracted several times with ethyl acetate and the aqueous phase is acidified with 2N hydrochloric acid. 3 g of crude product are isolated.

This crude product is dissolved in 1N sodium bicarbonate solution and the solution is acidified with 2N hydrochloric acid until it becomes slightly turbid and extracted several times with ethyl acetate. The organic extracts are discarded and the aqueous solution is adjusted to a pH value of 2 with 2N hydrochloric acid. The precipitate is filtered off, washed with water until free from chloride and dried in vacuo at 37° C. over potassium hydroxide. 2.51 g of the title compound are obtained.

NMR (d$_6$-DMSO, 60 MHz): δ=3.60 ppm (AB, 2—CH$_2$—), δ=4.16 ppm (AB, 3—CH$_2$—S—), δ=4.80 ppm (m, 2H, 6—CH—+7—CH—), δ=7.10 ppm (t, 1H,

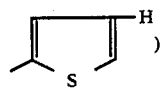

and δ=7.55 ppm (m, 2H,

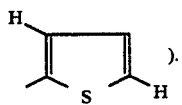

Elementary analysis: for C$_{14}$H$_{13}$N$_5$O$_3$S$_3$; calculated: C 42.5% H 3.3% N 17.7% O 12.2% S 24.3%. found: C 39.1% H 3.4% N 15.9% O 10.7% S 21.0%.

EXAMPLE 170

7-β-[2-(2-Amino-thiazol-4-yl)-2-syn-methoximino-acetamido]-3-[2-(thien-2-yl)-1H-1,3,4-triazol-5-yl-thiomethyl]-ceph-3-em-4-carboxylic acid The procedure is as according to Example 168, using 1.5 g (4 mmoles) of 7-amino-3-[2-(thien-2-yl)-1H-1,3,4-triazol-5-yl-thiomethyl]-ceph-3-em-4-carboxylic acid. 625 mg of the title compound are isolated. The product is identical to the compound described in Example 33.

EXAMPLE 171

7-β-[2-(2-Amino-thiazol-4-yl)-2-syn-methoximino-acetamido]-3-(5-carboxymethyl-4-methyl-1,3-thiazol-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.95 g (5 mmoles) of 5-carboxymethyl-2-mercapto-4-methyl-1,3-thiazole. The reaction solution is warmed to 60° C. for 6 hours. 1.3 g of the title compound are isolated.

R$_f$: 0.34 (n-butanol:water:ethanol:glacial acetic acid=10:4:3:3).

IR (KBr): 1,765 cm$^{-1}$ (β-lactam band).

NMR (d$_6$-DMSO, 60 MHz): δ=2.23 ppm (s, 3H, =C—CH$_3$), δ=3.73 ppm (s, 2H, =C—CH$_2$—COO—), δ=3.83 ppm (s, 3H, =N—OCH$_3$), δ=6.73 ppm (s, 1H,

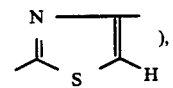

δ=7.17 ppm (s, broad, 2H, —NH$_2$) and δ=9.53 ppm (d, 1H, —CO—NH—).

EXAMPLE 172

7-β-Amino-3-(5-carboxymethyl-4-methyl-1,3-thiazol-2-yl-thiomethyl)-ceph-3-em-4-carboxylic acid 2.7 g (0.01 mole) of 7-aminocephalosporanic acid and 1.9 g (0.01 mole) of 5-carboxymethyl-2-mercapto-4-methyl-1,3-thiazole are suspended in 250 ml of water. Sodium bicarbonate is added until a clear solution has formed. The reaction solution is heated to 50° C. for 4 hours, whilst keeping the pH value constant at the neutral point. The solution is allowed to cool and is extracted several times with ethyl acetate and the aqueous phase is adjusted to a pH value of 2 with 2N HCl. The precipitate is filtered off, washed several times with alcohol and ether and dried. 3.7 g of the title compound of melting point 195°-196° C. (decomposition) are obtained.

NMR (d$_6$-DMSO, 60 MHz): δ=2.17 ppm (s, 3H, =C—CH$_3$), δ=3.52 ppm (AB, 2H, 2—CH$_2$—), δ=3.68 ppm (s, 2H, =C—CH$_2$—COO—), δ=4.31 ppm (AB, 2H, 3—CH$_2$—S—) and δ=4.80 ppm (m, 2H, 6—CH—+7—CH—).

EXAMPLE 173

7-β-[2-syn-Ethoximino-2-(2-amino-thiazol-4-yl)-acetamido]-3-(5-carboxymethyl-4-methyl-1,3-thiazol-2-yl-thiomethyl)-ceph-3-em-4-carboxylic acid The procedure is as according to Example 168, using 3.7 g (8 mmoles) of 2-syn-ethoximino-2-(2-tritylamino-thiazol-4-yl)-acetic acid and 1.6 g (4 mmoles) of 7-amino-3-(5-carboxymethyl-4-methyl-1,3-thiazol-2-yl-thiomethyl)-ceph-3-em-4-carboxylic acid. 584 mg of the title compound of melting point 200° C. (decomposition) are obtained.

R$_f$: 0.29 (n-butanol:water:ethanol:glacial acetic acid=10:4:3:3).

IR (KBr): 1,770 cm$^{-1}$ (β-lactam band).

NMR (d$_6$-DMSO, 60 MHz): δ=1.23 ppm (t, 3H, =N—O—C—CH$_3$), δ=2.23 ppm (s, 3H, =C—CH$_3$), δ=3.73 ppm (s, 2H, —CH$_2$—COO—), δ=4.10 ppm (q, 2H, =N—O—CH$_2$—C—), δ=5.11 ppm (d, 1H, 6—

CH—), δ=5.73 ppm (q, 1H, 7—CH—), δ=6.72 ppm (s, 1H,

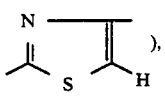

δ=7.15 ppm (s, broad, 2H, —NH₂) and δ=9.50 ppm (d, 1H, —CO—NH—).

EXAMPLE 174

7-β-[2-syn-Ethoximino-(2-amino-thiazol-4-yl)-acetamido]-3-(5-carboxymethyl-4-methyl-1,3-thiazol-2-yl-thiomethyl)-ceph-3-em-4-carboxylic acid The procedure is as according to Example 5, using 370 mg of 7-β-[2-ethoximino-(2-amino-thiazol-4-yl)-acetamido]-cephalosporanic acid, which was obtained according to Example 51, and 154 mg of 2-carboxymethyl-5-mercapto-4-methyl-1,3-thiazole. The reaction solution is warmed to 65° C. for 8 hours. 120 mg of the title compound are isolated. The product is identical to the compound described in Example 173.

EXAMPLE 175

7-β-[2-(2-Allylamino-thiazol-4-yl)-2-syn-methoximino-acetamido]-cephalosporanic acid The procedure is as according to Example 168, using 1.69 g (7 mmoles) of 2-(2-allylamino-thiazol-4-yl)-2-syn-methoximino-acetic acid and 956 mg (3.5 mmoles) of 7-aminocephalosporanic acid. 572 mg of the title compound of melting point 165°-170° (decomposition) are obtained.

R$_f$: 0.45 (n-butanol:water:ethanol:glacial acetic acid=10:4:3:3).

IR (KBr): 1,775 cm⁻¹ (β-lactam band) and 1,730 cm⁻¹ (acetate band).

NMR (d₆-DMSO, 60 MHz): δ=2.05 ppm (s, 3H, —O—CO—CH₃), δ=3.88 ppm (s, 3H, =N—OCH₃), δ=5.0-6.3 ppm (m, 5H, H₂C=CH—C—+6—CH—+-7—CH—), δ=6.8 ppm (s, 1H,

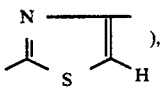

δ=7.93 ppm (t, 1H,

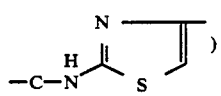

and δ=9.53 ppm (d, 1H, —CO—NH—).

EXAMPLE 176

7-β-[2-(2-Amino-thiazol-4-yl)-2-syn-methoximino-acetamido]-3-(benzoxazol-2-yl-thiomethyl)-ceph-3-em-4-carboxylic acid The procedure is as according to Example 5, using 544 mg (3.6 mmoles) of 2-mercapto-benzoxazole. The reaction solution is heated to 60° C. for 5.5 hours. 747 mg of the title compound are obtained.

R$_f$: 0.54 (ethyl acetate:isopropanol:water=4:3:2).
IR (KBr): 1,765 cm⁻¹ (β-lactam band).
NMR (d₆-DMSO, 60 MHz): δ=3.69 ppm (AB, 2H, 2—CH₂—), δ=3.85 ppm (s, 3H, =N—OCH₃), δ=4.45 ppm (AB, 2H, 3—CH₂—S—), δ=5.11 ppm (d, 1H, 6—CH—), δ=5.75 ppm (q, 1H, 7—CH—), δ=6.71 ppm (s, 1H,

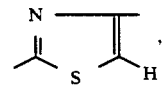

δ=7.0-7.9 ppm (m, 6H,

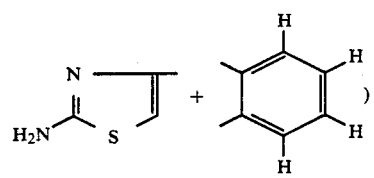

and δ=9.53 ppm (d, 1H, —CO—NH—).

EXAMPLE 177

7-β-[2-(2-Amino-thiazol-4-yl)-2-syn-methoximino-acetamido]-3-[4-amino-pyrazolo(3,4-d)pyrimidin-6-yl-thiomethyl]-ceph-3-em-4-carboxylic acid The procedure is as according to Example 5, using 601 mg (3.6 mmoles) of 4-amino-6-mercapto-pyrazolo(3,4-d)-pyrimidine. The reaction solution is warmed to 60°-65° C. for 15 hours. 1.02 g of the title compound are obtained.

R$_f$: 0.29 (ethyl acetate:isopropanol:water=4:3:2).
IR (KBr): 1,760 cm⁻¹ (β-lactam band).
NMR (d₆-DMSO, 60 MHz): δ=3.80 ppm (s, 3H, =N—OCH₃), δ=5.10 ppm (d, 1H, 6—CH—), δ=5.67 ppm (q, 1H, 7—CH—), δ=6.68 ppm (s, 1H,

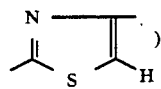

δ=7.13 ppm (s, broad, 2H,

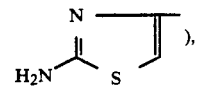

δ=7.64 ppm (s, broad, 2H,

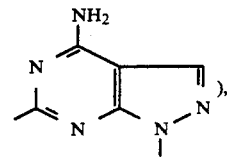

δ=7.97 ppm (s, broad, 1H,

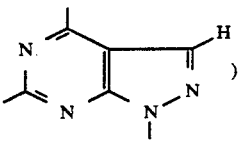

and δ=9.51 ppm (d, 1H, —CO—NH—).

EXAMPLE 178

7-β-[2-(2-Amino-thiazol-4-yl)-2-syn-methoximino-acetamido]-3-(6-methylthio-pyridazin-3-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximinoacetamido]-cephalosporanic acid and 0.87 g (5 mmoles) of 3-mercapto-6-methylthio-pyridazine. 0.4 g of the title compound is isolated.

$R_f$: 0.44 (n-butanol:water:glacial acetic acid:ethanol=10:4:3:3).

IR (KBr): 1,760 cm$^{-1}$ (β-lactam band).

NMR (d$_6$-DMSO, 60 MHz): δ=3.8 ppm (s, 3H, =N—OCH$_3$), δ=6.7 ppm (s, 1H,

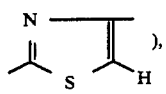

δ=7.13 ppm (s, broad, 2H, —NH$_2$), δ=7.43 ppm (s, 2H,

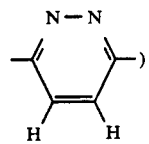

and δ=9.5 ppm (d, 1H, —CO—NH—).

EXAMPLE 179

7-β-[2-(2-Amino-thiazol-4-yl)-2-syn-methoximino-acetamido]-3-(6-carboxy-4-hydroxy-pyrimidin-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximinoacetamido]-cephalosporanic acid and 0.95 g (5.5 mmoles) of 6-carboxy-4-hydroxy-2-mercapto-pyrimidine. The reaction solution is warmed to 55° C. for 5 hours. The crude product isolated is stirred in ethanol, the mixture is filtered and the solvent is evaporated off. 0.65 g of the title compound is obtained.

$R_f$: 0.49 (n-butanol:water:ethanol:glacial acetic acid=10:4:3:3).

IR (KBr): 1,765 cm$^{-1}$ (β-lactam band).

NMR (d$_6$-DMSO, 60 MHz): 3.9 ppm (s, 3H, =N—OCH$_3$), δ=6.56 ppm (s, 1H,

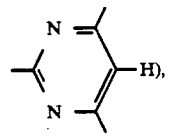

δ=6.67 ppm (s, 1H,

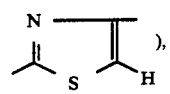

δ=7.13 ppm (s, broad, 2H, —NH$_2$) and δ=9.5 ppm (d, 1H, —CO—NH—).

EXAMPLE 180

7-β-[2-(2-Amino-thiazol-4-yl)-2-syn-methoximino-acetamido]-3-(2-amino-6-hydroxy-pyrimidin-4-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximinoacetamido]-cephalosporanic acid and 0.78 ... (5 mmoles) of 2-amino-6-hydroxy-4-mercapto-pyrimidine. The reaction solution is heated to 55° C. for 5 hours. 0.94 g of the title compound is isolated.

$R_f$: 0.55 (n-butanol:water:ethanol:glacial acetic acid=10:4:3:3).

IR (KBr): 1,760 cm$^{-1}$ (β-lactam band).

NMR (d$_6$-DMSO, 60 MHz): δ=3.83 ppm (s, 3H, =N—OCH$_3$), δ=5.4 ppm (s, 1H,

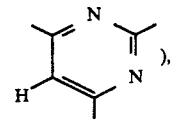

δ=6.6 ppm (s, broad, 2H,

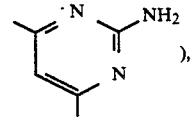

δ=6.7 ppm (s, 1H,

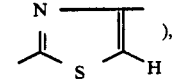

δ=7.13 ppm (s, broad, 2H,

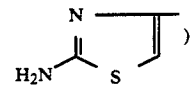

and δ=9.53 ppm (d, 1H, —CO—NH—).

EXAMPLE 181

7-β-[2-(2-Amino-thiazol-4-yl)-2-syn-methoximino-acetamido]-3-(4-amino-5-carboxy-pyrimidin-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.86 g (5 mmoles) of 4-amino-5-carboxy-2-mercapto-pyrimidine. The reaction solution is heated to 55° C. for 5 hours. The crude product is stirred with ethanol, undissolved material is filtered off and the solvent is evaporated off. 0.9 g of the title compound is obtained.

$R_f$: 0.58 (n-butanol:water:ethanol:glacial acetic acid=10:4:3:3).

IR (KBr): 1,760 cm$^{-1}$ (β-lactam band).

NMR (d$_6$-DMSO, 60 MHz): δ=3.82 ppm (s, 3H, =N—OCH$_3$), δ=6.70 ppm (s, 1H,

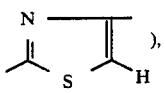

δ=7.15 ppm (s, broad, 2H,

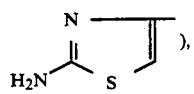

δ=7.93 ppm (s, broad, 2H,

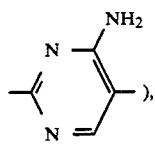

δ=8.50 ppm (s, 1H,

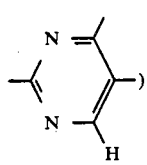

and δ=9.52 ppm (d, 1H, —CO—NH—).

EXAMPLE 182

7-β-[2-(2-Amino-thiazol-4-yl)-2-syn-methoximino-acetamido]-3-(4-hydroxy-6-methyl-pyrimidin-2-yl-thiomethyl)-ceph-3-em-4-carboxylic acid.

The procedure is as according to Example 5, using 2.3 g (5 mmoles) of 7-β-[2-(2-amino-thiazol-4-yl)-2-syn-methoximinoacetamido]-cephalosporanic acid and 0.65 g (5 mmoles) of 4-hydroxy-2-mercapto-6-methyl-pyrimidine. The reaction solution is heated to 55° C. for 5 hours. 0.79 g of the title compound of melting point 220°-230° C. (decomposition) is isolated.

R$_f$: 0.59 (n-butanol:water:ethanol:glacial acetic acid=10:4:3:3).

IR (KBr): 1,760 cm$^{-1}$ (β-lactam band).

NMR (d$_6$-DMSO, 60 MHz): δ=2.17 ppm (s, 3H, =C—CH$_3$), δ=3.83 ppm (s, 3H, =N—OCH$_3$), δ=5.95 ppm (s, 1H,

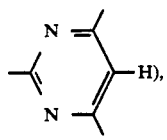

δ=6.72 ppm (s, 1H,

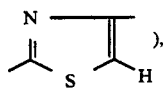

δ=7.16 ppm (s, broad, 2H, —NH$_2$) and δ=9.52 ppm (d, 1H, —CO—NH—).

EXAMPLE 183

7-β-[2-(2-Amino-thiazol-4-yl)-2-syn-methoximino-acetamido]-3-(5-nitro-pyrid-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.78 g (5 mmoles) of 2-mercapto-5-nitro-pyridine. The reaction solution is heated to 55° C. for 5 hours. The crude product isolated is purified by dissolving in 1N sodium bicarbonate solution and precipitating with 2N HCl. 0.55 g of the title compound of melting point 210° C. (decomposition) is obtained.

R$_f$: 0.62 (acetone:glacial acetic acid=10:1).

IR (KBr): 1,765 cm$^{-1}$ (β-lactam band).

NMR (d$_6$-DMSO, 60 MHz): δ=3.82 ppm (s, 3H, =N—OCH$_3$), δ=6.70 ppm (s, 1H,

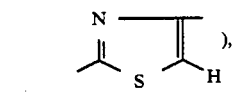

δ=7.13 ppm (s, broad, 2H, —NH$_2$), δ=7.55 ppm (m, 1H,

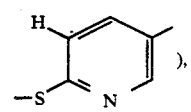

δ=8.33 ppm (m, 1H,

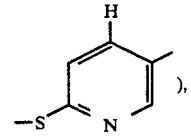

δ=9.12 ppm (m, 1H,

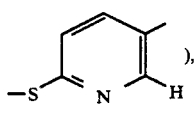

and δ=9.50 ppm (d, 1H, —CO—NH—).

EXAMPLE 184

7-β-[2-(2-Amino-thiazol-4-yl)-2-syn-methoximino-acetamido]-3-(1,1-dioxo-1,2,4-benzothiadiazin-3-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 1.07 g (5 mmoles) of 1,1-dioxo-3-mercapto-1,2,4-benzothiadiazine. The reaction solution is warmed to 55° C. for 5.5 hours. 1.5 g of the title compound of melting point 230° C. (decomposition) are isolated.

R$_f$: 0.38 (n-butanol:water:ethanol:glacial acetic acid=10:4:3:3).

IR (KBr): 1,765 cm$^{-1}$ (β-lactam band).

NMR (d$_6$-DMSO, 60 MHz): δ=3.8 ppm (s, 3H, =N—OCH$_3$), δ=6.7 ppm (s, 1H,

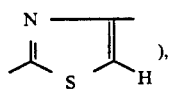

δ=7.0–7.9 ppm (m, 6H,

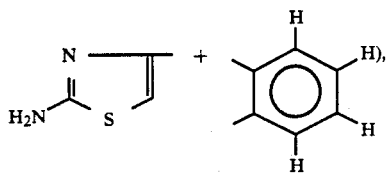

δ=9.53 ppm (d, 1H, —CO—NH—) and δ=12.5 ppm (s, broad, 1H, $$\mathrm{-C-N-SO_2-}) .$$
     H

EXAMPLE 185

7-β-[2-(2-Amino-thiazol-4-yl)-2-syn-methoximino-acetamido]-3-(5-chloro-benzothiazol-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 1.01 g (5 mmoles) of 5-chloro-2-mercapto-benzothiazole in 60 ml of water. The reaction solution is warmed to 60° C. for 8 hours. 0.9 g of the title compound is isolated.

$R_f$: 0.57 (n-butanol:water:ethanol:glacial acetic acid=10:4:3:3).

IR (KBr): 1,760 cm$^{-1}$ (β-lactam band).

NMR (d$_6$-DMSO, 60 MHz): δ=3.83 ppm (s, 3H, =N—OCH$_3$), δ=6.7 ppm (s, 1H,

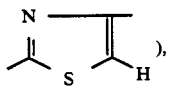

δ=7.1–8.1 ppm (m, 5H,

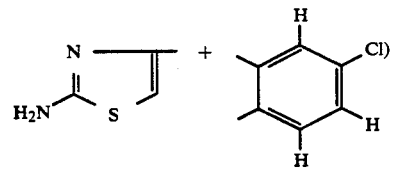

and δ=9.5 ppm (d, 1H, —CO—NH—).

EXAMPLE 186

7-β-[2-(2-Amino-thiazol-4-yl)-2-syn-methoximino-acetamido]-3-(4-methyl-pyrimidin-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.63 g of 2-mercapto-4-methyl-pyrimidine. The reaction solution is heated to 55° C. for 5 hours. 0.45 g of the title compound of melting point 170°–180° C. (decomposition) is isolated.

$R_f$: 0.64 (acetone:glacial acetic acid=10:1).

IR (KBr): 1,765 cm$^{-1}$ (β-lactam band).

NMR (d$_6$-DMSO, 60 MHz): δ=2.4 ppm (s, 3H, =C—CH$_3$), δ=3.83 ppm (s, 3H, =N—OCH$_3$), δ=6.73 ppm (s, 1H,

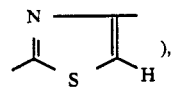

δ=7.08 ppm (d, 1H,

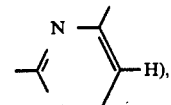

δ=8.42 ppm (d, 1H,

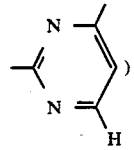

and δ=9.53 ppm (d, 1H, —CO—NH—).

EXAMPLE 187

7-β-[2-(2-Amino-thiazol-4-yl)-2-syn-methoximino-acetamido]-3-(5-methyl-4-phenyl-1,3-thiazol-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-4-phenyl-1,3-thiazole. The reaction solution is heated to 58° C. for 7 hours. 0.8 g of the title compound is isolated.

$R_f$: 0.59 (n-butanol:water:ethanol:glacial acetic acid=10:4:3:3).

IR (KBr): 1,765 cm$^{-1}$ (β-lactam band).

NMR (d$_6$-DMSO, 60 MHz): δ=2.33 ppm (s, 3H, =C—CH$_3$), δ=3.8 ppm (s, 3H, =N—OCH$_3$), δ=6.68 ppm (s, 1H,

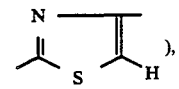

δ=7.13 ppm (s, broad, 2H, —NH$_2$), δ=7.43 ppm (m, 5H,

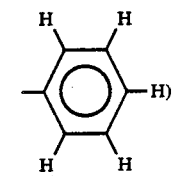

and δ=9.5 ppm (d, 1H, —CO—NH—).

EXAMPLE 188

7-β-[2-(2-Amino-thiazol-4-yl)-2-syn-methoximino-acetamido]-3-(4-methyl-1,3-thiazol-2-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 700 mg (5.3 mmoles) of 2-mercapto-4-methyl-1,3-thiazole in 80 ml of water. The reaction solution is heated to 58° C. for 7 hours. 800 mg of the title compound are isolated.

$R_f$: 0.45 (n-butanol:water:ethanol:glacial acetic acid=10:4:3:3).

IR (KBr): 1,770 cm$^{-1}$ (β-lactam band).

NMR (d$_6$-DMSO, 60 MHz): δ=2.33 ppm (s, 3H, =C—CH$_3$), δ=3.83 ppm (s, 3H, =N—OCH$_3$), δ=6.7 ppm (s, 1H,

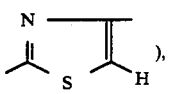

δ=7.17 ppm (m, 3H,

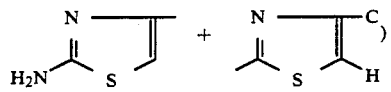

and δ=9.53 ppm (d, 1H, —CO—NH—).

EXAMPLE 189

7-β-[2-(2-Amino-thiazol-4-yl)-2-syn-methoximino-acetamido]-3-(pyrimidin-4-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.65 g (5.8 mmoles) of 4-mercapto-pyrimidine in 100 ml of water. The reaction solution is heated to 55° C. for 5 hours. 0.82 g of the title compound of melting point 210° C. (decomposition) is isolated.

$R_f$: 0.56 (acetone:glacial acetic acid=10:1).

IR (KBr): 1,770 cm$^{-1}$ (β-lactam band).

NMR (d$_6$-DMSO, 60 MHz): δ=3.8 ppm (s, 3H, =N—OCH$_3$), δ=6.68 ppm (s, 1H,

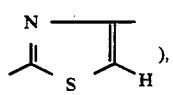

δ=7.13 ppm (s, broad, 2H, —NH$_2$), δ=7.4 ppm (m, 1H,

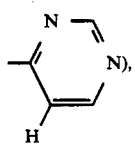

δ=8.4 ppm (d, 1H,

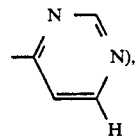

δ=8.85 ppm (d, 1H,

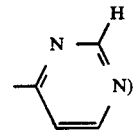

and δ=9.5 ppm (d, 1H, —CO—NH—).

EXAMPLE 190

7-β-[2-(2-Amino-thiazol-4-yl)-2-syn-methoximino-acetamido]-3-(quinolin-2-yl-thiomethyl)-ceph-3-em-4-carboxylic acid The procedure is as according to Example 5, using 580 mg (3.6 mmoles) of 2-mercapto-quinoline. The reaction solution is warmed to 60° C. for 6 hours and the crude product isolated is purified by trituration with ethyl acetate. 510 mg of the title compound are obtained.

$R_f$: 0.51 (ethyl acetate:methanol:glacial acetic acid=20:10:1).

IR (KBr): 1,770 cm$^{-1}$ (β-lactam band).

NMR (d$_6$-DMSO, 60 MHz): δ=3.81 ppm (s, =N—OCH$_3$), δ=5.07 ppm (d, 1H, 6—CH—), δ=5.67 ppm (q, 1H, 7—CH—), δ=6.67 ppm (s, 1H,

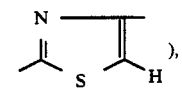

δ=7.1-8.3 ppm (m, 8H,

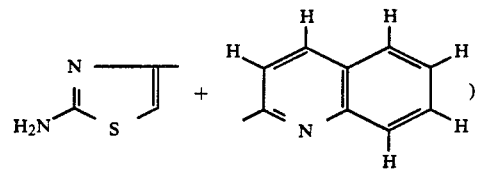

and δ=9.50 ppm (d, 1H, —CO—NH—).

EXAMPLE 191

7-β-[2-(2-Amino-thiazol-4-yl)-2-syn-methoximino-acetamido]-3-(2-amino-pyrimidin-4-yl-thiomethyl)-ceph-3-em-4-carboxylic acid The procedure is as according to Example 5, using 1.9 g (4 mmoles) of 7-β-[2-(amino-thiazol-4-yl)-2-syn-methoximino-acetamido]-cephalosporanic acid and 650 mg (4.5 mmoles) of 2-amino-4-mercapto-pyrimidine in 80 ml of water. The reaction solution is warmed to 50° C. under N$_2$ for 4 hours. 650 mg of the title compound are isolated.

$R_f$: 0.58 (n-butanol:water:ethanol:glacial acetic acid= 10:4:3:3).

IR (KBr): 1,762 cm$^{-1}$ (β-lactam band).

NMR (d$_6$-DMSO, 60 MHz): δ=3.54 ppm (AB, 2—CH$_2$—), δ=3.81 ppm (s, =N—OCH$_3$), δ=4.23 ppm (AB, 3—CH$_2$—S—), δ=5.11 ppm (d, 1H, 6—CH—), δ=5.72 ppm (q, 1H, 7—CH—), δ=6.55 ppm (d, 1H,

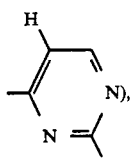

δ=6.71 ppm (s, 1H,

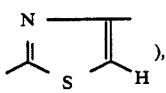

δ=6.9–7.5 ppm (broad, 4H,

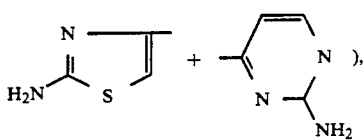

δ=7.93 ppm (d, 1H,

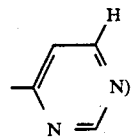

and δ=9.52 ppm (d, 1H, —CO—NH—).

EXAMPLE 192

7-β-[2-(2-Amino-thiazol-4-yl)-2-syn-methoximino-acetamido]-3-(1,3-oxazol-2-yl-thiomethyl)-ceph-3-em-4-carboxylic acid The procedure is as according to Example 5, using 364 mg (3.6 mmoles) of 2-mercapto-1,3-oxazole. The reaction solution is heated to 60° C. for 4 hours. 468 mg of the title compound are isolated.

R$_f$: 0.37 (ethyl acetate:methanol:glacial acetic acid=20:10:1).

IR (KBr): 1,766 cm$^{-1}$ (β-lactam band).

NMR (d$_6$-DMSO, 60 MHz): δ=3.58 ppm (AB, 2—CH$_2$—), δ=3.81 ppm (s, =N—OCH$_3$), δ=4.22 ppm (AB, 3—CH$_2$—S—), δ=5.07 ppm (d, 1H, 6—CH—), δ=5.71 ppm (q, 1H, 7—CH—), δ=6.68 ppm (s, 1H,

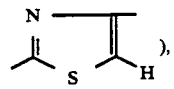

δ=7.11 ppm (s, broad, 2H, —NH$_2$), δ=7.21 ppm (d, 1H,

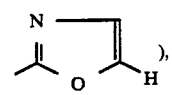

δ=8.09 ppm (d, 1H,

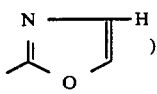

and δ=9.53 ppm (d, 1H, —CO—NH—).

EXAMPLE 193

7-β-[2-(2-Amino-thiazol-4-yl)-2-syn-methoximino-acetamido]-3-[5-chloro-s-triazolo(4,3-a)pyridin-3-yl-thiomethyl]-ceph-3-em-4-carboxylic acid The procedure is as according to Example 5, using 1.0 g (2 mmoles) of a 7-β-[2-(2-amino-thiazol-4-yl)-2-syn-methoximino-acetamido]-cephalosporanic acid-monoethanol adduct and 481 mg (2.6 mmoles) of 5-chloro-3-mercapto-s-triazolo(4,3-a)-pyridine in 60 ml of water. The reaction solution is heated to 60° C. for 2 hours. 415 mg of the title compound are isolated.

R$_f$: 0.30 (acetone:glacial acetic acid=10:1).

IR (KBr): 1,771 cm$^{-1}$ (β-lactam band).

NMR (d$_6$-DMSO, 60 MHz): δ=3.79 ppm (s, =N—OCH$_3$), δ=4.29 ppm (AB, 3—CH$_2$—S—), δ=5.06 ppm (d, 1H, 6—CH—), δ=5.69 ppm (q, 1H, 7—CH—), δ=6.70 ppm (s, 1H,

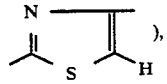

δ=7.0–7.8 ppm (m, 5H,

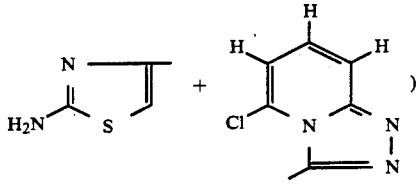

and δ=9.54 ppm (d, 1H, —CO—NH—).

EXAMPLE 194

7-β-[2-(2-Amino-thiazol-4-yl)-2-syn-methoximino-acetamido]-3-(N,N-diethyl-thiocarbamoyl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-ceph-3-em-4-carboxylic acid and 1.7 g (10 mmoles) of N,N-diethyl-dithiocarbamic acid in 80 ml of water. The reaction solution is warmed to 50° C. for 5 hours. 500 mg of the title compound of melting point 195° C. (decomposition) are isolated.

R$_f$: 0.38 (n-butanol:water:ethanol:glacial acetic acid=10:4:3:3).

IR (KBr): 1,760 cm$^{-1}$ (β-lactam band).

NMR (d$_6$-DMSO, 60 MHz): δ=1.18 ppm (t, 6H, —N—C—CH$_3$), δ=3.51 ppm (AB, 2H, 2—CH$_2$—), δ=3.81 ppm (s, 3H, =N—OCH$_3$), δ=4.15 ppm (m, 6H, 3—CH$_2$—S—+—N—CH$_2$—C), δ=5.11 ppm (d, 1H, 6—CH—), δ=5.71 ppm (q, 1H, 7—CH—), δ=6.71 ppm (s, 1H,

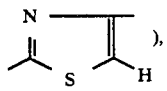

δ=7.15 ppm (s, 2H, —NH₂) and δ=9.50 ppm (d, 1H, —CO—NH—).

EXAMPLE 195

7-β-[2-(2-Amino-thiazol-4-yl)-2-syn-methoximino-acetamido]-3-(6-amino-2-hydroxy-pyrimidin-4-yl-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.61 g (5.5 mmoles) of 6-amino-2-hydroxy-4-mercapto-pyrimidine in 80 ml of water. The reaction solution is heated to 50° C. for 5 hours. 750 mg of the title compound are isolated.

R$_f$: 0.27 (n-butanol:water:ethanol:glacial acetic acid = 10:4:3:3).

IR (KBr): 1,760 cm$^{-1}$ (β-lactam band).

NMR (d₆-DMSO, 60 MHz): δ=3.79 ppm (s, =N—OCH₃), δ=5.10 ppm (d, 6—CH—), δ=5.69 ppm (q, 7—CH—), δ=6.71 ppm (s, 1H,

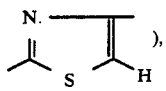

δ=7.14 ppm (s, broad, 2H, —NH₂) and δ= 9.50 ppm (d, 1H, —CO—NH—).

EXAMPLE 196

7-β-[2-(2-Amino-thiazol-4-yl)-2-syn-methoximino-acetamido]-3-(1-furfuryl-pyrimidin-6-one-4-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 1.0 g of 1-furfuryl-4-mercapto-pyrimidin-6-one. The reaction solution is heated to 50° C. for 5 hours. 0.5 g of the title compound of melting point 242° C. (decomposition) is isolated.

R$_f$: 0.39 (n-butanol:water:ethanol:glacial acetic acid = 10:4:3:3).

IR (KBr): 1,760 cm$^{-1}$ (β-lactam band).

EXAMPLE 197

7-β-[2-(2-Amino-thiazol-4-yl)-2-syn-methoximino-acetamido]-3-(1-methyl-pyrimidin-6-one-4-thiomethyl)-ceph-3-em-4-carboxylic acid The procedure is as according to Example 5, using 2.3 g (5 mmoles) of 7-β-[2-(2-amino-thiazol-4-yl)-2-syn-methoximino-acetamido]-cephalosporanic acid and 0.7 g (5 mmoles) of 4-mercapto-1-methyl-pyrimidin-6-one. The reaction solution is heated to 50° C. for 6 hours. 900 mg of the title compound are isolated.

R$_f$: 0.21 (n-butanol:water:ethanol:glacial acetic acid = 10:4:3:3).

IR (KBr): 1,758 cm$^{-1}$ (β-lactam band).

EXAMPLE 198

7-β-[2-(2-Amino-thiazol-4-yl)-2-syn-methoximino-acetamido]-3-(6-hydroxy-pyrimidin-4-yl-thiomethyl)-ceph-3-em-4-carboxylic acid The procedure is as according to Example 5, using 4.75 g (10 mmoles) of 7-β-[2-(2-amino-thiazol-4-yl)-2-syn-methoximino-acetamido]-cephalosporanic acid and 1.13 g (12 mmoles) of 6-hydroxy-4-mercapto-pyrimidine in 150 ml of water. The reaction solution is warmed to 50° C. for 5 hours. 1.57 g of the title compound are isolated.

IR (KBr): 1,760 cm$^{-1}$ (β-lactam band).

EXAMPLE 199

7-β-[2-(2-Amino-thiazol-4-yl)-2-syn-methoximino-acetamido]-3-(4-phenyl-1,3-thiazol-2-yl-thiomethyl)-ceph-3-em-4-carboxylic acid Analogously to Example 5, 1.5 g of the title compound are obtained from 2.1 g (4.7 mmoles) of 7-β-[2-(2-amino-thiazol-4-yl)-2-syn-methoximino-acetamido]-cephalosporanic acid and 1.36 g (7.05 mmoles) of 2-mercapto-5-phenyl-1,3-thiazole.

R$_f$: 0.59 (n-butanol:water:ethanol:glacial acetic acid = 10:4:3:3).

IR (KBr): 1,770 cm$^{-1}$ (β-lactam band).

NMR (d₆-DMSO, 60 MHz): δ=3.75 ppm (AB, 2H, 2—CH₂—), δ=3.85 ppm (s, 3H, =N—OCH₃), δ=4.40 ppm (AB, 2H, 3—CH₂—S—), δ=5.20 ppm (d, 1H, 6—CH—), δ=5.76 ppm (q, 1H, 7—CH—), δ=6.76 ppm (s, 1H,

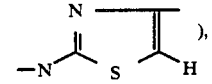

δ=7.20 ppm (s, 1H,

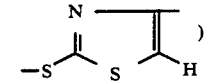

and δ=9.63 ppm (d, 1H, —CO—NH—).

EXAMPLE 200

7-β-[2-(2-Amino-thiazol-4-yl)-2-syn-methoximino-acetamido]-3-(3-phenyl-1,2,4-thiadiazol-5-yl-thiomethyl)-ceph-3-em-4-carboxylic acid Analogously to Example 5, 0.40 g of the title compound is obtained from 1.36 g (3 mmoles) of 7-β-[2-(2-amino-thiazol-4-yl)-2-syn-methoximino-acetamido]-cephalosporanic acid and 0.87 g (4.5 mmoles) of 3-phenyl-5-mercapto-1,2,4-thiadiazole.

R$_f$: 0.62 (n-butanol:water:ethanol:glacial acetic acid = 10:4:3:3).

IR (KBr): 1,767 cm$^{-1}$ (β-lactam band).

NMR (d₆-DMSO, 60 MHz): δ=3.76 ppm (AB, 2H, 2—CH₂—), δ=3.86 ppm (s, 3H, =N—OCH₃), δ=4.58 ppm (AB, 2H, 3—CH₂—S—) δ=5.20 ppm (d, 1H, 6—CH—), δ=5.80 ppm (q, 1H, 7—CH—), δ=6.80 ppm (s, 1H,

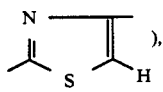

δ=7.21 ppm (s, 2H, —NH₂) and δ=9.62 ppm (d, 1H, —CO—NH—).

EXAMPLE 201

7-β-[2-(2-Amino-thiazol-4-yl)-2-syn-methoximino-acetamido]-3-(1-allyl-tetrazol-5-yl-thiomethyl)-ceph-3-em-4-carboxylic acid Analogously to Example 5, 0.33 g of the title compound is obtained from 1.36 g (3 mmoles) of 7-β-[2-(2-amino-thiazol-4-yl)-2-syn-methoximino-acetamido]-cephalosporanic acid and 0.74 g (4.5 mmoles) of the sodium salt of 1-allyl-5-mercaptotetrazole.

$R_f$: 0.48 (n-butanol:water:ethanol:glacial acetic acid=10:4:3:3).

IR (KBr): 1,762 cm⁻¹ (β-lactam band).

NMR (d₆-DMSO, 60 MHz): δ=3.80 ppm (s, 3H, =N—OCH₃), δ=4.90 ppm (AB, 2H, 3—CH₂—S—), δ=5.20 ppm (d, 1H, 6—CH—), δ=5.80 ppm (q, 1H, 7—CH—), δ=6.75 ppm (s, 1H,

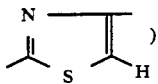

and δ=9.55 ppm (d, 1H, —CO—NH—).

EXAMPLE 202

7-β-[2-(2-Amino-thiazol-4-yl)-2-syn-methoximino-acetamido]-3-(benzothiazol-2-yl-thiomethyl)-ceph-3-em-4-carboxylic acid Analogously to Example 5, 0.9 g of the title compound is obtained from 1.36 g (3 mmoles) of 7-β-[2-(2-amino-thiazol-4-yl)-2-syn-methoximino-acetamido]-cephalosporanic acid and 0.75 g (4.5 mmoles) of 2-mercapto-benzothiazole.

$R_f$: 0.58 (n-butanol:water:ethanol:glacial acetic acid=10:4:3:3).

IR (KBr): 1,765 cm⁻¹ (β-lactam band).

NMR (d₆-DMSO, 60 MHz): δ=3.74 ppm (AB, 2H, 2—CH₂—), δ=3.85 ppm (s, 3H, =N—OCH₃), δ=4.75 ppm (AB, 2H, 3—CH₂—S—), δ=5.14 ppm (d, 1H, 6—CH—), δ=5.76 ppm (q, 1H, 7—CH—), δ=6.84 ppm (s, 1H,

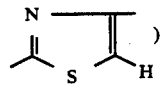

and δ=9.59 ppm (d, 1H, —CO—NH—).

EXAMPLE 203

7-β-[2-(2-Amino-thiazol-4-yl)-2-syn-methoximino-acetamido]-3-(3-hydroxy-pyridazin-6-yl-thiomethyl)-ceph-3-em-4-carboxylic acid Analogously to Example 5, 1.4 g of the title compound are obtained from 1.36 g (3 mmoles) of 7-β-[2-(2-amino-thiazol-4-yl)-2-syn-methoximino-acetamido]-cephalosporanic acid and 0.58 g (4.5 mmoles) of 3-hydroxy-6-mercapto-pyridazine.

$R_f$: 0.28 (n-butanol:water:ethanol:glacial acetic acid=10:4:3:3).

IR (KBr): 1,762 cm⁻¹ (β-lactam band).

NMR (d₆-DMSO, 60 MHz): δ=3.65 ppm (AB, 2H, 2—CH₂—), δ=3.87 ppm (s, 3H, =N—OCH₃), δ=4.90 ppm (AB, 2H, 3—CH₂—S—), δ=5.20 ppm (d, 1H, 6—CH—), δ=5.80 ppm (q, 1H, 7—CH—), δ=6.85 ppm (s, 1H,

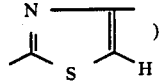

and δ=9.60 ppm (d, 1H, —CO—NH—).

EXAMPLE 204

7-β-[2-(2-Methylamino-thiazol-4-yl)-2-syn-methoximinoacetamido]-cephalosporanic acid

Stage 1

9.0 g of N-methylthiourea are stirred in 30 ml of ethanol and 60 ml of water with 25.2 g of ethyl 4-bromo-2-methoximino-acetoacetate at 20° for 1 hour, the mixture is cooled to 15° and adjusted to pH 5.0 with 2N NH₃ solution and the product is filtered off, washed with water and dried. 5.35 g of ethyl 2-(2-methylamino-thiazol-4-yl)-2-syn-methoximino-acetate of melting point 120°-121° are obtained.

Stage 2

9.73 g of the ethyl ester from stage 1 are boiled with 1.76 g of NaOH in 75 ml of ethanol for 30 minutes. The solution is cooled and diluted with 50 ml of ether and the product is filtered off. 8.7 g of sodium 2-(2-methylaminothiazol-4-yl)-2-syn-methoximino-acetate of melting point 280° (decomposition) are obtained.

$R_f$: 0.31 (n-butanol:water:ethanol:glacial acetic acid= 10:4:3:3).

Stage 3

8.5 g of the sodium salt from stage 2 are converted, in 80 ml of methylene chloride and 30 ml of ether with 40 ml of 1N HCl, into 4.6 g of 2-(2-methylamino-thiazol-4-yl)-2-syn-methoximino-acetic acid.

NMR (d₆-DMSO, 60 MHz): δ=2.82 ppm (s, 3H, CH₃—N), δ=3.88 ppm (s, 3H, =N—OCH₃), δ=6.90 ppm (s, 1H,

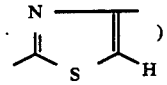

and δ=7.68 ppm (s, 1H, broad, NH).

Stage 4

3.8 g of the acid from stage 3 are converted, in 20 ml of methanol with ethanolic HCl solution and ether into the hydrochloride. 4.1 g of 2-(2-methylamino-thiazol-4-yl)-2-syn-methoximino-acetic acid hydrochloride are obtained.

Stage 5

2.51 g of the hydrochloride from stage 5 are dissolved in 20 ml of DMF and a solution of 5.0 g of benzhydryl 7-aminocephalosporanate in 20 ml of DMF is added. 2.27 g of dicyclohexylcarbodiimide are added at 0°, the mixture is subsequently stirred at 0° for 1 hour and at 20° for 2 hours and is filtered and the solvent is distilled off from the filtrate at 40° in vacuo (oil pump). The residue is stirred with ether, 10 ml of anisole and 10 ml of trifluoroacetic acid are added at 0° and the mixture is subsequently stirred at 20° for 1 hour and poured into 250 ml of ether. The product is filtered off, washed with ether, dissolved in 5 ml of ethanol and precipitated with potassium diethylacetate, 2 ml of ether being added. 1.40 g of the title compound in the form of the potassium salt are obtained.

R$_f$: 0.54 (n-butanol:water:ethanol:glacial acetic acid = 10:4:3:3).

IR (KBr): 1,770 cm$^{-1}$ ($\beta$-lactam band).

NMR (d$_6$-DMSO, 60 MHz): $\delta$=2.05 ppm (s, 3H, —O—CO—CH$_3$), $\delta$=2.98 ppm (s, 3H, CH$_3$—N>), $\delta$=3.85 ppm (s, 3H, =N—OCH$_3$), $\delta$=6.75 ppm (s, 1H,

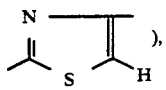

), $\delta$=8.00 ppm (s, 1H, —NH—C—) and $\delta$=9.60 ppm (d, 1H, —CO—NH).

EXAMPLE 205

7-$\beta$-[2-(2-Morpholino-thiazol-4-yl)-2-syn-methoximino-acetamido]cephalosporanic acid 1.03 g (4 mmoles) of 2-(2-morpholino-thiazol-4-yl)-2-syn-methoximino-acetic acid are dissolved in 40 ml of tetrahydrofuran. 460 mg (4 mmoles) of N-hydroxysuccinimide and 824 mg (4 mmoles) of dicyclohexylcarbodiimide are successively added, whilst cooling with ice, and the mixture is stirred at 0° C. for 1 hour. The dicyclohexylurea which has precipitated is filtered off and the filtrate is added dropwise to a solution of 956 mg (3.5 mmoles) of 7-amino-cephalosporanic acid and 1.31 ml (10.5 mmoles) of triethylamine in 50 ml of CHCl$_3$ at 0°. The mixture is stirred at 0° C. for 5 hours and then left to stand at room temperature for 12 hours. The solvent is removed in vacuo, the residue is taken up in 5% strength NaHCO$_3$ solution, the solution is extracted several times with ethyl acetate and the aqueous phase is adjusted to a pH value of 1.8 with 2N HCl. The reaction mixture is extracted several times with ethyl acetate, the extracts are dried over Na$_2$SO$_4$ and filtered and the solvent is removed. The residue solidifies on trituration with acetone/ether (1:1). 130 mg of the title compound of melting point 180° C. (decomposition) are obtained.

R$_f$: 0.49 (n-butanol:water:ethanol:glacial acetic acid = 10:4:3:3).

IR (KBr): 1,771 cm$^{-1}$ ($\beta$-lactam band). 1,725 cm$^{-1}$ (acetate band).

Preparation of the Starting Compound for Example 205 a) tert.-Butyl isothiocyanate 137 g of ammonium thiocyanate and 50 g of zinc-II chloride are dissolved in 500 ml of water. After adding 139 g of tert.-butyl chloride, the mixture is left to stand at room temperature for 96 hours, being occasionally shaken. The organic layer is separated off and washed with water. After drying over CaCl$_2$, it is again shaken thoroughly with 25 g of ZnCl$_2$ and the liquid is decanted off, washed with water and dried over CaCl$_2$. 43.6 g of the title compound are obtained as a yellowish oil which is used directly for stage b) without additional purification.

b) Morpholino-thiourea 14 g of tert.-butyl isothiocyanate are dissolved in 70 ml of petroleum ether. 10.6 g of morpholine are added dropwise, whilst cooling with ice. The precipitate which forms is filtered off, washed with petroleum ether and dried in air. The crude product is heated to 90°-95° C. in 70 ml of concentrated HCl for 30 minutes, whereupon tert.-butyl chloride escapes. 5% strength aqueous NaHCO$_3$ solution is added to the solution, whilst cooling. The crystals which have precipitated are filtered off and dried. 11.5 g of the title compound of melting point 168° are obtained.

R$_f$: 0.73 (toluene:ethanol=1:1).

c) Ethyl 2-(2-morpholino-thiazol-4-yl)-2-syn-methoximino-acetate 11.4 g (78 mmoles) of morpholino-thiourea are initially introduced with 10.8 ml (78 mmoles) of triethylamine and 100 ml of ethanol. 20.5 g (78 mmoles) of ethyl $\gamma$-bromo-$\alpha$-methoximino-acetoacetate in 20 ml of ethanol are added dropwise, whilst cooling with ice and passing a weak stream of N$_2$ through, and the mixture is then stirred at room temperature for a further 5 hours. It is left to stand overnight and, after removing the solvent, 29 g of the title compound are obtained as a yellowish oil, which is used directly for stage d) without additional purification.

R$_f$: 0.57 (toluene:ethanol=1:1).

d) 2-(2-Morpholino-thiazol-4-yl)-2-syn-methoximino-acetic acid 24 g of the oil obtained in stage c) are heated to the boil under reflux with 2N NaOH in ethanol. The solvent is distilled off, the residue is taken up in water and the solution is extracted several times with ether. After acidifying the aqueous phase with 2N HCl, 2.4 g of the title compound of melting point 132°-133° C. are obtained.

R$_f$: 0.12 (toluene:ethanol=1:1).

EXAMPLE 206

7-$\beta$-[2-(2-Amino-thiazol-4-yl)-2-syn-methoximino-acetamido]-3-[1-acetamido-ethyl-tetrazol-5-yl-thiomethyl]-ceph-3-em-4-carboxylic acid The procedure is as according to Example 5, using 673 mg (3.6 mmoles) of 1-acetamidoethyl-5-mercapto-tetrazole. The reaction solution is heated to 65° C. for 3 hours. 354 mg of the title compound are isolated.

R$_f$: 0.32 (acetone:glacial acetic acid=10:1).

IR (KBr): 1,766 cm$^{-1}$ ($\beta$-lactam band).

NMR (d$_6$-DMSO, 60 MHz): $\delta$=1.72 ppm (s, 3H, —CO—CH$_3$), $\delta$=3.83 ppm (s, 3H, =N—OCH$_3$), $\delta$=5.09 ppm (d, 1H, 6—CH—), $\delta$=5.75 ppm (q, 1H, 7—CH—), $\delta$=6.73 ppm (s, 1H,

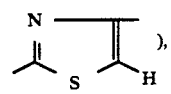

), $\delta$=7.99 ppm (t, 1H, $$\overset{H}{-C-C-N-CO-C-})$$

and δ=9.54 ppm (d, 1H, —CO—NH—).

EXAMPLE 207

7-β-[2-(2-Amino-thiazol-4-yl)-2-syn-methoximino-acetamido]-3-[s-triazolo(4,3-a)pyridin-3-yl-thiomethyl]-ceph-3-em-4-carboxylic acid The procedure is as according to Example 5, using 544 mg (3.6 mmoles) of 3-mercapto-s-triazolo(4,3-a)pyridine. The reaction solution is warmed to 65° C. for 3 hours. 620 mg of the title compound are isolated.

R_f: 0.20 (acetone:glacial acetic acid=10:1).

IR (KBr): 1,767 cm$^{-1}$ (β-lactam band).

NMR (d$_6$-DMSO, 60 MHz): δ=3.81 ppm (s, 3H, =N—OCH$_3$), δ=4.12 ppm (AB, 2H, 3—CH$_2$—S—), δ=5.07 ppm (d, 1H, 6—CH—), δ=5.70 ppm (q, 1H, 7—CH—), δ=6.74 ppm (s, 1H,

[structure: aminothiazole fragment]

δ=7.0–8.0 ppm (m, 5H,

[structure: aminothiazole + pyridotriazole fragments]

δ=8.44 ppm (m, 1H,

[structure: triazolopyridine fragment]

and δ=9.59 ppm (d, 1H, —CO—NH—).

EXAMPLE 208

7-β-[2-Amino-thiazol-4-yl)-2-syn-methoximino-acetamido]-3-[s-triazolo(4,3-a)pyridin-5-yl-thiomethyl]-ceph-3-em-4-carboxylic acid The procedure is as according to Example 5, using 544 mg (3.6 mmoles) of 5-mercapto-s-triazolo(4,3-a)pyridine. The reaction solution is warmed to 60° C. for 3 hours and the crude product isolated is purified by trituration with ethyl acetate. 765 mg of the title compound are obtained.

R_f: 0.24 (ethyl acetate:isopropanol:water=4:3:2).

IR (KBr): 1,762 cm$^{-1}$ (β-lactam band).

NMR (d$_6$-DMSO, 60 MHz): δ=3.65 ppm (AB, 2—CH$_2$—), δ=3.81 ppm (s, =N—OCH$_3$), δ=4.04 ppm (AB, 2H, 3—CH$_2$—S—), δ=5.10 ppm (d, 1H, 6—CH—), δ=5.67 ppm (q, 1H, 7—CH—), δ=6.72 ppm (s, 1H,

[structure: aminothiazole fragment]

δ=6.9–7.9 ppm (m, 5H,

[structure: aminothiazole + triazolopyridine]

δ=9.39 ppm (s, 1H,

[structure: triazolopyridine fragment]

and δ=9.53 ppm (d, 1H, —CO—NH—).

EXAMPLE 209

7-β-[2-(2-Amino-thiazol-4-yl)-2-syn-methoximino-acetamido]-3-(5-hydroxy-1,2,4-triazin-3-yl-thiomethyl)-ceph-3-em-4-carboxylic acid The procedure is as according to Example 5, using 465 mg (3.6 mmoles) of 5-hydroxy-3-mercapto-1,2,4-triazine. The reaction solution is warmed to 60° C. for 2.5 hours and the crude product isolated is purified by trituration with ethyl acetate. 341 mg of the title compound are obtained.

R_f: 0.32 (ethyl acetate:isopropanol:water=4:3:2).

IR (KBr): 1,757 cm$^{-1}$ (β-lactam band).

NMR (d$_6$-DMSO, 60 MHz): δ=3.85 ppm (s, =N—OCH$_3$), δ=4.69 ppm (AB, 2—CH$_2$—), δ=5.10 ppm (d, 1H, 6—CH—), δ=5.56 ppm (q, 1H, 7—CH—), δ=6.73 ppm (s, 1H,

[structure: aminothiazole fragment]

δ=7.17 ppm (s, broad, 2H, —NH$_2$), δ=7.68 ppm (s, 1H,

[structure: triazine fragment]

and δ=9.56 ppm (d, 1H, —CO—NH—).

EXAMPLE 210

7-β-[2-(2-Amino-thiazol-4-yl)-2-syn-oximino-acetamido]-3-(4,6-diamino-pyrimidin-2-yl-thiomethyl)-ceph-3-em-4-carboxylic acid 710 mg (1.53 mmoles) of the sodium salt of 7-β-[2-(2-amino-thiazol-4-yl)-2-syn-oximino-acetamido]-cephalosporanic acid and 284 mg (2 mmoles) of 4,6-diamino-2-mercapto-pyrimidine are dissolved in 50 ml of water and the solution is adjusted to pH 7 with solid NaHCO₃. The reaction solution is heated to 60° C. for 3 hours, whilst stirring and keeping the pH value constant. The solution is allowed to cool, concentrated to 10 ml in vacuo at 35° C. and acidified with 2N HCl. The precipitate is filtered off, washed with water until free from chloride and dried in vacuo at 37° C. over KOH. 336 mg of the title compound are obtained.

R$_f$: 0.40 (n-butanol:glacial acetic acid:water=3:1:1).

IR (KBr): 1,756 cm$^{-1}$ (β-lactam band).

NMR (d₆-DMSO, 60 MHz): δ=5.04 ppm (s, 1H,

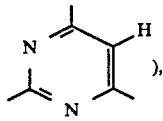

),

δ=5.10 ppm (d, 1H, 6—CH—), δ=5.71 ppm (q, 1H, 7—CH—), δ=6.10 ppm (s, broad, 2H,

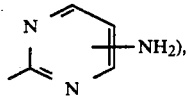

δ=6.64 ppm (s, broad, 3H,

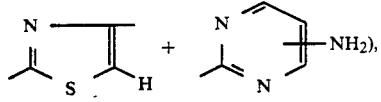

δ=7.09 ppm (s, broad, 2H,

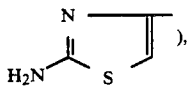

),

δ=9.37 ppm (d, 1H, —CO—NH—) and δ=11.25 ppm (s, broad, 1H, =N—O—H).

EXAMPLE 211

7-β-[2-(2-Amino-thiazol-4-yl)-2-oximino-acetamido]-3-(6-hydroxy-4-methyl-5-oxo-1,2,4-triazin-3-yl-thiomethyl)-ceph-3-em-4-carboxylic acid 710 mg (1.5 mmoles) of 7-β-[2-(2-amino-thiazol-4-yl)-2-syn-oximino-acetamido]-cephalosporanic acid and 318 mg (2 mmoles) of 6-hydroxy-3-mercapto-4-methyl-5-oxo-1,2,4-triazine are dissolved in 50 ml of water. The reaction mixture has a pH value of 2.5, and is adjusted to pH 7 with solid NaHCO₃, whereupon slight discoloration of the reaction solution occurs. The solution is heated to 60° C. for 3.5 hours, whilst stirring and keeping the pH value constant. After cooling, the solution is acidified with 2N HCl until it becomes slightly turbid (pH about 4.5) and extracted several times with ethyl acetate. The organic extracts are discarded and the aqueous phase is concentrated to 10 ml in vacuo at 35° C. The reaction product is precipitated from the solution which remains using 2N HCl, filtered off, washed with water and dried in vacuo at 37° C. over KOH. 479 mg of the title compound are obtained in the form of an anti:syn=2:1 mixture.

R$_f$: 0.37 (ethyl acetate:methanol:glacial acetic acid=20:10:1).

IR (KBr): 1,761 cm$^{-1}$ (β-lactam band).

NMR (d₆-DMSO, 60 MHz): syn: δ=3.26 ppm (s, —N—CH₃), δ=3.59 ppm (AB, 2—CH₂—), δ=4.09 ppm (AB, 3—CH₂—S—), δ=5.09 ppm (d, 6—CH—), δ=5.76 ppm (q, 7—CH—), δ=6.62 ppm (s,

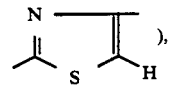

),

δ=7.20 ppm (s, broad, —NH₂), δ=9.39 ppm (d, —CO—NH—) and δ=11.26 ppm (s, broad, =N—OH); anti: δ=7.46 ppm (s,

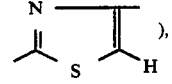

),

δ=9.22 ppm (d, —CO—NH—) and δ=12.38 ppm (s, broad, =N—OH).

EXAMPLE 212

7-β-[2-(2-Amino-thiazol-4-yl)-2-syn-methoximino-acetamido]-3-(5-carboxy-4-hydroxy-pyrimidin-2-yl-thiomethyl)-ceph-3-em-4-carboxylic acid The procedure is as according to Example 5, using 3.68 mg (7 mmoles) of 7-β-[2-(2-amino-thiazol-4-yl)-2-syn-methoximino-acetamido]-cephalosporanic acid and 1.2 g (7 mmoles) of 5-carboxy-4-hydroxy-2-mercapto-pyrimidine in 50 ml of water. The reaction solution is warmed to 50°-60° C. for 5 hours, whilst passing a weak stream of N₂ through. 1.36 g of the title compound of melting point 230° C. (decomposition) are isolated.

R$_f$: 0.69 (acetone:glacial acetic acid=10:1).

IR (KBr): 1,760 cm$^{-1}$ (β-lactam band).

NMR (d₆-DMSO, 60 MHz): δ=3.84 ppm (s, =N—OCH₃), δ=5.10 ppm (d, 6—CH—), δ=5.64 ppm (q, 7—CH—), δ=6.69 ppm (s, 1H,

δ=7.16 ppm (s, broad, 2H, —NH₂), δ=8.44 ppm (s, 1H,

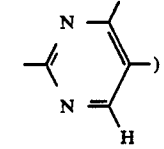

)

and δ=9.54 ppm (d, 1H, —CO—NH—).

EXAMPLE 213

7-β-[2-(2-Amino-thiazol-4-yl)-2-syn-oximino-acetamido]-3-(pyrimidin-4-yl-thiomethyl)-ceph-3-em-4-carboxylic acid 926 mg (2 mmoles) of sodium 7-[2-(2-amino-thiazol-4-yl)-2-syn-oximino-acetamido]-cephalosporanate are dissolved in 30 ml of $H_2O$, 224 mg (2 mmoles) of 4-mercaptopyrimidine are added and the mixture is warmed to 65° at pH 6.5 to 7.0 for 6 hours. 224 mg of 4-mercaptopyrimidine are then again added and the mixture is warmed to 65° C. at pH 6.5-7.0 for a further 3 hours. After cooling, the pH is adjusted to 4.5 with 2N HCl, the mixture is extracted twice with 20 ml of ethyl acetate each time and the extract is treated with 500 mg of active charcoal. The filtrate is cooled to 0° and adjusted to pH 2.0 with 2N HCl. The precipitate is filtered off, washed with water and dried in vacuo over $P_2O_5$. 290 mg of the title compound of melting point 260° C. are isolated.

$R_f$: 0.49 (ethyl acetate:isopropanol:water=4:3:2).

IR (KBr): 1,755 cm$^{-1}$ (β-lactam band).

NMR (d$_6$-DMSO, 60 MHz): δ=3.5 ppm (AB, 2H, 2—CH$_2$—), δ=4.4 ppm (AB, 2H, 3—CH$_2$—S—), δ=5.1 ppm (d, 1H, 6—CH—), δ=5.75 ppm (q, 1H, 7—CH—), δ=6.6 ppm (s, 1H,

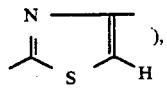

),

δ=7.1 ppm (s, broad, 2H, —NH$_2$), δ=7.5 ppm (2 x d, 1H,

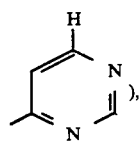

),

δ=8.4 ppm (d, 1H,

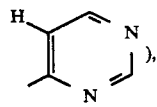

),

δ=8.9 ppm (d, 1H,

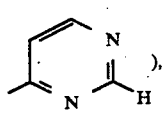

),

δ=9.3 ppm (d, 1H, —NHCO—) and δ=11.2 ppm (s, broad, 1H, =N—OH).

EXAMPLE 214

7-β-[2-(2-Amino-thiazol-4-yl)-2-syn-oximino-acetamido]-3-(4-ethyl-6-hydroxy-5-oxo-1,2,4-triazin-3-yl-thiomethyl)-ceph-3-em-4-carboxylic acid The procedure is as according to Example 210, using 695 mg (1.5 mmoles) of sodium 7-β-[2-(2-amino-thiazol-4-yl)-2-syn-oximino-acetamido]-cephalosporanate and 260 mg (1.5 mmoles) of 4-ethyl-6-hydroxy-3-mercapto-5-oxo-1,2,4-triazine in 50 ml of water. The reaction solution is heated to 60° C. for 3 hours, whilst keeping the pH value constant (pH=7). After again adding 17 mg (0.1 mmole) of the thiol, the mixture is heated to 60° C. for a further 1.5 hours. 394 mg of the title compound are isolated.

$R_f$: 0.18 (ethyl acetate:isopropanol:water=4:3:2).

IR (KBr): 1,758 cm$^{-1}$ (β-lactam band).

NMR (d$_6$-DMSO, 60 MHz): δ=1.17 ppm (t, 3H, —N—C—CH$_3$), δ=5.11 ppm (d, 1H, 6—CH—), δ=5.75 ppm (q, 1H, 7—CH—), δ=6.63 ppm (s, 1H,

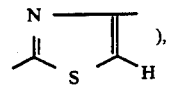

),

δ=7.07 ppm (s, broad, 2H, —NH$_2$), δ=9.40 ppm (d, 1H, —CO—NH—), δ=11.23 ppm (s, broad, 1H, =N—OH), and δ=12.38 ppm (s, broad, 1H, =C—OH).

EXAMPLE 215

7-β-[2-(2-Amino-thiazol-4-yl)-2-syn-oximino-acetamido]-3-(1-methyl-tetrazol-5-yl-thiomethyl)-ceph-3-em-4-carboxylic acid The procedure is as according to Example 210, using 695 mg (1.5 mmoles) of sodium 7-β-[2-(2-amino-thiazol-4-yl)-2-syn-oximino-acetamido]-cephalosporanate and 221 mg (1.6 mmoles) of sodium 5-mercapto-1-methyl-tetrazole in 50 ml of water. The reaction solution is warmed to 60°-65° C. for 5 hours. 412 mg of the title compound are isolated.

IR (Nujol): 1,770 cm$^{-1}$ (β-lactam band).

NMR (d$_6$-DMSO, 60 MHz): δ=6.65 ppm (s, 1H,

)

and δ=7.25 ppm (s, broad, 2H,

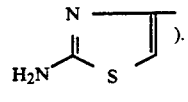

).

EXAMPLE 216

7-β-[2-(2-Amino-thiazol-4-yl)-2-syn-oximino-acetamido]-3-(2-methyl-1,3,4-thiadiazol-5-yl-thiomethyl)-ceph-3-em-4-carboxylic acid The procedure is as according to Example 210, using 1.39 g (3 mmoles) of sodium 7-β-[2-(2-amino-thiazol-4-yl)-2-syn-oximino-acetamido]-cephalosporanate and 422 mg (3.2 mmoles) of 5-mercapto-2-methyl-1,3,4-thiadiazole in 60 ml of water. The reaction solution is warmed to 60°-65° C. for 6 hours. 817 mg of the title compound are isolated.

NMR (d$_6$-DMSO, 60 MHz): δ=6.7 ppm (s, 1H,

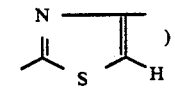

and δ=2.68 ppm (s, 3H,

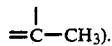

).

EXAMPLE 217

Sodium 7-β-[2-(2-amino-thiazol-4-yl)-2-syn-oximino-acetamido]-3-(2-methyl-1,3,4-thiadiazol-5-yl-thiomethyl)-ceph-3-em-4-carboxylate 0.8 g of the compound obtained according to Example 216 is suspended in 10 ml of methanol. 2 ml of a 1N solution of triethylamine in methanol are added and the mixture is stirred at room temperature for 5 minutes. The insoluble residue is filtered off and washed with a little methanol. 3 ml of a saturated methanolic sodium acetate solution are added to the filtrate and, after adding 50 ml of ethanol, the mixture is stirred at room temperature for 15 minutes. The precipitate is filtered off, washed with ethanol and then with ether and dried. 408 mg of the title compound are obtained. A further 143 mg of the title compound could be isolated by concentrating the mother liquor.

NMR (d₆-DMSO, 60 MHz): δ=2.66 ppm (s, 3H,

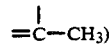

)

and δ=6.65 ppm (s, 1H,

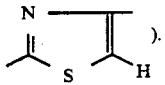

).

EXAMPLE 218

7-β-[2-(2-Amino-thiazol-4-yl)-2-syn-oximino-acetamido]-3-(5-carboxymethyl-4-methyl-1,3-thiazol-2-yl-thiomethyl)-ceph-3-em-4-carboxylic acid The procedure is as according to Example 210, using 289 mg (1.53 mmoles) of 5-carboxymethyl-2-mercapto-4-methyl-1,3-thiazole. The reaction solution is heated to 50°-60° C. for 8 hours. 218 mg of the title compound of melting point >210° C. (decomposition) are obtained.

R_f: 0.34 (ethyl acetate:glacial acetic acid:water=3:1:1).

IR (KBr): 1,766 cm⁻¹ (β-lactam band).

NMR (d₆-DMSO, 60 MHz): δ=2.25 ppm (s, 3H, =C—CH₃), δ=3.72 ppm (s, 2H, =C—CH₂—COO—), δ=4.24 ppm (AB, 2H, 3—CH₂—S—), δ=5.05 ppm (d, 1H, 6—CH—), δ=5.72 ppm (q, 1H, 7—CH—), δ=6.62 ppm (s, 1H,

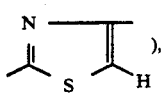

),

δ=7.04 ppm (s, broad, 2H, —NH₂), δ=9.35 ppm (d, 1H, —CO—NH—) and δ=11.26 ppm (s, broad, 1H, =N—OH).

EXAMPLE 219

7-β-[2-(2-Amino-thiazol-4-yl)-2-syn-oximino-acetamido]-3-[2-(thien-2-yl)-1H-1,3,4-triazol-5-yl-thiomethyl]-ceph-3-em-4-carboxylic acid The procedure is as according to Example 210, using 309 mg (1.7 mmoles) of 5-mercapto-2-(thien-2-yl)-1H-1,3,4-triazole. The reaction solution is heated to 60° C. for 4.2 hours. 440 mg of the title compound are isolated.

R_f: 0.42 (ethyl acetate:glacial acetic acid:water=3:1:1).

IR (KBr): 1,759 cm⁻¹ (β-lactam band).

NMR (d₆-DMSO, 60 MHz): δ=4.21 ppm (AB, 3—CH₂—S—), δ=5.10 ppm (d, 1H, 6—CH—), δ=5.72 ppm (q, 1H, 7—CH—), δ=6.61 ppm (s, 1H,

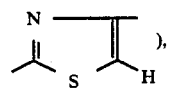

),

δ=7.04 ppm (broad, 2H, —NH₂), δ=7.12 ppm (t, 1H,

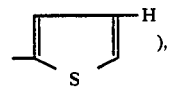

),

δ=7.63 ppm (m, 2H,

),

δ=9.37 ppm (d, 1H, —CO—NH—) and δ=11.21 ppm (s, broad, 1H, =N—OH).

EXAMPLE 220

7-β-[2-(2-Amino-thiazol-4-yl)-2-syn-methoximino-acetamido]-3-[tetrazolo(4,5-b)pyridazin-6-yl-thiomethyl]-ceph-3-em-4-carboxylic acid The procedure is as according to Example 5 using 551 mg (3.6 mmoles) of 6-mercapto-tetrazolo(4,5-b)pyridazine. The reaction solution is warmed to 65° C. for 8 hours. Then a further 153 mg (1 mmole) of the thiol are added and the mixture is heated again for 6 hours to 65° C. 659 g of the title compound are isolated.

R_f: 0.20 (ethyl acetate:glacial acetic acid:water=3:1:1).

IR (KBr): 1760 cm⁻¹ (β-lactam band).

NMR (d₆-DMSO, 60 MHz): δ=3.79 ppm (s, =N—OCH₃), δ=4.36 ppm (AB, 3—CH₂—S—), δ=5.10 ppm (d, 1H, 6—CH—), δ=5.76 ppm (q, 1H, 7—CH—), δ=6.69 ppm (s, 1H,

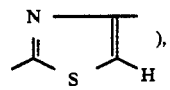

),

δ=7.15 ppm (s, broad, 2H, —NH₂), δ=7.71+8.53 ppm (d, 2H,

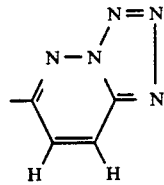

δ=9.52 ppm (d, 1H, —CO—NH—).

EXAMPLE 221

7-β-[2-(2-Amino-thiazol-4-yl)-2-syn-oximino-acetamido]-3-(pyrimidin-2-yl-thiomethyl)-ceph-3-em-4-carboxylic acid The procedure is as according to Example 210 using 695 mg (1.5 mmoles) of the sodium salt of 7-β-[2-(2-amino-thiazol-4-yl)-2-syn-oximino-acetamido]-cephalosporanic acid and 179 mg (1.6 mmoles) of 2-mercaptopyrimidine. The reaction solution is heated to 50° C. for 4.5 hours. After the addition of another 23 mg (0.2 mmole) of the thiol, the mixture is again heated to 60° C. for 2.5 hours. The isolated crude product is purified by trituration with ethyl acetate. 238 mg of the title compound are obtained.

R$_f$: 0.57 (ethyl acetate:glacial acetic acid:water=3:1:1).

IR (KBr): 1760 cm$^{-1}$ (β-lactam band).

NMR (d$_6$-DMSO, 60 MHz): δ=4.59 ppm (AB, 2H, 3—CH$_2$—S—), δ=5.09 ppm (d, 1H, 6—CH—), δ=5.69 ppm (q, 1H, 7—CH—), δ=6.63 ppm (s, 1H,

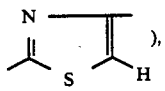

δ=7.04 ppm (s, broad, 2H, —NH$_2$), δ=7.15 ppm (m, 1H,

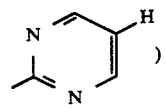

δ=8.56 ppm (d, 2H,

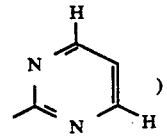

δ=9.35 ppm (d, 1H, —CO—NH—), δ=11.22 ppm (s, broad, 1H, =N—OH).

EXAMPLE 222

7-β-[2-(2-Amino-thiazol-4-yl)-2-syn-methoximino-acetamido]-3-(2-methoxycarbonylmethyl-1.3.4-oxadiazol-5-yl-thiomethyl)-ceph-3-em-4-carboxylic acid The procedure is as according to Example 5 using 627 mg (3.6 mmoles) of 5-mercapto-2-methoxycarbonylmethyl-1,3,4-oxadiazol. The reaction solution is warmed to 60° C. for 2.5 hours and the isolated crude product is purified by trituration with ethyl acetate. 437 g of the title compound are obtained.

R$_f$: (ethyl acetate:glacial acetic acid:water=3:1:1).

IR (KBr): 1766 cm$^{-1}$ (β-lactam band).

NMR (d$_6$-DMSO, 60 MHz): δ=3.61 ppm (s,

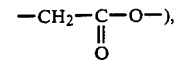

δ=3.77 ppm (s,

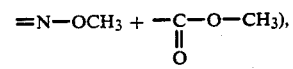

δ=4.17 ppm (AB, 3—CH$_2$—S—), δ=5.08 ppm (d, 1H, 6—CH—), δ=5.68 ppm (q, 1H, 7—CH—), δ=6.68 ppm (s, 1H,

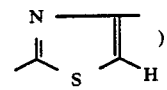

δ=7.13 ppm (s, broad, 2H, —NH$_2$), δ=9.51 ppm (d, 1H, —CO—NH—).

EXAMPLE 223

7-β-[2-(2-Amino-thiazol-4-yl)-2-syn-oximino-acetamido]-3-(2-acetamidomethyl-1,3,4-thiadiazol-5-yl-thiomethyl)-ceph-3-em-4-carboxylic acid 695 mg (1.5 mmoles) of sodium 7-β-[2-(2-amino-thiazol-4-yl)-2-syn-oximino-acetamide]-cephalosporanate are dissolved in 50 ml of water. The reaction solution has a pH of 5. After addition of 302 mg (1.6 mmoles) of 5-acetamidomethyl-1,3,4-thiadiazol-5-thiol the pH of the solution is 4. By adding NaHCO$_3$ the reaction solution is then adjusted to pH 6.5 and warmed to 60° C. for 2.5 hours while stirring and maintaining the pH constant. A further 19 mg (0.1 mmole) of the thiol are added and the mixture is warmed to 60° C. for another 4.5 hours. After addition of a further 19 mg (0.1 mmole) of the thiol, the reaction solution is warmed to 60° C. for another 6 hours. The reaction mixture is allowed to cool, filtered off and the filtrate is acidified with 2N hydrochloric acid. The precipitate is separated by filtration, washed with water and dried at 37° C. in vacuo 2 over KOH. 414 g of the title compound are isolated containing about 40% of anti-isomer.

R$_f$: 0.13 (ethyl acetate:glacial acetic acid:water=3:1:1).

IR (KBr): 1769 cm$^{-1}$ (β-lactam band).

NMR (d$_6$-DMSO, 60 MHz): Syn-Isomer: δ=1,84 ppm (s, 3H, —N—CO—CH$_3$), δ=4,40 ppm (AB, 3—CH$_2$—S—), δ=4,55 ppm (d, —CH$_2$—N—CO), δ=5,11 ppm (d, 1H, 6—CH—), δ=5,74 ppm (q, 1H, 7—CH—), δ=6,63 ppm (s,

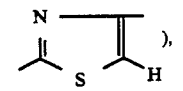

δ=7,12 ppm (s, broad, 2H, —NH$_2$), δ=8,74 ppm (t, broad, 1H, —C—NH—CO—), δ=9,43 ppm (d, —NH—CO—), δ=11,23 ppm (s, broad, =N—OH). Anti-Isomer: δ=7,45 ppm (s,

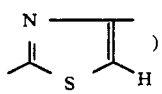

δ=9,25 ppm (d, —CO—NH—).

EXAMPLE 224

7-β-[2-(2-Amino-thiazol-4-yl)-2-syn-oximino-acetamido]-3-(purin-6-yl-thiomethyl)-ceph-3-em-4-carboxylic acid The procedure is as according to Example 210 using 695 mg (1.5 mmoles) of sodium 7-β-[2-(2-amino-thiazol-4-yl)-2-syn-oximino-acetamido]-cephalosporanate and 289 mg (1.7 mmoles) of 6-mercapto-purin-monohydrate. The reaction solution is warmed to 60° C. for 4.5 hours. 247 g of the title compound are isolated.

$R_f$ (ethyl acetate:glacial acetic acid:water=3:1:1).

IR (KBr): 1760 cm$^{-1}$ (β-lactam band).

NMR (d$_6$-DMSO, 60 MHz): δ=4.10 ppm (AB, 3—CH$_2$—S—), δ=5.11 ppm (d, 1H, 6—CH—), δ=5.73 ppm (q, 1H, 7—CH—), δ=6.62 ppm (s, 1H,

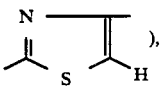

δ=7.04 ppm (s, broad, 2H, —NH$_2$), δ=8.42 ppm (s, 1H,

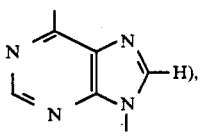

δ=8.63 ppm (s, 1H,

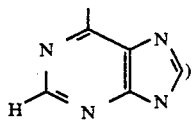

δ=9.37 ppm (d, 1H, —CO—NH—), δ=11.23 ppm (s, broad, 1H, =N—OH), δ=13.49 ppm (broad, 1H,

EXAMPLE 225

7-β-[2-(2-Amino-thiazol-4-yl)-2-syn-oximino-acetamido]-3-(quinolin-2-yl-thiomethyl)-ceph-3-em-4-carboxylic acid The procedure is as according to Example 210 using 695 mg (1.5 mmoles) of sodium 7-β-[2-(2-amino-thiazol-4-yl)-2-syn-oximino-acetamido]-cephalosporanate and 376 mg (1.7 mmoles) of 2-mercapto-quinolin. The reaction solution is warmed to 65° C. for 3.5 hours. 188 g of the title compound are obtained.

$R_f$: 0.42 (ethyl acetate:glacial acetic acid:water=3:1:1).

IR (KBr): 1762 cm$^{-1}$ (β-lactam band).

NMR (d$_6$-DMSO, 60 MHz): δ=5.07 ppm (d, 1H, 6—CH—), δ=5.70 ppm (q, 1H, 7—CH—), δ=6.61 ppm (s, 1H,

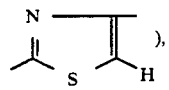

δ=7.03 ppm (s, broad, 2H, —NH$_2$), δ=7.1–8.3 ppm (m, 6H,

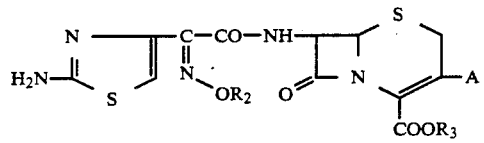

δ=9.36 ppm (d, 1H, —CO—NH—), δ=11.23 ppm (s, broad, =N—OH).

What is claimed is:

1. A cephem compound of the formula

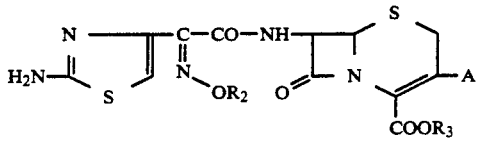

wherein $R_2$ is $C_1$-$C_4$-alkyl or $C_1$-$C_4$-alkyl substituted by carboxyl, and the group —$OR_2$ is in the syn-position;

$R_3$ is hydrogen, a physiologically acceptable ester group, or a physiologically acceptable cation; and A is —CH$_2$Y, Y is —SR$_5$, and $R_5$ is a 6-membered heterocycle which is triazinyl, or triazinyl which is partially or completely hydrogenated, said triazinyl or partially or completely hydrogenated triazinyl being unsubstituted or monosubstituted or polysubstituted by lower alkyl, carboxyloweralkyl, trifluoromethyl, aminoloweralkyl, acetylaminoloweralkyl, loweralkyloxycarbonyl-loweralkylcarboxamido, hydroxy, oxo, oxido, carboxy, furyl, thienyl, thiazolyl, or pyridyl.

2. A method for combating a bacterial infection in a patient suffering from such an infection, which method comprises administering to said patient a bactericidally effective amount of a compound as in claim 1.

3. A pharmaceutical composition for combating bacterial infections, said composition comprising a bactericidally effective amount of a compound as in claim 1 and a pharmaceutically acceptable carrier therefor.

4. A cephem compound of the formula wherein $R_2$ is $C_1$–$C_4$-alkyl and the group —$OR_2$ is in the syn-position;

$R_3$ is hydrogen, a physiologically acceptable ester group, or a physiologically acceptable cation; and A is —$CH_2Y$, Y is —$SR_5$, and $R_5$ is 1,2,4-triazin-3-yl substituted by up to three substituents selected from the group consisting of methyl, hydroxyl, oxo and —$CH_2CH_2CO_2H$.

5. A cephem compound as in claim 4 wherein $R_2$ is $CH_3$.

6. A cephem compound as in claim 4 wherein $R_2$ is $CH_3$ and $R_3$ is hydrogen.

7. A method for combating a bacterial infection in a patient suffering from such an infection, which method comprises administering to said patient a bactericidally effective amount of a compound as in claim 4.

8. A pharmaceutical composition for combating bacterial infections, said composition comprising a bactericidally effective amount of a compound as in claim 4 and a pharmaceutically acceptable carrier therefor.

9. A cephem compound of the formula

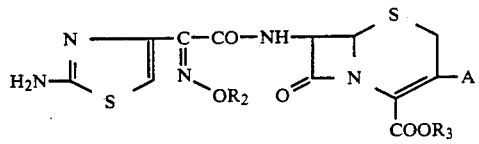

wherein $R_2$ is $C_1$–$C_4$-alkyl and the group —$OR_2$ is in the syn-position;

$R_3$ is hydrogen, a physiologically acceptable ester group, or a physiologically acceptable cation; and A is —$CH_2Y$, Y is —$SR_5$, and $R_5$ is 1,2,4-triazin-3-yl substituted by up to three substituents selected from the group consisting of up to two methyls, one oxo and one hydroxy.

10. A cephem compound as in claim 9 wherein $R_2$ is $CH_3$.

11. A cephem compound as in claim 9 wherein $R_2$ is $CH_3$ and $R_3$ is hydrogen.

12. A method for combating a bacterial infection in a patient suffering from such an infection, which method comprises administering to said patient a bactericidally effective amount of a compound as in claim 9.

13. A pharmaceutical composition for combating bacterial infections, said composition comprising a bactericidally effective amount of a compound as in claim 9 and a pharmaceutically acceptable carrier therefor.

* * * * *

UNITED STATES PATENT AND TRADEMARK OFFICE
CERTIFICATE OF CORRECTION

PATENT NO. : 5,089,490
DATED : February 18, 1992
INVENTOR(S) : Walter Durckheimer et al It is certified that error appears in the above-identified patent and that said Letters Patent is hereby corrected as shown below:

On the title page, at [62], after "Pat. No. 4,758,556." insert

--[30]    Foreign Application Priority Data

Apr. 2, 1977    [DE] Fed. Rep. of Germany    .....    2714880

Apr. 15, 1977    [DE] Fed. Rep. of Germany    .....    2716707--.

Signed and Sealed this

Twentieth Day of April, 1993

Attest:

MICHAEL K. KIRK

*Attesting Officer*    Acting Commissioner of Patents and Trademarks